US011857615B2

(12) United States Patent
Møller et al.

(10) Patent No.: US 11,857,615 B2
(45) Date of Patent: Jan. 2, 2024

(54) **PEPTIDES DERIVED FROM *ACINETOBACTER BAUMANNII* AND THEIR USE IN VACCINATION**

(71) Applicant: Evaxion Biotech ApS, København (DK)

(72) Inventors: Niels Iversen Møller, København (DK); Andreas Holm Mattsson, København (DK)

(73) Assignee: Evaxion Biotech A/S, Hørsholm (DK)

( * ) Notice: Subject to any disclaimer, the term of this patent is extended or adjusted under 35 U.S.C. 154(b) by 52 days.

(21) Appl. No.: 16/809,011

(22) Filed: Mar. 4, 2020

(65) Prior Publication Data

US 2020/0268866 A1     Aug. 27, 2020

Related U.S. Application Data

(63) Continuation of application No. 15/526,219, filed as application No. PCT/EP2015/076598 on Nov. 13, 2015, now abandoned.

(30) Foreign Application Priority Data

Nov. 13, 2014 (EP) .................................. 14193008

(51) Int. Cl.
   *A61K 39/104*     (2006.01)
   *C07K 14/21*     (2006.01)
   *A61K 39/00*     (2006.01)

(52) U.S. Cl.
CPC .......... *A61K 39/104* (2013.01); *C07K 14/212* (2013.01); *A61K 2039/543* (2013.01); *A61K 2039/55505* (2013.01); *A61K 2039/55566* (2013.01); *G01N 2333/22* (2013.01); *G01N 2469/20* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,683,202 A | 7/1987 | Mullis |
| 4,684,611 A | 8/1987 | Schilperoot et al. |
| 4,800,159 A | 1/1989 | Mullis et al. |
| 4,879,236 A | 11/1989 | Smith et al. |
| 4,952,500 A | 8/1990 | Finnerty et al. |
| 5,302,523 A | 4/1994 | Coffee et al. |
| 5,322,783 A | 6/1994 | Tomes et al. |
| 5,384,253 A | 1/1995 | Krzyzek et al. |
| 5,464,765 A | 11/1995 | Coffee et al. |
| 5,538,877 A | 7/1996 | Lundquist et al. |
| 5,538,880 A | 7/1996 | Lundquist et al. |
| 5,550,318 A | 8/1996 | Adams et al. |
| 5,563,055 A | 10/1996 | Townsend et al. |
| 5,580,859 A | 12/1996 | Felgner et al. |
| 5,589,466 A | 12/1996 | Felgner et al. |
| 5,591,616 A | 1/1997 | Hiei et al. |
| 5,610,042 A | 3/1997 | Chang et al. |
| 5,656,610 A | 8/1997 | Shuler et al. |
| 5,702,932 A | 12/1997 | Hoy et al. |
| 5,736,524 A | 4/1998 | Content et al. |
| 5,780,448 A | 7/1998 | Davis |
| 5,789,215 A | 8/1998 | Berns et al. |
| 5,843,650 A | 12/1998 | Segev |
| 5,846,709 A | 12/1998 | Segev |
| 5,846,783 A | 12/1998 | Wu et al. |
| 5,849,497 A | 12/1998 | Steinman |
| 5,849,546 A | 12/1998 | Sousa et al. |
| 5,849,547 A | 12/1998 | Cleuziat et al. |
| 5,858,652 A | 1/1999 | Laffler et al. |
| 5,866,366 A | 2/1999 | Kallender |
| 5,871,986 A | 2/1999 | Boyce |
| 5,916,776 A | 6/1999 | Kumar |
| 5,922,574 A | 7/1999 | Minter |
| 5,925,565 A | 7/1999 | Berlioz et al. |
| 5,928,905 A | 7/1999 | Stemmer et al. |
| 5,928,906 A | 7/1999 | Koster et al. |
| 5,932,451 A | 8/1999 | Wang et al. |
| 5,935,819 A | 8/1999 | Eichner et al. |
| 5,935,825 A | 8/1999 | Nishimura et al. |
| 5,939,291 A | 8/1999 | Loewy et al. |
| 5,942,391 A | 8/1999 | Zhang et al. |
| 5,945,100 A | 8/1999 | Fick |
| 5,981,274 A | 11/1999 | Tyrrell et al. |
| 5,994,624 A | 11/1999 | Trolinder et al. |
| 6,562,958 B1 | 5/2003 | Breton et al. |

FOREIGN PATENT DOCUMENTS

| | | |
|---|---|---|
| EP | 0365627 | 12/1993 |
| EP | 2599496 | 6/2013 |
| ES | 2366735 | 10/2011 |
| GB | 2202328 | 9/1988 |
| WO | WO9014837 | 12/1990 |
| WO | WO9409699 | 5/1994 |
| WO | WO9506128 | 3/1995 |
| WO | WO9820734 | 5/1998 |
| WO | WO2012158159 | 11/2012 |
| WO | WO2012158529 | 11/2012 |
| WO | WO2014048976 | 4/2014 |

OTHER PUBLICATIONS

Boersman et al. (Immunological Recognition of Peptides in Medicine and Biology, Edited by Zegers et al., Chapter 13, pp. 169-194).*
Adams, M. et al., "Acinetobacter baumannii AB0057 conserved hypothetical protein", XP002754301, (Dec. 16, 2008).
Adams, M. et al., "Comparative genome sequence analysis of multidrug-resistant acinetobacter baumannii" Journal of Bacteriology, vol. 190(24), pp. 8053-8064, XP002754301, (Oct. 2008).
Breton, G. et al., "DNA encoding Acinetobacter baumannii protein #2677", XP002754303, (Nov. 2003).

(Continued)

*Primary Examiner* — Brian Gangle
(74) *Attorney, Agent, or Firm* — McHale & Slavin, P.A.

(57) ABSTRACT

The present invention relates to proteins derived from *Acinetobacter baumanii*, nucleic acids encoding the proteins, antibodies specific for the proteins as well as methods of therapy, prophylaxis, and diagnosis that utilise the proteins, nucleic acids, and antibodies.

8 Claims, No Drawings

Specification includes a Sequence Listing.

(56) References Cited

OTHER PUBLICATIONS

Breton, G. et al., "Acinetobacter baumannii protein #2677", XP002754302, GSP:ADA35516, (Nov. 20, 2003).
Mcconnell, M. et al., "Vaccination with outer membrane complexes elicits rapid protective immunity to multidrug-resistant acinetobacter baumannii", Infection and Immunity, American Society for Microbiology, US, vol. 79(1), pp. 518-526, (Jan. 2011).
Goel, V. et al., "Monoclonal antibodies against the iron regulated outer membrane Proteins of Acinetobacter baumannii are bactericidal", BMC Microbiology, Biomed Central Ltd, GB, vol. 1(16), (XP021014761, (Aug. 9, 2001).
Jacobs, A. et al., "AB5075, a highly virulent isolate of acinetobacter baumannii, as a model strain for the evaluation of pathogenesis and antimicrobial treatments", MBIO, vol. 5(3), pp. e01076-14, (May-Jun. 2014).
Baig, A. et al., "Development and characterization of monoclonal antibodies for rapid detection of acinetobacter baumannii", Monoclonal Antibodies in Immunodiagnosis and Immunotherapy, vol. 33(4), pp. 291-298, XP055250018, (Aug. 29, 2014) Abstract.
Spellberg, B. et al., "Combating antimicrobial resistance: policy recommendations to save lives", Clin. Infect. Dis., vol. 52(S5), pp. S397-S428, (2011).
Spellberg, B. et al., "The epidemic of antibody-resistant infections: a call to action for the medical community from the Infectious Diseases Society of America", Clin. Infect. Dis., vol. 46(2), pp. 155-164, (2008).
Walker, B et al., "Looming global-scale failures and missing institutions", Science, vol. 325(5946), pp. 1345-1346, (2009) Abstract.
Doi, Y. et al., "Extensively drug-resistant acinetobacter baumannii", Emerg. Infect. Dis., vol. 15, pp. 980-982, (2009).
Perez, F. et al., "Why are we afraid of Acinetobacter baumannii?", Internet article: www.Expert-Reviews.com, pp. 269-271, (2008).
Hidron, A. et al., "Antimicrobial-resistant pathogens associated with healthcare-associated infections: annual summary of data reported to the national healthcare safety network at the centers for disease control and prevention", Infect. Control Hosp. Epidemiol., vol. 29(11), pp. 996-1011, (2008) Abstract.
Hoffman, M. et al., "Increasing resistance of acinetobacter species to imipenem in United States hospitals, 1999-2006", Infect. Control Hosp. Epidemiol., vol. 31, pp. 196-197, (2010) Abstract.
Kallen, A. et al., "Multidrug resistance among Gram-Negative pathogens that caused healthcare-associated Infections reported to the national healthcare safety network, 2006-2008", Infect. Control. Hosp. Epidemiol., vol. 31(5), pp. 528-531, (2010).
Lautenbach, E. et al., "Epidemiology and impact of Imipenem resistance in acinetobacter baumannii", Infect. Control Hosp. Epidemiol., vol. 30(12), pp. 1186-1192, (2009) Abstract.
Mera, R. et al., "Acinetobacter baumannii 2002-2008: increase of carbapenem-associated multiclass resistance in the United States", Drug Resist., vol. 16, pp. 209-215, (Sep. 2010) Abstract.
Perez, F. et al., "Antibiotic resistance determinants in *Acinetobacter* spp. and clinical outcomes in patients from a major military treatment facility", Am. J. Infect. Control, vol. 38(1), pp. 63-65, (Feb. 2010).
Rosenthal, V. et al., "Impact of international nosocomial infection control consortium (INICC) strategy on central line-associated bloodstream infection rates in the intensive care units of 15 developing countries", Am. J. Infect. Control, vol. 38(12), pp. 95-104, e102, (2010).
Falagas, M. et al., "Pandug-resistant Klebsiella pneumoniae, pseudomonas aeruginosa and acinetobacter baumannii Infections: characteristics and outcome in a series of 28 patients", Int. J. Antimicrob. Agents, vol. 32(5), pp. 450-454, (2008) Abstract.
Gordon, N. et al, "A review of clinical and microbiological outcomes following treatment of infections involving multidrug-resistant acinetobacter baumannii with tigecycline", J. Antimicrob. Chemother., vol. 63, pp. 775-780, (2009).

Metan, G. et al, "Factors influencing survival in patients with multi-drug-resistant acinetobacter bacteraemia", Eur. J. Intern. Med., vol. 20(5), pp. 540-544, (2009) Abstract.
Park, Y. et al, "Independent emergence of colistin-resistant *Acinetobacter* spp. isolates from Korea", Diagn. Microbiol. Infect. Dis., vol. 64(1), pp. 43-51, (2009) Abstract.
Donnelly, J. et al, "DNA vaccines", Annu. Rev. Immunol., vol. 15, pp. 617-648, (1997) Abstract.
Sunenshine, R., et al, "Multidrug-resistant acinetobacter infection mortality rate and length of hospitalization", Emeg. Infect. Dis., vol. 13(1), pp. 97-103, (Jan. 2007).
Munoz-Price, L. et al, "Acinetobacter baumannii: association between environmental contamination of patient rooms and occupant status", Infect. Control. Hosp. Epidemiol., vol. 1(10), pp. 1057-1062, (2013).
Tseng, Y. et al, "Prognosis of adult patients with bacteremia caused by extensively resistant acinetobacter baumannii", Diagn. Microbiol. Infect. Dis., vol. 59, pp. 181-190, (2007).
Adams, M. et al, "Resistance to colistin in acinetobacter baumannii associated with mutations in the PmrAB two-component system", Antimicrob. Agents Cheother, vol. 53(9), pp. 3628-3634, (Sep. 2009).
Hernan, R. et al, "Selection of colistin-resistant acinetobacter baumannii isolates in postneurosurgery meningitis in an intensive care unit with high presence of heteroresistance to colistin", Diagn. Microbiol. Infect. Dis., vol. 65(2), pp. 188-191, (2009) Abstract.
Livermore, D. et al, "Antimicrobial treatment and clinical outcome for infections with carbapenam-and multiply-resistant acinetobacter baumannii around London", Int. J. Antimicrob. Agents, vol. 35(1), pp. 19-24, (Jan. 2010) Abstract.
Robinson, H. et al, "DNA vaccines", Seminars in Immunol., vol. 9(5), pp. 271-283, (1997).
Wang, Y. et al, "In vitro activity of tigecycline and comparators on acinetobacter spp. isolates collected from patients with bacteremia and MIC change during the tigecycline evaluation and surveillance trial, 2004 to 2008", Diagn. Microbiol. Infect. Dis., vol. 68(1), pp. 73-79, (Sep. 2010).
Caricato, A. et a., "Risk factors and outcome of acinetobacter baumannii infection in severe trauma patients", Intensive Care Med., vol. 35, pp. 1964-1969, (2009).
D'Agata, E. et al, "An outbreak of acinetobacter baumannii: the importance of cross-transmission", Infect. Control Hosp. Epidemiol., vol. 21, pp. 588-591, (2000) Abstract.
Furniss, D. et al, "Acinetobacter infection is associated with acquired glucose intolerance in burn patients", J. Burn Care Rehabil., vol. 26(5), pp. 405-408, (2005) Abstract.
Zakuan, D. et al, "The prevalence and risk factors of nosocomial acinetobacter blood stream infections in tertiary teaching hospital in north-eastern Malaysia", Trop. Biomed., vol. 26(2), pp. 123-129, (2009).
Kohler, G. et al, "Continuous cultures of fused cells secreting antibody of predefined specificity", Nature, vol. 256, op. 495-496, (Aug. 1975) Abstract.
Valencia, R. et al, "Nosocomial outbreak of infection with pan-drug-resistant acinetobacter baummannii in a tertiary care university hospital", Infect. Control Hosp. Epidemiol., vol. 30(3), pp. 257-263, (Mar. 2009).
Rodriguez, C. et al, "Selection of colistin-resistant acinetobacter baumannii in postneurosurgical meningitis in an intensive care unit with high presence of heteroresistance to colistin", Diagn. Microbiol. Infect Dis., vol. 65(2), pp. 188-191, (Oct. 2009).
Lazar, E. et al, "Transforming growth Factor Alpha: Mutation of aspartic acid 47 and leucine 48 results in different biological activities", Molecular and Cellular Biology, vol. 8, No. 3, pp. 1247-1252, (Mar. 1988).
Petersen, B. et al, "NetTumP—neural network prediction of beta-turns by use of evolutionary information and predicted protein sequence features", PLoS ONE, Internet article: www.plosone.org, vol. 5(11), e15079, (Nov. 2010).
Burgess, W. et al, "Possible disassociation of the heparin-binding and mitogenic activities of heparin-binding (acidic fibroblast) growth factor-1 from its receptor-binding activities by site-directed mutagenesis of a single lysine residue", The Journal of Cellular Biology, vol. 111, pp. 2129-2138, (Nov. 1990).

(56) References Cited

OTHER PUBLICATIONS

Bowie, J. et al, "Deciphering the message in protein sequences: tolerance to amino acid substitutions", Science, vol. 247(4948), pp. 1306-1310, doi: 10.1126/science.2315699, (Mar. 1990) Abstract.

Cruse, J. et al, Illustrated Dictionary of Immunology, 2nd edition, CRC Press, pp. 46, 166, 382, (2003).

Cerqueira, G. et al, "The genome sequence of acinetobacter baylyi 107474", The Broad Institute Genome Sequencing Platform, The Broad Genome Sequencing Center for Infectious Disease, XP-002783437, Feb. 2013).

Vallenet, D. et al, "Comparative analysis of acinetobacters: Three genomes for three lifestyles", PLoS ONE, vol. 3 (3), e1805, XP-002783436, (Mar. 2008).

Breton, G. et al, "Acinetobacter baumannii protein #4107. Acinetobacter baumanii; bacterial disease; antibacterial; vaccine; plant biocontrol agent", Genome Terapeutics Corp., p. 1, XP-002783435, (May 2003).

\* cited by examiner

PEPTIDES DERIVED FROM *ACINETOBACTER BAUMANNII* AND THEIR USE IN VACCINATION

CROSS REFERENCE TO RELATED APPLICATIONS

In accordance with 37 C.F.R. 1.76, a claim of priority is included in an Application Data Sheet filed concurrently herewith. Accordingly, the present invention claims priority as a continuation of U.S. patent application Ser. No. 15/526,219, filed May 11, 2017, which is a § 371 national stage entry of International Application No. PCT/EP2015/076598, filed Nov. 13, 2015, which claims the benefit of the priority of European Patent Application No. 14193008.1, filed Nov. 13, 2014, the entire contents of each are incorporated herein by reference.

FIELD OF THE INVENTION

The present invention relates to the field of antimicrobial prophylaxis and therapy. In particular the present invention relates to novel proteins and polynucleotides derived from *Acinetobacter baumannii*. The invention further relates to vectors comprising the polynucleotides, transformed host organisms expressing the polynucleotides, antibodies (mono- or polyclonal) specific for the polypeptides as well as diagnostic, prophylactic and therapeutic uses and methods. Finally, also methods of preparation are part of the invention.

BACKGROUND OF THE INVENTION

Antibiotic resistance is recognized as one of the greatest threats to human health on the planet (2009; Choffnes et al., *Antibiotic Resistance: Implications for Global Health and Novel Intervention Strategies*, The National Academic Press, Washington, D.C., (2010); Smolinski et al., *Microbial Threats to Health: Emergence, Detection, and Response*, The Institute of Medicine, Washington D.C., (2003); Spellberg et al., *Clin Infect Dis* 52(55):397-428 (2011); Spellberg et al., *Clin Infect Dis* 46:155-164 (2008); Walker et al., *Science* 325-1345-1346 (2009). In the last decade, *Acinetobacter baumannii* has emerged as one of the most common and highly antibiotic-resistant pathogens in the United States (US) and throughout the world (Doi et al., *Emerg Infect Dis* 15:980-982 (2009); Higgins et al., *J Antimicrob Chemother* 65-233-238 (2010); Perez et al., *Antimicrob Agents Chemother* 51:3471-3484 (2007). Indeed, 50-70% of *A. baumannii* clinical isolates are now extensively drug resistant (XDR; i.e. resistant to carbapenems and all other antibiotics except colistin or tigecycline), reflecting a >15-fold increase in just the past 10 years (Dizbay et al., *Scand J Infect Dis* (2010); Hidron et al., *Infect Control Hosp Epidemiol* 29:996-1011 (2008); Hoffmann et al., *Infect Control Hosp Epidemiol* 31:196-197 (2010); Kallen et al., *Infect Control Hosp Epidemiol* 31:528-531 (2010); Lautenbach et al., *Infect Control Hosp Epidemolo* 30:1186-1192 (2009); Mera et al., *Drug Resist* 16:209-215 (2010); Perez et al., *Am J Infect Control* 38:63-65 (2010); Rosenthal et al., *Am J Infect Control* 38:95-104 e102 (2010). Infections caused by carbapenem-resistant, XDR *A. baumannii* are associated with prolonged hospitalization, tremendous health care costs, and high rates of death despite treatment (Doi et al., *Emerg Infect Dis* 15:980-982 (2009); Falagas et al., *Int J Antimicrob Agents* 32:450-454 (2008); Gordon and Wareham, *J Antimicrob Chemother* 63:775-780 (2009); Lautenbach et al., *Infect Control Hosp Epidemiol* 30:1186-1192 (2009); Metan et al., *Eur J Intern Med* 20:540-544 (2009); Park et al., *Diagn Microbiol Infect Dis* 64:43-51 (2009); Perez et al., *Am J Infect Control* 38:63-65 (2007); Sunenshine et al., *Emerg Infect Dis* 13:97-103 (2007). Indeed, bloodstream infections caused by XDR *A. baumannii* cause >50-60% mortality rates despite antibiotic therapy (Gordon and Wareham, *J Antimicrob Chemother* 63:775-780 (2009); Metan et al., *Eur J Intern Med* 20:540-544 (2009); Munoz-Price et al., *Infect Control Hosp Epidemiol* 1(10):1057-62 (2010); Park et al., *Diagn Microbiol Infect Dis* 64:43-51 (2009); Tseng et al., *Diagn Microbiol Infect Dis* 59:181-190 (2007). A major reason for these high mortality rates is that XDR *A. baumannii* infections are treatable only with sub-optimal second-line antibacterial agents, such as tigecycline and colistin. Even more concerning is the increasing resistance of *A. baumannii* to both colistin and tigecycline (Adams et al., *Antimicrob Agents Chemother* 53:3628-3634 (2009); Doi et al., *Emerg Infect Dis* 15:980-982 (2009); Falagas et al., *Int J Antimicrob Agents* 32:450-454 (2008); Hernan et al., *Diagn Microbiol Infect Dis* 65:188-191 (2009); Livermore et al., *Int J Antimicrob Agents* 35:19-24 (2010); Park et al., *Diagn Microbiol Infect Dis* 64:43-51 (2009); Valencia et al., *Infect Control Hosp Epidemiol* 30:257-263 (2009); Wang and Dowzicky, *Diagn Microbiol Infect Dis* 68:73-79 (2010). Such pan-drug resistant (PDR) *A. baumannii* infections are resistant to every FDA approved antibiotic, and are hence untreatable.

New methods to prevent and treat *A. baumannii* infections are critically needed, especially since no new drugs to treat these infections are in the antibacterial pipeline for the coming decade (Boucher et al., *Clin Infect Dis* 48:1-12 (2009); Spellberg et al., *Clin Infect Dis* 46:155-164 (2008). Since risk factors for *A. baumannii* infections are understood (Beavers et al., 2009; Caricato et al., *Intensive Care Med* 35:1964-1969 (2009); D'Agata et al., *Infect Control Hosp Epidemiol* 21:588-591 (2000); Furniss et al., *J Burn Care Rehabil* 26:405-408 (2005); Metan et al., *Eur J Intern Med* 20:540-544 (2009); Zakuan et al., *Trop Biomed* 26:123-129 (2009), vaccination of acutely at-risk patients is a promising method to prevent such infections, and antibody-based immunotherapy has promise to improve outcomes from infection.

The first full-genome sequence of *A. baumannii* was performed in 2007 (strain ATCC 17978) with a chromosome of 3976747 base pairs Vaccination is considered to be a very effective method of preventing infectious diseases in human and veterinary health care. Vaccination is the administration of immunogenically effective amounts of antigenic material (the vaccine) to produce immunity to a disease/disease-causing pathogenic agent. Vaccines have contributed to the eradication of smallpox, the near eradication of polio, and the control of a variety of diseases, including rubella, measles, mumps, chickenpox, typhoid fever.

Before "the genomic era", vaccines were based on killed or live attenuated, microorganisms, or parts purified from them. Subunit vaccines are considered as a modern upgrade of these types of vaccine, as the subunit vaccines contain one or more protective antigens, which are more or less the weak spot of the pathogen. Hence, in order to develop subunit vaccines, it is critical to identify the proteins, which are important for inducing protection and to eliminate others.

An antigen is said to be protective if it is able to induce protection from subsequent challenge by a disease-causing infectious agent in an appropriate animal model following immunization.

The empirical approach to subunit vaccine development, which includes several steps, begins with pathogen cultivation, followed by purification into components, and then testing of antigens for protection. Apart from being time and labour consuming, this approach has several limitations that can lead to failure. It is not possible to develop vaccines using this approach for microorganisms, which cannot easily be cultured and only allows for the identification of the antigens, which can be obtained in sufficient quantities. The empirical approach has a tendency to focus on the most abundant proteins, which in some cases are not immunoprotective. In other cases, the antigen expressed during in vivo infection is not expressed during in vitro cultivation. Furthermore, antigen discovery by use of the empirical approach demands an extreme amount of proteins in order to discover the protective antigens, which are like finding needles in the haystack. This renders it a very expensive approach, and it limits the vaccine development around diseases, which is caused by pathogens with a large genome or disease areas, which perform badly in a cost-effective perspective.

OBJECT OF THE INVENTION

It is an object of embodiments of the invention to provide *A. baumannii* derived antigenic polypeptides that may serve as constituents in vaccines against *A. baumannii* infections and in diagnosis of *A. baumannii* infections. It is also an object to provide nucleic acids, vectors, transformed cells, vaccine compositions, and other useful means for molecular cloning as well as for therapy and diagnosis with relevance for *A. baumannii.*

SUMMARY OF THE INVENTION

It has been found by the present inventor(s) that *A. baumannii*, expresses a number of hitherto unknown putatively surface exposed proteins which are candidates as vaccine targets as well as candidates as immunizing agents for preparation of antibodies that target *A. baumannii.*

So, in a first aspect the present invention relates to a polypeptide comprising a) an amino acid sequence selected from the group consisting of any one of SEQ ID NOs: 1-30, or
b) an amino acid sequence consisting of at least 5 contiguous amino acid residues from any one of SEQ ID NOs: 1-30, or
c) an amino acid sequence having a sequence identity of at least 60% with the amino acid sequence of a),
d) an amino acid sequence having a sequence identity of at least 60% with the amino acid sequence of b), or
e) an assembly of amino acids derived from any one of SEQ ID NOs: 1-30 which has essentially the same 3D conformation as in the protein from which said assembly is derived so as to constitute a B-cell epitope, said polypeptide being antigenic in a mammal.

In another aspect, the invention relates to an isolated nucleic acid fragment, which comprises i) a nucleotide sequence encoding a polypeptide of the invention, or
ii) a nucleotide sequence consisting of any one of SEQ ID NOs: 31-60.
iii) a nucleotide sequence consisting of at least 10 consecutive nucleotides in any one of SEQ ID NOs: 31-60,
iv) a nucleotide sequence having a sequence identity of at least 60% with the nucleotide sequence in i) or ii),
v) a nucleotide sequence having a sequence identity of at least 60% with the nucleotide sequence in iii),
vi) a nucleotide sequence complementary to the nucleotide sequence in i)-v), or
vii) a nucleotide sequence which hybridizes under stringent conditions with the nucleotide sequence in i)-vi).

In a third aspect, the invention relates to a vector comprising the nucleic acid of the invention, such as a cloning vector or an expression vector.

In fourth aspect, the invention relates to a cell which is transformed so as to carry the vector of the invention.

In a fifth aspect, the invention relates to a pharmaceutical composition comprising a polypeptide of the invention, a nucleic acid fragment of the invention, a vector of the invention, or a transformed cell of the invention, and a pharmaceutically acceptable carrier, vehicle or diluent.

In a sixth aspect, the invention relates to a method for inducing immunity in an animal by administering at least once an immunogenically effective amount of a polypeptide of the invention, a nucleic acid fragment of the invention, a vector of the invention, a transformed cell of the invention, or a pharmaceutical composition of the fifth aspect of the invention so as to induce adaptive immunity against *A. baumannii* in humans or animals.

In a seventh and eighth aspect, the invention relates to 1) a polyclonal antibody in which the antibodies specifically bind to at least one polypeptide of the invention, and which is essentially free from antibodies binding specifically to other *A. baumannii* polypeptides, and to 2) an isolated monoclonal antibody or antibody analogue which binds specifically to a polypeptide of the invention. In a related ninth aspect, the invention relates to a pharmaceutical composition comprising such a polyclonal or monoclonal antibody and a pharmaceutically acceptable carrier, vehicle or diluent.

In a $10^{th}$ aspect, the invention relates to a method for prophylaxis, treatment or amelioration of infection with *A. baumannii*, comprising administering a therapeutically effective amount of an antibody of the $7^{th}$ or $8^{th}$ aspect of the invention or a pharmaceutical composition of the eighth aspect to an individual in need thereof.

In an $11^{th}$ aspect, the invention relates to a method for determining, quantitatively or qualitatively, the presence of *A. baumannii*, in particular the presence of multi-resistant *A. baumannii*, in a sample, the method comprising contacting the sample with an antibody of aspects 8 or 9 of the invention and detecting the presence of antibody bound to material in the sample.

In an $12^{th}$ aspect of the invention is provided a method for determining, quantitatively or qualitatively, the presence of antibodies specific for *A. baumannii*, in particular the presence of antibodies specific for multi-resistant *A. baumannii*, in a sample, the method comprising contacting the sample with a polypeptide of the invention and detecting the presence of antibody that specifically bind said polypeptide.

In a $13^{th}$ aspect, the invention relates to a method for determining, quantitatively or qualitatively, the presence of a nucleic acid characteristic of *A. baumannii*, in particular the presence of a nucleic acid characteristic of multi-resistant *A. baumannii*, in a sample, the method comprising contacting the sample with a nucleic acid fragment of the invention and detecting the presence of nucleic acid in the sample that hybridizes to said nucleic acid fragment.

In a $14^{th}$ aspect, the invention relates to a method for the preparation of the polypeptide of the invention, comprising culturing a transformed cell of the present invention, which is capable of expressing the nucleic acid of the invention, under conditions that facilitate that the transformed cell expresses the nucleic acid fragment of the invention, which encodes a polypeptide of the invention, and subsequently recovering said polypeptide, or preparing said polypeptide by means of solid or liquid phase peptide synthesis.

In a 15$^{th}$ aspect, the invention relates to a method for determining whether a substance, such as an antibody, is potentially useful for treating infection with *A. baumannii*, the method comprising contacting the polypeptide of the invention with the substance and subsequently establishing whether the substance has at least one of the following characteristics:
1) the ability to bind specifically to said polypeptide,
2) the ability to compete with said polypeptide for specific binding to a ligand/receptor, and
3) the ability to specifically inactivate said polypeptide.

Finally, in a 16$^{th}$ aspect, the invention relates to a method for determining whether a substance, such as a nucleic acid, is potentially useful for treating infection with *A. baumannii*, the method comprising contacting the substance with the nucleic acid fragment of claim of the invention and subsequently establishing whether the substance has either the ability to
1) bind specifically to the nucleic acid fragment, or
2) bind specifically to a nucleic acid that hybridizes specifically with the nucleic acid fragment.

DETAILED DISCLOSURE OF THE INVENTION

Definitions

The term "polypeptide" is in the present context intended to mean both short peptides of from 2 to 10 amino acid residues, oligopeptides of from 11 to 100 amino acid residues, and polypeptides of more than 100 amino acid residues. Further-more, the term is also intended to include proteins, i.e. functional biomolecules comprising at least one polypeptide; when comprising at least two polypeptides, these may form complexes, be covalently linked, or may be non-covalently linked. The polypeptide (s) in a protein can be glycosylated and/or lipidated and/or comprise prosthetic groups.

The term "subsequence" means any consecutive stretch of at least 3 amino acids or, when relevant, of at least 3 nucleotides, derived directly from a naturally occurring amino acid sequence or nucleic acid sequence, respectively The term "amino acid sequence" s the order in which amino acid residues, connected by peptide bonds, lie in the chain in peptides and proteins.

The term "adjuvant" has its usual meaning in the art of vaccine technology, i.e. a substance or a composition of matter which is 1) not in itself capable of mounting a specific immune response against the immunogen of the vaccine, but which is 2) nevertheless capable of enhancing the immune response against the immunogen. Or, in other words, vaccination with the adjuvant alone does not provide an immune response against the immunogen, vaccination with the immunogen may or may not give rise to an immune response against the immunogen, but the combined vaccination with immunogen and adjuvant induces an immune response against the immunogen which is stronger than that induced by the immunogen alone.

"Sequence identity" is in the context of the present invention determined by comparing 2 optimally aligned sequences of equal length (e.g. DNA, RNA or amino acid) according to the following formula: $(N_{ref} - N_{dif}) \cdot 100/N_{ref}$ wherein $N_{ref}$ is the number of residues in one of the 2 sequences and $N_{dif}$ is the number of residues which are non-identical in the two sequences when they are aligned over their entire lengths and in the same direction. So, two sequences 5'-ATTCGGAACC-3' (SEQ ID No. 91) and 5'-ATACGGGACC-3' (SEQ ID NO. 92) will provide the sequence identity 80% ($N_{ref}=10$ and $N_{dif}=2$).

An "assembly of amino acids" means two or more amino acids bound together by physical or chemical means.

The "3D conformation" is the 3 dimensional structure of a biomolecule such as a protein. In monomeric polypeptides/proteins, the 3D conformation is also termed "the tertiary structure" and denotes the relative locations in 3 dimensional space of the amino acid residues forming the polypeptide.

"An immunogenic carrier" is a molecule or moiety to which an immunogen or a hapten can be coupled in order to enhance or enable the elicitation of an immune response against the immunogen/hapten. Immunogenic carriers are in classical cases relatively large molecules (such as tetanus toxoid, KLH, diphtheria toxoid etc.) which can be fused or conjugated to an immunogen/hapten, which is not sufficiently immunogenic in its own right—typically, the immunogenic carrier is capable of eliciting a strong T-helper lymphocyte response against the combined substance constituted by the immunogen and the immunogenic carrier, and this in turn provides for improved responses against the immunogen by B-lymphocytes and cytotoxic lymphocytes. More recently, the large carrier molecules have to a certain extent been substituted by so-called promiscuous T-helper epitopes, i.e. shorter peptides that are recognized by a large fraction of HLA haplotypes in a population, and which elicit T-helper lymphocyte responses.

A "T-helper lymphocyte response" is an immune response elicited on the basis of a peptide, which is able to bind to an MHC class II molecule (e.g. an HLA class II molecule) in an antigen-presenting cell and which stimulates T-helper lymphocytes in an animal species as a consequence of T-cell receptor recognition of the complex between the peptide and the MHC Class II molecule present.

An "immunogen" is a substance of matter which is capable of inducing an adaptive immune response in a host, whose immune system is confronted with the immunogen. As such, immunogens are a subset of the larger genus "antigens", which are substances that can be recognized specifically by the immune system (e.g. when bound by antibodies or, alternatively, when fragments of the are antigens bound to MHC molecules are being recognized by T-cell receptors) but which are not necessarily capable of inducing immunity—an antigen is, however, always capable of eliciting immunity, meaning that a host that has an established memory immunity against the antigen will mount a specific immune response against the antigen.

A "hapten" is a small molecule, which can neither induce or elicit an immune response, but if conjugated to an immunogenic carrier, antibodies or TCRs that recognize the hapten can be induced upon confrontation of the immune system with the hapten carrier conjugate.

An "adaptive immune response" is an immune response in response to confrontation with an antigen or immunogen, where the immune response is specific for antigene determinants of the antigen/immunogen—examples of adaptive immune responses are induction of antigen specific antibody production or antigen specific induction/activation of T helper lymphocytes or cytotoxic lymphocytes.

A "protective, adaptive immune response" is an antigen-specific immune response induced in a subject as a reaction to immunization (artificial or natural) with an antigen, where the immune response is capable of protecting the subject against subsequent challenges with the antigen or a pathology-related agent that includes the antigen. Typically, prophylactic vaccination aims at establishing a protective adaptive immune response against one or several pathogens.

"Stimulation of the immune system" means that a substance or composition of matter exhibits a general, non-specific immunostimulatory effect. A number of adjuvants and putative adjuvants (such as certain cytokines) share the ability to stimulate the immune system. The result of using an immunostimulating agent is an increased "alertness" of the immune system meaning that simultaneous or subsequent immunization with an immunogen induces a significantly more effective immune response compared to isolated use of the immunogen.

Hybridization under "stringent conditions" is herein defined as hybridization performed under conditions by which a probe will hybridize to its target sequence, to a detectably greater degree than to other sequences. Stringent conditions are target-sequence-dependent and will differ depending on the structure of the polynucleotide. By controlling the stringency of the hybridization and/or washing conditions, target sequences can be identified which are 100% complementary to a probe (homologous probing). Alternatively, stringency conditions can be adjusted to allow some mismatching in sequences so that lower degrees of similarity are detected (heterologous probing). Specificity is typically the function of post-hybridization washes, the critical factors being the ionic strength and temperature of the final wash solution. Generally, stringent wash temperature conditions are selected to be about 5° C. to about 2° C. lower than the melting point (Tm) for the specific sequence at a defined ionic strength and pH. The melting point, or denaturation, of DNA occurs over a narrow temperature range and represents the disruption of the double helix into its complementary single strands. The process is described by the temperature of the midpoint of transition, Tm, which is also called the melting temperature. Formulas are available in the art for the determination of melting temperatures.

The term "animal" is in the present context in general intended to denote an animal species (preferably mammalian), such as *Homo sapiens, Canis domesticus*, etc. and not just one single animal. However, the term also denotes a population of such an animal species, since it is important that the individuals immunized according to the method of the invention substantially all will mount an immune response against the immunogen of the present invention.

As used herein, the term "antibody" refers to a polypeptide or group of polypeptides composed of at least one antibody combining site. An "antibody combining site" is the three-dimensional binding space with an internal surface shape and charge distribution complementary to the features of an epitope of an antigen, which allows a binding of the antibody with the antigen. "Antibody" includes, for example, vertebrate antibodies, hybrid antibodies, chimeric antibodies, humanised antibodies, altered antibodies, univalent antibodies, Fab proteins, and single domain antibodies.

"Specific binding" denotes binding between two substances which goes beyond binding of either substance to randomly chosen substances and also goes beyond simple association between substances that tend to aggregate because they share the same overall hydrophobicity or hydrophilicity. As such, specific binding usually involves a combination of electrostatic and other interactions between two conformationally complementary areas on the two substances, meaning that the substances can "recognize" each other in a complex mixture.

The term "vector" is used to refer to a carrier nucleic acid molecule into which a heterologous nucleic acid sequence can be inserted for introduction into a cell where it can be replicated and expressed. The term further denotes certain biological vehicles useful for the same purpose, e.g. viral vectors and phage—both these infectious agents are capable of introducing a heterologous nucleic acid sequence The term "expression vector" refers to a vector containing a nucleic acid sequence coding for at least part of a gene product capable of being transcribed. In some cases, when the transcription product is an mRNA molecule, this is in turn translated into a protein, polypeptide, or peptide.

SPECIFIC EMBODIMENTS OF THE INVENTION

The Polypeptides of the Invention

In some embodiments the at least 5 contiguous amino acids referred to in option b) in the definition of the first aspect of the invention may preferably constitute at least or exactly or at most 6, such as at least or exactly or at most 7, at least or exactly or at most 8, at least or exactly or at most 9, at least or exactly or at most 10, at least or exactly or at most 11, at least or exactly or at most 12, at least or exactly or at most 13, at least or exactly or at most 14, at least or exactly or at most 15, at least or exactly or at most 16, at least or exactly or at most 17, at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27 at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35 and at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55 and at least or exactly or at most 56, at least or exactly or at most 57, at least or exactly or at most 58, at least or exactly or at most 59, or at least or exactly or at most 60 contiguous amino acid residues.

The number may, where applicable, be higher. Another way to phrase this is that for each of SEQ ID NOs: 1-30, the number of the contiguous amino acid residues is at least N−n, where N is the length of the sequence ID in question and n is any integer between 6 and N−1; that is, the at least 5 contiguous amino acids can be at least any number between 5 and the length of the reference sequence minus one, in increments of one. Consequently:

Insofar as embodiment b relates to SEQ ID NO: 2-30, the at least 5 contiguous amino acids referred to in option b) in the definition of the first aspect of the invention will preferably constitute at least or exactly or at most 61, at least or exactly or at most 62, at least or exactly or at most 63, at least or exactly or at most 64, at least or exactly or at most 65, at least or exactly or at most 66 contiguous amino acid residues.

Insofar as embodiment b relates to SEQ ID NO: 4-30, the at least 5 contiguous amino acids referred to in option b) in the definition of the first aspect of the invention will preferably constitute at least or exactly or at most 67, at least or exactly or at most 68, at least or exactly or at most 69, at least or exactly or at most 70, at least or exactly or at most 71, at least or exactly or at most 72, at least or exactly or at most 73 contiguous amino acid residues.

Insofar as embodiment b relates to SEQ ID NO: 5-30, the at least 5 contiguous amino acids referred to in option b) in the definition of the first aspect of the invention will preferably constitute at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108 contiguous amino acid residues.

Insofar as embodiment b relates to SEQ ID NO: 6-30, the at least 5 contiguous amino acids referred to in option b) in the definition of the first aspect of the invention will preferably constitute at least or exactly or at most 109, at least or exactly or at most 110, at least or exactly or at most 111, at least or exactly or at most 112, at least or exactly or at most 113, at least or exactly or at most 114 contiguous amino acid residues.

Insofar as embodiment b relates to SEQ ID NO: 7-30, the at least 5 contiguous amino acids referred to in option b) in the definition of the first aspect of the invention will preferably constitute at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126 contiguous amino acid residues.

Insofar as embodiment b relates to SEQ ID NO: 8-30, the at least 5 contiguous amino acids referred to in option b) in the definition of the first aspect of the invention will preferably constitute at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139 contiguous amino acid residues.

Insofar as embodiment b relates to SEQ ID NO: 9-30, the at least 5 contiguous amino acids referred to in option b) in the definition of the first aspect of the invention will preferably constitute at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159 contiguous amino acid residues.

Insofar as embodiment b relates to SEQ ID NO: 10-30, the at least 5 contiguous amino acids referred to in option b) in the definition of the first aspect of the invention will preferably constitute at least or exactly or at most 160, at least or exactly or at most 161, at least or exactly or at most 162 contiguous amino acid residues.

Insofar as embodiment b relates to SEQ ID NO: 11-30, the at least 5 contiguous amino acids referred to in option b) in the definition of the first aspect of the invention will preferably constitute at least or exactly or at most 163, at least or exactly or at most 164, at least or exactly or at most 165, at least or exactly or at most 166 contiguous amino acid residues.

Insofar as embodiment b relates to SEQ ID NO: 12-30, the at least 5 contiguous amino acids referred to in option b) in the definition of the first aspect of the invention will preferably constitute at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230 contiguous amino acid residues.

Insofar as embodiment b relates to SEQ ID NO: 13-30, the at least 5 contiguous amino acids referred to in option b) in the definition of the first aspect of the invention will preferably constitute at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238 contiguous amino acid residues.

Insofar as embodiment b relates to SEQ ID NO: 14-30, the at least 5 contiguous amino acids referred to in option b) in the definition of the first aspect of the invention will preferably constitute at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253 contiguous amino acid residues.

Insofar as embodiment b relates to SEQ ID NO: 15-30, the at least 5 contiguous amino acids referred to in option b) in the definition of the first aspect of the invention will preferably constitute at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 286, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294 contiguous amino acid residues.

Insofar as embodiment b relates to SEQ ID NO: 16-30, the at least 5 contiguous amino acids referred to in option b) in the definition of the first aspect of the invention will preferably constitute at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356 contiguous amino acid residues.

Insofar as embodiment b relates to SEQ ID NO: 17-30, the at least 5 contiguous amino acids referred to in option b) in the definition of the first aspect of the invention will preferably constitute at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367 contiguous amino acid residues.

Insofar as embodiment b relates to SEQ ID NO: 18-30, the at least 5 contiguous amino acids referred to in option b) in the definition of the first aspect of the invention will preferably constitute at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420 contiguous amino acid residues.

Insofar as embodiment b relates to SEQ ID NO: 19-30, the at least 5 contiguous amino acids referred to in option b) in the definition of the first aspect of the invention will preferably constitute at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445 contiguous amino acid residues.

Insofar as embodiment b relates to SEQ ID NO: 20-30, the at least 5 contiguous amino acids referred to in option b) in the definition of the first aspect of the invention will preferably constitute at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or at most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at most 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 692, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711 contiguous amino acid residues.

Insofar as embodiment b relates to SEQ ID NO: 21-30, the at least 5 contiguous amino acids referred to in option b) in the definition of the first aspect of the invention will preferably constitute at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727 contiguous amino acid residues.

Insofar as embodiment b relates to SEQ ID NO: 22-30, the at least 5 contiguous amino acids referred to in option b) in the definition of the first aspect of the invention will preferably constitute at least or exactly or at most 728 contiguous amino acid residues.

Insofar as embodiment b relates to SEQ ID NO: 23-30, the at least 5 contiguous amino acids referred to in option b) in the definition of the first aspect of the invention will preferably constitute at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754 contiguous amino acid residues.

Insofar as embodiment b relates to SEQ ID NO: 24-30, the at least 5 contiguous amino acids referred to in option b) in the definition of the first aspect of the invention will preferably constitute at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906 contiguous amino acid residues.

Insofar as embodiment b relates to SEQ ID NO: 25-30, the at least 5 contiguous amino acids referred to in option b) in the definition of the first aspect of the invention will preferably constitute at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974 contiguous amino acid residues.

Insofar as embodiment b relates to SEQ ID NO: 26-30, the at least 5 contiguous amino acids referred to in option b) in the definition of the first aspect of the invention will preferably constitute at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 988, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071 contiguous amino acid residues.

Insofar as embodiment b relates to SEQ ID NO: 27-30, the at least 5 contiguous amino acids referred to in option b) in the definition of the first aspect of the invention will preferably constitute at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, at least or exactly or at most 1109, at least or exactly or at most 1110 contiguous amino acid residues.

Insofar as embodiment b relates to SEQ ID NO: 28-30, the at least 5 contiguous amino acids referred to in option b) in the definition of the first aspect of the invention will preferably constitute at least or exactly or at most 1111, at least or exactly or at most 1112, at least or exactly or at most 1113, at least or exactly or at most 1114, at least or exactly or at most 1115, at least or exactly or at most 1116, at least or exactly or at most 1117, at least or exactly or at most 1118, at least or exactly or at most 1119, at least or exactly or at most 1120, at least or exactly or at most 1121, at least or exactly or at most 1122, at least or exactly or at most 1123, at least or exactly or at most 1124, at least or exactly or at most 1125, at least or exactly or at most 1126, at least or exactly or at most 1127, at least or exactly or at most 1128, at least or exactly or at most 1129, at least or exactly or at most 1130, at least or exactly or at most 1131, at least or exactly or at most 1132, at least or exactly or at most 1133, at least or exactly or at most 1134, at least or exactly or at most 1135, at least or exactly or at most 1136, at least or exactly or at most 1137, at least or exactly or at most 1138, at least or exactly or at most 1139, at least or exactly or at most 1140, at least or exactly or at most 1141, at least or exactly or at most 1142, at least or exactly or at most 1143, at least or exactly or at most 1144, at least or exactly or at most 1145, at least or exactly or at most 1146, at least or exactly or at most 1147, at least or exactly or at most 1148, at least or exactly or at most 1149, at least or exactly or at most 1150, at least or exactly or at most 1151, at least or exactly or at most 1152, at least or exactly or at most 1153, at least or exactly or at most 1154, at least or exactly or at most 1155, at least or exactly or at most 1156, at least or exactly or at most 1157, at least or exactly or at most 1158, at least or exactly or at most 1159, at least or exactly or at most 1160, at least or exactly or at most 1161, at least or exactly or at most 1162, at least or exactly or at most 1163, at least or exactly or at most 1164, at least or exactly or at most 1165, at least or exactly or at most 1166, at least or exactly or at most 1167, at least or exactly or at most 1168, at least or exactly or at most 1169, at least or exactly or at most 1170, at least or exactly or at most 1171, at least or exactly or at most 1172, at least or exactly or at most 1173, at least or exactly or at most 1174, at least or exactly or at most 1175, at least or exactly or at most 1176, at least or exactly or at most 1177, at least or exactly or at most 1178, at least or exactly or at most 1179, at least or exactly or at most 1180, at least or exactly or at most 1181, at least or exactly or at most 1182, at least or exactly or at most 1183, at least or exactly or at most 1184, at least or exactly or at most 1185, at least or exactly or at most 1186, at least or exactly or at most 1187, at least or exactly or at most 1188, at least or exactly or at most 1189, at least or exactly or at most 1190, at least or exactly or at most 1191, at least or exactly or at most 1192, at least or exactly or at most 1193, at least or exactly or at most 1194, at least or exactly or at most 1195, at least or exactly or at most 1196, at least or exactly or at most 1197, at least or exactly or at most 1198, at least or exactly or at most 1199, at least or exactly or at most 1200, at least or exactly or at most 1201, at least or exactly or at most 1202, at least or exactly or at most 1203, at least or exactly or at most 1204, at least or exactly or at most 1205, at least or exactly or at most 1206, at least or exactly or at most 1207, at least or exactly or at most 1208, at least or exactly or at most 1209, at least or exactly or at most 1210, at least or exactly or at most 1211, at least or exactly or at most 1212, at least or exactly or at most 1213, at least or exactly or at most 1214, at least or exactly or at most 1215, at least or exactly or at most 1216, at least or exactly or at most 1217, at least or exactly or at most 1218, at least or exactly or at most 1219, at least or exactly or at most 1220, at least or exactly or at most 1221, at least or exactly or at most 1222, at least or exactly or at most 1223, at least or exactly or at most 1224, at least or exactly or at most 1225, at least or exactly or at most 1226, at least or exactly or at most 1227, at least or exactly or at most 1228 contiguous amino acid residues.

Insofar as embodiment b relates to SEQ ID NO: 29-30, the at least 5 contiguous amino acids referred to in option b) in the definition of the first aspect of the invention will preferably constitute at least or exactly or at most 1229, at least or exactly or at most 1230, at least or exactly or at most 1231, at least or exactly or at most 1232, at least or exactly or at most 1233, at least or exactly or at most 1234, at least or exactly or at most 1235, at least or exactly or at most 1236, at least or exactly or at most 1237, at least or exactly or at most 1238, at least or exactly or at most 1239, at least or exactly or at most 1240, at least or exactly or at most 1241, at least or exactly or at most 1242, at least or exactly or at most 1243, at least or exactly or at most 1244, at least or exactly or at most 1245, at least or exactly or at most 1246, at least or exactly or at most 1247, at least or exactly or at most 1248, at least or exactly or at most 1249, at least or exactly or at most 1250, at least or exactly or at most 1251, at least or exactly or at most 1252, at least or exactly or at most 1253, at least or exactly or at most 1254, at least or exactly or at most 1255, at least or exactly or at most 1256, at least or exactly or at most 1257, at least or exactly or at most 1258, at least or exactly or at most 1259, at least or exactly or at most 1260, at least or exactly or at most 1261, at least or exactly or at most 1262, at least or exactly or at most 1263, at least or exactly or at most 1264, at least or exactly or at most 1265, at least or exactly or at most 1266, at least or exactly or at most 1267, at least or exactly or at most 1268, at least or exactly or at most 1269, at least or exactly or at most 1270, at least or exactly or at most 1271, at least or exactly or at most 1272, at least or exactly or at most 1273, at least or exactly or at most 1274, at least or exactly or at most 1275, at least or exactly or at most 1276, at least or exactly or at most 1277, at least or exactly or at most 1278, at least or exactly or at most 1279, at least or exactly or at most 1280, at least or exactly or at most 1281, at least or exactly or at most 1282, at least or exactly or at most 1283, at least or exactly or at most 1284 contiguous amino acid residues.

Insofar as embodiment b relates to SEQ ID NO: 30, the at least 5 contiguous amino acids referred to in option b) in the definition of the first aspect of the invention will preferably constitute at least or exactly or at most 1285, at least or exactly or at most 1286, at least or exactly or at most 1287, at least or exactly or at most 1288, at least or exactly or at most 1289, at least or exactly or at most 1290, at least or exactly or at most 1291, at least or exactly or at most 1292, at least or exactly or at most 1293, at least or exactly or at most 1294, at least or exactly or at most 1295, at least or exactly or at most 1296, at least or exactly or at most 1297, at least or exactly or at most 1298, at least or exactly or at most 1299, at least or exactly or at most 1300, at least or exactly or at most 1301, at least or exactly or at most 1302, at least or exactly or at most 1303, at least or exactly or at most 1304, at least or exactly or at most 1305, at least or exactly or at most 1306, at least or exactly or at most 1307, at least or exactly or at most 1308, at least or exactly or at most 1309, at least or exactly or at most 1310, at least or exactly or at most 1311, at least or exactly or at most 1312, at least or exactly or at most 1313, at least or exactly or at most 1314, at least or exactly or at most 1315, at least or exactly or at most 1316, at least or exactly or at most 1317, at least or exactly or at most 1318, at least or exactly or at most 1319, at least or exactly or at most 1320, at least or exactly or at most 1321, at least or exactly or at most 1322, at least or exactly or at most 1323, at least or exactly or at most 1324, at least or exactly or at most 1325, at least or exactly or at most 1326, at least or exactly or at most 1327, at least or exactly or at most 1328, at least or exactly or at most 1329, at least or exactly or at most 1330, at least or exactly or at most 1331, at least or exactly or at most 1332, at least or exactly or at most 1333, at least or exactly or at most 1334, at least or exactly or at most 1335, at least or exactly or at most 1336, at least or exactly or at most 1337, at least or exactly or at most 1338, at least or exactly or at most 1339, at least or exactly or at most 1340, at least or exactly or at most 1341, at least or exactly or at most 1342, at least or exactly or at most 1343, at least or exactly or at most 1344, at least or exactly or at most 1345, at least or exactly or at most 1346, at least or exactly or at most 1347, at least or exactly or at most 1348, at least or exactly or at most 1349, at least or exactly or at most 1350, at least or exactly or at most 1351, at least or exactly or at most 1352, at least or exactly or at most 1353, at least or exactly or at most 1354, at least or exactly or at most 1355, at least or exactly or at most 1356, at least or exactly or at most 1357, at least or exactly or at most 1358, at least or exactly or at most 1359, at least or exactly or at most 1360, at least or exactly or at most 1361, at least or exactly or at most 1362, at least or exactly or at most 1363, at least or exactly or at most 1364, at least or exactly or at most 1365, at least or exactly or at most 1366, at least or exactly or at most 1367, at least or exactly or at most 1368, at least or exactly or at most 1369, at least or exactly or at most 1370, at least or exactly or at most 1371, at least or exactly or at most 1372, at least or exactly or at most 1373, at least or exactly or at most 1374, at least or exactly or at most 1375, at least or exactly or at most 1376, at least or exactly or at most 1377, at least or exactly or at most 1378, at least or exactly or at most 1379, at least or exactly or at most 1380, at least or exactly or at most 1381, at least or exactly or at most 1382, at least or exactly or at most 1383, at least or exactly or at most 1384, at least or exactly or at most 1385, at least or exactly or at most 1386, at least or exactly or at most 1387, at least or exactly or at most 1388, at least or exactly or at most 1389, at least or exactly or at most 1390, at least or exactly or at most 1391, at least or exactly or at most 1392, at least or exactly or at most 1393, at least or exactly or at most 1394, at least or exactly or at most 1395, at least or exactly or at most 1396, at least or exactly or at most 1397, at least or exactly or at most 1398, at least or exactly or at most 1399, at least or exactly or at most 1400, at least or exactly or at most 1401, at least or exactly or at most 1402, at least or exactly or at most 1403, at least or exactly or at most 1404, at least or exactly or at most 1405, at least or exactly or at most 1406, at least or exactly or at most 1407, at least or exactly or at most 1408, at least or exactly or at most 1409, at least or exactly or at most 1410, at least or exactly or at most 1411, at least or exactly or at most 1412, at least or exactly or at most 1413, at least or exactly or at most 1414, at least or exactly or at most 1415, at least or exactly or at most 1416, at least or exactly or at most 1417, at least or exactly or at most 1418, at least or exactly or at most 1419, at least or exactly or at most 1420, at least or exactly or at most 1421, at least or exactly or at most 1422, at least or exactly or at most 1423, at least or exactly or at most 1424, at least or exactly or at most 1425, at least or exactly or at most 1426, at least or exactly or at most 1427, at least or exactly or at most 1428, at least or exactly or at most 1429, at least or exactly or at most 1430, at least or exactly or at most 1431, at least or exactly or at most 1432, at least or exactly or at most 1433, at least or exactly or at most 1434, at least or exactly or at most 1435, at least or exactly or at most 1436, at least or exactly or at most 1437, at least or exactly or at most 1438, at least or exactly or at most 1439, at least or exactly or at most 1440, at least or exactly or at most 1441, at least or exactly or at most 1442, at least or exactly or at most 1443, at least or exactly or at most 1444, at least or exactly or at most 1445, at least or exactly or at most 1446, at least or exactly or at most 1447, at least or exactly or at most 1448, at least or exactly or at most 1449, at least or exactly or at most 1450, at least or exactly or at most 1451, at least or exactly or at most 1452, at least or exactly or at most 1453, at least or exactly or at most 1454, at least or exactly or at most 1455, at least or exactly or at most 1456, at least or exactly or at most 1457, at least or exactly or at most 1458, at least or exactly or at most 1459, at least or exactly or at most 1460, at least or exactly or at most 1461, at least or exactly or at most 1462, at least or exactly or at most 1463, at least or exactly or at most 1464, at least or exactly or at most 1465, at least or exactly or at most 1466, at least or exactly or at most 1467, at least or exactly or at most 1468, at least or exactly or at most 1469, at least or exactly or at most 1470, at least or exactly or at most 1471, at least or exactly or at most 1472, at least or exactly or at most 1473, at least or exactly or at most 1474, at least or exactly or at most 1475, at least or exactly or at most 1476, at least or exactly or at most 1477, at least or exactly or at most 1478, at least or exactly or at most 1479, at least or exactly or at most 1480, at least or exactly or at most 1481, at least or exactly or at most 1482, at least or exactly or at most 1483, at least or exactly or at most 1484, at least or exactly or at most 1485, at least or exactly or at most 1486, at least or exactly or at most 1487, at least or exactly or at most 1488, at least or exactly or at most 1489, at least or exactly or at most 1490, at least or exactly or at most 1491, at least or exactly or at most 1492, at least or exactly or at most 1493, at least or exactly or at most 1494, at least or exactly or at most 1495, at least or exactly or at most 1496, at least or exactly or at most 1497, at least or exactly or at most 1498, at least or exactly or at most 1499, at least or exactly or at most 1500, at least or exactly or at most 1501, at least or exactly or at most 1502, at least or exactly or at most 1503, at least or exactly or at most 1504, at least or exactly or at most 1505, at least or exactly or at most 1506, at least or exactly or at most 1507, at least or exactly or at most 1508, at least or exactly or at most 1509, at least or exactly or at most 1510, at least or exactly or at most 1511, at least or exactly or at most 1512, at least or exactly or at most 1513, at least or exactly or at most 1514, at least or exactly or at most 1515, at least or exactly or at most 1516, at least or exactly or at most 1517, at least or exactly or at most 1518, at least or exactly or at most 1519, at least or exactly or at most 1520, at least or exactly or at most 1521, at least or exactly or at most 1522, at least or exactly or at most 1523, at least or exactly or at most 1524, at least or exactly or at most 1525, at least or exactly or at most 1526, at least or exactly or at most 1527, at least or exactly or at most 1528, at least or exactly or at most 1529, at least or exactly or at most 1530, at least or exactly or at most 1531, at least or exactly or at most 1532, at least or exactly or at most 1533, at least or exactly or at most 1534, at least or exactly or at most 1535, at least or exactly or at most 1536, at least or exactly or at most 1537, at least or exactly or at most 1538, at least or exactly or at most 1539, at least or exactly or at most 1540, at least or exactly or at most 1541, at least or exactly or at most 1542, at least or exactly or at most 1543, at least or exactly or at most 1544, at least or exactly or at most 1545, at least or exactly or at most 1546, at least or exactly or at most 1547, at least or exactly or at most 1548, at least or exactly or at most 1549, at least or exactly or at most 1550, at least or exactly or at most 1551, at least or exactly or at most 1552, at least or exactly or at most 1553, at least or exactly or at most 1554, at least or exactly or at most 1555, at least or exactly or at most 1556, at least or exactly or at most 1557, at least or exactly or at most 1558, at least or exactly or at most 1559, at least or exactly or at most 1560, at least or exactly or at most 1561, at least or exactly or at most 1562, at least or exactly or at most 1563, at least or exactly or at most 1564, at least or exactly or at most 1565, at least or exactly or at most 1566, at least or exactly or at most 1567, at least or exactly or at most 1568, at least or exactly or at most 1569, at least or exactly or at most 1570, at least or exactly or at most 1571, at least or exactly or at most 1572, at least or exactly or at most 1573, at least or exactly or at most 1574, at least or exactly or at most 1575, at least or exactly or at most 1576, at least or exactly or at most 1577, at least or exactly or at most 1578, at least or exactly or at most 1579, at least or exactly or at most 1580, at least or exactly or at most 1581, at least or exactly or at most 1582, at least or exactly or at most 1583, at least or exactly or at most 1584, at least or exactly or at most 1585, at least or exactly or at most 1586, at least or exactly or at most 1587, at least or exactly or at most 1588, at least or exactly or at most 1589, at least or exactly or at most 1590, at least or exactly or at most 1591, at least or exactly or at most 1592, at least or exactly or at most 1593, at least or exactly or at most 1594, at least or exactly or at most 1595, at least or exactly or at most 1596, at least or exactly or at most 1597, at least or exactly or at most 1598, at least or exactly or at most 1599, at least or exactly or at most 1600, at least or exactly or at most 1601, at least or exactly or at most 1602, at least or exactly or at most 1603, at least or exactly or at most 1604, at least or exactly or at most 1605, at least or exactly or at most 1606, at least or exactly or at most 1607, at least or exactly or at most 1608, at least or exactly or at most 1609, at least or exactly or at most 1610, at least or exactly or at most 1611, at least or exactly or at most 1612, at least or exactly or at most 1613, at least or exactly or at most 1614, at least or exactly or at most 1615, at least or exactly or at most 1616, at least or exactly or at most 1617, at least or exactly or at most 1618, at least or exactly or at most 1619, at least or exactly or at most 1620, at least or exactly or at most 1621, at least or exactly or at most 1622, at least or exactly or at most 1623, at least or exactly or at most 1624, at least or exactly or at most 1625, at least or exactly or at most 1626, at least or exactly or at most 1627, at least or exactly or at most 1628, at least or exactly or at most 1629, at least or exactly or at most 1630, at least or exactly or at most 1631, at least or exactly or at most 1632, at least or exactly or at most 1633, at least or exactly or at most 1634, at least or exactly or at most 1635, at least or exactly or at most 1636, at least or exactly or at most 1637, at least or exactly or at most 1638, at least or exactly or at most 1639, at least or exactly or at most 1640, at least or exactly or at most 1641, at least or exactly or at most 1642, at least or exactly or at most 1643, at least or exactly or at most 1644, at least or exactly or at most 1645, at least or exactly or at most 1646, at least or exactly or at most 1647, at least or exactly or at most 1648, at least or exactly or at most 1649, at least or exactly or at most 1650, at least or exactly or at most 1651, at least or exactly or at most 1652, at least or exactly or at most 1653, at least or exactly or at most 1654, at least or exactly or at most 1655, at least or exactly or at most 1656, at least or exactly or at most 1657, at least or exactly or at most 1658, at least or exactly or at most 1659, at least or exactly or at most 1660, at least or exactly or at most 1661, at least or exactly or at most 1662, at least or exactly or at most 1663, at least or exactly or at most 1664, at least or exactly or at most 1665, at least or exactly or at most 1666, at least or exactly or at most 1667, at least or exactly or at most 1668, at least or exactly or at most 1669, at least or exactly or at most 1670, at least or exactly or at most 1671, at least or exactly or at most 1672, at least or exactly or at most 1673, at least or exactly or at most 1674, at least or exactly or at most 1675, at least or exactly or at most 1676, at least or exactly or at most 1677, at least or exactly or at most 1678, at least or exactly or at most 1679, at least or exactly or at most 1680, at least or exactly or at most 1681, at least or exactly or at most 1682, at least or exactly or at most 1683, at least or exactly or at most 1684, at least or exactly or at most 1685, at least or exactly or at most 1686, at least or exactly or at most 1687, at least or exactly or at most 1688, at least or exactly or at most 1689, at least or exactly or at most 1690, at least or exactly or at most 1691, at least or exactly or at most 1692, at least or exactly or at most 1693, at least or exactly or at most 1694, at least or exactly or at most 1695, at least or exactly or at most 1696, at least or exactly or at most 1697, at least or exactly or at most 1698, at least or exactly or at most 1699, at least or exactly or at most 1700, at least or exactly or at most 1701, at least or exactly or at most 1702, at least or exactly or at most 1703, at least or exactly or at most 1704, at least or exactly or at most 1705, at least or exactly or at most 1706, at least or exactly or at most 1707, at least or exactly or at most 1708, at least or exactly or at most 1709, at least or exactly or at most 1710, at least or exactly or at most 1711, at least or exactly or at most 1712, at least or exactly or at most 1713, at least or exactly or at most 1714, at least or exactly or at most 1715, at least or exactly or at most 1716, at least or exactly or at most 1717, at least or exactly or at most 1718, at least or exactly or at most 1719, at least or exactly or at most 1720, at least or exactly or at most 1721, at least or exactly or at most 1722, at least or exactly or at most 1723, at least or exactly or at most 1724, at least or exactly or at most 1725, at least or exactly or at most 1726, at least or exactly or at most 1727, at least or exactly or at most 1728, at least or exactly or at most 1729, at least or exactly or at most 1730, at least or exactly or at most 1731, at least or exactly or at most 1732, at least or exactly or at most 1733, at least or exactly or at most 1734, at least or exactly or at most 1735, at least or exactly or at most 1736, at least or exactly or at most 1737, at least or exactly or at most 1738, at least or exactly or at most 1739, at least or exactly or at most 1740, at least or exactly or at most 1741, at least or exactly or at most 1742, at least or exactly or at most 1743, at least or exactly or at most 1744, at least or exactly or at most 1745, at least or exactly or at most 1746, at least or exactly or at most 1747, at least or exactly or at most 1748, at least or exactly or at most 1749, at least or exactly or at most 1750, at least or exactly or at most 1751, at least or exactly or at most 1752, at least or exactly or at most 1753, at least or exactly or at most 1754, at least or exactly or at most 1755, at least or exactly or at most 1756, at least or exactly or at most 1757, at least or exactly or at most 1758, at least or exactly or at most 1759, at least or exactly or at most 1760, at least or exactly or at most 1761, at least or exactly or at most 1762, at least or exactly or at most 1763, at least or exactly or at most 1764, at least or exactly or at most 1765, at least or exactly or at most 1766, at least or exactly or at most 1767, at least or exactly or at most 1768, at least or exactly or at most 1769, at least or exactly or at most 1770, at least or exactly or at most 1771, at least or exactly or at most 1772, at least or exactly or at most 1773, at least or exactly or at most 1774, at least or exactly or at most 1775, at least or exactly or at most 1776, at least or exactly or at most 1777, at least or exactly or at most 1778, at least or exactly or at most 1779, at least or exactly or at most 1780, at least or exactly or at most 1781, at least or exactly or at most 1782, at least or exactly or at most 1783, at least or exactly or at most 1784, at least or exactly or at most 1785, at least or exactly or at most 1786, at least or exactly or at most 1787, at least or exactly or at most 1788, at least or exactly or at most 1789, at least or exactly or at most 1790, at least or exactly or at most 1791, at least or exactly or at most 1792, at least or exactly or at most 1793, at least or exactly or at most 1794, at least or exactly or at most 1795, at least or exactly or at most 1796, at least or exactly or at most 1797, at least or exactly or at most 1798, at least or exactly or at most 1799, at least or exactly or at most 1800, at least or exactly or at most 1801, at least or exactly or at most 1802, at least or exactly or at most 1803, at least or exactly or at most 1804, at least or exactly or at most 1805, at least or exactly or at most 1806, at least or exactly or at most 1807, at least or exactly or at most 1808, at least or exactly or at most 1809, at least or exactly or at most 1810, at least or exactly or at most 1811, at least or exactly or at most 1812, at least or exactly or at most 1813, at least or exactly or at most 1814, at least or exactly or at most 1815, at least or exactly or at most 1816, at least or exactly or at most 1817, at least or exactly or at most 1818, at least or exactly or at most 1819, at least or exactly or at most 1820, at least or exactly or at most 1821, at least or exactly or at most 1822, at least or exactly or at most 1823, at least or exactly or at most 1824, at least or exactly or at most 1825, at least or exactly or at most 1826, at least or exactly or at most 1827, at least or exactly or at most 1828, at least or exactly or at most 1829, at least or exactly or at most 1830, at least or exactly or at most 1831, at least or exactly or at most 1832, at least or exactly or at most 1833, at least or exactly or at most 1834, at least or exactly or at most 1835, at least or exactly or at most 1836, at least or exactly or at most 1837, at least or exactly or at most 1838, at least or exactly or at most 1839, at least or exactly or at most 1840, at least or exactly or at most 1841, at least or exactly or at most 1842, at least or exactly or at most 1843, at least or exactly or at most 1844, at least or exactly or at most 1845, at least or exactly or at most 1846, at least or exactly or at most 1847, at least or exactly or at most 1848, at least or exactly or at most 1849, at least or exactly or at most 1850, at least or exactly or at most 1851, at least or exactly or at most 1852, at least or exactly or at most 1853, at least or exactly or at most 1854, at least or exactly or at most 1855, at least or exactly or at most 1856, at least or exactly or at most 1857, at least or exactly or at most 1858, at least or exactly or at most 1859, at least or exactly or at most 1860, at least or exactly or at most 1861, at least or exactly or at most 1862, at least or exactly or at most 1863, at least or exactly or at most 1864, at least or exactly or at most 1865, at least or exactly or at most 1866, at least or exactly or at most 1867, at least or exactly or at most 1868, at least or exactly or at most 1869, at least or exactly or at most 1870, at least or exactly or at most 1871, at least or exactly or at most 1872, at least or exactly or at most 1873, at least or exactly or at most 1874, at least or exactly or at most 1875, at least or exactly or at most 1876, at least or exactly or at most 1877, at least or exactly or at most 1878, at least or exactly or at most 1879, at least or exactly or at most 1880, at least or exactly or at most 1881, at least or exactly or at most 1882, at least or exactly or at most 1883, at least or exactly or at most 1884, at least or exactly or at most 1885, at least or exactly or at most 1886, at least or exactly or at most 1887, at least or exactly or at most 1888, at least or exactly or at most 1889, at least or exactly or at most 1890, at least or exactly or at most 1891, at least or exactly or at most 1892, at least or exactly or at most 1893, at least or exactly or at most 1894, at least or exactly or at most 1895, at least or exactly or at most 1896, at least or exactly or at most 1897, at least or exactly or at most 1898, at least or exactly or at most 1899, at least or exactly or at most 1900, at least or exactly or at most 1901, at least or exactly or at most 1902, at least or exactly or at most 1903, at least or exactly or at most 1904, at least or exactly or at most 1905, at least or exactly or at most 1906, at least or exactly or at most 1907, at least or exactly or at most 1908, at least or exactly or at most 1909, at least or exactly or at most 1910, at least or exactly or at most 1911, at least or exactly or at most 1912, at least or exactly or at most 1913, at least or exactly or at most 1914, at least or exactly or at most 1915, at least or exactly or at most 1916, at least or exactly or at most 1917, at least or exactly or at most 1918, at least or exactly or at most 1919, at least or exactly or at most 1920, at least or exactly or at most 1921, at least or exactly or at most 1922, at least or exactly or at most 1923, at least or exactly or at most 1924, at least or exactly or at most 1925, at least or exactly or at most 1926, at least or exactly or at most 1927, at least or exactly or at most 1928, at least or exactly or at most 1929, at least or exactly or at most 1930, at least or exactly or at most 1931, at least or exactly or at most 1932, at least or exactly or at most 1933, at least or exactly or at most 1934, at least or exactly or at most 1935, at least or exactly or at most 1936, at least or exactly or at most 1937, at least or exactly or at most 1938, at least or exactly or at most 1939, at least or exactly or at most 1940, at least or exactly or at most 1941, at least or exactly or at most 1942, at least or exactly or at most 1943, at least or exactly or at most 1944, at least or exactly or at most 1945, at least or exactly or at most 1946, at least or exactly or at most 1947, at least or exactly or at most 1948, at least or exactly or at most 1949, at least or exactly or at most 1950, at least or exactly or at most 1951, at least or exactly or at most 1952, at least or exactly or at most 1953, at least or exactly or at most 1954, at least or exactly or at most 1955, at least or exactly or at most 1956, at least or exactly or at most 1957, at least or exactly or at most 1958, at least or exactly or at most 1959, at least or exactly or at most 1960, at least or exactly or at most 1961, at least or exactly or at most 1962, at least or exactly or at most 1963, at least or exactly or at most 1964, at least or exactly or at most 1965, at least or exactly or at most 1966, at least or exactly or at most 1967, at least or exactly or at most 1968, at least or exactly or at most 1969, at least or exactly or at most 1970, at least or exactly or at most 1971, at least or exactly or at most 1972, at least or exactly or at most 1973, at least or exactly or at most 1974, at least or exactly or at most 1975, at least or exactly or at most 1976, at least or exactly or at most 1977, at least or exactly or at most 1978, at least or exactly or at most 1979, at least or exactly or at most 1980, at least or exactly or at most 1981, at least or exactly or at most 1982, at least or exactly or at most 1983, at least or exactly or at most 1984, at least or exactly or at most 1985, at least or exactly or at most 1986, at least or exactly or at most 1987, at least or exactly or at most 1988, at least or exactly or at most 1989, at least or exactly or at most 1990, at least or exactly or at most 1991, at least or exactly or at most 1992, at least or exactly or at most 1993, at least or exactly or at most 1994, at least or exactly or at most 1995, at least or exactly or at most 1996, at least or exactly or at most 1997, at least or exactly or at most 1998, at least or exactly or at most 1999, at least or exactly or at most 2000, at least or exactly or at most 2001, at least or exactly or at most 2002, at least or exactly or at most 2003, at least or exactly or at most 2004, at least or exactly or at most 2005, at least or exactly or at most 2006, at least or exactly or at most 2007, at least or exactly or at most 2008, at least or exactly or at most 2009, at least or exactly or at most 2010, at least or exactly or at most 2011, at least or exactly or at most 2012, at least or exactly or at most 2013, at least or exactly or at most 2014, at least or exactly or at most 2015, at least or exactly or at most 2016, at least or exactly or at most 2017, at least or exactly or at most 2018, at least or exactly or at most 2019, at least or exactly or at most 2020, at least or exactly or at most 2021, at least or exactly or at most 2022, at least or exactly or at most 2023, at least or exactly or at most 2024, at least or exactly or at most 2025, at least or exactly or at most 2026, at least or exactly or at most 2027, at least or exactly or at most 2028, at least or exactly or at most 2029, at least or exactly or at most 2030, at least or exactly or at most 2031, at least or exactly or at most 2032, at least or exactly or at most 2033, at least or exactly or at most 2034, at least or exactly or at most 2035, at least or exactly or at most 2036, at least or exactly or at most 2037, at least or exactly or at most 2038, at least or exactly or at most 2039, at least or exactly or at most 2040, at least or exactly or at most 2041, at least or exactly or at most 2042, at least or exactly or at most 2043, at least or exactly or at most 2044, at least or exactly or at most 2045, at least or exactly or at most 2046, at least or exactly or at most 2047, at least or exactly or at most 2048, at least or exactly or at most 2049, at least or exactly or at most 2050, at least or exactly or at most 2051, at least or exactly or at most 2052, at least or exactly or at most 2053, at least or exactly or at most 2054, at least or exactly or at most 2055, at least or exactly or at most 2056, at least or exactly or at most 2057, at least or exactly or at most 2058, at least or exactly or at most 2059, at least or exactly or at most 2060, at least or exactly or at most 2061, at least or exactly or at most 2062, at least or exactly or at most 2063, at least or exactly or at most 2064, at least or exactly or at most 2065, at least or exactly or at most 2066, at least or exactly or at most 2067, at least or exactly or at most 2068, at least or exactly or at most 2069, at least or exactly or at most 2070, at least or exactly or at most 2071, at least or exactly or at most 2072, at least or exactly or at most 2073, at least or exactly or at most 2074, at least or exactly or at most 2075, at least or exactly or at most 2076, at least or exactly or at most 2077, at least or exactly or at most 2078, at least or exactly or at most 2079, at least or exactly or at most 2080, at least or exactly or at most 2081, at least or exactly or at most 2082, at least or exactly or at most 2083, at least or exactly or at most 2084, at least or exactly or at most 2085, at least or exactly or at most 2086, at least or exactly or at most 2087, at least or exactly or at most 2088, at least or exactly or at most 2089, at least or exactly or at most 2090, at least or exactly or at most 2091, at least or exactly or at most 2092, at least or exactly or at most 2093, at least or exactly or at most 2094, at least or exactly or at most 2095, at least or exactly or at most 2096, at least or exactly or at most 2097, at least or exactly or at most 2098, at least or exactly or at most 2099, at least or exactly or at most 2100, at least or exactly or at most 2101, at least or exactly or at most 2102, at least or exactly or at most 2103, at least or exactly or at most 2104, at least or exactly or at most 2105, at least or exactly or at most 2106, at least or exactly or at most 2107, at least or exactly or at most 2108, at least or exactly or at most 2109, at least or exactly or at most 2110, at least or exactly or at most 2111, at least or exactly or at most 2112, at least or exactly or at most 2113, at least or exactly or at most 2114, at least or exactly or at most 2115, at least or exactly or at most 2116, at least or exactly or at most 2117, at least or exactly or at most 2118, at least or exactly or at most 2119, at least or exactly or at most 2120, at least or exactly or at most 2121, at least or exactly or at most 2122, at least or exactly or at most 2123, at least or exactly or at most 2124, at least or exactly or at most 2125, at least or exactly or at most 2126, at least or exactly or at most 2127, at least or exactly or at most 2128, at least or exactly or at most 2129, at least or exactly or at most 2130, at least or exactly or at most 2131, at least or exactly or at most 2132, at least or exactly or at most 2133, at least or exactly or at most 2134, at least or exactly or at most 2135, at least or exactly or at most 2136, at least or exactly or at most 2137, at least or exactly or at most 2138, at least or exactly or at most 2139, at least or exactly or at most 2140, at least or exactly or at most 2141, at least or exactly or at most 2142, at least or exactly or at most 2143, at least or exactly or at most 2144, at least or exactly or at most 2145, at least or exactly or at most 2146, at least or exactly or at most 2147, at least or exactly or at most 2148, at least or exactly or at most 2149, at least or exactly or at most 2150, at least or exactly or at most 2151, at least or exactly or at most 2152, at least or exactly or at most 2153, at least or exactly or at most 2154, at least or exactly or at most 2155, at least or exactly or at most 2156, at least or exactly or at most 2157, at least or exactly or at most 2158, at least or exactly or at most 2159, at least or exactly or at most 2160, at least or exactly or at most 2161, at least or exactly or at most 2162, at least or exactly or at most 2163, at least or exactly or at most 2164, at least or exactly or at most 2165, at least or exactly or at most 2166, at least or exactly or at most 2167, at least or exactly or at most 2168, at least or exactly or at most 2169, at least or exactly or at most 2170, at least or exactly or at most 2171, at least or exactly or at most 2172, at least or exactly or at most 2173, at least or exactly or at most 2174, at least or exactly or at most 2175, at least or exactly or at most 2176, at least or exactly or at most 2177, at least or exactly or at most 2178, at least or exactly or at most 2179, at least or exactly or at most 2180, at least or exactly or at most 2181, at least or exactly or at most 2182, at least or exactly or at most 2183, at least or exactly or at most 2184, at least or exactly or at most 2185, at least or exactly or at most 2186, at least or exactly or at most 2187, at least or exactly or at most 2188, at least or exactly or at most 2189, at least or exactly or at most 2190, at least or exactly or at most 2191, at least or exactly or at most 2192, at least or exactly or at most 2193, at least or exactly or at most 2194, at least or exactly or at most 2195, at least or exactly or at most 2196, at least or exactly or at most 2197, at least or exactly or at most 2198, at least or exactly or at most 2199, at least or exactly or at most 2200, at least or exactly or at most 2201, at least or exactly or at most 2202, at least or exactly or at most 2203, at least or exactly or at most 2204, at least or exactly or at most 2205, at least or exactly or at most 2206, at least or exactly or at most 2207, at least or exactly or at most 2208, at least or exactly or at most 2209, at least or exactly or at most 2210, at least or exactly or at most 2211, at least or exactly or at most 2212, at least or exactly or at most 2213, at least or exactly or at most 2214, at least or exactly or at most 2215, at least or exactly or at most 2216, at least or exactly or at most 2217, at least or exactly or at most 2218, at least or exactly or at most 2219, at least or exactly or at most 2220, at least or exactly or at most 2221, at least or exactly or at most 2222, at least or exactly or at most 2223, at least or exactly or at most 2224, at least or exactly or at most 2225, at least or exactly or at most 2226, at least or exactly or at most 2227, at least or exactly or at most 2228, at least or exactly or at most 2229, at least or exactly or at most 2230, at least or exactly or at most 2231, at least or exactly or at most 2232, at least or exactly or at most 2233, at least or exactly or at most 2234, at least or exactly or at most 2235, at least or exactly or at most 2236, at least or exactly or at most 2237, at least or exactly or at most 2238, at least or exactly or at most 2239, at least or exactly or at most 2240, at least or exactly or at most 2241, at least or exactly or at most 2242, at least or exactly or at most 2243, at least or exactly or at most 2244, at least or exactly or at most 2245, at least or exactly or at most 2246, at least or exactly or at most 2247, at least or exactly or at most 2248, at least or exactly or at most 2249, at least or exactly or at most 2250, at least or exactly or at most 2251, at least or exactly or at most 2252, at least or exactly or at most 2253, at least or exactly or at most 2254, at least or exactly or at most 2255, at least or exactly or at most 2256, at least or exactly or at most 2257, at least or exactly or at most 2258, at least or exactly or at most 2259, at least or exactly or at most 2260, at least or exactly or at most 2261, at least or exactly or at most 2262, at least or exactly or at most 2263, at least or exactly or at most 2264, at least or exactly or at most 2265, at least or exactly or at most 2266, at least or exactly or at most 2267, at least or exactly or at most 2268, at least or exactly or at most 2269, at least or exactly or at most 2270, at least or exactly or at most 2271, at least or exactly or at most 2272, at least or exactly or at most 2273, at least or exactly or at most 2274, at least or exactly or at most 2275, at least or exactly or at most 2276, at least or exactly or at most 2277, at least or exactly or at most 2278, at least or exactly or at most 2279, at least or exactly or at most 2280, at least or exactly or at most 2281, at least or exactly or at most 2282, at least or exactly or at most 2283, at least or exactly or at most 2284, at least or exactly or at most 2285, at least or exactly or at most 2286, at least or exactly or at most 2287, at least or exactly or at most 2288, at least or exactly or at most 2289, at least or exactly or at most 2290, at least or exactly or at most 2291, at least or exactly or at most 2292, at least or exactly or at most 2293, at least or exactly or at most 2294, at least or exactly or at most 2295, at least or exactly or at most 2296, at least or exactly or at most 2297, at least or exactly or at most 2298, at least or exactly or at most 2299, at least or exactly or at most 2300, at least or exactly or at most 2301, at least or exactly or at most 2302, at least or exactly or at most 2303, at least or exactly or at most 2304, at least or exactly or at most 2305, at least or exactly or at most 2306, at least or exactly or at most 2307, at least or exactly or at most 2308, at least or exactly or at most 2309, at least or exactly or at most 2310, at least or exactly or at most 2311, at least or exactly or at most 2312, at least or exactly or at most 2313, at least or exactly or at most 2314, at least or exactly or at most 2315, at least or exactly or at most 2316, at least or exactly or at most 2317, at least or exactly or at most 2318, at least or exactly or at most 2319, at least or exactly or at most 2320, at least or exactly or at most 2321, at least or exactly or at most 2322, at least or exactly or at most 2323, at least or exactly or at most 2324, at least or exactly or at most 2325, at least or exactly or at most 2326, at least or exactly or at most 2327, at least or exactly or at most 2328, at least or exactly or at most 2329, at least or exactly or at most 2330, at least or exactly or at most 2331, at least or exactly or at most 2332, at least or exactly or at most 2333, at least or exactly or at most 2334, at least or exactly or at most 2335, at least or exactly or at most 2336, at least or exactly or at most 2337, at least or exactly or at most 2338, at least or exactly or at most 2339, at least or exactly or at most 2340, at least or exactly or at most 2341, at least or exactly or at most 2342, at least or exactly or at most 2343, at least or exactly or at most 2344, at least or exactly or at most 2345, at least or exactly or at most 2346, at least or exactly or at most 2347, at least or exactly or at most 2348, at least or exactly or at most 2349, at least or exactly or at most 2350, at least or exactly or at most 2351, at least or exactly or at most 2352, at least or exactly or at most 2353, at least or exactly or at most 2354, at least or exactly or at most 2355, at least or exactly or at most 2356, at least or exactly or at most 2357, at least or exactly or at most 2358, at least or exactly or at most 2359, at least or exactly or at most 2360, at least or exactly or at most 2361, at least or exactly or at most 2362, at least or exactly or at most 2363, at least or exactly or at most 2364, at least or exactly or at most 2365, at least or exactly or at most 2366, at least or exactly or at most 2367, at least or exactly or at most 2368, at least or exactly or at most 2369, at least or exactly or at most 2370, at least or exactly or at most 2371, at least or exactly or at most 2372, at least or exactly or at most 2373, at least or exactly or at most 2374, at least or exactly or at most 2375, at least or exactly or at most 2376, at least or exactly or at most 2377, at least or exactly or at most 2378, at least or exactly or at most 2379, at least or exactly or at most 2380, at least or exactly or at most 2381, at least or exactly or at most 2382, at least or exactly or at most 2383, at least or exactly or at most 2384, at least or exactly or at most 2385, at least or exactly or at most 2386, at least or exactly or at most 2387, at least or exactly or at most 2388, at least or exactly or at most 2389, at least or exactly or at most 2390, at least or exactly or at most 2391, at least or exactly or at most 2392, at least or exactly or at most 2393, at least or exactly or at most 2394, at least or exactly or at most 2395, at least or exactly or at most 2396, at least or exactly or at most 2397, at least or exactly or at most 2398, at least or exactly or at most 2399, at least or exactly or at most 2400, at least or exactly or at most 2401, at least or exactly or at most 2402, at least or exactly or at most 2403, at least or exactly or at most 2404, at least or exactly or at most 2405, at least or exactly or at most 2406, at least or exactly or at most 2407, at least or exactly or at most 2408, at least or exactly or at most 2409, at least or exactly or at most 2410, at least or exactly or at most 2411, at least or exactly or at most 2412, at least or exactly or at most 2413, at least or exactly or at most 2414, at least or exactly or at most 2415, at least or exactly or at most 2416, at least or exactly or at most 2417, at least or exactly or at most 2418, at least or exactly or at most 2419, at least or exactly or at most 2420, at least or exactly or at most 2421, at least or exactly or at most 2422, at least or exactly or at most 2423, at least or exactly or at most 2424, at least or exactly or at most 2425, at least or exactly or at most 2426, at least or exactly or at most 2427, at least or exactly or at most 2428, at least or exactly or at most 2429, at least or exactly or at most 2430, at least or exactly or at most 2431, at least or exactly or at most 2432, at least or exactly or at most 2433, at least or exactly or at most 2434, at least or exactly or at most 2435, at least or exactly or at most 2436, at least or exactly or at most 2437, at least or exactly or at most 2438, at least or exactly or at most 2439, at least or exactly or at most 2440, at least or exactly or at most 2441, at least or exactly or at most 2442, at least or exactly or at most 2443, at least or exactly or at most 2444, at least or exactly or at most 2445, at least or exactly or at most 2446, at least or exactly or at most 2447, at least or exactly or at most 2448, at least or exactly or at most 2449, at least or exactly or at most 2450, at least or exactly or at most 2451, at least or exactly or at most 2452, at least or exactly or at most 2453, at least or exactly or at most 2454, at least or exactly or at most 2455, at least or exactly or at most 2456, at least or exactly or at most 2457, at least or exactly or at most 2458, at least or exactly or at most 2459, at least or exactly or at most 2460, at least or exactly or at most 2461, at least or exactly or at most 2462, at least or exactly or at most 2463, at least or exactly or at most 2464, at least or exactly or at most 2465, at least or exactly or at most 2466, at least or exactly or at most 2467, at least or exactly or at most 2468, at least or exactly or at most 2469, at least or exactly or at most 2470, at least or exactly or at most 2471, at least or exactly or at most 2472, at least or exactly or at most 2473, at least or exactly or at most 2474, at least or exactly or at most 2475, at least or exactly or at most 2476, at least or exactly or at most 2477, at least or exactly or at most 2478, at least or exactly or at most 2479, at least or exactly or at most 2480, at least or exactly or at most 2481, at least or exactly or at most 2482, at least or exactly or at most 2483, at least or exactly or at most 2484, at least or exactly or at most 2485, at least or exactly or at most 2486, at least or exactly or at most 2487, at least or exactly or at most 2488, at least or exactly or at most 2489, at least or exactly or at most 2490, at least or exactly or at most 2491, at least or exactly or at most 2492, at least or exactly or at most 2493, at least or exactly or at most 2494, at least or exactly or at most 2495, at least or exactly or at most 2496, at least or exactly or at most 2497, at least or exactly or at most 2498, at least or exactly or at most 2499, at least or exactly or at most 2500, at least or exactly or at most 2501, at least or exactly or at most 2502, at least or exactly or at most 2503, at least or exactly or at most 2504, at least or exactly or at most 2505, at least or exactly or at most 2506, at least or exactly or at most 2507, at least or exactly or at most 2508, at least or exactly or at most 2509, at least or exactly or at most 2510, at least or exactly or at most 2511, at least or exactly or at most 2512, at least or exactly or at most 2513, at least or exactly or at most 2514, at least or exactly or at most 2515, at least or exactly or at most 2516, at least or exactly or at most 2517, at least or exactly or at most 2518, at least or exactly or at most 2519, at least or exactly or at most 2520, at least or exactly or at most 2521, at least or exactly or at most 2522, at least or exactly or at most 2523, at least or exactly or at most 2524, at least or exactly or at most 2525, at least or exactly or at most 2526, at least or exactly or at most 2527, at least or exactly or at most 2528, at least or exactly or at most 2529, at least or exactly or at most 2530, at least or exactly or at most 2531, at least or exactly or at most 2532, at least or exactly or at most 2533, at least or exactly or at most 2534, at least or exactly or at most 2535, at least or exactly or at most 2536, at least or exactly or at most 2537, at least or exactly or at most 2538, at least or exactly or at most 2539, at least or exactly or at most 2540, at least or exactly or at most 2541, at least or exactly or at most 2542, at least or exactly or at most 2543, at least or exactly or at most 2544, at least or exactly or at most 2545, at least or exactly or at most 2546, at least or exactly or at most 2547, at least or exactly or at most 2548, at least or exactly or at most 2549, at least or exactly or at most 2550, at least or exactly or at most 2551, at least or exactly or at most 2552, at least or exactly or at most 2553, at least or exactly or at most 2554, at least or exactly or at most 2555, at least or exactly or at most 2556, at least or exactly or at most 2557, at least or exactly or at most 2558, at least or exactly or at most 2559, at least or exactly or at most 2560, at least or exactly or at most 2561, at least or exactly or at most 2562, at least or exactly or at most 2563, at least or exactly or at most 2564, at least or exactly or at most 2565, at least or exactly or at most 2566, at least or exactly or at most 2567, at least or exactly or at most 2568, at least or exactly or at most 2569, at least or exactly or at most 2570, at least or exactly or at most 2571, at least or exactly or at most 2572, at least or exactly or at most 2573, at least or exactly or at most 2574, at least or exactly or at most 2575, at least or exactly or at most 2576, at least or exactly or at most 2577, at least or exactly or at most 2578, at least or exactly or at most 2579, at least or exactly or at most 2580, at least or exactly or at most 2581, at least or exactly or at most 2582, at least or exactly or at most 2583, at least or exactly or at most 2584, at least or exactly or at most 2585, at least or exactly or at most 2586, at least or exactly or at most 2587, at least or exactly or at most 2588, at least or exactly or at most 2589, at least or exactly or at most 2590, at least or exactly or at most 2591, at least or exactly or at most 2592, at least or exactly or at most 2593, at least or exactly or at most 2594, at least or exactly or at most 2595, at least or exactly or at most 2596, at least or exactly or at most 2597, at least or exactly or at most 2598, at least or exactly or at most 2599, at least or exactly or at most 2600, at least or exactly or at most 2601, at least or exactly or at most 2602, at least or exactly or at most 2603, at least or exactly or at most 2604, at least or exactly or at most 2605, at least or exactly or at most 2606, at least or exactly or at most 2607, at least or exactly or at most 2608, at least or exactly or at most 2609, at least or exactly or at most 2610, at least or exactly or at most 2611, at least or exactly or at most 2612, at least or exactly or at most 2613, at least or exactly or at most 2614, at least or exactly or at most 2615, at least or exactly or at most 2616, at least or exactly or at most 2617, at least or exactly or at most 2618, at least or exactly or at most 2619, at least or exactly or at most 2620, at least or exactly or at most 2621, at least or exactly or at most 2622, at least or exactly or at most 2623, at least or exactly or at most 2624, at least or exactly or at most 2625, at least or exactly or at most 2626, at least or exactly or at most 2627, at least or exactly or at most 2628, at least or exactly or at most 2629, at least or exactly or at most 2630, at least or exactly or at most 2631, at least or exactly or at most 2632, at least or exactly or at most 2633, at least or exactly or at most 2634, at least or exactly or at most 2635, at least or exactly or at most 2636, at least or exactly or at most 2637, at least or exactly or at most 2638, at least or exactly or at most 2639, at least or exactly or at most 2640, at least or exactly or at most 2641, at least or exactly or at most 2642, at least or exactly or at most 2643, at least or exactly or at most 2644, at least or exactly or at most 2645, at least or exactly or at most 2646, at least or exactly or at most 2647, at least or exactly or at most 2648, at least or exactly or at most 2649, at least or exactly or at most 2650, at least or exactly or at most 2651, at least or exactly or at most 2652, at least or exactly or at most 2653, at least or exactly or at most 2654, at least or exactly or at most 2655, at least or exactly or at most 2656, at least or exactly or at most 2657, at least or exactly or at most 2658, at least or exactly or at most 2659, at least or exactly or at most 2660, at least or exactly or at most 2661, at least or exactly or at most 2662, at least or exactly or at most 2663, at least or exactly or at most 2664, at least or exactly or at most 2665, at least or exactly or at most 2666, at least or exactly or at most 2667, at least or exactly or at most 2668, at least or exactly or at most 2669, at least or exactly or at most 2670, at least or exactly or at most 2671, at least or exactly or at most 2672, at least or exactly or at most 2673, at least or exactly or at most 2674, at least or exactly or at most 2675, at least or exactly or at most 2676, at least or exactly or at most 2677, at least or exactly or at most 2678, at least or exactly or at most 2679, at least or exactly or at most 2680, at least or exactly or at most 2681, at least or exactly or at most 2682, at least or exactly or at most 2683, at least or exactly or at most 2684, at least or exactly or at most 2685, at least or exactly or at most 2686, at least or exactly or at most 2687, at least or exactly or at most 2688, at least or exactly or at most 2689, at least or exactly or at most 2690, at least or exactly or at most 2691, at least or exactly or at most 2692, at least or exactly or at most 2693, at least or exactly or at most 2694, at least or exactly or at most 2695, at least or exactly or at most 2696, at least or exactly or at most 2697, at least or exactly or at most 2698, at least or exactly or at most 2699, at least or exactly or at most 2700, at least or exactly or at most 2701, at least or exactly or at most 2702, at least or exactly or at most 2703, at least or exactly or at most 2704, at least or exactly or at most 2705, at least or exactly or at most 2706, at least or exactly or at most 2707, at least or exactly or at most 2708, at least or exactly or at most 2709, at least or exactly or at most 2710, at least or exactly or at most 2711, at least or exactly or at most 2712, at least or exactly or at most 2713, at least or exactly or at most 2714, at least or exactly or at most 2715, at least or exactly or at most 2716, at least or exactly or at most 2717, at least or exactly or at most 2718, at least or exactly or at most 2719, at least or exactly or at most 2720, at least or exactly or at most 2721, at least or exactly or at most 2722, at least or exactly or at most 2723, at least or exactly or at most 2724, at least or exactly or at most 2725, at least or exactly or at most 2726, at least or exactly or at most 2727, at least or exactly or at most 2728, at least or exactly or at most 2729, at least or exactly or at most 2730, at least or exactly or at most 2731, at least or exactly or at most 2732, at least or exactly or at most 2733, at least or exactly or at most 2734, at least or exactly or at most 2735, at least or exactly or at most 2736, at least or exactly or at most 2737, at least or exactly or at most 2738, at least or exactly or at most 2739, at least or exactly or at most 2740, at least or exactly or at most 2741, at least or exactly or at most 2742, at least or exactly or at most 2743, at least or exactly or at most 2744, at least or exactly or at most 2745, at least or exactly or at most 2746, at least or exactly or at most 2747, at least or exactly or at most 2748, at least or exactly or at most 2749, at least or exactly or at most 2750, at least or exactly or at most 2751, at least or exactly or at most 2752, at least or exactly or at most 2753, at least or exactly or at most 2754, at least or exactly or at most 2755, at least or exactly or at most 2756, at least or exactly or at most 2757, at least or exactly or at most 2758, at least or exactly or at most 2759, at least or exactly or at most 2760, at least or exactly or at most 2761, at least or exactly or at most 2762, at least or exactly or at most 2763, at least or exactly or at most 2764, at least or exactly or at most 2765, at least or exactly or at most 2766, at least or exactly or at most 2767, at least or exactly or at most 2768, at least or exactly or at most 2769, at least or exactly or at most 2770, at least or exactly or at most 2771, at least or exactly or at most 2772, at least or exactly or at most 2773, at least or exactly or at most 2774, at least or exactly or at most 2775, at least or exactly or at most 2776, at least or exactly or at most 2777, at least or exactly or at most 2778, at least or exactly or at most 2779, at least or exactly or at most 2780, at least or exactly or at most 2781, at least or exactly or at most 2782, at least or exactly or at most 2783, at least or exactly or at most 2784, at least or exactly or at most 2785, at least or exactly or at most 2786, at least or exactly or at most 2787, at least or exactly or at most 2788, at least or exactly or at most 2789, at least or exactly or at most 2790, at least or exactly or at most 2791, at least or exactly or at most 2792, at least or exactly or at most 2793, at least or exactly or at most 2794, at least or exactly or at most 2795, at least or exactly or at most 2796, at least or exactly or at most 2797, at least or exactly or at most 2798, at least or exactly or at most 2799, at least or exactly or at most 2800, at least or exactly or at most 2801, at least or exactly or at most 2802, at least or exactly or at most 2803, at least or exactly or at most 2804, at least or exactly or at most 2805, at least or exactly or at most 2806, at least or exactly or at most 2807, at least or exactly or at most 2808, at least or exactly or at most 2809, at least or exactly or at most 2810, at least or exactly or at most 2811, at least or exactly or at most 2812, at least or exactly or at most 2813, at least or exactly or at most 2814, at least or exactly or at most 2815, at least or exactly or at most 2816, at least or exactly or at most 2817, at least or exactly or at most 2818, at least or exactly or at most 2819, at least or exactly or at most 2820, at least or exactly or at most 2821, at least or exactly or at most 2822, at least or exactly or at most 2823, at least or exactly or at most 2824, at least or exactly or at most 2825, at least or exactly or at most 2826, at least or exactly or at most 2827, at least or exactly or at most 2828, at least or exactly or at most 2829, at least or exactly or at most 2830, at least or exactly or at most 2831, at least or exactly or at most 2832, at least or exactly or at most 2833, at least or exactly or at most 2834, at least or exactly or at most 2835, at least or exactly or at most 2836, at least or exactly or at most 2837, at least or exactly or at most 2838, at least or exactly or at most 2839, at least or exactly or at most 2840, at least or exactly or at most 2841, at least or exactly or at most 2842, at least or exactly or at most 2843, at least or exactly or at most 2844, at least or exactly or at most 2845, at least or exactly or at most 2846, at least or exactly or at most 2847, at least or exactly or at most 2848, at least or exactly or at most 2849, at least or exactly or at most 2850, at least or exactly or at most 2851, at least or exactly or at most 2852, at least or exactly or at most 2853, at least or exactly or at most 2854, at least or exactly or at most 2855, at least or exactly or at most 2856, at least or exactly or at most 2857, at least or exactly or at most 2858, at least or exactly or at most 2859, at least or exactly or at most 2860, at least or exactly or at most 2861, at least or exactly or at most 2862, at least or exactly or at most 2863, at least or exactly or at most 2864, at least or exactly or at most 2865, at least or exactly or at most 2866, at least or exactly or at most 2867, at least or exactly or at most 2868, at least or exactly or at most 2869, at least or exactly or at most 2870, at least or exactly or at most 2871, at least or exactly or at most 2872, at least or exactly or at most 2873, at least or exactly or at most 2874, at least or exactly or at most 2875, at least or exactly or at most 2876, at least or exactly or at most 2877, at least or exactly or at most 2878, at least or exactly or at most 2879, at least or exactly or at most 2880, at least or exactly or at most 2881, at least or exactly or at most 2882, at least or exactly or at most 2883, at least or exactly or at most 2884, at least or exactly or at most 2885, at least or exactly or at most 2886, at least or exactly or at most 2887, at least or exactly or at most 2888, at least or exactly or at most 2889, at least or exactly or at most 2890, at least or exactly or at most 2891, at least or exactly or at most 2892, at least or exactly or at most 2893, at least or exactly or at most 2894, at least or exactly or at most 2895, at least or exactly or at most 2896, at least or exactly or at most 2897, at least or exactly or at most 2898, at least or exactly or at most 2899, at least or exactly or at most 2900, at least or exactly or at most 2901, at least or exactly or at most 2902, at least or exactly or at most 2903, at least or exactly or at most 2904, at least or exactly or at most 2905, at least or exactly or at most 2906, at least or exactly or at most 2907, at least or exactly or at most 2908, at least or exactly or at most 2909, at least or exactly or at most 2910, at least or exactly or at most 2911, at least or exactly or at most 2912, at least or exactly or at most 2913, at least or exactly or at most 2914, at least or exactly or at most 2915, at least or exactly or at most 2916, at least or exactly or at most 2917, at least or exactly or at most 2918, at least or exactly or at most 2919, at least or exactly or at most 2920, at least or exactly or at most 2921, at least or exactly or at most 2922, at least or exactly or at most 2923, at least or exactly or at most 2924, at least or exactly or at most 2925, at least or exactly or at most 2926, at least or exactly or at most 2927, at least or exactly or at most 2928, at least or exactly or at most 2929, at least or exactly or at most 2930, at least or exactly or at most 2931, at least or exactly or at most 2932, at least or exactly or at most 2933, at least or exactly or at most 2934, at least or exactly or at most 2935, at least or exactly or at most 2936, at least or exactly or at most 2937, at least or exactly or at most 2938, at least or exactly or at most 2939, at least or exactly or at most 2940, at least or exactly or at most 2941, at least or exactly or at most 2942, at least or exactly or at most 2943, at least or exactly or at most 2944, at least or exactly or at most 2945, at least or exactly or at most 2946, at least or exactly or at most 2947, at least or exactly or at most 2948, at least or exactly or at most 2949, at least or exactly or at most 2950, at least or exactly or at most 2951, at least or exactly or at most 2952, at least or exactly or at most 2953, at least or exactly or at most 2954, at least or exactly or at most 2955, at least or exactly or at most 2956, at least or exactly or at most 2957, at least or exactly or at most 2958, at least or exactly or at most 2959, at least or exactly or at most 2960, at least or exactly or at most 2961, at least or exactly or at most 2962, at least or exactly or at most 2963, at least or exactly or at most 2964, at least or exactly or at most 2965, at least or exactly or at most 2966, at least or exactly or at most 2967, at least or exactly or at most 2968, at least or exactly or at most 2969, at least or exactly or at most 2970, at least or exactly or at most 2971, at least or exactly or at most 2972, at least or exactly or at most 2973, at least or exactly or at most 2974, at least or exactly or at most 2975, at least or exactly or at most 2976, at least or exactly or at most 2977, at least or exactly or at most 2978, at least or exactly or at most 2979, at least or exactly or at most 2980, at least or exactly or at most 2981, at least or exactly or at most 2982, at least or exactly or at most 2983, at least or exactly or at most 2984, at least or exactly or at most 2985, at least or exactly or at most 2986, at least or exactly or at most 2987, at least or exactly or at most 2988, at least or exactly or at most 2989, at least or exactly or at most 2990, at least or exactly or at most 2991, at least or exactly or at most 2992, at least or exactly or at most 2993, at least or exactly or at most 2994, at least or exactly or at most 2995, at least or exactly or at most 2996, at least or exactly or at most 2997, at least or exactly or at most 2998, at least or exactly or at most 2999, at least or exactly or at most 3000, at least or exactly or at most 3001, at least or exactly or at most 3002, at least or exactly or at most 3003, at least or exactly or at most 3004, at least or exactly or at most 3005, at least or exactly or at most 3006, at least or exactly or at most 3007, at least or exactly or at most 3008, at least or exactly or at most 3009, at least or exactly or at most 3010, at least or exactly or at most 3011, at least or exactly or at most 3012, at least or exactly or at most 3013, at least or exactly or at most 3014, at least or exactly or at most 3015, at least or exactly or at most 3016, at least or exactly or at most 3017, at least or exactly or at most 3018, at least or exactly or at most 3019, at least or exactly or at most 3020, at least or exactly or at most 3021, at least or exactly or at most 3022, at least or exactly or at most 3023, at least or exactly or at most 3024, at least or exactly or at most 3025, at least or exactly or at most 3026, at least or exactly or at most 3027, at least or exactly or at most 3028, at least or exactly or at most 3029, at least or exactly or at most 3030, at least or exactly or at most 3031, at least or exactly or at most 3032, at least or exactly or at most 3033, at least or exactly or at most 3034, at least or exactly or at most 3035, at least or exactly or at most 3036, at least or exactly or at most 3037, at least or exactly or at most 3038, at least or exactly or at most 3039, at least or exactly or at most 3040, at least or exactly or at most 3041, at least or exactly or at most 3042, at least or exactly or at most 3043, at least or exactly or at most 3044, at least or exactly or at most 3045, at least or exactly or at most 3046, at least or exactly or at most 3047 contiguous amino acid residues.

In some embodiments, the polypeptide of the invention also has a sequence identity with the amino acid sequence of a) defined above of at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%. Similarly, the polypeptide of the invention in some embodiments also has a sequence identity with the amino acid sequence of b) defined above of at least 60%, such as at least 65%, at least 70%, at least 75%, at least 80%, at least 85%, at least 90%, at least 91%, at least 92%, at least 93%, at least 94%, at least 95%, at least 96%, at least 97%, at least 98%, and at least 99%.

In the embodiments defined by option b) above, the polypeptide of the invention is also one that has at least 5 contiguous amino acid residues defined for option b) above and also has its N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 38, 39, 40, 42, 43, 44, 45, 46, 47, 48, 49, 50, 51, 52, 53, 54, 55, and 56 in any one of SEQ ID NOs: 1-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 57, 58, 59, 60, 61 and 62 in any on of SEQ ID NOs: 2-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 63, 64, 65, 66, 67, 68, and 69 in any one of SEQ ID NOs: 4-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, and 104 in any one of SEQ ID NOs: 5-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 105, 106, 107, 108, 109, 110, and 110 in any one of SEQ ID NOs: 6-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 111, 112, 113, 114, 115, 116, 117, 118, 119, 120, 121, and 122 in any one of SEQ ID NOs: 7-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 123, 124, 125, 126, 127, 128, 129, 130, 131, 132, 133, 134, and 135 in any one of SEQ ID NOs: 8-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 136, 137, 138, 139, 140, 141, 142, 143, 144, 145, 146, 147, 148, 149, 150, 151, 152, 153, 154, and 155 in any one of SEQ ID NOs: 9-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 156, 157, and 158 in any one of SEQ ID NOs: 10-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 159, 160, 161, and 162 in any one of SEQ ID NOs: 11-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, and 226 in any one of SEQ ID NOs: 12-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 227, 228, 229, 230, 231, 232, 233, and 234 in any one of SEQ ID NOs: 13-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 235, 236, 237, 238, 239, 240, 241, 242, 243, 244, 245, 246, 247, 248, and 249 in SEQ ID NOs: 14-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, and 290 in any one of SEQ ID NOs: 15-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, and 352 in any one of SEQ ID NOs: 16-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 353, 354, 355, 356, 357, 358, 359, 360, 361, 362, and 363 in any one of SEQ ID NOs: 17-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, and 416 in any one of SEQ ID NOs: 18-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 417, 418, 419, 420, 421, 422, 423, 424, 425, 426, 427, 428, 429, 430, 431, 432, 433, 434, 435, 436, 437, 438, 439, 440, and 441 in any one of SEQ ID NOs: 19-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, and 707 in any one of SEQ ID NOs: 20-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 708, 709, 710, 711, 712, 713, 714, 715, 716, 717, 718, 719, 720, 721, 722 and 723 in any one of SEQ ID NOs: 21-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to amino acid residue 724 in any one of SEQ ID NOs: 22-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 725, 726, 727, 728, 729, 730, 731, 732, 733, 734, 735, 736, 737, 738, 739, 740, 741, 742, 743, 744, 745, 746, 747, 748, 749, and 750 in any one of SEQ ID NOs: 23-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, and 902 in any one of SEQ ID NOs: 24-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, and 970 in any one of SEQ ID NOs: 25-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, and 1067 in any one of SEQ ID NOs: 26-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 1068, 1069, 1070, 1071, 1072, 1073, 1074, 1075, 1076, 1077, 1078, 1079, 1080, 1081, 1082, 1083, 1084, 1085, 1086, 1087, 1088, 1089, 1090, 1091, 1092, 1093, 1094, 1095, 1096, 1097, 1098, 1099, 1100, 1101, 1102, 1103, 1104, 1105, and 1106 in any one of SEQ ID NOs: 27-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 1107, 1108, 1109, 1110, 1111, 1112, 1113, 1114, 1115, 1116, 1117, 1118, 1119, 1120, 1121, 1122, 1123, 1124, 1125, 1126, 1127, 1128, 1129, 1130, 1131, 1132, 1133, 1134, 1135, 1136, 1137, 1138, 1139, 1140, 1141, 1142, 1143, 1144, 1145, 1146, 1147, 1148, 1149, 1150, 1151, 1152, 1153, 1154, 1155, 1156, 1157, 1158, 1159, 1160, 1161, 1162, 1163, 1164, 1165, 1166, 1167, 1168, 1169, 1170, 1171, 1172, 1173, 1174, 1175, 1176, 1177, 1178, 1179, 1180, 1181, 1182, 1183, 1184, 1185, 1186, 1187, 1188, 1189, 1190, 1191, 1192, 1193, 1194, 1195, 1196, 1197, 1198, 1199, 1200, 1201, 1202, 1203, 1204, 1205, 1206, 1207, 1208, 1209, 1210, 1211, 1212, 1213, 1214, 1215, 1216, 1217, 1218, 1219, 1220, 1221, 1222, 1223, and 1224 in any one of SEQ ID NOs: 28-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues In the embodiments defined by option b) above, the polypeptide of the invention is also one that has at least 5 contiguous amino acid residues defined for option b) above and also has its N-terminal amino acid residue corresponding to any one of amino acid residues 1225, 1226, 1227, 1228, 1229, 1230, 1231, 1232, 1233, 1234, 1235, 1236, 1237, 1238, 1239, 1240, 1241, 1242, 1243, 1244, 1245, 1246, 1247, 1248, 1249, 1250, 1251, 1252, 1253, 1254, 1255, 1256, 1257, 1258, 1259, 1260, 1261, 1262, 1263, 1264, 1265, 1266, 1267, 1268, 1269, 1270, 1271, 1272, 1273, 1274, 1275, 1276, 1277, 1278, 1279, and 1280 in any one of SEQ ID NOs: 29-30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

In the embodiments defined by option b) above, the polypeptide of the invention is also one that has at least 5 contiguous amino acid residues defined for option b) above and also has its N-terminal amino acid residue corresponding to any one of amino acid residues 1281, 1282, 1283, 1284, 1285, 1286, 1287, 1288, 1289, 1290, 1291, 1292, 1293, 1294, 1295, 1296, 1297, 1298, 1299, 1300, 1301, 1302, 1303, 1304, 1305, 1306, 1307, 1308, 1309, 1310, 1311, 1312, 1313, 1314, 1315, 1316, 1317, 1318, 1319, 1320, 1321, 1322, 1323, 1324, 1325, 1326, 1327, 1328, 1329, 1330, 1331, 1332, 1333, 1334, 1335, 1336, 1337, 1338, 1339, 1340, 1341, 1342, 1343, 1344, 1345, 1346, 1347, 1348, 1349, 1350, 1351, 1352, 1353, 1354, 1355, 1356, 1357, 1358, 1359, 1360, 1361, 1362, 1363, 1364, 1365, 1366, 1367, 1368, 1369, 1370, 1371, 1372, 1373, 1374, 1375, 1376, 1377, 1378, 1379, 1380, 1381, 1382, 1383, 1384, 1385, 1386, 1387, 1388, 1389, 1390, 1391, 1392, 1393, 1394, 1395, 1396, 1397, 1398, 1399, 1400, 1401, 1402, 1403, 1404, 1405, 1406, 1407, 1408, 1409, 1410, 1411, 1412, 1413, 1414, 1415, 1416, 1417, 1418, 1419, 1420, 1421, 1422, 1423, 1424, 1425, 1426, 1427, 1428, 1429, 1430, 1431, 1432, 1433, 1434, 1435, 1436, 1437, 1438, 1439, 1440, 1441, 1442, 1443, 1444, 1445, 1446, 1447, 1448, 1449, 1450, 1451, 1452, 1453, 1454, 1455, 1456, 1457, 1458, 1459, 1460, 1461, 1462, 1463, 1464, 1465, 1466, 1467, 1468, 1469, 1470, 1471, 1472, 1473, 1474, 1475, 1476, 1477, 1478, 1479, 1480, 1481, 1482, 1483, 1484, 1485, 1486, 1487, 1488, 1489, 1490, 1491, 1492, 1493, 1494, 1495, 1496, 1497, 1498, 1499, 1500, 1501, 1502, 1503, 1504, 1505, 1506, 1507, 1508, 1509, 1510, 1511, 1512, 1513, 1514, 1515, 1516, 1517, 1518, 1519, 1520, 1521, 1522, 1523, 1524, 1525, 1526, 1527, 1528, 1529, 1530, 1531, 1532, 1533, 1534, 1535, 1536, 1537, 1538, 1539, 1540, 1541, 1542, 1543, 1544, 1545, 1546, 1547, 1548, 1549, 1550, 1551, 1552, 1553, 1554, 1555, 1556, 1557, 1558, 1559, 1560, 1561, 1562, 1563, 1564, 1565, 1566, 1567, 1568, 1569, 1570, 1571, 1572, 1573, 1574, 1575, 1576, 1577, 1578, 1579, 1580, 1581, 1582, 1583, 1584, 1585, 1586, 1587, 1588, 1589, 1590, 1591, 1592, 1593, 1594, 1595, 1596, 1597, 1598, 1599, 1600, 1601, 1602, 1603, 1604, 1605, 1606, 1607, 1608, 1609, 1610, 1611, 1612, 1613, 1614, 1615, 1616, 1617, 1618, 1619, 1620, 1621, 1622, 1623, 1624, 1625, 1626, 1627, 1628, 1629, 1630, 1631, 1632, 1633, 1634, 1635, 1636, 1637, 1638, 1639, 1640, 1641, 1642, 1643, 1644, 1645, 1646, 1647, 1648, 1649, 1650, 1651, 1652, 1653, 1654, 1655, 1656, 1657, 1658, 1659, 1660, 1661, 1662, 1663, 1664, 1665, 1666, 1667, 1668, 1669, 1670, 1671, 1672, 1673, 1674, 1675, 1676, 1677, 1678, 1679, 1680, 1681, 1682, 1683, 1684, 1685, 1686, 1687, 1688, 1689, 1690, 1691, 1692, 1693, 1694, 1695, 1696, 1697, 1698, 1699, 1700, 1701, 1702, 1703, 1704, 1705, 1706, 1707, 1708, 1709, 1710, 1711, 1712, 1713, 1714, 1715, 1716, 1717, 1718, 1719, 1720, 1721, 1722, 1723, 1724, 1725, 1726, 1727, 1728, 1729, 1730, 1731, 1732, 1733, 1734, 1735, 1736, 1737, 1738, 1739, 1740, 1741, 1742, 1743, 1744, 1745, 1746, 1747, 1748, 1749, 1750, 1751, 1752, 1753, 1754, 1755, 1756, 1757, 1758, 1759, 1760, 1761, 1762, 1763, 1764, 1765, 1766, 1767, 1768, 1769, 1770, 1771, 1772, 1773, 1774, 1775, 1776, 1777, 1778, 1779, 1780, 1781, 1782, 1783, 1784, 1785, 1786, 1787, 1788, 1789, 1790, 1791, 1792, 1793, 1794, 1795, 1796, 1797, 1798, 1799, 1800, 1801, 1802, 1803, 1804, 1805, 1806, 1807, 1808, 1809, 1810, 1811, 1812, 1813, 1814, 1815, 1816, 1817, 1818, 1819, 1820, 1821, 1822, 1823, 1824, 1825, 1826, 1827, 1828, 1829, 1830, 1831, 1832, 1833, 1834, 1835, 1836, 1837, 1838, 1839, 1840, 1841, 1842, 1843, 1844, 1845, 1846, 1847, 1848, 1849, 1850, 1851, 1852, 1853, 1854, 1855, 1856, 1857, 1858, 1859, 1860, 1861, 1862, 1863, 1864, 1865, 1866, 1867, 1868, 1869, 1870, 1871, 1872, 1873, 1874, 1875, 1876, 1877, 1878, 1879, 1880, 1881, 1882, 1883, 1884, 1885, 1886, 1887, 1888, 1889, 1890, 1891, 1892, 1893, 1894, 1895, 1896, 1897, 1898, 1899, 1900, 1901, 1902, 1903, 1904, 1905, 1906, 1907, 1908, 1909, 1910, 1911, 1912, 1913, 1914, 1915, 1916, 1917, 1918, 1919, 1920, 1921, 1922, 1923, 1924, 1925, 1926, 1927, 1928, 1929, 1930, 1931, 1932, 1933, 1934, 1935, 1936, 1937, 1938, 1939, 1940, 1941, 1942, 1943, 1944, 1945, 1946, 1947, 1948, 1949, 1950, 1951, 1952, 1953, 1954, 1955, 1956, 1957, 1958, 1959, 1960, 1961, 1962, 1963, 1964, 1965, 1966, 1967, 1968, 1969, 1970, 1971, 1972, 1973, 1974, 1975, 1976, 1977, 1978, 1979, 1980, 1981, 1982, 1983, 1984, 1985, 1986, 1987, 1988, 1989, 1990, 1991, 1992, 1993, 1994, 1995, 1996, 1997, 1998, 1999, 2000, 2001, 2002, 2003, 2004, 2005, 2006, 2007, 2008, 2009, 2010, 2011, 2012, 2013, 2014, 2015, 2016, 2017, 2018, 2019, 2020, 2021, 2022, 2023, 2024, 2025, 2026, 2027, 2028, 2029, 2030, 2031, 2032, 2033, 2034, 2035, 2036, 2037, 2038, 2039, 2040, 2041, 2042, 2043, 2044, 2045, 2046, 2047, 2048, 2049, 2050, 2051, 2052, 2053, 2054, 2055, 2056, 2057, 2058, 2059, 2060, 2061, 2062, 2063, 2064, 2065, 2066, 2067, 2068, 2069, 2070, 2071, 2072, 2073, 2074, 2075, 2076, 2077, 2078, 2079, 2080, 2081, 2082, 2083, 2084, 2085, 2086, 2087, 2088, 2089, 2090, 2091, 2092, 2093, 2094, 2095, 2096, 2097, 2098, 2099, 2100, 2101, 2102, 2103, 2104, 2105, 2106, 2107, 2108, 2109, 2110, 2110, 2111, 2112, 2113, 2114, 2115, 2116, 2117, 2118, 2119, 2120, 2121, 2122, 2123, 2124, 2125, 2126, 2127, 2128, 2129, 2130, 2131, 2132, 2133, 2134, 2135, 2136, 2137, 2138, 2139, 2140, 2141, 2142, 2143, 2144, 2145, 2146, 2147, 2148, 2149, 2150, 2151, 2152, 2153, 2154, 2155, 2156, 2157, 2158, 2159, 2160, 2171, 2172, 2173, 2174, 2175, 2176, 2177, 2178, 2179, 2180, 2181, 2182, 2183, 2184, 2185, 2186, 2187, 2188, 2189, 2190, 2191, 2192, 2193, 2194, 2195, 2196, 2197, 2198, 2199, 2200, 2201, 2202, 2203, 2204, 2205, 2206, 2207, 2208, 2209, 2210, 2211, 2212, 2213, 2214, 2215, 2216, 2217, 2218, 2219, 2220, 2221, 2222, 2223, 2224, 2225, 2226, 2227, 2228, 2229, 2230, 2231, 2232, 2233, 2234, 2235, 2236, 2237, 2238, 2239, 2240, 2241, 2242, 2243, 2244, 2245, 2246, 2247, 2248, 2249, 2250, 2251, 2252, 2253, 2254, 2255, 2256, 2257, 2258, 2259, 2260, 2271, 2272, 2273, 2274, 2275, 2276, 2277, 2278, 2279, 2280, 2281, 2282, 2283, 2284, 2285, 2286, 2287, 2288, 2289, 2290, 2291, 2292, 2293, 2294, 2295, 2296, 2297, 2298, 2299, 2300, 2301, 2302, 2303, 2304, 2305, 2306, 2307, 2308, 2309, 2310, 2311, 2312, 2313, 2314, 2315, 2316, 2317, 2318, 2319, 2320, 2321, 2322, 2323, 2324, 2325, 2326, 2327, 2328, 2329, 2330, 2331, 2332, 2333, 2334, 2335, 2336, 2337, 2338, 2339, 2340, 2341, 2342, 2343, 2344, 2345, 2346, 2347, 2348, 2349, 2350, 2351, 2352, 2353, 2354, 2355, 2356, 2357, 2358, 2359, 2360, 2361, 2362, 2363, 2364, 2365, 2366, 2367, 2368, 2369, 2370, 2371, 2372, 2373, 2374, 2375, 2376, 2377, 2378, 2379, 2380, 2381, 2382, 2383, 2384, 2385, 2386, 2387, 2388, 2389, 2390, 2391, 2392, 2393, 2394, 2395, 2396, 2397, 2398, 2399, 2400, 2401, 2402, 2403, 2404, 2405, 2406, 2407, 2408, 2409, 2410, 2411, 2412, 2413, 2414, 2415, 2416, 2417, 2418, 2419, 2420, 2421, 2422, 2423, 2424, 2425, 2426, 2427, 2428, 2429, 2430, 2431, 2432, 2433, 2434, 2435, 2436, 2437, 2438, 2439, 2440, 2441, 2442, 2443, 2444, 2445, 2446, 2447, 2448, 2449, 2450, 2451, 2452, 2453, 2454, 2455, 2456, 2457, 2458, 2459, 2460, 2461, 2462, 2463, 2464, 2465, 2466, 2467, 2468, 2469, 2470, 2471, 2472, 2473, 2474, 2475, 2476, 2477, 2478, 2479, 2480, 2481, 2482, 2483, 2484, 2485, 2486, 2487, 2488, 2489, 2490, 2491, 2492, 2493, 2494, 2495, 2496, 2497, 2498, 2499, 2500, 2501, 2502, 2503, 2504, 2505, 2506, 2507, 2508, 2509, 2510, 2511, 2512, 2513, 2514, 2515, 2516, 2517, 2518, 2519, 2520, 2521, 2522, 2523, 2524, 2525, 2526, 2527, 2528, 2529, 2530, 2531, 2532, 2533, 2534, 2535, 2536, 2537, 2538, 2539, 2540, 2541, 2542, 2543, 2544, 2545, 2546, 2547, 2548, 2549, 2550, 2551, 2552, 2553, 2554, 2555, 2556, 2557, 2558, 2559, 2560, 2561, 2562, 2563, 2564, 2565, 2566, 2567, 2568, 2569, 2570, 2571, 2572, 2573, 2574, 2575, 2576, 2577, 2578, 2579, 2580, 2581, 2582, 2583, 2584, 2585, 2586, 2587, 2588, 2589, 2590, 2591, 2592, 2593, 2594, 2595, 2596, 2597, 2598, 2599, 2600, 2601, 2602, 2603, 2604, 2605, 2606, 2607, 2608, 2609, 2610, 2611, 2612, 2613, 2614, 2615, 2616, 2617, 2618, 2619, 2620, 2621, 2622, 2623, 2624, 2625, 2626, 2627, 2628, 2629, 2630, 2631, 2632, 2633, 2634, 2635, 2636, 2637, 2638, 2639, 2640, 2641, 2642, 2643, 2644, 2645, 2646, 2647, 2648, 2649, 2650, 2651, 2652, 2653, 2654, 2655, 2656, 2657, 2658, 2659, 2660, 2661, 2662, 2663, 2664, 2665, 2666, 2667, 2668, 2669, 2670, 2671, 2672, 2673, 2674, 2675, 2676, 2677, 2678, 2679, 2680, 2681, 2682, 2683, 2684, 2685, 2686, 2687, 2688, 2689, 2690, 2691, 2692, 2693, 2694, 2695, 2696, 2697, 2698, 2699, 2700, 2701, 2702, 2703, 2704, 2705, 2706, 2707, 2708, 2709, 2710, 2711, 2712, 2713, 2714, 2715, 2716, 2717, 2718, 2719, 2720, 2721, 2722, 2723, 2724, 2725, 2726, 2727, 2728, 2729, 2730, 2731, 2732, 2733, 2734, 2735, 2736, 2737, 2738, 2739, 2740, 2741, 2742, 2743, 2744, 2745, 2746, 2747, 2748, 2749, 2750, 2751, 2752, 2753, 2754, 2755, 2756, 2757, 2758, 2759, 2760, 2761, 2762, 2763, 2764, 2765, 2766, 2767, 2768, 2769, 2770, 2771, 2772, 2773, 2774, 2775, 2776, 2777, 2778, 2779, 2780, 2781, 2782, 2783, 2784, 2785, 2786, 2787, 2788, 2789, 2790, 2791, 2792, 2793, 2794, 2795, 2796, 2797, 2798, 2799, 2800, 2801, 2802, 2803, 2804, 2805, 2806, 2807, 2808, 2809, 2810, 2811, 2812, 2813, 2814, 2815, 2816, 2817, 2818, 2819, 2820, 2821, 2822, 2823, 2824, 2825, 2826, 2827, 2828, 2829, 2830, 2831, 2832, 2833, 2834, 2835, 2836, 2837, 2838, 2839, 2840, 2841, 2842, 2843, 2844, 2845, 2846, 2847, 2848, 2849, 2850, 2851, 2852, 2853, 2854, 2855, 2856, 2857, 2858, 2859, 2860, 2861, 2862, 2863, 2864, 2865, 2866, 2867, 2868, 2869, 2870, 2871, 2872, 2873, 2874, 2875, 2876, 2877, 2878, 2879, 2880, 2881, 2882, 2883, 2884, 2885, 2886, 2887, 2888, 2889, 2890, 2891, 2892, 2893, 2894, 2895, 2896, 2897, 2898, 2899, 2900, 2901, 2902, 2903, 2904, 2905, 2906, 2907, 2908, 2909, 2910, 2911, 2912, 2913, 2914, 2915, 2916, 2917, 2918, 2919, 2920, 2921, 2922, 2923, 2924, 2925, 2926, 2927, 2928, 2929, 2930, 2931, 2932, 2933, 2934, 2935, 2936, 2937, 2938, 2939, 2940, 2941, 2942, 2943, 2944, 2945, 2946, 2947, 2948, 2949, 2950, 2951, 2952, 2953, 2954, 2955, 2956, 2957, 2958, 2959, 2960, 2961, 2962, 2963, 2964, 2965, 2966, 2967, 2968, 2969, 2970, 2971, 2972, 2973, 2974, 2975, 2976, 2977, 2978, 2979, 2980, 2981, 2982, 2983, 2984, 2985, 2986, 2987, 2988, 2989, 2990, 2991, 2992, 2993, 2994, 2995, 2996, 2997, 2998, 2999, 3000, 3001, 3002, 3003, 3004, 3005, 3006, 3007, 3008, 3009, 3010, 3011, 3012, 3013, 3014, 3015, 3016, 3017, 3018, 3019, 3020, 3021, 3022, 3023, 3024, 3025, 3026, 3027, 3028, 3029, 3030, 3031, 3032, 3033, 3034, 3035, 3036, 3037, 3038, 3039, 3040, 3042, and 3043 in any one of SEQ ID NOs: 30, if the length of the at least 5 amino acid residues so permit—if the length of the at least 5 amino acids are higher than 5, the N-terminal first residue will not be higher numbered than N−L+1, where N is the number of amino acid residues of the reference sequence and L is the number of amino acids defined for option b.

The polypeptide of the invention is in certain embodiments also fused or conjugated to an immunogenic carrier molecule; or, phrased otherwise, the polypeptide of the invention also includes such an immunogenic carrier molecule in addition to the material derived from SEQ ID NOs. 1-30. The immunogenic carrier molecule is a typically polypeptide that induces T-helper lymphocyte responses in a majority of humans, such as immunogenic carrier proteins selected from the group consisting of keyhole limpet hemocyanino or a fragment thereof, tetanus toxoid or a fragment thereof, dipththeria toxoid or a fragment thereof. Other suitable carrier molecules are discussed infra. One further fusion partner, which is preferably incorporated is a "His tag", i.e. a stretch of amino acids, which is rich or only consists of histidinyl residues so as to facilitate protein purification.

In preferred embodiments, the polypeptide of the invention detailed above is capable of inducing an adaptive immune response against the polypeptide in a mammal, in particular in a human being. Preferably, the adaptive immune response is a protective adaptive immune response against infection with *A baumanii*. The polypeptide may in these cases induce a humeral and/or a cellular immune response.

Epitopes

SEQ ID NOs: 1-30 include antigenic determinants (epitopes) that are as such recognized by antibodies and/or when bound to MHC molecules by T-cell receptors. For the purposes of the present invention, B-cell epitopes (i.e. antibody binding epitopes) are of particular relevance.

It is relatively uncomplicated to identify linear B-cell epitopes—one very simple approach entails that antibodies raised against *A. baumannii* or *A. baumannii* derived proteins disclosed herein are tested for binding to overlapping oligomeric peptides derived from any one of SEQ ID NO: 1-30. Thereby, the regions of the *A. baumannii* polypeptide which are responsible for or contribute to binding to the antibodies can be identified.

Alternatively, or additionally, one can produce mutated versions of the polypeptides of the invention, e.g. version where each single non-alanine residue in SEQ ID NOs.: 1-30 are point mutated to alanine—this method also assists in identifying complex assembled B-cell epitopes; this is the case when binding of the same antibody is modified by exchanging amino acids in different areas of the full-length polypeptide.

Also, in silico methods for B-cell epitope prediction can be employed: useful state-of-the-art systems for β-turn prediction is provided in Petersen B et al. (November 2010), *Plos One* 5(11): e15079; prediction of linear B-cell epitopes, cf: Larsen 3 E P et al. (April 2006), Immunome Research, 2:2; prediction of solvent exposed amino acids: Petersen B et al (July 2009), BMC Structural Biology, 9:51.

The Nucleic Acid Fragments of the Invention

The nucleic acid fragment of the invention referred to above is preferably is a DNA fragment (such as SEQ ID NOs: 31-60) or an RNA fragment (such as SEQ ID NOs 61-90).

The nucleic acid fragment of the invention typically consists of at least or exactly or at most 11, such as at least or exactly or at most 12, at least or exactly or at most 13, at least or exactly or at most 14, at least or exactly or at most 15, at least or exactly or at most 16, at least or exactly or at most 17 at least or exactly or at most 18, at least or exactly or at most 19, at least or exactly or at most 20, at least or exactly or at most 21, at least or exactly or at most 22, at least or exactly or at most 23, at least or exactly or at most 24, at least or exactly or at most 25, at least or exactly or at most 26, at least or exactly or at most 27, at least or exactly or at most 28, at least or exactly or at most 29, at least or exactly or at most 30, at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76, at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 153, at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 166, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182 and at least or exactly or at most 183 consecutive nucleotides in any one of SEQ ID NOs: 31-90. Longer fragments are contemplated, i.e. fragments having at least or exactly or at most 200, at least or exactly or at most 300 at least or exactly or at most 400, at least or exactly or at most 500, at least or exactly or at most 600, at least or exactly or at most 700, at least or exactly or at most 800, at least or exactly or at most 900, at least or exactly or at most 1000, at least or exactly or at most 1500, at least or exactly or at most 2000, at least or exactly or at most 2500, at least or exactly or at most 3000, at least or exactly or at most 3500, and at least or exactly or at most 4000 nucleotides from those of SEQ ID NOs: 31-90 that encompass fragments of such lengths.

Particularly preferred nucleic acid fragments (DNA or RNA) are those fragments of any one of SEQ ID NOs 31-90, which encode a polypeptide of the present invention discussed supra.

The nucleic acid fragment of the invention discussed above typically has a sequence identity with the nucleotide sequence defined for i) or ii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The nucleic acid fragment of the invention discussed above may also have a sequence identity with the nucleotide sequence defined for iii) above, which is at least 65%, such as at least 70%, at least 75%, at least 80%, at least 85%, at least 90%, at least 91%, at least 92%, at least 93%, at least 94%, at least 95%, at least 96%, at least 97%, at least 98%, and at least 99%.

The Vectors of the Invention

Vectors of the invention fall into several categories discussed infra. One preferred vector of the invention comprises in operable linkage and in the 5'-3' direction, an expression control region comprising an enhancer/promoter for driving expression of the nucleic acid fragment defined for option i) above, optionally a signal peptide coding sequence, a nucleotide sequence defined for option i), and optionally a terminator. Hence, such a vector constitutes an expression vector useful for effecting production in cells of the polypeptide of the invention. Since the polypeptides of the invention are bacterial of origin, recombinant production is conveniently effected in bacterial host cells, so here it is preferred that the expression control region drives expression in prokaryotic cell such as a bacterium, e.g. in E coll. However, if the vector is to drive expression in mammalian cell (as would be the case for a DNA vaccine vector), the expression control region should be adapted to this particular use.

At any rate, certain vectors of the invention are capable of autonomous replication.

Also, the vector of the invention may be one that is capable of being integrated into the genome of a host cell—this is particularly useful if the vector is use in the production of stably transformed cells, where the progeny will also include the genetic information introduced via the vector. Alternatively, vectors incapable of being integrated into the genome of a mammalian host cell are useful in e.g. DNA vaccination.

Typically, the vector of the invention is selected from the group consisting of a virus, such as a attenuated virus (which may in itself be useful as a vaccine agent), a bacteriophage, a plasmid, a minichromosome, and a cosmid.

A more detailed discussion of vectors of the invention is provided in the following:

Polypeptides of the invention may be encoded by a nucleic acid molecule comprised in a vector. A nucleic acid sequence can be "heterologous," which means that it is in a context foreign to the cell in which the vector is being introduced, which includes a sequence homologous to a sequence in the cell but in a position within the host cell where it is ordinarily not found. Vectors include naked DNAs, RNAs, plasmids, cosmids, viruses (bacteriophage, animal viruses, and plant viruses), and artificial chromosomes (e.g., YACs). One of skill in the art would be well equipped to construct a vector through standard recombinant techniques (for example Sambrook et al, 2001; Ausubel et al, 1996, both incorporated herein by reference). In addition to encoding the polypeptides of this invention, a vector of the present invention may encode polypeptide sequences such as a tag or immunogenicity enhancing peptide (e.g. an immunogenic carrier or a fusion partner that stimulates the immune system, such as a cytokine or active fragment thereof). Useful vectors encoding such fusion proteins include pIN vectors (Inouye et al, 1985), vectors encoding a stretch of histidines, and pGEX vectors, for use in generating glutathione S-transferase (GST) soluble fusion proteins for later purification and separation or cleavage.

Vectors of the invention may be used in a host cell to produce a polypeptide of the invention that may subsequently be purified for administration to a subject or the vector may be purified for direct administration to a subject for expression of the protein in the subject (as is the case when administering a nucleic acid vaccine).

Expression vectors can contain a variety of "control sequences," which refer to nucleic acid sequences necessary for the transcription and possibly translation of an operably linked coding sequence in a particular host organism. In addition to control sequences that govern transcription and translation, vectors and expression vectors may contain nucleic acid sequences that serve other functions as well and are described infra.

1. Promoters and Enhancers

A "promoter" is a control sequence. The promoter is typically a region of a nucleic acid sequence at which initiation and rate of transcription are controlled. It may contain genetic elements at which regulatory proteins and molecules may bind such as RNA polymerase and other transcription factors. The phrases "operatively positioned," "operatively linked," "under control," and "under transcriptional control" mean that a promoter is in a correct functional location and/or orientation in relation to a nucleic acid sequence to control transcriptional initiation and expression of that sequence. A promoter may or may not be used in conjunction with an "enhancer," which refers to a cis-acting regulatory sequence involved in the transcriptional activation of a nucleic acid sequence.

A promoter may be one naturally associated with a gene or sequence, as may be obtained by isolating the 5' non-coding sequences located upstream of the coding segment or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural state. Such promoters or enhancers may include promoters or enhancers of other genes, and promoters or enhancers isolated from any other prokaryotic, viral, or eukaryotic cell, and promoters or enhancers not "naturally occurring," i.e., containing different elements of different transcriptional regulatory regions, and/or mutations that alter expression. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202, 5,928,906, each incorporated herein by reference).

Naturally, it may be important to employ a promoter and/or enhancer that effectively direct(s) the expression of the DNA segment in the cell type or organism chosen for expression. Those of skill in the art of molecular biology generally know the use of promoters, enhancers, and cell type combinations for protein expression (see Sambrook et al, 2001, incorporated herein by reference). The promoters employed may be constitutive, tissue-specific, or inducible and in certain embodiments may direct high level expression of the introduced DNA segment under specified conditions, such as large-scale production of recombinant proteins or peptides.

Examples of inducible elements, which are regions of a nucleic acid sequence that can be activated in response to a specific stimulus, include but are not limited to Immunoglobulin Heavy Chain (Banerji et al, 1983; Gilles et al, 1983; Grosschedl et al, 1985; Atchinson et al, 1986, 1987; toiler et al, 1987; Weinberger et al, 1984; Kiledjian et al, 1988; Porton et al; 1990), Immunoglobulin Light Chain (Queen et al, 1983; Picard et al, 1984), T Cell Receptor (Luria et al, 1987; Winoto et al, 1989; Redondo et al; 1990), HLA DQα and/or DQβ (Sullivan et al, 1987), 13-Interferon (Goodbourn et al, 1986; Fujita et al, 1987; Goodbourn et al, 1988), Interleukin-2 (Greene et al, 1989), Interleukin-2 Receptor (Greene et al, 1989; Lin et al, 1990), MHC Class II 5 (Koch et al, 1989), MHC Class II HLA-DRα (Sherman et al, 1989), β-Actin (Kawamoto et al, 1988; Ng et al; 1989), Muscle Creatine Kinase (MCK) (Jaynes et al, 1988; Horlick et al, 1989; Johnson et al, 1989), Prealbumin (Transthyretin) (Costa et al, 1988), Elastase I (Omitz et al, 1987), Metallothionein (MTII) (Karin et al, 1987; Culotta et al, 1989), Collagenase (Pinkert et al, 1987; Angel et al, 1987), Albumin (Pinkert et al, 1987; Tranche et al, 1989, 1990), α-Fetoprotein (Godbout et al, 1988; Campere et al, 1989), γ-Globin (Bodine et al, 1987; Perez-Stable et al, 1990), β-Globin (Trudel et al, 1987), c-fos (Cohen et al, 1987), c-HA-ras (Triesman, 1986; Deschamps et al, 1985), Insulin (Edlund et al, 1985), Neural Cell Adhesion Molecule (NCAM) (Hirsh et al, 1990), αl-Antitrypain (Larimer et al, 1990), H2B (TH2B) Histone (Hwang et al, 1990), Mouse and/or Type I Collagen (Ripe et al, 1989), Glucose-Regulated Proteins (GRP94 and GRP78) (Chang et al, 1989), Rat Growth Hormone (Larsen et al, 1986), Human Serum Amyloid A (SAA) (Edbrooke et al, 1989), Troponin I (TN I) (Yutzey et al, 1989), Platelet-Derived Growth Factor (PDGF) (Pech et al, 1989), Duchenne Muscular Dystrophy (Klamut et al, 1990), SV40 (Banerji et al, 1981; Moreau et al, 1981; Sleigh et al, 1985; Firak et al, 1986; Herr et al, 1986; Imbra et al, 1986; Kadesch et al, 1986; Wang et al, 1986; Ondek et al, 1987; Kuhl et al, 1987; Schaffner et al, 1988), Polyoma (Swartzendruber et al, 1975; Vasseur et al, 1980; Katinka et al, 1980, 1981; Tyndell et al, 1981; Dandolo et al, 1983; de Villiers et al, 1984; Hen et al, 1986; Satake et al, 1988; Campbell et al, 1988), Retroviruses (Kriegler et al, 1982, 1983; Levinson et al, 1982; Kriegler et al, 1983, 1984a, b, 1988; Bosze et al, 1986; Miksicek et al, 1986; Celander et al, 1987; Thiesen et al, 1988; Celander et al, 1988; Choi et al, 1988; Reisman et al, 1989), Papilloma Virus (Campo et al, 1983; Lusky et al, 1983; Spandidos and Wilkie, 1983; Spalholz et al, 1985; Lusky et al, 1986; Cripe et al, 1987; Gloss et al, 1987; Hirochika et al, 1987; Stephens et al, 1987), Hepatitis B Virus (Bulla et al, 1986; Jameel et al, 1986; Shaul et al, 1987; Spandau et al, 1988; Vannice et al, 1988), Human Immunodeficiency Virus (Muesing et al, 1987; Hauber et al, 1988; Jakobovits et al, 1988; Feng et al, 1988; Takebe et al, 1988; Rosen et al, 1988; Berkhout et al, 1989; Laspia et al, 1989; Sharp et al, 1989; Braddock et al, 1989), Cytomegalovirus (CMV) IE (Weber et al, 1984; Boshart et al, 1985; Foecking et al, 1986), Gibbon Ape Leukemia Virus (Holbrook et al, 1987; Quinn et al, 1989).

Inducible Elements include, but are not limited to MT II—Phorbol Ester (TFA)/Heavy metals (Palmiter et al, 1982; Haslinger et al, 1985; Searle et al, 1985; Stuart et al, 1985; Imagawa et al, 1987, Karin et al, 1987; Angel et al, 1987b; McNeall et al, 1989); MMTV (mouse mammary tumor virus)—Glucocorticoids (Huang et al, 1981; Lee et al, 1981; Majors et al, 1983; Chandler et al, 1983; Lee et al, 1984; Ponta et al, 1985; Sakai et al, 1988); β-Interferon—poly(rl) x/poly(rc) (Tavernier et al, 1983); Adenovirus 5 E2—EIA (Imperiale et al, 1984); Collagenase—Phorbol Ester (TPA) (Angel et al, 1987a); Stromelysin—Phorbol Ester (TPA) (Angel et al, 1987b); SV40—Phorbol Ester (TPA) (Angel et al, 1987b); Murine MX Gene—Interferon, Newcastle Disease Virus (Hug et al, 1988); GRP78 Gene—A23187 (Resendez et al, 1988); α-2-Macroglobulin—IL-6 (Kunz et al, 1989); Vimentin—Serum (Rittling et al, 1989); MHC Class I Gene H-2κb—Interferon (Blanar et al, 1989); HSP70—E1A/SV40 Large T Antigen (Taylor et al, 1989, 1990a, 1990b); Proliferin—Phorbol Ester/TPA (Mordacq et al, 1989); Tumor Necrosis Factor—PMA (Hensel et al, 1989); and Thyroid Stimulating Hormonea Gene—Thyroid Hormone (Chatterjee et al, 1989).

Also contemplated as useful in the present invention are the dectin-1 and dectin-2 promoters. Additionally any promoter/enhancer combination (as per the Eukaryotic Promoter Data Base EPDB) could also be used to drive expression of structural genes encoding oligosaccharide processing enzymes, protein folding accessory proteins, selectable marker proteins or a heterologous protein of interest.

The particular promoter that is employed to control the expression of peptide or protein encoding polynucleotide of the invention is not believed to be critical, so long as it is capable of expressing the polynucleotide in a targeted cell, preferably a bacterial cell. Where a human cell is targeted, it is preferable to position the polynucleotide coding region adjacent to and under the control of a promoter that is capable of being expressed in a human cell. Generally speaking, such a promoter might include either a bacterial, human or viral promoter.

In various embodiments, the human cytomegalovirus (CMV) immediate early gene promoter, the SV40 early promoter, and the Rous sarcoma virus long terminal repeat can be used to obtain high level expression of a related polynucleotide to this invention. The use of other viral or mammalian cellular or bacterial phage promoters, which are well known in the art, to achieve expression of polynucleotides is contemplated as well.

In embodiments in which a vector is administered to a subject for expression of the protein, it is contemplated that a desirable promoter for use with the vector is one that is not down-regulated by cytokines or one that is strong enough that even if down-regulated, it produces an effective amount of the protein/polypeptide of the current invention in a subject to elicit an immune response. Non-limiting examples of these are CMV IE and RSV LTR. In other embodiments, a promoter that is up-regulated in the presence of cytokines is employed. The MHC I promoter increases expression in the presence of IFN-γ.

Tissue specific promoters can be used, particularly if expression is in cells in which expression of an antigen is desirable, such as dendritic cells or macrophages. The mammalian MHC I and MHC II promoters are examples of such tissue-specific promoters. 2. Initiation Signals and Internal Ribosome Binding Sites (IRES)

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic and may be operable in bacteria or mammalian cells. The efficiency of expression may be enhanced by the inclusion of appropriate transcription enhancer elements.

In certain embodiments of the invention, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, herein incorporated by reference).

2. Multiple Cloning Sites

Vectors can include a multiple cloning site (MCS), which is a nucleic acid region that contains multiple restriction enzyme sites, any of which can be used in conjunction with standard recombinant technology to digest the vector. (See Carbonelli et al, 1999, Levenson et al, 1998, and Cocea, 1997, incorporated herein by reference.) Frequently, a vector is linearized or fragmented using a restriction enzyme that cuts within the MCS to enable exogenous sequences to be ligated to the vector. Techniques involving restriction enzymes and ligation reactions are well known to those of skill in the art of recombinant technology.

3. Splicing Sites

Most transcribed eukaryotic RNA molecules will undergo RNA splicing to remove introns from the primary transcripts. If relevant in the context of vectors of the present invention, vectors containing genomic eukaryotic sequences may require donor and/or acceptor splicing sites to ensure proper processing of the transcript for protein expression. (See Chandler et al, 1997, incorporated herein by reference.)

4. Termination Signals

The vectors or constructs of the present invention will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (poly A) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message.

Terminators contemplated for use in the invention include any known terminator of transcription described herein or known to one of ordinary skill in the art, including but not limited to, for example, the bovine growth hormone terminator or viral termination sequences, such as the SV40 terminator. In certain embodiments, the termination signal may be a lack of transcribable or translatable sequence, such as due to a sequence truncation.

5. Polyadenylation Signals

In expression, particularly eukaryotic expression (as is relevant in nucleic acid vaccination), one will typically include a polyadenylation signal to effect proper polyadenylation of the transcript. The nature of the polyadenylation signal is not believed to be crucial to the successful practice of the invention, and/or any such sequence may be employed. Preferred embodiments include the SV40 polyadenylation signal and/or the bovine growth hormone polyadenylation signal, convenient and/or known to function well in various target cells.

Polyadenylation may increase the stability of the transcript or may facilitate cytoplasmic transport.

6. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

7. Selectable and Screenable Markers

In certain embodiments of the invention, cells containing a nucleic acid construct of the present invention may be identified in vitro or in vivo by encoding a screenable or selectable marker in the expression vector. When transcribed and translated, a marker confers an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, markers that confer resistance to neomycin, puromycin, hygromycin, DHFR, GPT, zeocin or histidinol are useful selectable markers. In addition to markers conferring a phenotype that allows for the discrimination of transformants based on the implementation of conditions, other types of markers including screenable markers such as GFP for colorimetric analysis. Alternatively, screenable enzymes such as herpes simplex virus thymidine kinase (tk) or chloramphenicol acetyltransferase (CAT) may be utilized. One of skill in the art would also know how to employ immunologic markers that can be used in conjunction with FACS analysis. The marker used is not believed to be important, so long as it is capable of being expressed simultaneously with the nucleic acid encoding a protein of the invention. Further examples of selectable and screenable markers are well known to one of skill in the art.

The Transformed Cells of the Invention

Transformed cells of the invention are useful as organisms for producing the polypeptide of the invention, but also as simple "containers" of nucleic acids and vectors of the invention.

Certain transformed cells of the invention are capable of replicating the nucleic acid fragment defined for option i) of the second aspect of the invention. Preferred transformed cells of the invention are capable of expressing the nucleic acid fragment defined for option i).

For recombinant production it is convenient, but not a prerequisite that the transformed cell according is prokaryotic, such as a bacterium, but generally both prokaryotic cells and eukaryotic cells may be used.

Suitable prokaryotic cells are bacterial cells selected from the group consisting of *Escherichia* (such as *E. coli.*), *Bacillus* [e.g. *Bacillus subtilis*], *Salmonella*, and *Mycobacterium* [preferably non-pathogenic, e.g. *M. bovis* BCG].

Eukaryotic cells can be in the form of yeasts (such as *Saccharomyces cerevisiae*) and protozoans. Alternatively, the transformed eukaryotic cells are derived from a multicellular organism such as a fungus, an insect cell, a plant cell, or a mammalian cell.

For production purposes, it is advantageous that the transformed cell of the invention is stably transformed by having the nucleic acid defined above for option i) stably integrated into its genome, and in certain embodiments it is also preferred that the transformed cell secretes or carries on its surface the polypeptide of the invention, since this facilitates recovery of the polypeptides produced. A particular version of this embodiment is one where the transformed cell is a bacterium and secretion of the polypeptide of the invention is into the periplasmic space.

As noted above, stably transformed cells are preferred—these i.a. allows that cell lines comprised of transformed cells as defined herein may be established—such cell lines are particularly preferred aspects of the invention.

Further details on cells and cell lines are presented in the following:

Suitable cells for recombinant nucleic acid expression of the nucleic acid fragments of the present invention are prokaryotes and eukaryotes. Examples of prokaryotic cells include *E. coli*; members of the *Staphylococcus* genus, such as *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *Pseudomonas fluorescens*. Examples of eukaryotic cells include mammalian cells; insect cells; yeast cells such as members of the *Saccharomyces* genus (e.g. *S. cerevisiae*), members of the *Pichia* genus (e.g. *P. pastoris*), members of the *Hansenula* genus (e.g. *H. polymorpha*), members of the *Kluyveromyces* genus (e.g. *K. lactis* or *K. fragilis*) and members of the *Schizosaccharomyces* genus (e.g. *S. pombe*).

Techniques for recombinant gene production, introduction into a cell, and recombinant gene expression are well known in the art. Examples of such techniques are provided in references such as Ausubel, Current Protocols in Molecular Biology, John Wiley, 1987-2002, and Sambrook et al., Molecular Cloning, A Laboratory Manual, 2 nd Edition, Cold Spring Harbor Laboratory Press, 1989.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector or expressing a heterologous gene encoded by a vector. A host cell can, and has been, used as a recipient for vectors or viruses. A host cell may be "transfected" or "transformed," which refers to a process by which exogenous nucleic acid, such as a recombinant protein-encoding sequence, is transferred or introduced into the host cell. A transformed cell includes the primary subject cell and its progeny.

Host cells may be derived from prokaryotes or eukaryotes, including bacteria, yeast cells, insect cells, and mammalian cells for replication of the vector or expression of part or all of the nucleic acid sequence(s). Numerous cell lines and cultures are available for use as a host cell, and they can be obtained through the American Type Culture Collection (ATCC), which is an organization that serves as an archive for living cultures and genetic materials (www.atcc.org) or from other depository institutions such as Deutsche Sammlung vor Micrroorganismen and Zellkulturen (DSM). An appropriate host can be determined by one of skill in the art based on the vector backbone and the desired result. A plasmid or cosmid, for example, can be introduced into a prokaryote host cell for replication of many vectors or expression of encoded proteins. Bacterial cells used as host cells for vector replication and/or expression include *Staphylococcus* strains, DH5a, JMI 09, and KCB, as well as a number of commercially available bacterial hosts such as SURE® Competent Cells and SOLOP ACK™ Gold Cells (STRATAGENE®, La Jolla, CA). Alternatively, bacterial cells such as *E. coli* LE392 could be used as host cells for phage viruses. Appropriate yeast cells include *Saccharomyces cerevisiae, Saccharomyces pombe*, and *Pichia pastoris*.

Examples of eukaryotic host cells for replication and/or expression of a vector include HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ Baculovirus expression system from CLONTECH®

In addition to the disclosed expression systems of the invention, other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

Amplification of Nucleic Acids

Nucleic acids used as a template for amplification may be isolated from cells, tissues or other samples according to standard methodologies (Sambrook et al, 2001). In certain embodiments, analysis is performed on whole cell or tissue homogenates or biological fluid samples without substantial purification of the template nucleic acid. The nucleic acid may be genomic DNA or fractionated or whole cell RNA. Where RNA is used, it may be desired to first convert the RNA to a complementary DNA.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

Pairs of primers designed to selectively hybridize to nucleic acids corresponding to sequences of genes identified herein are contacted with the template nucleic acid under conditions that permit selective hybridization. Depending upon the desired application, high stringency hybridization conditions may be selected that will only allow hybridization to sequences that are completely complementary to the primers. In other embodiments, hybridization may occur under reduced stringency to allow for amplification of nucleic acids containing one or more mismatches with the primer sequences. Once hybridized, the template-primer complex is contacted with one or more enzymes that facilitate template-dependent nucleic acid synthesis. Multiple rounds of amplification, also referred to as "cycles," are conducted until a sufficient amount of amplification product is produced.

The amplification product may be detected or quantified. In certain applications, the detection may be performed by visual means. Alternatively, the detection may involve indirect identification of the product via chemiluminescence, radioactive scintigraphy of incorporated radiolabel or fluorescent label or even via a system using electrical and/or thermal impulse signals (Bellus, 1994).

A number of template dependent processes are available to amplify the oligonucleotide sequences present in a given template sample. One of the best known amplification methods is the polymerase chain reaction (referred to as PCR™) which is described in detail in U.S. Pat. Nos.

4,683,195, 4,683,202 and 4,800,159, and in Innis et al., 1988, each of which is incorporated herein by reference in their entirety.

Alternative methods for amplification of target nucleic acid sequences that may be used in the practice of the present invention are disclosed in U.S. Pat. Nos. 5,843,650, 5,846,709, 5,846,783, 5,849,546, 5,849,497, 5,849,547, 5,858,652, 5,866,366, 5,916,776, 5,922,574, 5,928,905, 5,928,906, 5,932,451, 5,935,825, 5,939,291 and 5,942,391, GB Application No. 2 202 328, and in PCT Application No. PCT/US89/01025, each of which is incorporated herein by reference in its entirety.

Methods of Gene Transfer

Suitable methods for nucleic acid delivery to effect expression of compositions of the present invention are believed to include virtually any method by which a nucleic acid (e.g., DNA, including viral and nonviral vectors) can be introduced into a cell, a tissue or an organism, as described herein or as would be known to one of ordinary skill in the art. Such methods include, but are not limited to, direct delivery of DNA such as by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference); by calcium phosphate precipitation (Graham and Van Der Eb, 1973; Chen and Okayama, 1987; Rippe et al., 1990); by using DEAE dextran followed by polyethylene glycol (Gopal, 1985); by direct sonic loading (Fechheimer et al, 1987); by liposome mediated transfection (Nicolau and Sene, 1982; Fraley et al, 1979; Nicolau et al, 1987; Wong et al, 1980; Kaneda et al, 1989; Kato et al, 1991); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al, 1990; U.S. Pat. Nos. 5,302,523 and 5,464,765, each incorporated herein by reference); by *Agrobacterium* mediated transformation (U.S. Pat. Nos. 5,591,616 and 5,563,055, each incorporated herein by reference); or by PEG mediated transformation of protoplasts (Omirulleh et al, 1993; U.S. Pat. Nos. 4,684,611 and 4,952,500, each incorporated herein by reference); by desiccation/inhibition mediated DNA uptake (Potrykus et al, 1985). Through the application of techniques such as these, organelle(s), cell(s), tissue(s) or organism(s) may be stably or transiently transformed.

The Antibodies of the Invention—and their Production/Isolation

Antibodies directed against the proteins of the invention are useful for affinity chromatography, immunoassays, and for distinguishing/identifying *staphylococcus* proteins as well as for passive immunisation and therapy.

Antibodies to the proteins of the invention, both polyclonal and monoclonal, may be prepared by conventional methods. In general, the protein is first used to immunize a suitable animal, preferably a mouse, rat, rabbit or goat. Rabbits and goats are preferred for the preparation of polyclonal sera due to the volume of serum obtainable, and the availability of labeled anti-rabbit and anti-goat antibodies. Immunization is generally performed by mixing or emulsifying the protein in saline, preferably in an adjuvant such as Freund's complete adjuvant, and injecting the mixture or emulsion parenterally (generally subcutaneously or intramuscularly). A dose of 50-200 μg/injection is typically sufficient. Immunization is generally boosted 2-6 weeks later with one or more injections of the protein in saline, preferably using Freund's incomplete adjuvant. One may alternatively generate antibodies by in vitro immunization using methods known in the art, which for the purposes of this invention is considered equivalent to in vivo immunization. Polyclonal antiserum is obtained by bleeding the immunized animal into a glass or plastic container, incubating the blood at 25 C for one hour, followed by incubating at 4 C for 2-18 hours. The serum is recovered by centrifugation (eg. 1,000 g for 10 minutes). About 20-50 ml per bleed may be obtained from rabbits.

Monoclonal antibodies are prepared using the standard method of Kohler & Milstein [*Nature* (1975) 256: 495-96], or a modification thereof. Typically, a mouse or rat is immunized as described above. However, rather than bleeding the animal to extract serum, the spleen (and optionally several large lymph nodes) is removed and dissociated into single cells. If desired, the spleen cells may be screened (after removal of nonspecifically adherent cells) by applying a cell suspension to a plate or well coated with the protein antigen. B-cells expressing membrane-bound immunoglobulin specific for the antigen bind to the plate, and are not rinsed away with the rest of the suspension. Resulting B-cells, or all dissociated spleen cells, are then induced to fuse with myeloma cells to form hybridomas, and are cultured in a selective I aedium (elg. hypexanthine, aminopterin, thymidine medium, "HAT"). The resulting hybridomas are plated by limiting dilution, and are assayed for production of antibodies, which bind specifically to the immunizing antigen (and which do not bind to unrelated antigens). The selected MAb-secreting hybridomas are then cultured either in vitro (eg. in tissue culture bottles or hollow fiber reactors), or in vivo (as ascites in mice).

If desired, the antibodies (whether polyclonal or monoclonal) may be labeled using conventional techniques. Suitable labels include fluorophores, chromophores, radioactive atoms (particularly $32p$ and $125I$), electron-dense reagents, enzymes, and ligands having specific binding partners. Enzymes are typically detected by their activity. For example, horseradish peroxidase is usually detected by its ability to convert 3,3',5,5'-tetramethylbenzidine (TMB) to a blue pigment, quantifiable with a spectrophotometer. "Specific binding partner" refers to a protein capable of binding a ligand molecule with high specificity, as for example in the case of an antigen and a monoclonal antibody specific therefor. Other specific binding partners include biotin and avidin or streptavidin, IgG and protein A, and the numerous receptor-ligand couples known in the art. It should be understood that the above description is not meant to categorize the various labels into distinct classes, as the same label may serve in several different modes. For example, $115I$ may serve as a radioactive label or as an electron-dense reagent. HRP may serve as enzyme or as antigen for a MAb. Further, one may combine various labels for desired effect. For example, MAbs and avidin also require labels in the practice of this invention: thus, one might label a MAb with biotin, and detect its presence with avidin labeled with, $125I$, or with an anti-biotin MAb labeled with HRP. Other permutations and possibilities will be readily apparent to those of ordinary skill in the art, and are considered as equivalents within the scope of the instant invention.

According to the invention, the isolated monoclonal antibody or antibody analogue is preferably a monoclonal antibody selected from a multi-domain antibody such as a murine antibody, a chimeric antibody such as a humanized antibody, a fully human antibody, and single-domain antibody of a llama or a camel, or which is an antibody analogue selected from a fragment of an antibody such as an Fab or an F(ab')$_2$, an scFV; cf. also the definition of the term "antibody" presented above.

Compositions of the Invention; Vaccines

Pharmaceutical compositions, in particular vaccines, according to the invention may either be prophylactic (ie. to prevent infection) or therapeutic (ie, to treat disease after infection).

Such vaccines comprise immunising antigen(s), immunogen(s), polypeptide(s), protein(s) or nucleic acid(s), usually in combination with "pharmaceutically acceptable carriers", which include any carrier that does not itself induce the production of antibodies harmful to the individual receiving the composition. Suitable carriers are typically large, slowly metabolized macromolecules such as proteins, polysaccharides, polylactic acids, polyglycolic acids, polymeric amino acids, amino acid copolymers, lipid aggregates (such as oil droplets or liposomes), and inactive virus particles.

Such carriers are well known to those of ordinary skill in the art. Additionally, these carriers may function as immunostimulating agents ("adjuvants"). Furthermore, the antigen or immunogen may be conjugated to a bacterial toxoid, such as a toxoid from diphtheria, tetanus, cholera, H. pylori, etc. pathogen, cf. the description of immunogenic carriers supra.

The pharmaceutical compositions of the invention thus typically contain an immunological adjuvant, which is commonly an aluminium based adjuvant or one of the other adjuvants described in the following:

Preferred adjuvants to enhance effectiveness of the composition include, but are not limited to: (1) aluminum salts (alum), such as aluminum hydroxide, aluminum phosphate, aluminum sulfate, etc; (2) oil-in-water emulsion formulations (with or without other specific immunostimulating agents such as muramyl peptides (see below) or bacterial cell wall components), such as for example (a) MF59 (WO 90/14837; Chapter 10 in Vaccine design: the subunit and adjuvant approach, eds. Powell & Newman, Plenum Press 1995), containing 5% Squalene, 0.5% Tween 80, and 0.5% Span 85 (optionally containing various amounts of MTP-PE (see below), although not required) formulated into submicron particles using a microfluidizer such as Model 110Y microfluidizer (Microfluidics, Newton, MA), (b) SAF, containing 10% Squalane, 0.4% Tween 80, 5% pluronic-blocked polymer L121, and thr-MDP (see below) either microfluidized into a submicron emulsion or vortexed to generate a larger particle size emulsion, and (c) Ribi adjuvant system (RAS), (Ribi Immunochem, Hamilton, MT) containing 2% Squalene, 0.2% Tween 80, and one or more bacterial cell wall components from the group consisting of monophosphoryl lipid A (MPL), trehalose dimycolate (TDM), and cell wall skeleton (CWS), preferably MPL+CWS (Detox™); (3) saponin adjuvants such as Stimulon™ (Cambridge Bioscience, Worcester, MA) may be used or particles generated therefrom such as ISCOMs (immunostimulating complexes); (4) Complete Freund's Adjuvant (CFA) and Incomplete Freund's Adjuvant (IFA); (5) cytokines, such as interleukins (eg. IL-1, IL-2, IL-4, IL-5, IL-6, IL-7, IL-12, etc.), interferons (eg. gamma interferon), macrophage colony stimulating factor (M-CSF), tumor necrosis factor (TNF), etc.; and (6) other substances that act as immunostimulating agents to enhance the effectiveness of the composition. Alum and MF59™ adjuvants are preferred.

As mentioned above, muramyl peptides include, but are not limited to, N-acetyl-muramyl-L-threonyl-D-isoglutamine (thr-MDP), N-acetyl-normuramyl-L-alanyl-D-isogluta-tamine (nor-MDP), N-acetylmuramyl-L-alanyl-D-isoglutaminyl-L-alanine-2"-2'-dipalmitoyl-sn-glycero-3-hydroxyphosphoryloxy)-ethylamine (MTP-PE), etc.

The immunogenic compositions (eg. the immunising antigen or immunogen or polypeptide or protein or nucleic acid, pharmaceutically acceptable carrier, and adjuvant) typically will contain diluents, such as water, saline, glycerol, ethanol, etc. Additionally, auxiliary substances, such as wetting or emulsifying agents, pH buffering substances, and the like, may be present in such vehicles.

Typically, the immunogenic compositions are prepared as injectables, either as liquid solutions or suspensions; solid forms suitable for solution in, or suspension in, liquid vehicles prior to injection may also be prepared. The preparation also may be emulsified or encapsulated in liposomes for enhanced adjuvant effect, as discussed above under pharmaceutically acceptable carriers.

Immunogenic compositions used as vaccines comprise an immunologically effective amount of the antigenic or immunogenic polypeptides, as well as any other of the above-mentioned components, as needed. By "immunologically effective amount", it is meant that the administration of that amount to an individual, either in a single dose or as part of a series, is effective for treatment or prevention. This amount varies depending upon the health and physical condition of the individual to be treated, the taxonomic group of individual to be treated (eg. nonhuman primate, primate, etc.), the capacity of the individual's immune system to synthesize antibodies or generally mount an immune response, the degree of protection desired, the formulation of the vaccine, the treating doctor's assessment of the medical situation, and other relevant factors. It is expected that the amount will fall in a relatively broad range that can be determined through routine trials. However, for the purposes of protein vaccination, the amount administered per immunization is typically in the range between 0.5 µg and 500 mg (however, often not higher than 5,000 µg), and very often in the range between 10 and 200 µg.

The immunogenic compositions are conventionally administered parenterally, eg, by injection, either subcutaneously, intramuscularly, or transdermally/transcutaneously (eg. WO 98/20734). Additional formulations suitable for other modes of administration include oral and pulmonary formulations, suppositories, and transdermal applications. In the case of nucleic acid vaccination, also the intravenous or intraarterial routes may be applicable.

Dosage treatment may be a single dose schedule or a multiple dose schedule. The vaccine may be administered in conjunction with other immunoregulatory agents.

As an alternative to protein-based vaccines, DNA vaccination (also termed nucleic acid vaccination or gene vaccination) may be used [eg. Robinson & Torres (1997) Seminars in Immunol 9: 271-283; Donnelly et al. (1997) Annu Rev Immunol 15: 617-648; later herein].

A further aspect of the invention is the recognition that combination vaccines can be provided, wherein 2 or more antigens disclosed herein are combined to enhance the immune response by the vaccinated animal, including to optimize initial immune response and duration of immunity. For the purposes of this aspect of the invention, multiple antigenic fragments derived from the same, longer protein can also be used, such as the use a combination of different lengths of polypeptide sequence fragments from one protein.

Thus, embodiments of the invention relate to a composition (or the use as a vaccine of) comprising 2 distinct (i.e. non-identical) proteinaceaous immunogens disclosed herein wherein the first of said immunogens is SEQ ID NO: 1 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 2 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 3 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 4 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 5 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 6 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 7 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 8 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 9 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 10 or a variant or fragment thereof disclosed herein in combination with a proteinaceous immunogen selected from any one of SEQ 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 11 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 12 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 13 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 14 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 15 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 16 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 17 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 18 or a variant or fragment thereof disclosed herein in combination with a proteinaceous immunogen selected from any one of SEQ NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 19 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 20 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 21 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 22 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 23 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 24 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 25 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 26 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 27 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 28 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 29 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Thus, embodiments of the invention relate to a composition (or the use as a vaccine of) comprising 2 distinct (i.e. non-identical) proteinaceous immunogens disclosed herein wherein the first of said immunogens is SEQ ID NO: 30 or a variant or fragment thereof disclosed herein in combination with a proteinaceous immunogen selected from any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30, or a variant or fragment disclosed herein of any one of SEQ ID NOs: 1, 2, 3, 4, 5, 6, 7, 8, 9, 10, 11, 12, 13, 14, 15, 16, 17, 18, 19, 20, 21, 22, 23, 24, 25, 26, 27, 28, 29, and 30.

Treatment Methods of the Invention

The method of the sixth aspect of the invention generally relates to induction of immunity and as such also entails method that relate to treatment, prophylaxis and amelioration of disease.

When immunization methods entail that a polypeptide of the invention or a composition comprising such a polypeptide is administered the animal (e.g. the human) typically receives between 0.5 and 5,000 µg of the polypeptide of the invention per administration.

In preferred embodiments of the sixth aspect, the immunization scheme includes that the animal (e.g. the human) receives a priming administration and one or more booster administrations.

Preferred embodiments of the $6^{th}$ aspect of the invention comprise that the administration is for the purpose of inducing protective immunity against *A. baumannii*. In this embodiment it is particularly preferred that the protective immunity is effective in reducing the risk of attracting infection with *A. baumannii* or is effective in treating or ameliorating infection with *A. baumannii*.

As mentioned herein, the preferred vaccines of the invention induce humoral immunity, so it is preferred that the administration is for the purpose of inducing antibodies specific for *A. baumannii* and wherein said antibodies or B-lymphocytes producing said antibodies are subsequently recovered from the animal.

But, as also mentioned the method of the $6^{th}$ aspect may also be useful in antibody production, so in other embodiments the administration is for the purpose of inducing antibodies specific for *A. baumannii* and wherein B-lymphocytes producing said antibodies are subsequently recovered from the animal and used for preparation of monoclonal antibodies.

Pharmaceutical compositions can as mentioned above comprise polypeptides, antibodies, or nucleic acids of the invention. The pharmaceutical compositions will comprise a therapeutically effective amount thereof.

The term "therapeutically effective amount" or "prophylactically effective amount" as used herein refers to an amount of a therapeutic agent to treat, ameliorate, or prevent a desired disease or condition, or to exhibit a detectable therapeutic or preventative effect. The effect can be detected by, for example, chemical markers or antigen levels. Therapeutic effects also include reduction in physical symptoms, such as decreased body temperature. The precise effective amount for a subject will depend upon the subject's size and health, the nature and extent of the condition, and the therapeutics or combination of therapeutics selected for administration. Thus, it is not useful to specify an exact effective amount in advance. Reference is however made to the ranges for dosages of immunologically effective amounts of polypeptides, cf. above.

However, the effective amount for a given situation can be determined by routine experimentation and is within the judgement of the clinician.

For purposes of the present invention, an effective dose will be from about 0.01 mg/kg to 50 mg/kg or 0.05 mg/kg to about 10 mg/kg of the DNA or RNA constructs in the individual to which it is administered.

A pharmaceutical composition can also contain a pharmaceutically acceptable carrier. The term "pharmaceutically acceptable carrier" refers to a carrier for administration of a therapeutic agent, such as antibodies or a polypeptide, genes, and other therapeutic agents. The term refers to any pharmaceutical carrier that does not itself induce the production of antibodies harmful to the individual receiving the composition, and which may be administered without undue toxicity. Suitable carriers may be large, slowly metabolized macromolecules such as proteins, polysaccharides, polylactic acids, polyglycolic acids, polymeric amino acids, amino acid copolymers, and inactive virus particles. Such carriers are well known to those of ordinary skill in the art.

Pharmaceutically acceptable salts can be used therein, for example, mineral acid salts such as hydrochlorides, hydrobromides, phosphates, sulfates, and the like; and the salts of organic acids such as acetates, propionates, malonates, benzoates, and the like. A thorough discussion of pharmaceutically acceptable excipients is available in Remington's Pharmaceutical Sciences (Mack Pub. Co., N. J. 1991).

Pharmaceutically acceptable carriers in therapeutic compositions may contain liquids such as water, saline, glycerol and ethanol. Additionally, auxiliary substances, such as wetting or emulsifying agents, pH buffering substances, and the like, may be present in such vehicles. Typically, the therapeutic compositions are prepared as injectables, either as liquid solutions or suspensions; solid forms suitable for solution in, or suspension in, liquid vehicles prior to injection may also be prepared. Liposomes are included within the definition of a pharmaceutically acceptable carrier.

As is apparent from the claims, the invention also relates to related embodiments to the treatment and prophylaxis disclosed herein: the invention also includes embodiments where the polypeptide of the invention is for use as a pharmaceutical, in particular for use as a pharmaceutical in the treatment, prophylaxis or amelioration of infection with A. baumannii;

the nucleic acid fragment of the invention or the vector of the invention is for use as a pharmaceutical, in particular for use as a pharmaceutical in the treatment, prophylaxis or amelioration of infection with A. baumannii;

the transformed cell of the invention is for use as a pharmaceutical, in particular for use as a pharmaceutical in the treatment, prophylaxis or amelioration of infection with A. baumannii.

the antibody, antibody fragment or antibody analogue of the invention is for use as a pharmaceutical, in particular for use as a pharmaceutical in the treatment, prophylaxis or amelioration of infection with A. baumannii.

Example 1

Immunization Study
Experimental 16 individual proteins derived from A. baumanii (where 1 protein is a positive control) were tested. 16 mice were included in each group. The study was divided into 4 separate experiments comprising testing of 5 groups, that is 4 protein groups and 1 control group (adjuvant only). The 4 experiments are run in parallel, that is staggered with 7-14 days between each immunization. Hence the studies had a duration of 70-98 days (~2.3-3.3 months):

Challenge strain: A. baumanii AB5075.
Mouse strain: C57BL/6 (inbred).
Dose: 25 µg protein in each immunization.
Immunization route and interval: 3× subcutaneous with 14 days intervals.
Inoculation route (challenge): intranasal.
End point: Lethal challenge.
Adjuvant: Priming immunization: Alum+incomplete Freund's adjuvant (IFA). 1st and second boost: Alum.
Bled and ELISA: Mice were bled 4 days prior to challenge and ELISAs were run.
Mouse Tag: Each mouse was tagged, hence making it possible to track the mouse-specific antibody titer with survival.
Trial type: Double blinded.
Number of mice per group: 16 mice.
Monitoring period: 7-10 days.
Experiment 1

Group 1 was immunized with the protein AB57_3582-22-253, i.e. SEQ ID NO: 14, amino acid residues 22-253.

Study Group 3 was immunized with the protein AB57_1088-22-159, i.e. SEQ ID NO: 9, amino acid residues 22-159.

Group 5 (the negative control) received phosphate buffered saline (PBS).

Groups 2 and 4 were immunized with proteins irrelevant for the present invention and did not provide protection. Data are hence not shown.

Experiment 2

Group 1 was immunized with a protein consisting of amino acids 2-346 of the protein having ATCC accession number 17978.

Group 2 was immunized with a cocktail of AB57_2465-45-550, AB57_2465-551-906, AB57_1136-35-420, and AB57_1136-421-1071, i.e. 2 fragments of SEQ ID NO: 24 (amino acid residues 45 to 550 and 551 to 906, respectively) and 2 fragments of SEQ ID NO: 25 (amino acid residues 35 to 420 and 421 to 1071, respectively).

Group 3 was immunized with a cocktail of the proteins AB57_1893-26-711, AB57_1893-48-176, AB57_1893-478-711, and AB57_1893-26-477, i.e. 4 fragments of SEQ ID NO: 20 (amino acid residues 26-711, 48-176, 478-711, and 26-477, respectively).

Group 4 was immunized with the protein AB57_2233-22-162, i.e. a fragment of SEQ ID NO: 10 (amino acids 22-162).

Group 5 (the negative control) received phosphate buffered saline (PBS).

Experiment 3

Group 1 was immunized with the protein (AB57_3370-27-356), i.e. a fragment of SEQ ID NO: 16 (amino acid reissues 27-356)

Group 2 was immunized with a cocktail of the proteins AB57_1059-1-754+AB57_1059-25-754+AB57_1059-25-466+AB57_1059-58-177, i.e. the complete protein having SEQ ID NO: 23, as well a 3 fragments thereof (amino acid residues 25-754, 25-466, and 58-177, respectively).

Group 3 was immunized with the protein AB57_1621-1-367, i.e. SEQ ID NO: 17.

Group 4 was immunized with a cocktail of the proteins AB57_3396-23-691+AB57_3396-306-691+AB57_3396-23-305, i.e. 3 fragments of a positive control (the protein having accession number ACJ 41966).

Group 5 (the negative control) received phosphate buffered saline (PBS).

Experiment 4

Group 1 was immunized with a cocktail of the 4 proteins AB57_0478-1-550, AB57_0478-551-1110, AB57_2309-22-294, and AB57_2309-1-294, i.e. 2 fragments of SEQ ID NO: 27 (amino acids 1-550 and 551-1110, respectively) and a fragment (amino acids 22-294) and the full-length version of SEQ ID NO: 15.

Group 2 was immunized with a cocktail of the 4 proteins AB57_0053-19-108, AB57_1336-19-114, AB57_0830-1-166, and AB57_3389-22-126, i.e. amino acids 19-108 of SEQ ID NO: 5, amino acids 19-114 of SEQ ID NO: 6, the entire sequence SEQ ID NO: 11, and amino acids 22-126 of SEQ ID NO: 7.

Group 3 was immunized with a cocktail of the 3 proteins AB57_3081-2651-3047, AB57_0596-29-580, and AB57_0596-581-727, i.e. amino acids 2651-3047 of SEQ ID NO: 30, and 2 fragments of SEQ ID NO: 21 (amino acids 29-580 and 581-727, respectively).

Group 4 was immunized with a cocktail of the 2 proteins AB57_3778-23-230 and AB57_1830-35-238, i.e. amino acids 22-230 of SEQ ID NO: 12 and amino acids 35-238 of SEQ ID NO: 13.

Group 5 (the negative control) received phosphate buffered saline (PBS).

Results

| Group | Survival | Day 0 | Day 1 | Day 2 | Day 3 | Day 4 | Day 5 | Day 6 | Day 7 |
|---|---|---|---|---|---|---|---|---|---|
| Experiment 1 | | | | | | | | | |
| 1 | # Mice alive | 13 | 13 | 2 | 2 | 2 | 2 | 2 | 2 |
|   | % Survival | N/A | 100.0 | 15.4 | 15.4 | 15.4 | 15.4 | 15.4 | 15.4 |
| 3 | # Mice alive | 15 | 15 | 0 | 0 | 0 | 0 | 0 | 0 |
|   | % Survival | N/A | 100 | 0 | 0 | 0 | 0 | 0 | 0 |
| 5 | # Mice alive | 12 | 12 | 0 | 0 | 0 | 0 | 0 | 0 |
|   | % Survival | N/A | 100.0 | 0 | 0 | 0 | 0 | 0 | 0 |
| Experiment 2 | | | | | | | | | |
| 1 | # Mice alive | 12 | 12 | 3 | 2 | 2 | 2 | 2 | 2 |
|   | % Survival | N/A | 100.0 | 25.0 | 16.7 | 16.7 | 16.7 | 16.7 | 16.7 |
| 2 | # Mice alive | 10 | 10 | 5 | 4 | 4 | 4 | 4 | 3 |
|   | % Survival | N/A | 100 | 50 | 40 | 40 | 40 | 40 | 30 |
| 3 | # Mice alive | 13 | 13 | 0 | 0 | 0 | 0 | 0 | 0 |
|   | % Survival | N/A | 100 | 0 | 0 | 0 | 0 | 0 | 0 |
| 4 | # Mice alive | 9 | 9 | 0 | 0 | 0 | 0 | 0 | 0 |
|   | % Survival | N/A | 100 | 0 | 0 | 0 | 0 | 0 | 0 |
| 5 | # Mice alive | 13 | 13 | 2 | 1 | 1 | 1 | 1 | 1 |
|   | % Survival |  | 100.0 | 15.4 | 7.7 | 7.7 | 7.7 | 7.7 | 7.7 |
| Experiment 3 | | | | | | | | | |
| 1 | # Mice alive | 15 | 11 | 3 | 3 | 3 | 3 | 3 | 3 |
|   | % Survival | N/A | 73.3 | 20.0 | 20.0 | 20.0 | 20.0 | 20.0 | 20.0 |
| 2 | # Mice alive | 16 | 15 | 8 | 8 | 7 | 7 | 7 | 7 |
|   | % Survival | N/A | 93.8 | 50.0 | 50.0 | 43.8 | 43.8 | 43.8 | 43.8 |
| 3 | # Mice alive | 16 | 13 | 0 |  |  |  |  |  |
|   | % Survival | N/A | 81.3 | 0.0 |  |  |  |  |  |
| 4 | # Mice alive | 16 | 15 | 6 | 6 | 6 | 6 | 6 | 6 |
|   | % Survival | N/A | 93.8 | 37.5 | 37.5 | 37.5 | 37.5 | 37.5 | 37.5 |
| 5 | # Mice alive | 15 | 13 | 1 | 0 |  |  |  |  |
|   | % Survival |  | 86.7 | 6.7 | 0.0 |  |  |  |  |
| Experiment 4 | | | | | | | | | |
| 1 | # Mice alive | 12 | 12 | 9 | 7 | 6 | 6 | 6 | 6 |
|   | % Survival | N/A | 100 | 75 | 58 | 50 | 50 | 50 | 50 |
| 2 | # Mice alive | 13 | 13 | 5 | 2 | 2 | 2 | 2 | 2 |
|   | % Survival | N/A | 100 | 38 | 15 | 15 | 15 | 15 | 15 |
| 3 | # Mice alive | 10 | 10 | 5 | 2 | 2 | 2 | 2 | 2 |
|   | % Survival | N/A | 100 | 50 | 20 | 20 | 20 | 20 | 20 |
| 4 | # Mice alive | 13 | 13 | 4 | 0 | 0 | 0 | 0 | 0 |
|   | % Survival | N/A | 100 | 31 | 0 | 0 | 0 | 0 | 0 |
| 5 | # Mice alive | 13 | 13 | 1 | 1 | 1 | 1 | 1 | 1 |
|   | % Survival |  | 100.0 | 7.7 | 7.7 | 7.7 | 7.7 | 7.7 | 7.7 |

The above observations has let the inventors to the following conclusions:

Proteins tested that provide significant protection against challenge:
1: AB57_1059-1-754, AB57_1059-25-754, AB57_1059-25-466, and AB57_1059-58-177;
2: AB57_3396-23-691 (positive control), AB57_3396-306-691 (positive controls, and AB_3396-23-305 (positive control);
3: AB57_0478-1-550 and AB57_0478-551-1110; 4: AB57_2309-22-294 and AB57_2309-22-294.

A number of proteins tested are found to possibly provide protection against challenge infection:
1: AB57_3582-22-253;
2: AB57_2465-45-550 and AB57_2465-551-906;
3: AB57_1136-35-420 and AB57_1136-421-1071;
4. AB573370-27-356.

Amino Acid Sequences of the Proteins of the Invention:
In the present specification and claims, the amino acid sequences of the proteins are identified via the SEQ ID NOs. set forth in the sequence listing and the table below. However, alternative designations are used in the examples, according to the following table:

| Designation: | SEQ ID NO: |
|---|---|
| AB57_1759 | 1 |
| AB57_1009 | 2 |
| AB57_1902 | 3 |

-continued

| Designation: | SEQ ID NO: |
|---|---|
| AB57_1614 | 4 |
| AB57_0053 | 5 |
| AB57_1336 | 6 |
| AB57_3389 | 7 |
| AB57_3578 | 8 |
| AB57_1088 | 9 |
| AB57_2233 | 10 |
| AB57_0830 | 11 |
| AB57_3778 | 12 |
| AB57_1830 | 13 |
| AB57_3582 | 14 |
| AB57_2309 | 15 |
| AB57_3370 | 16 |
| AB57_1621 | 17 |
| AB57_0504 | 18 |
| AB57_0619 | 19 |
| AB57_1893 | 20 |
| AB57_0596 | 21 |
| AB57_2870 | 22 |
| AB57_1059 | 23 |
| AB57_2465 | 24 |
| AB57_0791 | 25 |
| AB57_1136 | 26 |
| AB57_0478 | 27 |
| AB57_1048 | 28 |
| AB57_3621 | 29 |
| AB57_3081 | 30 |

When designating a fragment of one of these proteins, this is done using the nomenclature AB57_XXXX-A-p1-p2, where XXXX is any of the 4 digit numbers following "AB57" in the table above, and p1 and p2 are the start and end amino acids relative to the entire sequence of the protein. For instance AB57_3081-50-200 is the fragment of AB57_3081 that has the amino acid sequence defined by residues 50 to 200 of AB57_3081.

SEQ ID NO: 1
MTQLINKGGFRERANRSRKYQQSENKQVALPSKKYQPQTKLQDNQSEMIQ
AKAGTAETSD

SEQ ID NO: 2
MKLAKTLLATTLALTAASTFAASKEDQAHNTAGEEKVVVSTQEQANTANA
ASDAVGSASEAAPATR

SEQ ID NO: 3
MIDEEKPLNFEDDDEPLDFEDEEFIDDKKEDEMYNSITKDGSSVDPADDG
TRHIRPEDGDPIEIDE

SEQ ID NO: 4
MSTTNNQANQRNNQQQQQQQNDNRNQQQHGNQQQNDQQQQNNQQQQQNDN
RGQQQGSNQKDSGQQNSNNNQQR

SEQ ID NO: 5
MSAKLVVTLLATSLLTVGCVAYTDDPYYRGGYGYHDHDDDRYDRNDGRRY
SEWERKRWEERKRLYEQQRKDIREQQKDRREWEKRHREWEKKRLEDRDHD
HRDYRHDD

SEQ ID NO: 6
MNKLLVALGLAATVALVGCNKDKAPETGATTGEHLENAAQQATADIKSAG
DQAASDIATATDNASAKIDAAADHAADATAKAAAETEATARKATADTAQA
VENAAADVKKDAQH

SEQ ID NO: 7
MKMTAKIALFSAAIVTMGSLAACQSTTQPPKPEHGMMQDGPRDGHHHRMK
HREFTPEQKAAWEQHRAERKARFEQIQKACEGKVVGQTVNVQVGDKTLEG
TCNLRFEPKRPQPPVNAPAPVATQAK

SEQ ID NO: 8
MKAIKILCITSSILVSSSLFAETPQPQQVNEATSKTMPYGDNPSLGRVLL
YKTGKGIQNLGDSIQGASEKTSNKISEKWKDTKEFTAEKAEVVQQKADTA
KVFTEQKIEQAKQNITSSRNGENIPIEQGELSKSSTTAN

SEQ ID NO: 9
MKKSLLAIALMSTLLVACNKHENKTETTSDASTPVQTAQSNNNEAVDTAH
TAENSLDWDGKYKGTLPCADCEGIKTELELKDDKTYELTETYLGKGDANP
FETHGKFTFDKDNTSVITLDDKAQNRKFFIGENTATALDMEGKKVEGSLA
EHYVLKKED

SEQ ID NO: 10
MANKKLLICAAIAAGLLLTACVKKETPKEEEQDKVETAVSEPQPQKPAKF
ESLESVDTQEAQVQEQPQVEVHREETANTTTEIRRETRPARSDESSQTQV
AEQPKSETPKVEPKPEKKPEPKAEPKPEKAQSKPAAKATEPANTEDDAVA
AAIAAATPALKN

SEQ ID NO: 11
MTTENKLDELKANAADAKVQGEKALDDLKENVKEKQTAGKEAIADKVDEL
KTKAADAKVQGEKALEDLKENVKEKQAAAKEAVEDKASDLKGKLDDAQHS
LQDKFDHLRTEAAHKLDDAKAKAAELKEEAATKFDELKTQATAKFDELKK
TATEKLNKLKNHDSAE

SEQ ID NO: 12
MHTRRILLAFSLAASAASVAFADYQNINQSTDSDRLEQLSKTLSQGSYTH
PDDLDLPASAKVSVTLREKTVELNNDSLAKKYGTTTAKNSFKTSSSNPYS
WLVSHPLPDTVRVSSNFGGRTMGGRAEHHGGLDMAAPSGTPIYATGPGIV
TKSGWGTGYGQYVEINHGNGYLTRYAHASRLMVRVGDQVSAGDHIANVGC
TGRCTGPHLHYEVVKDGQRKNPSTYLAMLP

SEQ ID NO: 13
MGMTFTDIENKSAKRLIGIAAVIFLHLLVAYILMSGLANNIQKPAEKPVE
LQIIQDIKPPPPPKPEEPKPKEKPPEPPKMVEKVAKVPEPPKEVEKVATP
VQKTTPVAQTTKVATPAPAAPSTPSPSPVAAPAPVAAAAPALKPAGVTRG
VSEGSAGCEKPEYPREALMNEEQGTVRIRVLVDTSGKVIDAKVKKSSGSK
TLDKAATKAYSLCTFKPAMKDGVPQQDWYEIEYPFVIE

SEQ ID NO: 14
MKMMKTAIVTASVLASASIFAQSAGVNAGASAQVNVQPGGLVSGVANTVK
NTAHTVGNTAKHAGHVAADTTVKATKKTTGKVTELSSKAATGTKEVASEA
VTGTKHFATEAATGTKNLATKAATGTKNLAVEAKADTKAHLDAVKTKVAE
KQADQKEFTAEKQADAQARVDAVKARVAQNQAEQKEFVADTKADAQAKLN
TAQPAHGVNAQTGVNVGVNVAGINANANVNAGAQASTQKGEKKSFIKGLF
GTN

SEQ ID NO: 15
MQMKKHSLLFIALMSTTSLYANIPIESRGLSQNDGSASNTSSSNISVPTN
LNWELMQKNQQLENDIRTLRGQLEEQANDIEQLKKDLANRYTDLDQRLEL
LHQKVDPDSATQDDSSNATSDNTTPASAPAPQTTESNKVAAVPATQTSEQ
QPSAPTTTTQPAPAAAQNQSNSLELEKAAYTVALDAYKQGGAKKAIAPMQ
NFIKNHPNSIYTGNAYFWLAEFHLATDPVNYNEAKKNYNVVANQYPNSSK
APRALYQLYSIAKDVDKNTVSANQYKNKLLSQYPKSEEAKFFNK

SEQ ID NO: 16
MSMNNKQRWMGGVVLLGGGVLLAALLLKGNEEIKQVDVQPQTSTSPKLQA
KPKQSAQEGQMVQLQPLAVDVETEKRLLEEQRRSREKAVAEQEARAAEFL
AMQQQAEADAARKAAAEYAAINARRAAAQESSDNIPPEVAGSENKAKGQQ
TDTKKSVDLAKADADKKAAEAKRLAEADKKAAEAKRQAEADKKAAEAKRQ
AEADKKAAEAKRQAEADKKAAEAKRQAEADKKAAEAKRQAEADKKAAEAK
RKAEAEKKAEAEKARELLENGDKKWMVQVALAANQANADAVVSKLRAKGY
KVTTSPTSKGIRIMVGPAKDRDTADTTRKKITSDASLNMKSAWVIDWVPL
DQRKSD

SEQ ID NO: 17
MANTRYEDDNNSSGTSNRGFASMDPERVREIASKGGRAAHASGNAHEFTS
EEAREAGRAAHASGNAHEFTSEEAREAGALSHKNDDRNGRGRSRYDDDED
DDRGRSSGRGRGRSRYDDDDEDDDRGRSGGRGRGRGRDDDDEDDDRGRSG

GRGRGRSRDDDDDEDDDRGSGGRGRGRSRRDDDDDEDDDRGSGGRGRGRS

RRDDDDDEDDDRGSGGRGRGRSRYDDDDDEDDDRGSGGRGRGRSRADDDD

EDDDRGSGGRGRGRSRYDDDDDEDDDRGSGGRGRGRSRRDDDDDEDDDRG

RSGGRGRGRSRYDDDDDEDDDRGSGGRGRGRSRRDDDDDDDDRRGRSDGR

GQNSRNQKRDAYGRFTS

SEQ ID NO: 18
MLYVIPFIILLVVAVILKKRENSQKQEATSPKNINRKSGKKASAKSSKSS

REKIKAKVIEENIPAIPQSNPVPEALRHNIQQLIQEKQFSAAEAQVNQAL

KKDNTQHELYLLLLEIHIAQKDEFAIQQLISHIRSLGLNEIAAQAETRQK

EYESSSQPDAIDFPQAQTYEEPKNTDTTAQFDELTTSSSEASFDDLQKDY

TPVKQEPAIEIEPLEFNFSFEQNSATENTNQPAQQPELSSTQETNELADL

EFSFDLAPLHETEEKSQAVEVKADQENSINALDFNFDLNPSSSETKSVQQ

APSLDEIKLIEQAPLEATSIAPLEFSLDEPALVPAPELETQNHIDVVNEA

ATQTQIEDPLLEAFPELKQINENELDLKLAEQYIKFGANQAARNLLQGDE

QKFNTEQQQHAKNLLNRIAS

SEQ ID NO: 19
MPKIKPIKLVIIVVCIAIIAVLAWKFLKPKQQQPQYITAEVTRGDIENNV

LATGTLDATKLISVGAQVSGQVKKMYVQLGDQVKQGQLIAQIDSTTQENS

LKTSDANIKNLEAQRLQQIASLNEKQLEYRRQQQMYAQDATPRADLESAE

AAYKTAQAQVKALDAQIESAKITRSTAQTNIGYTRIVAPTDGTVVAIVTE

EGQTVNANQSAPTIVKIAKLQNMTIKAQVSEADIMKVEKGQQVYFTTLGD

ETKRYATLRQIEPAPDSISSESNSTTSSTTSSAVYYNALFDVPNTDGKLR

IDMTAQVYIVLNSAKNALLVPSSALSSKQFSGQRKQGQSADKASSTPSAE

RKHQGNGVRLERLNLTPEQKQLIEQGKATLSVVRVLQADGTTKPTQILVG

INNRVNAQVLAGLKQGDQVVIADSSENSAASANSGNNRRRGPMGM

SEQ ID NO: 20
MNIPPRPFKLSVIACAICYANLTYAQDAQVQALQTIQVKASNAEQSSEQT

KAYNVKNSSSATKLNIEAKETPQTINVVTRQQIEDFGLTSTRDVLRNTPG

VTVSNQETERTTYMARGFEISNILTDGVGFPLSGYNYNNTNPDTYFYDRV

EVVKGADSLTNAFGDPSATINNIRKRPTQEFQASGGVSYGSWDTQRYEAD

VSGSILPSGKVRGRIMGYEQTGDSYLDRYSAEKNGFAGIVEADLTDSTLL

TAGYSQEQNKPNANNWGALPLLDANGKQISYDRSYNPNPDWAHWDNETQN

AFVELKQKLNDQWNAKLTYNYLDTKHNSRLLYYYGYPKADGSGVSLTPWG

GQEHQEKHAVDFNLEGTYKLENREHEATLGYSYVRNHQQDKQSTGTINDS

NVIKSTTTDWASWTPQSITWSDFTEAANYKQNINSIYAATRLHLNEDLKL

LLGANYVQAESKGESYSSPMSYSESKVSPYVGLTYNFTPEYTGYMSYTSI

FRPQTGIDKDTNQALKPIEGKSYEMGVKSSWLDDRLTGTLSVFKTEQNNY

PLRNSDGNPLNRKVPTSDLESQGVEVGLSGQITDVNLSEGYAQFSIKDT

KNGGEARTYNPNQTLNLLTTYTPPVLPKLKVGAGLQWQDGIKLYDSNVNG

TIKQDAYALVNLMASYEVNDHITLQANGNNIFDKKYLNSFPDGQAFYGAP

ANYTVAVKFKY

SEQ ID NO: 21
MKLQTIACAVAIATGGLFFSHTMNEARAATNTAAVSQSIQPTQEQALVAR

QLATLVDRQHYLNMRLDANTSNRILDMYLDSLDPDHSLFLDAEVQNYKKL

YGSNFGASLKAGNLTGPFAIHQQYRERLKQFYEFMLAELKKPQNLKQPNT

FIEVDREKAPYFKTSAEQQNHWRKMLVSQLINLTISREEEQAKQKALKEN

PSLADGQDLTGPEDLTPAQTLTKRYTRQLERISRVKSDDVLDKTLNAMLA

TYDPHSNYYPPIDAIELNRQTTLQLEGIGVSIRPERGNEDYTKIETIVEG

GPASKSGQVKSGDRIVGVAQEGGKMIDVVGWSSSEIVGLIRGKRGTKVTL

KLLGAGASMSQARNVTLVRDVIQEEDAGVRSRTVEVTRDGKKHLLGVIEI

PSFYFDYRSRRAGQQYRSVSEDTANAFEALKAKKVEGIIIDLRNDPGGSL

EEVARMLGQVIKSGPVVQIRDGNGNVSVFEDNDGGQQIYTGPLAVLVNLA

SASASEIYSAAIQDYERGIIIGSTTTGKGTAQVQLDTLAYGQATLTQRKF

YRVTGGSTQNKGVVPDIKLVDIYNEEFGERKSKNALKWDTIPTAPFKREG

SVQPYVAKLSQLSEQRVAVDPQFKYLNKRTAIAKVTSDQKQVVLDIDKRR

AELLSLEKQTLDAENERRIATGQKPFPNWESYQASLDALAESRAKMKANQ

RPALPEEETEVNEAANVLMDYAKLQNR

SEQ ID NO: 22
MTRIIVASKEGLDVLQDGQLNKVVLNQPTIIQIGVSQKDIASMEKQGGSL

VIHLKNGETIVLENFFNEATNTTEHSLVFPTEQGKFVEAQFDAQGKVIDY

RGLNHVTDLAYTSTSPSAATMAVDNDPSFSMGNVLKAGLAVLAAEGLYLW

AFDKDDKDDSPSTPDLIAPAAPTATLADDTVTVTGKTEANAKIYIKDAAG

NTVASGVADASGNYTIKLDKPLVNGDKLNVIAQDAAGNNSKVTVVTGTKD

TIAPDVPQAQLSDDGSLLTGKAEANAKITVYDATGKVLGTVFANKDGIYS

LKLTPPLTSEAGGKVVAEDAAGNKSEEVKIIAGKDTIPPASPFVEVNKEG

SVIHGKTEANAKVQIKDADGKVIGSGTADAQGEFQITLSPALKEAQKGTV

VVEDAAGNVSKPVEITPGFDSIAPDKPTVQINTDGTSVTGTAEANAKIEI

KDTTGKVIGSGTADANGKFTISISPALTDNKHASVSAIDNAGNKSEVVDI

VGTKDTTPPAKPILNSVDDDVGAVKGAITAGSETDDARPKLTGSGEANAT

LTIYDNGVAIGVVTVTSGRSWSFTFDKDLALGKHTITLTQTDAAGLTSEA

SSPFTFYVVAPKAASLSETSVDILSTEGPSLADSVGLHTLKVAQNTTTET

NNPQKSVPLDDLLKSSTASESDPIAKLLSSTALKTTQASEPIEVNASVGQ

TTSNPNHPLPDTTSSVLQNLLDQTYPVV

SEQ ID NO: 23
MSKRIIQSVLSVSVLASMMSMAFAAQNEQEQAEQTLEKPAEPVKLETIFV

TAEEQVKQSLGVSVITKEDLEKLPVRNDISDYVRRMPGVNLTGNSATGQR

GNNRQIDIRGMGPENTLILVDGKPINSRNSVRYGWKGERDTRGDSNWVPA

EAIESIEVLRGPAAARYGSGAAGGVVNIITKKVTNETHGSVEFYTSQPED

SKEGSSNRVGENVSGPLIKDVLSYRLYGNYNKTEADDVDINKSIGSTAAG

REGVKNKDISGRLAWQATDQQTVLLDISSSKQGNIYSGDSQLNANAEADA

ILSQLIGKETNTMYRDSYALTHEGDWSWGKSKLVAQYDKTHNKRLPEGLA

GSVEGKINNLDDKATSRLETLRFNGEANIPFEYYLPQVLTVGTEWVEDRE

KDNVSTTQGKDSSGSGYGDQLAKGDRSKMESRIASAYIEDNLKVTDSTDV

-continued
VLGLRFDDHSKSGSNWSPSLNITQKLNDNFTLKGGVAKAYKAPNMYQNAE
GYLLSTNGNGCPANIESRCLLQGNGDLKPETSVNKELGIQFQRDIVNASL
TWFRNDYKDKIVAGTHVVGTVDGSSTNANTGAVTNTKWNILRWENTPKAL
IQGFEGSLGLDFGDIRWTNNFTYMMDSKDKQTGNPLSLVPIYTINSIFDY
DITDQLDVNFVFTQYGRQKSRQFAENRLESGIGSGGANSALKPSTVKSYS
TAGINVGYKFSDQISTRVGVSNLFDKQILRDSNSISQTYNEPGRAYYASL
KYSF SEQ ID NO: 24
MPSKIKFKQSTLSHSMHLILKMQSIPKLICSSLLLSLCVTPCYAQSSAET
VIPEANQTVTDSLVQQTNTNNPSDVPITDVATLVTQAQQQQDSLAILQQQ
EQFPNQIEEFKPITLDNLEDLPVMPVDQNMANEIYRVAEEAKNEAQNFQN
GTQKQPEMVVSDASQAELHEINQAPVNIDQLMHEIQSDSKIVVEANETGK
TLPELTAAVEEPPEEKGFFRRIFNKIRPPRVIPMEQIPRITAEVTGAPDD
LAKNIKGKLSTFTQESFEDFNAALPQLRSLSNQAAQAVGYYNAEFRFEKL
SASRVRVNVTPNEPVRINEQNIEFTGAGAKQPQFQVIRLVPDQDVGDIFN
HGLYETTKSRIVDAASDNGYFDAYWRLHDVKVSQPENKADINLKYETGER
YKLGKVEFRMSDPSKPLPLNMNILESMAPWKEGDDYAFWRVNVLANNLIN
SRYFNYTLVDSIKPDPIEKPLELPPDLQALVDQQNVDIDESKLLPLEQQQ
LAKARQLASSSKEVTQNVVDEKQFAGTESVQAAPASLKAATVQHEEQESE
QDRLQAQAREEKRIPVIVTLNADKLNSLETGIGYGTDTGARLRSQYRRSI
VNKYGHSFDANLELSQIRQSIDGRYSIPYKHPLNDYFNIVGGYERETRDD
IGPDVSLLTESAVLGGERVIKKPLGNWQHTIGVRYRLDRLTQKGNVDISE
LPDAFKTAASEQEALLFSYETSKTSSNTRLNPTKAFKQTYKLELGSESLL
SDANMAIATAGWRFIYSLGENDDHQFVGRSDFSYIFTDEFDKVPYNLRFF
TGGDQTIRGFDYKSLSPEDNGYKIGGQALAVGSLEYNYQFKEGWRAAVFS
DFGNAYDKSFSNPTAYSVGVGIRWKSPIGPIRLDVASGISDDNHPIRLHF
FIGPQL SEQ ID NO: 25
MFIKSILSSITSIIPLPENSNTSSNLGNGSGDGLLNGISSGNGEHNYGIG
NGIADDASITAPITIPLNLSGNSITLIGNSSSSSVNSSPTTTSNNVNDND
VTNNGNGSTIGSGTGNGSGDGLLNGAASGNGEHNYGIGNGIADDASITAP
LSIPINLAGNSITLIGDSSSSSVNNSATNTSNTVNDNDTTYNGNGSGGGN
GSGDGLLNGIGSGNGEQNYGIGNGIADDASITAPITLPINLSGNSITLIG
NSSASSVNSSPTTTSNTVNDNDTTYNGNGTGDSGVSALGGSGNGSGDGAG
NGIASGNGEHNYGIGNGNGDDVDITAPITGVLNISGNSFTLIGNSSSSSV
NTAPTTTSNTVNDNDTIDNGNSGGTGSGSGNGSGDGLLNGAASGNGEHNY
GIGNGNGDDVDITAPITGVFNFSGNSFSIIGNSSSSSINTAPTTTTNTVN
DNDVTDNGNDGGGLVGGSSGNGSGDGLLNGAASGNGEHNYGIGNGNGDDA
DFTFPLTGVLNFSGNSLSGFGSSSSDSVNVAPTTATNTVNDNDTIDNANT
GGLGDGSGNGSGDGLLNGAASGNGEHNYGIGNGNGDDADFTLPFTGGLNI
LGNALSGIGGSSTDSINISPTTTSNTVNDNDTTNNGNTSGGVIGSGDSGN
GSGDGLLNGISSGNGEHNYGIGNGNGDDVDVVAPITTPLNVLGNSFSFIG -continued
GEGTGDILGPITGIIGGIGGDGDILSPITGIIGGIGGDGDILSPITGIIG
SIGGIGGDLGDNPLTGIIQSGIDVLQNLESLKTGLINTGIDTIAGTIIGV
FPDAEHPVGDFADLGKLLFETSRDSVNGTLEAISDLAGADLEGASGSITG
VIDTLITNGSTASTIIQHIVGDDLVTENGGLLGSITTIIGGVDSGDGGLL
GGLDGLISINYGDSDNSNSIDVEDILGNILGSVGSNQGIAVGEPDPTGGS
LIHTISLNTVNQLTDQLLHALPTV SEQ ID NO: 26
MYKPTTFVWQPSAASLFKITVLSSALAALGITTGCSSTPQSAKTSKTKQV
SGAGYLDASSLDSLEDLLSATDMRAVEGDRLLILKHGDVWKRMAVGFKMD
LNHWDPRIEAQRSWFISRQPYLDRLSARASRYLYHTVKEAERRGLPTELA
LLPVIESSYDPAATSSAAAAGLWQFIPSTGRIYGLQQTGMYDGRRDVVES
TRAAYEFLGSLYNQFGSWELALAAYNAGPGRIQQAINRNQAAGLPTDYWS
LKLPQETMNYVPRFLAVAQIIKNPRAYGVSLPPIANRPHFREVTLSAPLS
LNEIASVTGLSRAELYALNPGYRGETVDPASPMRILIPADISPSVDNKLK
GMKAGGSSGWWASVTSPSKPTTTTSTSVTVRTTPSTPAQPVRPSTPAKTS
SSSVTVKTTTPRGSDALAAFAASADVPSAPRIPVAVTPAANIKPVRTEPP
ISATEREKILAAVRAEGEKETVDQALEPQATQAEKDQVVAELKALAPQGT
EIVDPYDGKIKLTAIQTSQSVAEQQGKEVSKGFAYPKTLAEDATLANSED
AQRNKDKPYIKTDTDVVVVQPKGKRSTYTVQPGDTLAVIAMKNGVNWRDV
AKWNQIDPEKTLFVGTSLYLYDAKPQEAETTAKSAAKPDVYVVQANDSLT
GVANQFNLSVKQLAEYNDLSVTDGLFVGQKLQLKEPKGNRAAKVEPKAIQ
ASTRRIATKSYTVKAGEYLKLIADRYALSNQELADLTPGLSAGSNLIVGQ
KINVPAKEITVDEVDDSKASGKYEKLAAGPSYKTESYKVQRGDTLSSIAT
KSKISLAELAELNNLKANSHVQLGQTLKVPAGASVPDQYVVQSGDSLNAI
AAKYNLQTSYLADLNGLSRTAGLRAGQRLKLTGEVETTSKVSAKNTKEET
PETYTVKSGDSLGNIANRYHLQLDYLAALNGLSRNSNVRVGQRLKLTGDL
PTVETAKTDTAKSSPKAVVAGKNTEKYTVKAGESLNAIASRAGISVRELA
EMNALKANANLQRGQNIVIPKTVVEYKVKRGDTLIGLASKYGLETTLLAE
LNNLTPSTQLRIGDIIKVPNL SEQ ID NO: 27
MKRMLINATHAEEVRVALITGNRLYDFDLENRTREQKKSNIYKGHVTRVE
PSLEAVFVEYGAGRQGFLSMREIANSYFQADPRQTSNIRELITEGTELLV
QVEKEERGNKGAALSTFISLAGRYLVLMPNNPKGGGISRQISGSVREELK
EILASLNVPRGMSVIVRTAGIGRTQEELQLDLQHLLDLWAQIQGTASSGP
SPMLVHQEAGVVTRAIRDYLRDDVAEILIDSEQAYNEAYNFVKAVMPRQL
DKLKTYTLNEPLFAHFGIESQIQTAYEREVKLPSGGSIVIDQTEALVSID
INSAKSTRGHDVEETALNTNLEAAEEIARQLRLRDIGGLVVIDFIDMTKE
RNQRMVEAKLREATQSDRARIQFGQLSRFGLMEMSRQRLRPSLEEATGYV
CPRCHGTGMVRDLRSLSLSIMRKVEEIALRERHGEVQVEVPVEIAAFLLN
EKRHSLVYLEQTSGVRVTVLPHPHLETPHYEIAYNPDGFAPSSYERTEAT
RSSEKELGYESSEWHLEEADHGHAHVTATASTHAAAQKKANHATQPVAQP
SAQKAASPCAWLENLFVQKQAQTVDQSRSAQNAAAAIEQMVNTGAVSRGQ

```
FGQVAVPAVAEVAPVQSNNAYISQSPVKQDVRERVEKDDKSQQQRQNNKK
RKHKEQREQHHQSHEQQHQVHEEVVQLSRQEQRELKRQQKRQQQQDQQHQ
NNDVQHTENAVPRRDRNNQQRPNRPNRHRDPSVLNENQNTLVVVDEKQIK
VDVIDAPKEDVMNTALIINVDQGQSEIVALTPERRHVERVETTSTEVAQE
PTPAPVVAEKAAVVETKEEAQPSQEAAQPQIKRASNDPRMRRQQREAKH
AKAATPSIAPSQIPTLAQHTIGSLIRHVYGEDCTVLIEQFGLVPTFNRAL
QKFAEQYASTLVVEVTAETEEKKPVTRDAELPSHKPAEEAEPAPVLPLTP
PQAPAPRVANDPRERRRLAKLAAEQAFEQVKQQHSAQEEVATPAPVAEET
VAAPTAETQATVEPAQQPLELNQSTEVVQPEAAPAEEKATEETVAEAPAA
KEPAPSKAASKAKAAAEETVAPTEATTDAESEDVKADKDKPSRPRRPRGR
PPKKANPVAE
```

SEQ ID NO: 28
```
MSTLATLKALLAKRILIIDGAMGTMIQRHKLEEADYRGERFADWAHDLKG
NNDLLVLTQPQIIQGIHEAYLDAGADIIETNSFNGTRVSMSDYHMEDLVP
EINREAARLAKAACEKYSTPDKPRFVAGVLGPTSRTCSISPDVNNPAFRN
ISFDELKENYIEATHALIEGGADIILIETVFDTLNCKAAIFAVKEVFKQI
GRELPIMISGTITDASGRTLTGQTAEAFWNSVRHGDLLSIGFNCALGADA
MRPHVKTISDVADTFVSAHPNAGLPNAFGEYDETPEQTAAFLKEFAESGL
INITGGCCGTTPDHIRAIANAVKDIAPRQVPETVPACRLSGLEPFNIYDD
SLFVNVGERTNVTGSKKFLRLIREENFAEALEVAQQQVEAGAQIIDINMD
EGMLDSQNAMVHFLNLVASEPDISRVPIMIDSSKWEIIEAGLKCVQGKPV
VNSISLKEGYDEFVEKARLCRQYGAAIIVMAFDEVGQADTAERKREICKR
SYDILVNEVGFPAEDIIFDPNVFAVATGIEEHNNYAVDFIEATGWIKQNL
PHAMISGGVSNVSFSFRGNEPVREAIHSVFLYHAIKQGMTMGIVNAGQMA
IYDDIPTELKEAVEDVILNQNQGESGQAATEKLLEVAEKYRGQGGATKEA
ENLEWRNESVEKRLEYALVKGITTYIDQDTEEARLKSKRPLDVIEGPLMD
GMNVVGDLFGSGKMFLPQVVKSARVMKQAVAWLNPYIEAEKTEGQSKGKV
LMATVKGDVEDIGKNIVGVVLGCNGYDIVDLGVMVPCEKILQTAIDEKCD
IIGLSGLITPSLDEMVFVAKEMQRKGFNIPLLIGGATTSKAHTAVKIDPQ
YQNDAVIYVADASRAVGVATTLLSKEMRGAFIEEHRAEYAKIRERLANKQ
PKAAKLTYKESVENGFKIDESYVPPKPNLLGTQVLKNYPLATLVDYFDWT
PFFISWSLTGKFPKILEDEVVGEATDLYNQAQAMLKDIIDNNRFDARAV
FGMFPAQRTDADTVSVFDEAGQNVTHTFEHLRQQSDKVTGKPNLSLADYI
RADREQQDYLGGFTVSIFGAEELANEYKAKGDDYSAILVQSLADRFAEAF
AEHLHERIRKEFWGYKADEQLSNEELIKEKYVGIRPAPGYPACPEHSEKA
VLFDWLGSTDKIGTKLTEHFAMMPPSSVSGFYYSHPQSEYFNVGKISQDQ
LEDYAKRKGWTLDEAKRWLAPNLDDSIV
```

SEQ ID NO: 29
```
MKLKLKNFKPNNLWYAVCSSSMIFTWLMTSSVVQASDLQIYASPTAGKKT
IVMMLDTSGSMTNNSYGENRLAMLKNGMNAFLASNNPVLNDTRVGLGNES
ANGDSRSGQILVAAAPLGDASTLNTVGSQRYKLKQAVANLTAGGSTPSAH
AYAEAAAYLMGTTTYSETNYAIRKDSYIKRVRRSDNRTEYSYCTNYRDSQ
IDTANLWQPCRSNSYWSSWSTNNPGVDNATAYDTSSDWTYYYTYYYTTFN
YAVANADSGIPKSKSNDTASNPNIVVDRNATNSNAVYQSPLPAVANRQSC
DGQGIYELSDGEPNNTTNTRSASVMSTALGSTFGADFNCSGGLSNTTADS
GWACMGEFAKELFDKTKNPAGVSIQTAFVGFGSDFSSLNSSDVKNACRLS
SRTQSDRKGDDACSPNQSTNAVAAPGYGNGGFFPTQSSQGVTDSVIAFIN
NLDKVPLEPLTTGAISVPYDALNPKNLQEYGYLRAFEPNPANTYLTWRGN
LKKYHVVLSGANAGAFEANSGGLVYNASGAFRTGTKDYWNSSTYTDGGKV
FLGGSYANVPLPIAGQPETRDAEGNITKYYYAVQSKIRNLFTDVSAVAAD
GSLTKISTSGTNLLKIPAAPPEETNPFDTVANTASYVLGKFDPSTGQNIL
KAFPISLKLKILNYLGYSTDINATTLPSSLVTSNEPYLSMGGSIHSLPVQ
LTYNGTLDDNGNLTSAREQSILYGTMEGGLHIVDASSGIEQMVFVPADIL
NDSVASKALVVGQSDASAPAEGMDGAWVSDPAYNITTVGSGSSAVSKVTA
KQMNIYGGMRMGGSSYYGLDVLSPTSPKLLFRIGADQNDYSRMGQSWSKP
VLANIRYNGSIRRVLIVGGGYDQCYEKPNITLTDACFTNGKAKGNAVYII
DAKTGQRLWWTSDTGSNTDNANMKHSIVSRISTLDRDADGLVDHLYFGDL
GGQIFRVDLNNNQTKTNSTYSSFGVRVVRLANLATNDSTYDGTNDYTGGN
APRFYEPPTVTIHDYGIHTFITVGIASGDRSTPLDVYPLTGREGMTPASA
LSGRPVNNVYGIIDRDFVKKNLMSLTDNQLETKDITRTGLRKNPQILRTG
ETRVAQIFFPTTGVGKGGWYRSLSSTSDGTEKANNSFRIKGGLKAFEEPM
AITGNLIILVYDPQGTGIVAADPCLPRVVGETDRQTYCLPFGACLNSDGS
IDQNKENHSGFETQTGTNCPVGASECNKNVIGSGIRSVTFVPTEDNPPTT
NSCGKLKLSGNEQGTGQWQCTSHLVPTRWYERYR
```

SEQ ID NO: 30
```
MTDAAGNTSEQAVQKVVVDTTAPQAGELTLSDLSDTGISATDQITQDKNF
NLKLEGQESGSRVTYLVSTDEGKTWQETTIAQKDLTDGVYQYKAVVTDAA
GNTSETAVQKVVVDTTTPQAGELTLSDLNDTGVSVTDQITQDKNFNLKLE
GQETGSRVTYLVSTDEGKTWQETTIAQKDLADGVYKYKAVVTDAAGNTSE
TAVQKVVVDTTAPQAGKLTLSDLNDTGVSATDQITQDNSFTLKLAQPIVI
GEQAALLDHYEVSKDEGKTWQETTADQKDLADGIYQYKAIVTDLAGNISE
SAIQKVVVDNSLNVESTTVIVKPITEDNTISLVEKDQVISIRLEIANLPT
DLNSSLTSVNTTLGNVTYNFHFDEVTQEWVTEIPAEFLWSVEPQTNISIE
ISLTDQAGNTAIIKHTQNYNVDHTPNSPTLDSLTFNNIDGAIISGSAYKG
SKVDIYNKNGDWLASTITNEEGKFTLQDLSINSNQEVYAVATYNGYSSEN
SSIGLVTEVPAISITRISPEGVISGYATEGSHFIVKDQNGNILQEFNSNV
FDSSGITPFSVMALGEVRPFILSLDQPLEEGAQIIISIDKDNISGHPQYI
TADYTPAVFLETPQFDISGETLSVHVNEPNSFIRAFSGEGNLIATGFTDE
QGFASLQVFQFLKEGETVSVQVVDKNQNTSETLIEVPNFAYIPHVERITQ
EGLISGVAEDNSTVIVRDADGNELGKVTLGDDNSWSDFSHFSLSVNRPLI
DGEKISVQIIDNKGLMSPEQNIIVDLTPPPAPTELNENDAGDLVYGHAEP
FSEILVKDGQGNILNKWFWNNWTDESGSFSIELGTFLTNAETVYVTATDV
NGNVSLAAQIQAPNYAFAPYVDSFTSDGVISGQAENNSTLVVKDAKGDVV
```

-continued

```
AEIKVGEDNGWNGSSYFKLQLDRPLVDGEQFFLSIKDARGQVSADTVITA
DTVAPTPASNLVFSEDGSYLTGVAELNTTIQVFDHNGQLVNIWNNTINSD
GTFTIYLGSNNLHGEAFTVTVKDQAGNVSEAISINAPLDDIAPNPIKNIL
LDANGQNFTAQAEANSQIEVFDSLGNQTGWGSTDSAGNVSGSFNQTYLHG
EELTFVVIDRAGNRSIEFKQNALIDTIAPNPIANIIFNEDGQSFTAQAEA
GSSIDVLDQTGNKIGFGYTDSSGNVSGYFQQVYLHGEELTFVVIDRAGNR
SAEVKQSALNDDVVPNPIENIVLDLNGQNFTAQAEANSQIEIKNNNGDVV
GYGSADSAGNVSGYLYQVHLHGEELTFIVVDRAGNRSTEVKQNALIDDIA
PNPIENIVLDINGQNFTAQAEANTQIEVKNAVGEIVGLGYVDGAGNVSGY
LYQVYLHGEELTFVVVDRAGNRSTEVKQNALIDDIAPNPIENIVLDINGQ
NFTAQAEANTQIEVKNAVGEIVGLGYVDGAGNVSGYLYQVYLHGEELTFV
VVDRAGNRSTEVKQNALIDDIAPNPIENILLDANGQNFTAQAEANTQIEV
KNTAGEVIGSGSTDSMGNVSGYFYQVYLHGEELTFVVVDRAGNRSTEVKQ
NALIDDIAPNAIENIIFNENGQNFTAQAEANSKVEVKNAAGFVVGSGYVD
SVGNVSGYLNQVYLKGEELTFVVIDQAGNRSIEVKQTAFLDNTAPENATN
LVFSEDGSYLSGMAFPNATIQIFDQYGQLLNQWNNNVNWDGTFNIYLNSN
YMHGEVFKVVVVDHAGNLSGEVTVKAPLDDIAPVAASDLVFNEDGSSLSG
VAEPNTFIQIFDQNGQQMNTWSQSVNADGTFTIFFGTYNLHGEEFTVIVK
DLAGNVSEAVSVKAPLDDIAPKPIKNIVFDANGQSFTAQAEANSQIEIFD
SFGSQIGWGSTDSTGSVTGYFYQVYLHGEELTFVVIDRVGNRSDEMKLNA
LMDTIAPKPIENIIFNENGQNFTAQAEANSFISVKNAAGEFVGYGYVDST
GNVSGHENQVYLKGEELTFIVIDKAGNQSIEYKQNALTDDIAPNPIENIV
```

```
LNKNGQNFTAQAEADSQIEVKNTAGEVVGSGYVDSIGNVSGSFNQVYLHG
EELTFVVVDRAGNRSTFVKQNALIDDIAPNQIENIVFDVNGQYFTGHAEA
DTRIEVLDQEGNRAGWGYVDSQGNVIGYFNQVYLHGEELTFIVVDIAGNR
SVEVKQNALIDNVAPPAAANITLTSDGLLFGEAEPNSTVEIIDQYGAVIT
TTYVWYDGTFNQWINLSQYQTQNLSIVVKDQAGNRSEVVHELVPVFTNSP
IAATELKLDIDGHILTGKATVGMSVVVTSTDGQTINGGWNNAVNEDGSFA
IQLNDYYLQGQTLQVRVYDQNTNQYSLISEIIAPLDNIAPVINEVVINND
GYGITGQTDSKAIIQVMDADGDLRAEFQADETGYFNASIYPPILRGEQLF
ITAIDLAKNISKPFNITFNADTNAPPSAEHIVVSENGFFIEGTAVAISTV
HIFDVHSNHVATNVADEAGNFNIQLYPPLASGQILRIVVEYNGYQSAYTE
ITAPIDTVAPNAATQLLLFDGNVLSGQAFAYSIVNIFDANNNLVGQTNVG
SDGAFLTHLWYEYWHGETLTVKVVDANQNVSVGTTIVAINDTVVPDVVTQ
LAIDEWGSLTGRVESYATVELTYHFTDQPLSVTSTTALANGMFFIYLDRN
ATSLDLTVIDRAGNRSETISQIISDLPTVIIDHFKGDATDNTYNIDTIDD
FVQFYIVEPYAIYKDVWIDNSYMYSDWVIEGHYEQIWFVDGYYESQWATS
GYSTVQNIYQNQNGITYIDNGTADSDYSRYEQQYYDEVNGQWQEGYELTY
IRSEEGWVDTSHYFDVYIDTSHYFEVWVDTSHYQDINVENSYWESQLVES
GRRDVDLGGHDKIISSVNYSLVGLYQTVNDPTTVDSFLESGRYVEDLELV
GSAHLNATGNALDNLLTGNSGNNVLNGRFGNDTYITNEGTDTIVFQLLNS
QDATGGNGHDTVLDFTLGDIRTNLQADKIDLSFLLIDYSKDVSALAKFIT
VEQDAGNTTISLDRDGEGTMFNSVSLLTLNQVNTTLDELLNNQQIIV
```

---

The invention claimed is:

1. A pharmaceutical composition comprising a polypeptide, an immunological adjuvant, and a pharmaceutically acceptable carrier, vehicle or diluent, wherein said polypeptide consists of:
   a) SEQ ID NO: 27, or
   b) an amino acid sequence consisting of between 30 and 509 contiguous amino acid residues of the amino acid sequence in a), or
   c) an amino acid sequence having a sequence identity of at least 80% with the amino acid sequence of a) or b), where sequence identity is determined by comparing the sequence of option a) or b) with a sequence of equal length therewith according to the formula: $(N_{ref} - N_{dif}) \cdot 100/N_{ref}$, wherein $N_{ref}$ is the number of residues in each of the 2 compared sequences and $N_{dif}$ is the number of residues which are non-identical in the two sequences when they are aligned over their entire lengths and in the same direction, wherein the amino acid sequence of a), b), or c) is optionally fused to an immunogenic carrier molecule, said polypeptide being antigenic in an animal.

2. The pharmaceutical composition according to claim 1, wherein the adjuvant is an aluminium based adjuvant.

3. The pharmaceutical composition according to claim 1, wherein the at least 30 contiguous amino acids are at least or exactly or at most 31, at least or exactly or at most 32, at least or exactly or at most 33, at least or exactly or at most 34, at least or exactly or at most 35, at least or exactly or at most 36, at least or exactly or at most 37, at least or exactly or at most 38, at least or exactly or at most 39, at least or exactly or at most 40, at least or exactly or at most 41, at least or exactly or at most 42, at least or exactly or at most 43, at least or exactly or at most 44, at least or exactly or at most 45, at least or exactly or at most 46, at least or exactly or at most 47, at least or exactly or at most 48, at least or exactly or at most 49, at least or exactly or at most 50, at least or exactly or at most 51, at least or exactly or at most 52, at least or exactly or at most 53, at least or exactly or at most 54, at least or exactly or at most 55, at least or exactly or at most 56, at least or exactly or at most 57, at least or exactly or at most 58, at least or exactly or at most 59, at least or exactly or at most 60, at least or exactly or at most 61, at least or exactly or at most 62, at least or exactly or at most 63, at least or exactly or at most 64, at least or exactly or at most 65, at least or exactly or at most 66, at least or exactly or at most 67, at least or exactly or at most 68, at least or exactly or at most 69, at least or exactly or at most 70, at least or exactly or at most 71, at least or exactly or at most 72, at least or exactly or at most 73, at least or exactly or at most 74, at least or exactly or at most 75, at least or exactly or at most 76 at least or exactly or at most 77, at least or exactly or at most 78, at least or exactly or at most 79, at least or exactly or at most 80, at least or exactly or at most 81, at least or exactly or at most 82, at least or exactly or at most 83, at least or exactly or at most 84, at least or exactly or at most 85, at least or exactly or at most 86, at least or exactly or at most 87, at least or exactly or at most 88, at least or exactly or at most 89, at least or exactly or at most 90, at least or exactly or at most 91, at least or exactly or at most 92, at least or exactly or at most 93, at least or exactly or at most 94, at least or exactly or at most 95, at least or exactly or at most 96, at least or exactly or at most 97, at least or exactly or at most 98, at least or exactly or at most 99, at least or exactly or at most 100, at least or exactly or at most 101, at least or exactly or at most 102, at least or exactly or at most 103, at least or exactly or at most 104, at least or exactly or at most 105, at least or exactly or at most 106, at least or exactly or at most 107, at least or exactly or at most 108, at least or exactly or at most 109, at least or exactly or at most 110, at least or exactly or at most 111, at least or exactly or at most 112, at least or exactly or at most 113, at least or exactly or at most 114, at least or exactly or at most 115, at least or exactly or at most 116, at least or exactly or at most 117, at least or exactly or at most 118, at least or exactly or at most 119, at least or exactly or at most 120, at least or exactly or at most 121, at least or exactly or at most 122, at least or exactly or at most 123, at least or exactly or at most 124, at least or exactly or at most 125, at least or exactly or at most 126, at least or exactly or at most 127, at least or exactly or at most 128, at least or exactly or at most 129, at least or exactly or at most 130, at least or exactly or at most 131, at least or exactly or at most 132, at least or exactly or at most 133, at least or exactly or at most 134, at least, or exactly or at most 135, at least or exactly or at most 136, at least or exactly or at most 137, at least or exactly or at most 138, at least or exactly or at most 139, at least or exactly or at most 140, at least or exactly or at most 141, at least or exactly or at most 142, at least or exactly or at most 143, at least or exactly or at most 144, at least or exactly or at most 145, at least or exactly or at most 146, at least or exactly or at most 147, at least or exactly or at most 148, at least or exactly or at most 149, at least or exactly or at most 150, at least or exactly or at most 151, at least or exactly or at most 152, at least or exactly or at most 15 at least or exactly or at most 154, at least or exactly or at most 155, at least or exactly or at most 156, at least or exactly or at most 157, at least or exactly or at most 158, at least or exactly or at most 159, at least or exactly or at most 160, at least or exactly or at most 161, at least or exactly or at most 162, at least or exactly or at most 163, at least or exactly or at most 164, at least or exactly or at most 165, at least or exactly or at most 16S, at least or exactly or at most 167, at least or exactly or at most 168, at least or exactly or at most 169, at least or exactly or at most 170, at least or exactly or at most 171, at least or exactly or at most 172, at least or exactly or at most 173, at least or exactly or at most 174, at least or exactly or at most 175, at least or exactly or at most 176, at least or exactly or at most 177, at least or exactly or at most 178, at least or exactly or at most 179, at least or exactly or at most 180, at least or exactly or at most 181, at least or exactly or at most 182, at least or exactly or at most 183, at least or exactly or at most 184, at least or exactly or at most 185, at least or exactly or at most 186, at least or exactly or at most 187, at least or exactly or at most 188, at least or exactly or at most 189, at least or exactly or at most 190, at least or exactly or at most 191, at least or exactly or at most 192, at least or exactly or at most 193, at least or exactly or at most 194, at least or exactly or at most 195, at least or exactly or at most 196, at least or exactly or at most 197, at least or exactly or at most 198, at least or exactly or at most 199, at least or exactly or at most 200, at least or exactly or at most 201, at least or exactly or at most 202, at least or exactly or at most 203, at least or exactly or at most 204, at least or exactly or at most 205, at least or exactly or at most 206, at least or exactly or at most 207, at least or exactly or at most 208, at least or exactly or at most 209, at least or exactly or at most 210, at least or exactly or at most 211, at least or exactly or at most 212, at least or exactly or at most 213, at least or exactly or at most 214, at least or exactly or at most 215, at least or exactly or at most 216, at least or exactly or at most 217, at least or exactly or at most 218, at least or exactly or at most 219, at least or exactly or at most 220, at least or exactly or at most 221, at least or exactly or at most 222, at least or exactly or at most 223, at least or exactly or at most 224, at least or exactly or at most 225, at least or exactly or at most 226, at least or exactly or at most 227, at least or exactly or at most 228, at least or exactly or at most 229, at least or exactly or at most 230, at least or exactly or at most 231, at least or exactly or at most 232, at least or exactly or at most 233, at least or exactly or at most 234, at least or exactly or at most 235, at least or exactly or at most 236, at least or exactly or at most 237, at least or exactly or at most 238, at least or exactly or at most 239, at least or exactly or at most 240, at least or exactly or at most 241, at least or exactly or at most 242, at least or exactly or at most 243, at least or exactly or at most 244, at least or exactly or at most 245, at least or exactly or at most 246, at least or exactly or at most 247, at least or exactly or at most 248, at least or exactly or at most 249, at least or exactly or at most 250, at least or exactly or at most 251, at least or exactly or at most 252, at least or exactly or at most 253, at least or exactly or at most 254, at least or exactly or at most 255, at least or exactly or at most 256, at least or exactly or at most 257, at least or exactly or at most 258, at least or exactly or at most 259, at least or exactly or at most 260, at least or exactly or at most 261, at least or exactly or at most 262, at least or exactly or at most 263, at least or exactly or at most 264, at least or exactly or at most 265, at least or exactly or at most 266, at least or exactly or at most 267, at least or exactly or at most 268, at least or exactly or at most 269, at least or exactly or at most 270, at least or exactly or at most 271, at least or exactly or at most 272, at least or exactly or at most 273, at least or exactly or at most 274, at least or exactly or at most 275, at least or exactly or at most 276, at least or exactly or at most 277, at least or exactly or at most 278, at least or exactly or at most 279, at least or exactly or at most 280, at least or exactly or at most 281, at least or exactly or at most 282, at least or exactly or at most 283, at least or exactly or at most 284, at least or exactly or at most 285, at least or exactly or at most 266, at least or exactly or at most 287, at least or exactly or at most 288, at least or exactly or at most 289, at least or exactly or at most 290, at least or exactly or at most 291, at least or exactly or at most 292, at least or exactly or at most 293, at least or exactly or at most 294, at least or exactly or at most 295, at least or exactly or at most 296, at least or exactly or at most 297, at least or exactly or at most 298, at least or exactly or at most 299, at least or exactly or at most 300, at least or exactly or at most 301, at least or exactly or at most 302, at least or exactly or at most 303, at least or exactly or at most 304, at least or exactly or at most 305, at least or exactly or at most 306, at least or exactly or at most 307, at least or exactly or at most 308, at least or exactly or at most 309, at least or exactly or at most 310, at least or exactly or at most 311, at least or exactly or at most 312, at least or exactly or at most 313, at least or exactly or at most 314, at least or exactly or at most 315, at least or exactly or at most 316, at least or exactly or at most 317, at least or exactly or at most 318, at least or exactly or at most 319, at least or exactly or at most 320, at least or exactly or at most 321, at least or exactly or at most 322, at least or exactly or at most 323, at least or exactly or at most 324, at least or exactly or at most 325, at least or exactly or at most 326, at least or exactly or at most 327, at least or exactly or at most 328, at least or exactly or at most 329, at least or exactly or at most 330, at least or exactly or at most 331, at least or exactly or at most 332, at least or exactly or at most 333, at least or exactly or at most 334, at least or exactly or at most 335, at least or exactly or at most 336, at least or exactly or at most 337, at least or exactly or at most 338, at least or exactly or at most 339, at least or exactly or at most 340, at least or exactly or at most 341, at least or exactly or at most 342, at least or exactly or at most 343, at least or exactly or at most 344, at least or exactly or at most 345, at least or exactly or at most 346, at least or exactly or at most 347, at least or exactly or at most 348, at least or exactly or at most 349, at least or exactly or at most 350, at least or exactly or at most 351, at least or exactly or at most 352, at least or exactly or at most 353, at least or exactly or at most 354, at least or exactly or at most 355, at least or exactly or at most 356, at least or exactly or at most 357, at least or exactly or at most 358, at least or exactly or at most 359, at least or exactly or at most 360, at least or exactly or at most 361, at least or exactly or at most 362, at least or exactly or at most 363, at least or exactly or at most 364, at least or exactly or at most 365, at least or exactly or at most 366, at least or exactly or at most 367, at least or exactly or at most 368, at least or exactly or at most 369, at least or exactly or at most 370, at least or exactly or at most 371, at least or exactly or at most 372, at least or exactly or at most 373, at least or exactly or at most 374, at least or exactly or at most 375, at least or exactly or at most 376, at least or exactly or at most 377, at least or exactly or at most 378, at least or exactly or at most 379, at least or exactly or at most 380, at least or exactly or at most 381, at least or exactly or at most 382, at least or exactly or at most 383, at least or exactly or at most 384, at least or exactly or at most 385, at least or exactly or at most 386, at least or exactly or at most 387, at least or exactly or at most 388, at least or exactly or at most 389, at least or exactly or at most 390, at least or exactly or at most 391, at least or exactly or at most 392, at least or exactly or at most 393, at least or exactly or at most 394, at least or exactly or at most 395, at least or exactly or at most 396, at least or exactly or at most 397, at least or exactly or at most 398, at least or exactly or at most 399, at least or exactly or at most 400, at least or exactly or at most 401, at least or exactly or at most 402, at least or exactly or at most 403, at least or exactly or at most 404, at least or exactly or at most 405, at least or exactly or at most 406, at least or exactly or at most 407, at least or exactly or at most 408, at least or exactly or at most 409, at least or exactly or at most 410, at least or exactly or at most 411, at least or exactly or at most 412, at least or exactly or at most 413, at least or exactly or at most 414, at least or exactly or at most 415, at least or exactly or at most 416, at least or exactly or at most 417, at least or exactly or at most 418, at least or exactly or at most 419, at least or exactly or at most 420, at least or exactly or at most 421, at least or exactly or at most 422, at least or exactly or at most 423, at least or exactly or at most 424, at least or exactly or at most 425, at least or exactly or at most 426, at least or exactly or at most 427, at least or exactly or at most 428, at least or exactly or at most 429, at least or exactly or at most 430, at least or exactly or at most 431, at least or exactly or at most 432, at least or exactly or at most 433, at least or exactly or at most 434, at least or exactly or at most 435, at least or exactly or at most 436, at least or exactly or at most 437, at least or exactly or at most 438, at least or exactly or at most 439, at least or exactly or at most 440, at least or exactly or at most 441, at least or exactly or at most 442, at least or exactly or at most 443, at least or exactly or at most 444, at least or exactly or at most 445, at least or exactly or at most 446, at least or exactly or at most 447, at least or exactly or at most 448, at least or exactly or at most 449, at least or exactly or at most 450, at least or exactly or at most 451, at least or exactly or at most 452, at least or exactly or at most 453, at least or exactly or at most 454, at least or exactly or at most 455, at least or exactly or at most 456, at least or exactly or at most 457, at least or exactly or at most 458, at least or exactly or at most 459, at least or exactly or at most 460, at least or exactly or at most 461, at least or exactly or at most 462, at least or exactly or at most 463, at least or exactly or at most 464, at least or exactly or at most 465, at least or exactly or at most 466, at least or exactly or at most 467, at least or exactly or at most 468, at least or exactly or at most 469, at least or exactly or at most 470, at least or exactly or at most 471, at least or exactly or at most 472, at least or exactly or at most 473, at least or exactly or at most 474, at least or exactly or at most 475, at least or exactly or at most 476, at least or exactly or at most 477, at least or exactly or at most 478, at least or exactly or at most 479, at least or exactly or at most 480, at least or exactly or at most 481, at least or exactly or at most 482, at least or exactly or at most 483, at least or exactly or at most 484, at least or exactly or at most 485, at least or exactly or at most 486, at least or exactly or at most 487, at least or exactly or at most 488, at least or exactly or at most 489, at least or exactly or at most 490, at least or exactly or at most 491, at least or exactly or at most 492, at least or exactly or at most 493, at least or exactly or at most 494, at least or exactly or at most 495, at least or exactly or at most 496, at least or exactly or at most 497, at least or exactly or at most 498, at least or exactly or at most 499, at least or exactly or at most 500, at least or exactly or at most 501, at least or exactly or at most 502, at least or exactly or at most 503, at least or exactly or at most 504, at least or exactly or at most 505, at least or exactly or at most 506, at least or exactly or at most 507, at least or exactly or at most 508, at least or exactly or at most 509, at least or exactly or at most 510, at least or exactly or at most 511, at least or exactly or at most 512, at least or exactly or at most 513, at least or exactly or at most 514, at least or exactly or at most 515, at least or exactly or at most 516, at least or exactly or at most 517, at least or exactly or at most 518, at least or exactly or at most 519, at least or exactly or at most 520, at least or exactly or at most 521, at least or exactly or at most 522, at least or exactly or at most 523, at least or exactly or at most 524, at least or exactly or at most 525, at least or exactly or at most 526, at least or exactly or at most 527, at least or exactly or at most 528, at least or exactly or at most 529, at least or exactly or at most 530, at least or exactly or at most 531, at least or exactly or at most 532, at least or exactly or at most 533, at least or exactly or at most 534, at least or exactly or at most 535, at least or exactly or at most 536, at least or exactly or at most 537, at least or exactly or at most 538, at least or exactly or at most 539, at least or exactly or at most 540, at least or exactly or at most 541, at least or exactly or at most 542, at least or exactly or at most 543, at least or exactly or at most 544, at least or exactly or at most 545, at least or exactly or at most 546, at least or exactly or at most 547, at least or exactly or at most 548, at least or exactly or at most 549, at least or exactly or at most 550, at least or exactly or at most 551, at least or exactly or at most 552, at least or exactly or at most 553, at least or exactly or at most 554, at least or exactly or at most 555, at least or exactly or at most 556, at least or exactly or at most 557, at least or exactly or at most 558, at least or exactly or at most 559, at least or exactly or at most 560, at least or exactly or at most 561, at least or exactly or at most 562, at least or exactly or at most 563, at least or exactly or at most 564, at least or exactly or at most 565, at least or exactly or at most 566, at least or exactly or at most 567, at least or exactly or at most 568, at least or exactly or at most 569, at least or exactly or at most 570, at least or exactly or at most 571, at least or exactly or at most 572, at least or exactly or at most 573, at least or exactly or at most 574, at least or exactly or at most 575, at least or exactly or at most 576, at least or exactly or at most 577, at least or exactly or at most 578, at least or exactly or at most 579, at least or exactly or at most 580, at least or exactly or at most 581, at least or exactly or at most 582, at least or exactly or at most 583, at least or exactly or at most 584, at least or exactly or at most 585, at least or exactly or at most 586, at least or exactly or at most 587, at least or exactly or at most 588, at least or exactly or at most 589, at least or exactly or at most 590, at least or exactly or at most 591, at least or exactly or at most 592, at least or exactly or at most 593, at least or exactly or at most 594, at least or exactly or at most 595, at least or exactly or at most 596, at least or exactly or at most 597, at least or exactly or at most 598, at least or exactly or at most 599, at least or exactly or at most 600, at least or exactly or at most 601, at least or exactly or at most 602, at least or exactly or at most 603, at least or exactly or at most 604, at least or exactly or at most 605, at least or exactly or at most 606, at least or exactly or at most 607, at least or exactly or at most 608, at least or exactly or at most 609, at least or exactly or at most 610, at least or exactly or at most 611, at least or exactly or at most 612, at least or exactly or t most 613, at least or exactly or at most 614, at least or exactly or at most 615, at least or exactly or at most 616, at least or exactly or at most 617, at least or exactly or at most 618, at least or exactly or at most 619, at least or exactly or at most 620, at least or exactly or at mast 621, at least or exactly or at most 622, at least or exactly or at most 623, at least or exactly or at most 624, at least or exactly or at most 625, at least or exactly or at most 626, at least or exactly or at most 627, at least or exactly or at most 628, at least or exactly or at most 629, at least, or exactly or at most 630, at least or exactly or at most 631, at least or exactly or at most 632, at least or exactly or at most 633, at least or exactly or at most 634, at least or exactly or at most 635, at least or exactly or at most 636, at least or exactly or at most 637, at least or exactly or at most 638, at least or exactly or at most 639, at least or exactly or at most 640, at least or exactly or at most 641, at least or exactly or at most 642, at least or exactly or at most 643, at least or exactly or at most 644, at least or exactly or at most 645, at least or exactly or at most 646, at least or exactly or at most 647, at least or exactly or at most 648, at least or exactly or at most 649, at least or exactly or at most 650, at least or exactly or at most 651, at least or exactly or at most 652, at least or exactly or at most 653, at least or exactly or at most 654, at least or exactly or at most 655, at least or exactly or at most 656, at least or exactly or at most 657, at least or exactly or at most 658, at least or exactly or at most 659, at least or exactly or at most 660, at least or exactly or at most 661, at least or exactly or at most 662, at least or exactly or at most 663, at least or exactly or at most 664, at least or exactly or at most 665, at least or exactly or at most 666, at least or exactly or at most 667, at least or exactly or at most 668, at least or exactly or at most 669, at least or exactly or at most 670, at least or exactly or at most 671, at least or exactly or at most 672, at least or exactly or at most 673, at least or exactly or at most 674, at least or exactly or at most 675, at least or exactly or at most 676, at least or exactly or at most 677, at least or exactly or at most 678, at least or exactly or at most 679, at least or exactly or at most 680, at least or exactly or at most 681, at least or exactly or at most 682, at least or exactly or at most 683, at least or exactly or at most 684, at least or exactly or at most 685, at least or exactly or at most 686, at least or exactly or at most 687, at least or exactly or at most 688, at least or exactly or at most 689, at least or exactly or at most 690, at least or exactly or at most 691, at least or exactly or at most 592, at least or exactly or at most 693, at least or exactly or at most 694, at least or exactly or at most 695, at least or exactly or at most 696, at least or exactly or at most 697, at least or exactly or at most 698, at least or exactly or at most 699, at least or exactly or at most 700, at least or exactly or at most 701, at least or exactly or at most 702, at least or exactly or at most 703, at least or exactly or at most 704, at least or exactly or at most 705, at least or exactly or at most 706, at least or exactly or at most 707, at least or exactly or at most 708, at least or exactly or at most 709, at least or exactly or at most 710, at least or exactly or at most 711, at least or exactly or at most 712, at least or exactly or at most 713, at least or exactly or at most 714, at least or exactly or at most 715, at least or exactly or at most 716, at least or exactly or at most 717, at least or exactly or at most 718, at least or exactly or at most 719, at least or exactly or at most 720, at least or exactly or at most 721, at least or exactly or at most 722, at least or exactly or at most 723, at least or exactly or at most 724, at least or exactly or at most 725, at least or exactly or at most 726, at least or exactly or at most 727, at least or exactly or at most 728, at least or exactly or at most 729, at least or exactly or at most 730, at least or exactly or at most 731, at least or exactly or at most 732, at least or exactly or at most 733, at least or exactly or at most 734, at least or exactly or at most 735, at least or exactly or at most 736, at least or exactly or at most 737, at least or exactly or at most 738, at least or exactly or at most 739, at least or exactly or at most 740, at least or exactly or at most 741, at least or exactly or at most 742, at least or exactly or at most 743, at least or exactly or at most 744, at least or exactly or at most 745, at least or exactly or at most 746, at least or exactly or at most 747, at least or exactly or at most 748, at least or exactly or at most 749, at least or exactly or at most 750, at least or exactly or at most 751, at least or exactly or at most 752, at least or exactly or at most 753, at least or exactly or at most 754, at least or exactly or at most 755, at least or exactly or at most 756, at least or exactly or at most 757, at least or exactly or at most 758, at least or exactly or at most 759, at least or exactly or at most 760, at least or exactly or at most 761, at least or exactly or at most 762, at least or exactly or at most 763, at least or exactly or at most 764, at least or exactly or at most 765, at least or exactly or at most 766, at least or exactly or at most 767, at least or exactly or at most 768, at least or exactly or at most 769, at least or exactly or at most 770, at least or exactly or at most 771, at least or exactly or at most 772, at least or exactly or at most 773, at least or exactly or at most 774, at least or exactly or at most 775, at least or exactly or at most 776, at least or exactly or at most 777, at least or exactly or at most 778, at least or exactly or at most 779, at least or exactly or at most 780, at least or exactly or at most 781, at least or exactly or at most 782, at least or exactly or at most 783, at least or exactly or at most 784, at least or exactly or at most 785, at least or exactly or at most 786, at least or exactly or at most 787, at least or exactly or at most 788, at least or exactly or at most 789, at least or exactly or at most 790, at least or exactly or at most 791, at least or exactly or at most 792, at least or exactly or at most 793, at least or exactly or at most 794, at least or exactly or at most 795, at least or exactly or at most 796, at least or exactly or at most 797, at least or exactly or at most 798, at least or exactly or at most 799, at least or exactly or at most 800, at least or exactly or at most 801, at least or exactly or at most 802, at least or exactly or at most 803, at least or exactly or at most 804, at least or exactly or at most 805, at least or exactly or at most 806, at least or exactly or at most 807, at least or exactly or at most 808, at least or exactly or at most 809, at least or exactly or at most 810, at least or exactly or at most 811, at least or exactly or at most 812, at least or exactly or at most 813, at least or exactly or at most 814, at least or exactly or at most 815, at least or exactly or at most 816, at least or exactly or at most 817, at least or exactly or at most 818, at least or exactly or at most 819, at least or exactly or at most 820, at least or exactly or at most 821, at least or exactly or at most 822, at least or exactly or at most 823, at least or exactly or at most 824, at least or exactly or at most 825, at least or exactly or at most 826, at least or exactly or at most 827, at least or exactly or at most 828, at least or exactly or at most 829, at least or exactly or at most 830, at least or exactly or at most 831, at least or exactly or at most 832, at least or exactly or at most 833, at least or exactly or at most 834, at least or exactly or at most 835, at least or exactly or at most 836, at least or exactly or at most 837, at least or exactly or at most 838, at least or exactly or at most 839, at least or exactly or at most 840, at least or exactly or at most 841, at least or exactly or at most 842, at least or exactly or at most 843, at least or exactly or at most 844, at least or exactly or at most 845, at least or exactly or at most 846, at least or exactly or at most 847, at least or exactly or at most 848, at least or exactly or at most 849, at least or exactly or at most 850, at least or exactly or at most 851, at least or exactly or at most 852, at least or exactly or at most 853, at least or exactly or at most 854, at least or exactly or at most 855, at least or exactly or at most 856, at least or exactly or at most 857, at least or exactly or at most 858, at least or exactly or at most 859, at least or exactly or at most 860, at least or exactly or at most 861, at least or exactly or at most 862, at least or exactly or at most 863, at least or exactly or at most 864, at least or exactly or at most 865, at least or exactly or at most 866, at least or exactly or at most 867, at least or exactly or at most 868, at least or exactly or at most 869, at least or exactly or at most 870, at least or exactly or at most 871, at least or exactly or at most 872, at least or exactly or at most 873, at least or exactly or at most 874, at least or exactly or at most 875, at least or exactly or at most 876, at least or exactly or at most 877, at least or exactly or at most 878, at least or exactly or at most 879, at least or exactly or at most 880, at least or exactly or at most 881, at least or exactly or at most 882, at least or exactly or at most 883, at least or exactly or at most 884, at least or exactly or at most 885, at least or exactly or at most 886, at least or exactly or at most 887, at least or exactly or at most 888, at least or exactly or at most 889, at least or exactly or at most 890, at least or exactly or at most 891, at least or exactly or at most 892, at least or exactly or at most 893, at least or exactly or at most 894, at least or exactly or at most 895, at least or exactly or at most 896, at least or exactly or at most 897, at least or exactly or at most 898, at least or exactly or at most 899, at least or exactly or at most 900, at least or exactly or at most 901, at least or exactly or at most 902, at least or exactly or at most 903, at least or exactly or at most 904, at least or exactly or at most 905, at least or exactly or at most 906, at least or exactly or at most 907, at least or exactly or at most 908, at least or exactly or at most 909, at least or exactly or at most 910, at least or exactly or at most 911, at least or exactly or at most 912, at least or exactly or at most 913, at least or exactly or at most 914, at least or exactly or at most 915, at least or exactly or at most 916, at least or exactly or at most 917, at least or exactly or at most 918, at least or exactly or at most 919, at least or exactly or at most 920, at least or exactly or at most 921, at least or exactly or at most 922, at least or exactly or at most 923, at least or exactly or at most 924, at least or exactly or at most 925, at least or exactly or at most 926, at least or exactly or at most 927, at least or exactly or at most 928, at least or exactly or at most 929, at least or exactly or at most 930, at least or exactly or at most 931, at least or exactly or at most 932, at least or exactly or at most 933, at least or exactly or at most 934, at least or exactly or at most 935, at least or exactly or at most 936, at least or exactly or at most 937, at least or exactly or at most 938, at least or exactly or at most 939, at least or exactly or at most 940, at least or exactly or at most 941, at least or exactly or at most 942, at least or exactly or at most 943, at least or exactly or at most 944, at least or exactly or at most 945, at least or exactly or at most 946, at least or exactly or at most 947, at least or exactly or at most 948, at least or exactly or at most 949, at least or exactly or at most 950, at least or exactly or at most 951, at least or exactly or at most 952, at least or exactly or at most 953, at least or exactly or at most 954, at least or exactly or at most 955, at least or exactly or at most 956, at least or exactly or at most 957, at least or exactly or at most 958, at least or exactly or at most 959, at least or exactly or at most 960, at least or exactly or at most 961, at least or exactly or at most 962, at least or exactly or at most 963, at least or exactly or at most 964, at least or exactly or at most 965, at least or exactly or at most 966, at least or exactly or at most 967, at least or exactly or at most 968, at least or exactly or at most 969, at least or exactly or at most 970, at least or exactly or at most 971, at least or exactly or at most 972, at least or exactly or at most 973, at least or exactly or at most 974, at least or exactly or at most 975, at least or exactly or at most 976, at least or exactly or at most 977, at least or exactly or at most 978, at least or exactly or at most 979, at least or exactly or at most 980, at least or exactly or at most 981, at least or exactly or at most 982, at least or exactly or at most 983, at least or exactly or at most 984, at least or exactly or at most 985, at least or exactly or at most 986, at least or exactly or at most 987, at least or exactly or at most 968, at least or exactly or at most 989, at least or exactly or at most 990, at least or exactly or at most 991, at least or exactly or at most 992, at least or exactly or at most 993, at least or exactly or at most 994, at least or exactly or at most 995, at least or exactly or at most 996, at least or exactly or at most 997, at least or exactly or at most 998, at least or exactly or at most 999, at least or exactly or at most 1000, at least or exactly or at most 1001, at least or exactly or at most 1002, at least or exactly or at most 1003, at least or exactly or at most 1004, at least or exactly or at most 1005, at least or exactly or at most 1006, at least or exactly or at most 1007, at least or exactly or at most 1008, at least or exactly or at most 1009, at least or exactly or at most 1010, at least or exactly or at most 1011, at least or exactly or at most 1012, at least or exactly or at most 1013, at least or exactly or at most 1014, at least or exactly or at most 1015, at least or exactly or at most 1016, at least or exactly or at most 1017, at least or exactly or at most 1018, at least or exactly or at most 1019, at least or exactly or at most 1020, at least or exactly or at most 1021, at least or exactly or at most 1022, at least or exactly or at most 1023, at least or exactly or at most 1024, at least or exactly or at most 1025, at least or exactly or at most 1026, at least or exactly or at most 1027, at least or exactly or at most 1028, at least or exactly or at most 1029, at least or exactly or at most 1030, at least or exactly or at most 1031, at least or exactly or at most 1032, at least or exactly or at most 1033, at least or exactly or at most 1034, at least or exactly or at most 1035, at least or exactly or at most 1036, at least or exactly or at most 1037, at least or exactly or at most 1038, at least or exactly or at most 1039, at least or exactly or at most 1040, at least or exactly or at most 1041, at least or exactly or at most 1042, at least or exactly or at most 1043, at least or exactly or at most 1044, at least or exactly or at most 1045, at least or exactly or at most 1046, at least or exactly or at most 1047, at least or exactly or at most 1048, at least or exactly or at most 1049, at least or exactly or at most 1050, at least or exactly or at most 1051, at least or exactly or at most 1052, at least or exactly or at most 1053, at least or exactly or at most 1054, at least or exactly or at most 1055, at least or exactly or at most 1056, at least or exactly or at most 1057, at least or exactly or at most 1058, at least or exactly or at most 1059, at least or exactly or at most 1060, at least or exactly or at most 1061, at least or exactly or at most 1062, at least or exactly or at most 1063, at least or exactly or at most 1064, at least or exactly or at most 1065, at least or exactly or at most 1066, at least or exactly or at most 1067, at least or exactly or at most 1068, at least or exactly or at most 1069, at least or exactly or at most 1070, at least or exactly or at most 1071, at least or exactly or at most 1072, at least or exactly or at most 1073, at least or exactly or at most 1074, at least or exactly or at most 1075, at least or exactly or at most 1076, at least or exactly or at most 1077, at least or exactly or at most 1078, at least or exactly or at most 1079, at least or exactly or at most 1080, at least or exactly or at most 1081, at least or exactly or at most 1082, at least or exactly or at most 1083, at least or exactly or at most 1084, at least or exactly or at most 1085, at least or exactly or at most 1086, at least or exactly or at most 1087, at least or exactly or at most 1088, at least or exactly or at most 1089, at least or exactly or at most 1090, at least or exactly or at most 1091, at least or exactly or at most 1092, at least or exactly or at most 1093, at least or exactly or at most 1094, at least or exactly or at most 1095, at least or exactly or at most 1096, at least or exactly or at most 1097, at least or exactly or at most 1098, at least or exactly or at most 1099, at least or exactly or at most 1100, at least or exactly or at most 1101, at least or exactly or at most 1102, at least or exactly or at most 1103, at least or exactly or at most 1104, at least or exactly or at most 1105, at least or exactly or at most 1106, at least or exactly or at most 1107, at least or exactly or at most 1108, or exactly or at most 1109 contiguous amino acid residues.

4. The pharmaceutical composition according to claim 1, wherein the sequence identity in c) is at least 85%, at least 90%, at least 91%, at least 92%, at least 93%, at least 94%, at least 95%, at least 96%, at least 97%, at least 98 or at least 99%.

5. The pharmaceutical composition according to claim 1, wherein the at least 30 contiguous amino acid residues has an N-terminal amino acid residue corresponding to any one of amino acid residues 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, 920, 921, 922, 923, 924, 925, 926, 927, 928, 929, 930, 931, 932, 933, 934, 935, 936, 937, 938, 939, 940, 941, 942, 943, 944, 945, 946, 947, 948, 949, 950, 951, 952, 953, 954, 955, 956, 957, 958, 959, 960, 961, 962, 963, 964, 965, 966, 967, 968, 969, 970, 971, 972, 973, 974, 975, 976, 977, 978, 979, 980, 981, 982, 983, 984, 985, 986, 987, 988, 989, 990, 991, 992, 993, 994, 995, 996, 997, 998, 999, 1000, 1001, 1002, 1003, 1004, 1005, 1006, 1007, 1008, 1009, 1010, 1011, 1012, 1013, 1014, 1015, 1016, 1017, 1018, 1019, 1020, 1021, 1022, 1023, 1024, 1025, 1026, 1027, 1028, 1029, 1030, 1031, 1032, 1033, 1034, 1035, 1036, 1037, 1038, 1039, 1040, 1041, 1042, 1043, 1044, 1045, 1046, 1047, 1048, 1049, 1050, 1051, 1052, 1053, 1054, 1055, 1056, 1057, 1058, 1059, 1060, 1061, 1062, 1063, 1064, 1065, 1066, 1067, 1068, 1069, 1070, 1071, 1072, 1073, 1074, 1075, 1076, 1077, 1078, 1079, 1080, and 1081 in SEQ ID NO: 27.

6. The pharmaceutical composition according to claim 1, wherein the polypeptide is fused or conjugated to an immunogenic carrier molecule.

7. The pharmaceutical composition according to claim 6, wherein the immunogenic carrier molecule is a polypeptide that induces T-helper lymphocyte responses in a majority of humans.

8. The pharmaceutical composition according to claim 7, wherein the immunogenic carrier molecule is an immunogenic carrier protein selected from the group consisting of keyhole limpet hemocyanin or a fragment thereof, tetanus toxoid or a fragment thereof, diphtheria toxoid or a fragment thereof.

* * * * *

SEQUENCE LISTING

```
<160> NUMBER OF SEQ ID NOS: 92

<210> SEQ ID NO 1
<211> LENGTH: 60
<212> TYPE: PRT
<213> ORGANISM: Acinetobacter baumannii

<400> SEQUENCE: 1

Met Thr Gln Leu Ile Asn Lys Gly Gly Phe Arg Glu Arg Ala Asn Arg
1               5                   10                  15

Ser Arg Lys Tyr Gln Gln Ser Glu Asn Lys Gln Val Ala Leu Pro Ser
            20                  25                  30

Lys Lys Tyr Gln Pro Gln Thr Lys Leu Gln Asp Asn Gln Ser Glu Met
        35                  40                  45

Ile Gln Ala Lys Ala Gly Thr Ala Glu Thr Ser Asp
    50                  55                  60

<210> SEQ ID NO 2
<211> LENGTH: 66
<212> TYPE: PRT
<213> ORGANISM: Acinetobacter baumannii

<400> SEQUENCE: 2

Met Lys Leu Ala Lys Thr Leu Leu Ala Thr Thr Leu Ala Leu Thr Ala
1               5                   10                  15
```

Ala Ser Thr Phe Ala Ala Ser Lys His Asp Gln Ala His Asn Thr Ala
        20                  25                  30

Gly Glu Glu Lys Val Val Val Ser Thr Gln Glu Gln Ala Asn Thr Ala
            35                  40                  45

Asn Ala Ala Ser Asp Ala Val Gly Ser Ala Ser Glu Ala Ala Pro Ala
    50                  55                  60

Thr Arg
65

<210> SEQ ID NO 3
<211> LENGTH: 66
<212> TYPE: PRT
<213> ORGANISM: Acinetobacter baumannii

<400> SEQUENCE: 3

Met Ile Asp Glu Glu Lys Pro Leu Asn Phe Glu Asp Asp Glu Pro
1               5                   10                  15

Leu Asp Phe Glu Asp Glu Glu Phe Ile Asp Asp Lys Lys Glu Asp Glu
            20                  25                  30

Met Tyr Asn Ser Ile Thr Lys Asp Gly Ser Ser Val Asp Pro Ala Asp
        35                  40                  45

Asp Gly Thr Arg His Ile Arg Pro Glu Asp Gly Asp Pro Ile Glu Ile
    50                  55                  60

Asp Glu
65

<210> SEQ ID NO 4
<211> LENGTH: 73
<212> TYPE: PRT
<213> ORGANISM: Acinetobacter baumannii

<400> SEQUENCE: 4

Met Ser Thr Thr Asn Asn Gln Ala Asn Gln Arg Asn Asn Gln Gln Gln
1               5                   10                  15

Gln Gln Gln Gln Asn Asp Asn Arg Asn Gln Gln Gln His Gly Asn Gln
            20                  25                  30

Gln Gln Asn Asp Gln Gln Gln Asn Gln Gln Gln Gln Gln Asn
        35                  40                  45

Asp Asn Arg Gly Gln Gln Gln Gly Ser Asn Gln Lys Asp Ser Gly Gln
    50                  55                  60

Gln Asn Ser Asn Asn Asn Gln Gln Arg
65                  70

<210> SEQ ID NO 5
<211> LENGTH: 108
<212> TYPE: PRT
<213> ORGANISM: Acinetobacter baumannii

<400> SEQUENCE: 5

Met Ser Ala Lys Leu Val Val Thr Leu Leu Ala Thr Ser Leu Leu Thr
1               5                   10                  15

Val Gly Cys Val Ala Tyr Thr Asp Asp Pro Tyr Tyr Arg Gly Gly Tyr
            20                  25                  30

Gly Tyr His Asp His Asp Asp Arg Tyr Asp Arg Asn Asp Gly Arg
        35                  40                  45

Arg Tyr Ser Glu Trp Glu Arg Lys Arg Trp Glu Arg Lys Arg Leu
    50                  55                  60

-continued

Tyr Glu Gln Gln Arg Lys Asp Ile Arg Glu Gln Lys Asp Arg Arg
 65                  70                  75                  80

Glu Trp Glu Lys Arg His Arg Glu Trp Glu Lys Lys Arg Leu Glu Asp
                 85                  90                  95

Arg Asp His Asp His Arg Asp Tyr Arg His Asp Asp
            100                 105

<210> SEQ ID NO 6
<211> LENGTH: 114
<212> TYPE: PRT
<213> ORGANISM: Acinetobacter baumannii

<400> SEQUENCE: 6

Met Asn Lys Leu Leu Val Ala Leu Gly Leu Ala Ala Thr Val Ala Leu
1               5                   10                  15

Val Gly Cys Asn Lys Asp Lys Ala Pro Glu Thr Gly Ala Thr Thr Gly
                20                  25                  30

Glu His Leu Glu Asn Ala Ala Gln Gln Ala Thr Ala Asp Ile Lys Ser
            35                  40                  45

Ala Gly Asp Gln Ala Ala Ser Asp Ile Ala Thr Ala Thr Asp Asn Ala
    50                  55                  60

Ser Ala Lys Ile Asp Ala Ala Asp His Ala Ala Asp Ala Thr Ala
65                  70                  75                  80

Lys Ala Ala Ala Glu Thr Glu Thr Ala Arg Lys Ala Thr Ala Asp
                85                  90                  95

Thr Ala Gln Ala Val Glu Asn Ala Ala Ala Asp Val Lys Lys Asp Ala
            100                 105                 110

Gln His

<210> SEQ ID NO 7
<211> LENGTH: 126
<212> TYPE: PRT
<213> ORGANISM: ACINETOBACTER BAUMANNII

<400> SEQUENCE: 7

Met Lys Met Thr Ala Lys Ile Ala Leu Phe Ser Ala Ala Ile Val Thr
1               5                   10                  15

Met Gly Ser Leu Ala Ala Cys Gln Ser Thr Thr Gln Pro Pro Lys Pro
                20                  25                  30

Glu His Gly Met Met Gln Asp Gly Pro Arg Asp Gly His His Arg
            35                  40                  45

Met Lys His Arg Glu Phe Thr Pro Glu Gln Lys Ala Ala Trp Glu Gln
    50                  55                  60

His Arg Ala Glu Arg Lys Ala Arg Phe Glu Gln Ile Gln Lys Ala Cys
65                  70                  75                  80

Glu Gly Lys Val Val Gly Gln Thr Val Asn Val Gln Val Gly Asp Lys
                85                  90                  95

Thr Leu Glu Gly Thr Cys Asn Leu Arg Phe Glu Pro Lys Arg Pro Gln
            100                 105                 110

Pro Pro Val Asn Ala Pro Ala Pro Val Ala Thr Gln Ala Lys
        115                 120                 125

<210> SEQ ID NO 8
<211> LENGTH: 139
<212> TYPE: PRT
<213> ORGANISM: Acinetobacter baumannii

<400> SEQUENCE: 8

Met Lys Ala Ile Lys Ile Leu Cys Ile Thr Ser Ser Ile Leu Val Ser
1               5                   10                  15

Ser Ser Leu Phe Ala Glu Thr Pro Gln Pro Gln Gln Val Asn Glu Ala
            20                  25                  30

Thr Ser Lys Thr Met Pro Tyr Gly Asp Asn Pro Ser Leu Gly Arg Val
            35                  40                  45

Leu Leu Tyr Lys Thr Gly Lys Gly Ile Gln Asn Leu Gly Asp Ser Ile
        50                  55                  60

Gln Gly Ala Ser Glu Lys Thr Ser Asn Lys Ile Ser Glu Lys Trp Lys
65                  70                  75                  80

Asp Thr Lys Glu Phe Thr Ala Glu Lys Ala Glu Val Val Gln Gln Lys
                85                  90                  95

Ala Asp Thr Ala Lys Val Phe Thr Glu Gln Lys Ile Glu Gln Ala Lys
            100                 105                 110

Gln Asn Ile Thr Ser Ser Arg Asn Gly Glu Asn Ile Pro Ile Glu Gln
            115                 120                 125

Gly Glu Leu Ser Lys Ser Ser Thr Thr Ala Asn
        130                 135

<210> SEQ ID NO 9
<211> LENGTH: 159
<212> TYPE: PRT
<213> ORGANISM: Acinetobacter baumannii

<400> SEQUENCE: 9

Met Lys Lys Ser Leu Leu Ala Ile Ala Leu Met Ser Thr Leu Leu Val
1               5                   10                  15

Ala Cys Asn Lys His Glu Asn Lys Thr Glu Thr Thr Ser Asp Ala Ser
            20                  25                  30

Thr Pro Val Gln Thr Ala Gln Ser Asn Asn Asn Glu Ala Val Asp Thr
            35                  40                  45

Ala His Thr Ala Glu Asn Ser Leu Asp Trp Asp Gly Lys Tyr Lys Gly
        50                  55                  60

Thr Leu Pro Cys Ala Asp Cys Glu Gly Ile Lys Thr Glu Leu Glu Leu
65                  70                  75                  80

Lys Asp Asp Lys Thr Tyr Glu Leu Thr Glu Thr Tyr Leu Gly Lys Gly
                85                  90                  95

Asp Ala Asn Pro Phe Glu Thr His Gly Lys Phe Thr Phe Asp Lys Asp
            100                 105                 110

Asn Thr Ser Val Ile Thr Leu Asp Asp Lys Ala Gln Asn Arg Lys Phe
            115                 120                 125

Phe Ile Gly Glu Asn Thr Ala Thr Ala Leu Asp Met Glu Gly Lys Lys
        130                 135                 140

Val Glu Gly Ser Leu Ala Glu His Tyr Val Leu Lys Lys Glu Asp
145                 150                 155

<210> SEQ ID NO 10
<211> LENGTH: 162
<212> TYPE: PRT
<213> ORGANISM: Acinetobacter baumannii

<400> SEQUENCE: 10

Met Ala Asn Lys Lys Leu Leu Ile Cys Ala Ala Ile Ala Ala Gly Leu
1               5                   10                  15

Leu Leu Thr Ala Cys Val Lys Lys Glu Thr Pro Lys Glu Glu Glu Gln
            20                  25                  30

```
Asp Lys Val Glu Thr Ala Val Ser Glu Pro Gln Pro Gln Lys Pro Ala
        35                  40                  45
Lys Phe Glu Ser Leu Glu Ser Val Asp Thr Gln Glu Ala Gln Val Gln
 50                  55                  60
Glu Gln Pro Gln Val Val His Arg Glu Thr Ala Asn Thr Thr
 65                  70                  75                  80
Thr Glu Ile Arg Arg Glu Thr Arg Pro Ala Arg Ser Asp Glu Ser Ser
                 85                  90                  95
Gln Thr Gln Val Ala Glu Gln Pro Lys Ser Glu Thr Pro Lys Val Glu
                100                 105                 110
Pro Lys Pro Glu Lys Lys Pro Glu Pro Lys Ala Glu Pro Lys Pro Glu
                115                 120                 125
Lys Ala Gln Ser Lys Pro Ala Ala Lys Ala Thr Glu Pro Ala Asn Thr
        130                 135                 140
Glu Asp Asp Ala Val Ala Ala Ile Ala Ala Ala Thr Pro Ala Leu
145                 150                 155                 160
Lys Asn

<210> SEQ ID NO 11
<211> LENGTH: 166
<212> TYPE: PRT
<213> ORGANISM: Acinetobacter baumannii

<400> SEQUENCE: 11

Met Thr Thr Glu Asn Lys Leu Asp Glu Leu Lys Ala Asn Ala Ala Asp
1               5                   10                  15
Ala Lys Val Gln Gly Glu Lys Ala Leu Asp Asp Leu Lys Glu Asn Val
                20                  25                  30
Lys Glu Lys Gln Thr Ala Gly Lys Glu Ala Ile Ala Asp Lys Val Asp
        35                  40                  45
Glu Leu Lys Thr Lys Ala Ala Asp Ala Lys Val Gln Gly Glu Lys Ala
 50                  55                  60
Leu Glu Asp Leu Lys Glu Asn Val Lys Glu Lys Gln Ala Ala Ala Lys
 65                  70                  75                  80
Glu Ala Val Glu Asp Lys Ala Ser Asp Leu Lys Gly Lys Leu Asp Asp
                 85                  90                  95
Ala Gln His Ser Leu Gln Asp Lys Phe Asp His Leu Arg Thr Glu Ala
                100                 105                 110
Ala His Lys Leu Asp Asp Ala Lys Ala Lys Ala Ala Glu Leu Lys Glu
        115                 120                 125
Glu Ala Ala Thr Lys Phe Asp Glu Leu Lys Thr Gln Ala Thr Ala Lys
        130                 135                 140
Phe Asp Glu Leu Lys Lys Thr Ala Thr Glu Lys Leu Asn Lys Leu Lys
145                 150                 155                 160
Asn His Asp Ser Ala Glu
                165

<210> SEQ ID NO 12
<211> LENGTH: 230
<212> TYPE: PRT
<213> ORGANISM: Acinetobacter baumannii

<400> SEQUENCE: 12

Met His Thr Arg Arg Ile Leu Leu Ala Phe Ser Leu Ala Ala Ser Ala
1               5                   10                  15
```

```
Ala Ser Val Ala Phe Ala Asp Tyr Gln Asn Ile Asn Gln Ser Thr Asp
            20                  25                  30

Ser Asp Arg Leu Glu Gln Leu Ser Lys Thr Leu Ser Gln Gly Ser Tyr
        35                  40                  45

Thr His Pro Asp Asp Leu Asp Leu Pro Ala Ser Ala Lys Val Ser Val
50                  55                  60

Thr Leu Arg Glu Lys Thr Val Glu Leu Asn Asn Asp Ser Leu Ala Lys
65                  70                  75                  80

Lys Tyr Gly Thr Thr Thr Ala Lys Asn Ser Phe Lys Thr Ser Ser Ser
                85                  90                  95

Asn Pro Tyr Ser Trp Leu Val Ser His Pro Leu Pro Asp Thr Val Arg
            100                 105                 110

Val Ser Ser Asn Phe Gly Gly Arg Thr Met Gly Gly Arg Ala Glu His
        115                 120                 125

His Gly Gly Leu Asp Met Ala Ala Pro Ser Gly Thr Pro Ile Tyr Ala
130                 135                 140

Thr Gly Pro Gly Ile Val Thr Lys Ser Gly Trp Gly Thr Gly Tyr Gly
145                 150                 155                 160

Gln Tyr Val Glu Ile Asn His Gly Asn Gly Tyr Leu Thr Arg Tyr Ala
                165                 170                 175

His Ala Ser Arg Leu Met Val Arg Val Gly Asp Gln Val Ser Ala Gly
            180                 185                 190

Asp His Ile Ala Asn Val Gly Cys Thr Gly Arg Cys Thr Gly Pro His
        195                 200                 205

Leu His Tyr Glu Val Val Lys Asp Gly Gln Arg Lys Asn Pro Ser Thr
210                 215                 220

Tyr Leu Ala Met Leu Pro
225                 230

<210> SEQ ID NO 13
<211> LENGTH: 238
<212> TYPE: PRT
<213> ORGANISM: Acinetobacter baumannii

<400> SEQUENCE: 13

Met Gly Met Thr Phe Thr Asp Ile Glu Asn Lys Ser Ala Lys Arg Leu
1               5                   10                  15

Ile Gly Ile Ala Ala Val Ile Phe Leu His Leu Leu Val Ala Tyr Ile
            20                  25                  30

Leu Met Ser Gly Leu Ala Asn Asn Ile Gln Lys Pro Ala Glu Lys Pro
        35                  40                  45

Val Glu Leu Gln Ile Ile Gln Asp Ile Lys Pro Pro Pro Pro Pro Lys
50                  55                  60

Pro Glu Glu Pro Lys Pro Lys Glu Lys Pro Glu Pro Pro Lys Pro Met
65                  70                  75                  80

Val Glu Lys Val Ala Lys Val Pro Glu Pro Pro Lys Glu Val Glu Lys
                85                  90                  95

Val Ala Thr Pro Val Gln Lys Thr Thr Pro Val Ala Gln Thr Thr Lys
            100                 105                 110

Val Ala Thr Pro Ala Pro Ala Pro Ser Thr Pro Ser Pro Ser Pro
        115                 120                 125

Val Ala Ala Pro Ala Pro Val Ala Ala Ala Pro Ala Leu Lys Pro
130                 135                 140

Ala Gly Val Thr Arg Gly Val Ser Glu Gly Ser Ala Gly Cys Glu Lys
145                 150                 155                 160
```

Pro Glu Tyr Pro Arg Glu Ala Leu Met Asn Glu Gln Gly Thr Val
                165                 170                 175

Arg Ile Arg Val Leu Val Asp Thr Ser Gly Lys Val Ile Asp Ala Lys
            180                 185                 190

Val Lys Lys Ser Ser Gly Ser Lys Thr Leu Asp Lys Ala Ala Thr Lys
        195                 200                 205

Ala Tyr Ser Leu Cys Thr Phe Lys Pro Ala Met Lys Asp Gly Val Pro
    210                 215                 220

Gln Gln Asp Trp Tyr Glu Ile Glu Tyr Pro Phe Val Ile Glu
225                 230                 235

<210> SEQ ID NO 14
<211> LENGTH: 253
<212> TYPE: PRT
<213> ORGANISM: Acinetobacter baumannii

<400> SEQUENCE: 14

Met Lys Met Met Lys Thr Ala Ile Val Thr Ala Ser Val Leu Ala Ser
1               5                   10                  15

Ala Ser Ile Phe Ala Gln Ser Ala Gly Val Asn Ala Gly Ala Ser Ala
            20                  25                  30

Gln Val Asn Val Gln Pro Gly Gly Leu Val Ser Gly Val Ala Asn Thr
        35                  40                  45

Val Lys Asn Thr Ala His Thr Val Gly Asn Thr Ala Lys His Ala Gly
    50                  55                  60

His Val Ala Ala Asp Thr Thr Val Lys Ala Thr Lys Lys Thr Thr Gly
65                  70                  75                  80

Lys Val Thr Glu Leu Ser Ser Lys Ala Ala Thr Gly Thr Lys His Val
                85                  90                  95

Ala Ser Glu Ala Val Thr Gly Thr Lys His Phe Ala Thr Glu Ala Ala
            100                 105                 110

Thr Gly Thr Lys Asn Leu Ala Thr Lys Ala Ala Thr Gly Thr Lys Asn
        115                 120                 125

Leu Ala Val Glu Ala Lys Ala Asp Thr Lys Ala His Leu Asp Ala Val
    130                 135                 140

Lys Thr Lys Val Ala Glu Lys Gln Ala Asp Gln Lys Glu Phe Thr Ala
145                 150                 155                 160

Glu Lys Gln Ala Asp Ala Gln Ala Arg Val Asp Ala Val Lys Ala Arg
                165                 170                 175

Val Ala Gln Asn Gln Ala Glu Gln Lys Glu Phe Val Ala Asp Thr Lys
            180                 185                 190

Ala Asp Ala Gln Ala Lys Leu Asn Thr Ala Gln Pro Ala His Gly Val
        195                 200                 205

Asn Ala Gln Thr Gly Val Asn Val Gly Val Asn Val Ala Gly Ile Asn
    210                 215                 220

Ala Asn Ala Asn Val Asn Ala Gly Ala Gln Ala Ser Thr Gln Lys Gly
225                 230                 235                 240

Glu Lys Lys Ser Phe Ile Lys Gly Leu Phe Gly Thr Asn
                245                 250

<210> SEQ ID NO 15
<211> LENGTH: 294
<212> TYPE: PRT
<213> ORGANISM: Acinetobacter baumannii

<400> SEQUENCE: 15

Met Gln Met Lys Lys His Ser Leu Leu Phe Ile Ala Leu Met Ser Thr
1               5                   10                  15

Thr Ser Leu Tyr Ala Asn Ile Pro Ile Glu Ser Arg Gly Leu Ser Gln
            20                  25                  30

Asn Asp Gly Ser Ala Ser Asn Thr Ser Ser Asn Ile Ser Val Pro
        35                  40                  45

Thr Asn Leu Asn Trp Glu Leu Met Gln Lys Asn Gln Gln Leu Glu Asn
50                  55                  60

Asp Ile Arg Thr Leu Arg Gly Gln Leu Glu Glu Gln Ala Asn Asp Ile
65                  70                  75                  80

Glu Gln Leu Lys Lys Asp Leu Ala Asn Arg Tyr Thr Asp Leu Asp Gln
                85                  90                  95

Arg Leu Glu Leu Leu His Gln Lys Val Asp Pro Asp Ser Ala Thr Gln
            100                 105                 110

Asp Asp Ser Ser Asn Ala Thr Ser Asp Asn Thr Thr Pro Ala Ser Ala
        115                 120                 125

Pro Ala Pro Gln Thr Thr Glu Ser Asn Lys Val Ala Ala Val Pro Ala
130                 135                 140

Thr Gln Thr Ser Glu Gln Gln Pro Ser Ala Pro Thr Thr Thr Thr Gln
145                 150                 155                 160

Pro Ala Pro Ala Ala Ala Gln Asn Gln Ser Asn Ser Leu Glu Leu Glu
            165                 170                 175

Lys Ala Ala Tyr Thr Val Ala Leu Asp Ala Tyr Lys Gln Gly Gly Ala
        180                 185                 190

Lys Lys Ala Ile Ala Pro Met Gln Asn Phe Ile Lys Asn His Pro Asn
            195                 200                 205

Ser Ile Tyr Thr Gly Asn Ala Tyr Phe Trp Leu Ala Glu Phe His Leu
210                 215                 220

Ala Thr Asp Pro Val Asn Tyr Asn Glu Ala Lys Lys Asn Tyr Asn Val
225                 230                 235                 240

Val Ala Asn Gln Tyr Pro Asn Ser Ser Lys Ala Pro Arg Ala Leu Tyr
            245                 250                 255

Gln Leu Tyr Ser Ile Ala Lys Asp Val Asp Lys Asn Thr Val Ser Ala
        260                 265                 270

Asn Gln Tyr Lys Asn Lys Leu Leu Ser Gln Tyr Pro Lys Ser Glu Glu
            275                 280                 285

Ala Lys Phe Phe Asn Lys
        290

<210> SEQ ID NO 16
<211> LENGTH: 356
<212> TYPE: PRT
<213> ORGANISM: Acinetobacter baumannii

<400> SEQUENCE: 16

Met Ser Met Asn Asn Lys Gln Arg Trp Met Gly Gly Val Val Leu Leu
1               5                   10                  15

Gly Gly Gly Val Leu Leu Ala Ala Leu Leu Leu Lys Gly Asn Glu Glu
            20                  25                  30

Ile Lys Gln Val Asp Val Gln Pro Gln Thr Ser Thr Ser Pro Lys Leu
        35                  40                  45

Gln Ala Lys Pro Lys Gln Ser Ala Gln Glu Gly Gln Met Val Gln Leu
50                  55                  60

Gln Pro Leu Ala Val Asp Val Glu Thr Glu Lys Arg Leu Leu Glu Glu

```
            65                  70                  75                  80
        Gln Arg Arg Ser Arg Glu Lys Ala Val Ala Glu Gln Glu Ala Arg Ala
                        85                  90                  95

Ala Glu Phe Leu Ala Met Gln Gln Ala Glu Ala Asp Ala Ala Arg
                    100                 105                 110

Lys Ala Ala Ala Glu Tyr Ala Ala Ile Asn Ala Arg Arg Ala Ala Ala
                    115                 120                 125

Gln Glu Ser Ser Asp Asn Ile Pro Pro Glu Val Ala Gly Ser Glu Asn
                130                 135                 140

Lys Ala Lys Gly Gln Gln Thr Asp Thr Lys Lys Ser Val Asp Leu Ala
        145                 150                 155                 160

Lys Ala Asp Ala Asp Lys Lys Ala Ala Glu Ala Lys Arg Leu Ala Glu
                        165                 170                 175

Ala Asp Lys Lys Ala Ala Glu Ala Lys Arg Gln Ala Glu Ala Asp Lys
                    180                 185                 190

Lys Ala Ala Glu Ala Lys Arg Gln Ala Glu Ala Asp Lys Lys Ala Ala
                    195                 200                 205

Glu Ala Lys Arg Gln Ala Glu Ala Asp Lys Lys Ala Ala Glu Ala Lys
                210                 215                 220

Arg Gln Ala Glu Ala Asp Lys Lys Ala Ala Glu Ala Lys Arg Gln Ala
        225                 230                 235                 240

Glu Ala Asp Lys Lys Ala Ala Glu Ala Lys Arg Lys Ala Glu Ala Glu
                        245                 250                 255

Lys Lys Ala Glu Ala Glu Lys Ala Arg Glu Leu Leu Glu Asn Gly Asp
                    260                 265                 270

Lys Lys Trp Met Val Gln Val Ala Leu Ala Ala Asn Gln Ala Asn Ala
                275                 280                 285

Asp Ala Val Val Ser Lys Leu Arg Ala Lys Gly Tyr Lys Val Thr Thr
            290                 295                 300

Ser Pro Thr Ser Lys Gly Ile Arg Ile Met Val Gly Pro Ala Lys Asp
        305                 310                 315                 320

Arg Asp Thr Ala Asp Thr Thr Arg Lys Lys Ile Thr Ser Asp Ala Ser
                        325                 330                 335

Leu Asn Met Lys Ser Ala Trp Val Ile Asp Trp Val Pro Leu Asp Gln
                    340                 345                 350

Arg Lys Ser Asp
                355

<210> SEQ ID NO 17
<211> LENGTH: 367
<212> TYPE: PRT
<213> ORGANISM: Acinetobacter baumannii

<400> SEQUENCE: 17

Met Ala Asn Thr Arg Tyr Glu Asp Asp Asn Asn Ser Ser Gly Thr Ser
        1               5                   10                  15

Asn Arg Gly Phe Ala Ser Met Asp Pro Glu Arg Val Arg Glu Ile Ala
                    20                  25                  30

Ser Lys Gly Gly Arg Ala Ala His Ala Ser Gly Asn Ala His Glu Phe
                35                  40                  45

Thr Ser Glu Glu Ala Arg Glu Ala Gly Arg Ala Ala His Ala Ser Gly
            50                  55                  60

Asn Ala His Glu Phe Thr Ser Glu Glu Ala Arg Glu Ala Gly Ala Leu
        65                  70                  75                  80
```

Ser His Lys Asn Asp Asp Arg Asn Gly Arg Gly Ser Arg Tyr Asp
                85                  90                  95
Asp Asp Glu Asp Asp Asp Arg Gly Arg Ser Gly Arg Gly Arg Gly
            100                 105                 110
Arg Ser Arg Tyr Asp Asp Asp Glu Asp Asp Arg Gly Arg Ser
        115                 120                 125
Gly Gly Arg Gly Arg Gly Arg Gly Asp Asp Asp Glu Asp Asp
    130                 135                 140
Asp Arg Gly Arg Ser Gly Gly Arg Gly Arg Ser Arg Asp Asp
145                 150                 155                 160
Asp Asp Glu Asp Asp Arg Gly Arg Ser Gly Gly Arg Gly Arg Gly
            165                 170                 175
Arg Ser Arg Arg Asp Asp Asp Glu Asp Asp Arg Gly Arg Ser
        180                 185                 190
Gly Gly Arg Gly Arg Gly Arg Ser Arg Arg Asp Asp Asp Glu Asp
    195                 200                 205
Asp Asp Arg Gly Arg Ser Gly Gly Arg Gly Arg Ser Arg Tyr
        210                 215                 220
Asp Asp Asp Asp Glu Asp Asp Arg Gly Arg Ser Gly Gly Arg Gly
225                 230                 235                 240
Arg Gly Arg Ser Arg Arg Asp Asp Asp Glu Asp Asp Arg Gly
            245                 250                 255
Arg Ser Gly Gly Arg Gly Arg Gly Arg Ser Arg Tyr Asp Asp Asp
        260                 265                 270
Glu Asp Asp Asp Arg Gly Arg Ser Gly Gly Arg Gly Arg Ser
        275                 280                 285
Arg Arg Asp Asp Asp Glu Asp Asp Arg Gly Arg Ser Gly Gly
290                 295                 300
Arg Gly Arg Gly Arg Ser Arg Tyr Asp Asp Asp Glu Asp Asp Asp
305                 310                 315                 320
Arg Gly Arg Ser Gly Gly Arg Gly Arg Ser Arg Ser Arg Asp Asp
            325                 330                 335
Asp Asp Asp Asp Asp Asp Arg Arg Gly Arg Ser Asp Gly Arg Gly Gln
        340                 345                 350
Asn Ser Arg Asn Gln Lys Arg Asp Ala Tyr Gly Arg Phe Thr Ser
        355                 360                 365

<210> SEQ ID NO 18
<211> LENGTH: 420
<212> TYPE: PRT
<213> ORGANISM: Acinetobacter baumannii

<400> SEQUENCE: 18

Met Leu Tyr Val Ile Pro Phe Ile Ile Leu Leu Val Val Ala Val Ile
1               5                   10                  15
Leu Lys Lys Arg Glu Asn Ser Gln Lys Gln Glu Ala Thr Ser Pro Lys
                20                  25                  30
Asn Ile Asn Arg Lys Ser Gly Lys Lys Ala Ser Ala Lys Ser Ser Lys
            35                  40                  45
Ser Ser Arg Glu Lys Ile Lys Ala Lys Val Ile Glu Glu Asn Ile Pro
        50                  55                  60
Ala Ile Pro Gln Ser Asn Pro Val Pro Glu Ala Leu Arg His Asn Ile
65                  70                  75                  80
Gln Gln Leu Ile Gln Glu Lys Gln Phe Ser Ala Ala Glu Ala Gln Val
                85                  90                  95

```
Asn Gln Ala Leu Lys Lys Asp Asn Thr Gln His Glu Leu Tyr Leu Leu
                100                 105                 110

Leu Leu Glu Ile His Ile Ala Gln Lys Asp Glu Phe Ala Ile Gln Gln
            115                 120                 125

Leu Ile Ser His Ile Arg Ser Leu Gly Leu Asn Glu Ile Ala Ala Gln
        130                 135                 140

Ala Glu Thr Arg Gln Lys Glu Tyr Glu Ser Ser Gln Pro Asp Ala
145                 150                 155                 160

Ile Asp Phe Pro Gln Ala Gln Thr Tyr Glu Glu Pro Lys Asn Thr Asp
                165                 170                 175

Thr Thr Ala Gln Phe Asp Glu Leu Thr Thr Ser Ser Glu Ala Ser
            180                 185                 190

Phe Asp Asp Leu Gln Lys Asp Tyr Thr Pro Val Lys Gln Glu Pro Ala
                195                 200                 205

Ile Glu Ile Glu Pro Leu Glu Phe Asn Phe Ser Phe Glu Gln Asn Ser
            210                 215                 220

Ala Thr Glu Asn Thr Asn Gln Pro Ala Gln Gln Pro Glu Leu Ser Ser
225                 230                 235                 240

Thr Gln Glu Thr Asn Glu Leu Ala Asp Leu Glu Phe Ser Phe Asp Leu
                245                 250                 255

Ala Pro Leu His Glu Thr Glu Glu Lys Ser Gln Ala Val Glu Val Lys
            260                 265                 270

Ala Asp Gln Glu Asn Ser Ile Asn Ala Leu Asp Phe Asn Phe Asp Leu
                275                 280                 285

Asn Pro Ser Ser Ser Glu Thr Lys Ser Val Gln Gln Ala Pro Ser Leu
            290                 295                 300

Asp Glu Ile Lys Leu Ile Glu Gln Ala Pro Leu Glu Ala Thr Ser Ile
305                 310                 315                 320

Ala Pro Leu Glu Phe Ser Leu Asp Gly Pro Ala Leu Val Pro Ala Pro
                325                 330                 335

Glu Leu Glu Thr Gln Asn His Ile Asp Val Val Asn Glu Ala Ala Thr
            340                 345                 350

Gln Thr Gln Ile Glu Asp Pro Leu Leu Glu Ala Phe Pro Glu Leu Lys
            355                 360                 365

Gln Ile Asn Glu Asn Glu Leu Asp Leu Lys Leu Ala Glu Gln Tyr Ile
            370                 375                 380

Lys Phe Gly Ala Asn Gln Ala Ala Arg Asn Leu Leu Gln Gly Asp Glu
385                 390                 395                 400

Gln Lys Phe Asn Thr Glu Gln Gln Gln His Ala Lys Asn Leu Leu Asn
                405                 410                 415

Arg Ile Ala Ser
            420

<210> SEQ ID NO 19
<211> LENGTH: 445
<212> TYPE: PRT
<213> ORGANISM: Acinetobacter baumannii

<400> SEQUENCE: 19

Met Pro Lys Ile Lys Pro Ile Lys Leu Val Ile Ile Val Val Cys Ile
1               5                   10                  15

Ala Ile Ile Ala Val Leu Ala Trp Lys Phe Leu Lys Pro Lys Gln Gln
            20                  25                  30

Gln Pro Gln Tyr Ile Thr Ala Glu Val Thr Arg Gly Asp Ile Glu Asn
```

```
            35                  40                  45
Asn Val Leu Ala Thr Gly Thr Leu Asp Ala Thr Lys Leu Ile Ser Val
 50                  55                  60
Gly Ala Gln Val Ser Gly Gln Val Lys Lys Met Tyr Val Gln Leu Gly
 65                  70                  75                  80
Asp Gln Val Lys Gln Gly Leu Ile Ala Gln Ile Asp Ser Thr Thr
                 85                  90                  95
Gln Glu Asn Ser Leu Lys Thr Ser Asp Ala Asn Ile Lys Asn Leu Glu
                100                 105                 110
Ala Gln Arg Leu Gln Gln Ile Ala Ser Leu Asn Glu Lys Gln Leu Glu
                115                 120                 125
Tyr Arg Arg Gln Gln Gln Met Tyr Ala Gln Asp Ala Thr Pro Arg Ala
                130                 135                 140
Asp Leu Glu Ser Ala Glu Ala Ala Tyr Lys Thr Ala Gln Ala Gln Val
145                 150                 155                 160
Lys Ala Leu Asp Ala Gln Ile Glu Ser Ala Lys Ile Thr Arg Ser Thr
                165                 170                 175
Ala Gln Thr Asn Ile Gly Tyr Thr Arg Ile Val Ala Pro Thr Asp Gly
                180                 185                 190
Thr Val Val Ala Ile Val Thr Glu Glu Gly Gln Thr Val Asn Ala Asn
                195                 200                 205
Gln Ser Ala Pro Thr Ile Val Lys Ile Ala Lys Leu Gln Asn Met Thr
210                 215                 220
Ile Lys Ala Gln Val Ser Glu Ala Asp Ile Met Lys Val Glu Lys Gly
225                 230                 235                 240
Gln Gln Val Tyr Phe Thr Thr Leu Gly Asp Glu Thr Lys Arg Tyr Ala
                245                 250                 255
Thr Leu Arg Gln Ile Glu Pro Ala Pro Asp Ser Ile Ser Ser Glu Ser
                260                 265                 270
Asn Ser Thr Thr Ser Ser Thr Thr Ser Ser Ala Val Tyr Tyr Asn Ala
                275                 280                 285
Leu Phe Asp Val Pro Asn Thr Asp Gly Lys Leu Arg Ile Asp Met Thr
290                 295                 300
Ala Gln Val Tyr Ile Val Leu Asn Ser Ala Lys Asn Ala Leu Leu Val
305                 310                 315                 320
Pro Ser Ser Ala Leu Ser Ser Lys Gln Phe Ser Gly Gln Arg Lys Gln
                325                 330                 335
Gly Gln Ser Ala Asp Lys Ala Ser Ser Thr Pro Ser Ala Glu Arg Lys
                340                 345                 350
His Gln Gly Asn Gly Val Arg Leu Glu Arg Leu Asn Leu Thr Pro Glu
                355                 360                 365
Gln Lys Gln Leu Ile Glu Gln Gly Lys Ala Thr Leu Ser Val Val Arg
                370                 375                 380
Val Leu Gln Ala Asp Gly Thr Thr Lys Pro Thr Gln Ile Leu Val Gly
385                 390                 395                 400
Ile Asn Asn Arg Val Asn Ala Gln Val Leu Ala Gly Leu Lys Gln Gly
                405                 410                 415
Asp Gln Val Val Ile Ala Asp Ser Ser Glu Asn Ser Ala Ala Ser Ala
                420                 425                 430
Asn Ser Gly Asn Asn Arg Arg Arg Gly Pro Met Gly Met
                435                 440                 445

<210> SEQ ID NO 20
```

<211> LENGTH: 711
<212> TYPE: PRT
<213> ORGANISM: Acinetobacter baumannii

<400> SEQUENCE: 20

```
Met Asn Ile Pro Pro Arg Pro Phe Lys Leu Ser Val Ile Ala Cys Ala
1               5                   10                  15

Ile Cys Tyr Ala Asn Leu Thr Tyr Ala Gln Asp Ala Gln Val Gln Ala
            20                  25                  30

Leu Gln Thr Ile Gln Val Lys Ala Ser Asn Ala Glu Gln Ser Ser Glu
        35                  40                  45

Gln Thr Lys Ala Tyr Asn Val Lys Asn Ser Ser Ala Thr Lys Leu
50                  55                  60

Asn Ile Glu Ala Lys Glu Thr Pro Gln Thr Ile Asn Val Val Thr Arg
65                  70                  75                  80

Gln Gln Ile Glu Asp Phe Gly Leu Thr Ser Thr Arg Asp Val Leu Arg
                85                  90                  95

Asn Thr Pro Gly Val Thr Val Ser Asn Gln Glu Thr Glu Arg Thr Thr
            100                 105                 110

Tyr Met Ala Arg Gly Phe Glu Ile Ser Asn Ile Leu Thr Asp Gly Val
        115                 120                 125

Gly Phe Pro Leu Ser Gly Tyr Asn Tyr Asn Asn Thr Asn Pro Asp Thr
    130                 135                 140

Tyr Phe Tyr Asp Arg Val Glu Val Val Lys Gly Ala Asp Ser Leu Thr
145                 150                 155                 160

Asn Ala Phe Gly Asp Pro Ser Ala Thr Ile Asn Asn Ile Arg Lys Arg
                165                 170                 175

Pro Thr Gln Glu Phe Gln Ala Ser Gly Gly Val Ser Tyr Gly Ser Trp
            180                 185                 190

Asp Thr Gln Arg Tyr Glu Ala Asp Val Ser Gly Ser Ile Leu Pro Ser
        195                 200                 205

Gly Lys Val Arg Gly Arg Ile Met Gly Tyr Glu Gln Thr Gly Asp Ser
    210                 215                 220

Tyr Leu Asp Arg Tyr Ser Ala Glu Lys Asn Gly Phe Ala Gly Ile Val
225                 230                 235                 240

Glu Ala Asp Leu Thr Asp Ser Thr Leu Leu Thr Ala Gly Tyr Ser Gln
                245                 250                 255

Glu Gln Asn Lys Pro Asn Ala Asn Asn Trp Gly Ala Leu Pro Leu Leu
            260                 265                 270

Asp Ala Asn Gly Lys Gln Ile Ser Tyr Asp Arg Ser Tyr Asn Pro Asn
        275                 280                 285

Pro Asp Trp Ala His Trp Asp Asn Glu Thr Gln Asn Ala Phe Val Glu
    290                 295                 300

Leu Lys Gln Lys Leu Asn Asp Gln Trp Asn Ala Lys Leu Thr Tyr Asn
305                 310                 315                 320

Tyr Leu Asp Thr Lys His Asn Ser Arg Leu Tyr Tyr Gly Tyr
                325                 330                 335

Pro Lys Ala Asp Gly Ser Gly Val Ser Leu Thr Pro Trp Gly Gly Gln
            340                 345                 350

Glu His Gln Glu Lys His Ala Val Asp Phe Asn Leu Glu Gly Thr Tyr
        355                 360                 365

Lys Leu Phe Asn Arg Glu His Glu Ala Thr Leu Gly Tyr Ser Tyr Val
    370                 375                 380

Arg Asn His Gln Gln Asp Lys Gln Ser Thr Gly Thr Ile Asn Asp Ser
```

```
                385                 390                 395                 400
Asn Val Ile Lys Ser Thr Thr Thr Asp Trp Ala Ser Trp Thr Pro Gln
                405                 410                 415

Ser Ile Thr Trp Ser Asp Phe Thr Glu Ala Ala Asn Tyr Lys Gln Asn
                420                 425                 430

Ile Asn Ser Ile Tyr Ala Ala Thr Arg Leu His Leu Asn Glu Asp Leu
                435                 440                 445

Lys Leu Leu Leu Gly Ala Asn Tyr Val Gln Ala Glu Ser Lys Gly Glu
                450                 455                 460

Ser Tyr Ser Ser Pro Met Ser Tyr Ser Glu Ser Lys Val Ser Pro Tyr
465                 470                 475                 480

Val Gly Leu Thr Tyr Asn Phe Thr Pro Glu Tyr Thr Gly Tyr Met Ser
                485                 490                 495

Tyr Thr Ser Ile Phe Arg Pro Gln Thr Gly Ile Asp Lys Asp Thr Asn
                500                 505                 510

Gln Ala Leu Lys Pro Ile Glu Gly Lys Ser Tyr Glu Met Gly Val Lys
                515                 520                 525

Ser Ser Trp Leu Asp Asp Arg Leu Thr Gly Thr Leu Ser Val Phe Lys
530                 535                 540

Thr Glu Gln Asn Asn Tyr Pro Leu Arg Asn Ser Asp Gly Asn Pro Leu
545                 550                 555                 560

Asn Arg Lys Val Pro Thr Ser Asp Leu Glu Ser Gln Gly Val Glu Val
                565                 570                 575

Gly Leu Ser Gly Gln Ile Thr Asp Asn Val Asn Leu Ser Phe Gly Tyr
                580                 585                 590

Ala Gln Phe Ser Ile Lys Asp Thr Lys Asn Gly Gly Glu Ala Arg Thr
                595                 600                 605

Tyr Asn Pro Asn Gln Thr Leu Asn Leu Leu Thr Thr Tyr Thr Pro Pro
                610                 615                 620

Val Leu Pro Lys Leu Lys Val Gly Ala Gly Leu Gln Trp Gln Asp Gly
625                 630                 635                 640

Ile Lys Leu Tyr Asp Ser Asn Val Asn Gly Thr Ile Lys Gln Asp Ala
                645                 650                 655

Tyr Ala Leu Val Asn Leu Met Ala Ser Tyr Glu Val Asn Asp His Ile
                660                 665                 670

Thr Leu Gln Ala Asn Gly Asn Asn Ile Phe Asp Lys Lys Tyr Leu Asn
                675                 680                 685

Ser Phe Pro Asp Gly Gln Ala Phe Tyr Gly Ala Pro Ala Asn Tyr Thr
                690                 695                 700

Val Ala Val Lys Phe Lys Tyr
705                 710

<210> SEQ ID NO 21
<211> LENGTH: 727
<212> TYPE: PRT
<213> ORGANISM: Acinetobacter baumannii

<400> SEQUENCE: 21

Met Lys Leu Gln Thr Ile Ala Cys Ala Val Ala Ile Ala Thr Gly Gly
1               5                   10                  15

Leu Phe Phe Ser His Thr Met Asn Glu Ala Arg Ala Ala Thr Asn Thr
                20                  25                  30

Ala Ala Val Ser Gln Ser Ile Gln Pro Thr Gln Glu Gln Ala Leu Val
                35                  40                  45
```

```
Ala Arg Gln Leu Ala Thr Leu Val Asp Arg Gln His Tyr Leu Asn Met
 50                  55                  60

Arg Leu Asp Ala Asn Thr Ser Asn Arg Ile Leu Asp Met Tyr Leu Asp
 65                  70                  75                  80

Ser Leu Asp Pro Asp His Ser Leu Phe Leu Asp Ala Glu Val Gln Asn
                 85                  90                  95

Tyr Lys Lys Leu Tyr Gly Ser Asn Phe Gly Ala Ser Leu Lys Ala Gly
                100                 105                 110

Asn Leu Thr Gly Pro Phe Ala Ile His Gln Gln Tyr Arg Glu Arg Leu
            115                 120                 125

Lys Gln Phe Tyr Glu Phe Met Leu Ala Glu Leu Lys Lys Pro Gln Asn
130                 135                 140

Leu Lys Gln Pro Asn Thr Phe Ile Glu Val Asp Arg Glu Lys Ala Pro
145                 150                 155                 160

Tyr Phe Lys Thr Ser Ala Glu Gln Gln Asn His Trp Arg Lys Met Leu
                165                 170                 175

Val Ser Gln Leu Ile Asn Leu Thr Ile Ser Arg Glu Glu Glu Gln Ala
            180                 185                 190

Lys Gln Lys Ala Leu Lys Glu Asn Pro Ser Leu Ala Asp Gly Gln Asp
195                 200                 205

Leu Thr Gly Pro Glu Asp Leu Thr Pro Ala Gln Thr Leu Thr Lys Arg
210                 215                 220

Tyr Thr Arg Gln Leu Glu Arg Ile Ser Arg Val Lys Ser Asp Asp Val
225                 230                 235                 240

Leu Asp Lys Thr Leu Asn Ala Met Leu Ala Thr Tyr Asp Pro His Ser
            245                 250                 255

Asn Tyr Tyr Pro Pro Ile Asp Ala Ile Glu Leu Asn Arg Gln Thr Thr
            260                 265                 270

Leu Gln Leu Glu Gly Ile Gly Val Ser Ile Arg Pro Glu Arg Gly Asn
        275                 280                 285

Glu Asp Tyr Thr Lys Ile Glu Thr Ile Val Glu Gly Gly Pro Ala Ser
290                 295                 300

Lys Ser Gly Gln Val Lys Ser Gly Asp Arg Ile Val Gly Val Ala Gln
305                 310                 315                 320

Glu Gly Gly Lys Met Ile Asp Val Val Gly Trp Ser Ser Glu Ile
            325                 330                 335

Val Gly Leu Ile Arg Gly Lys Arg Gly Thr Lys Val Thr Leu Lys Leu
            340                 345                 350

Leu Gly Ala Gly Ala Ser Met Ser Gln Ala Arg Asn Val Thr Leu Val
            355                 360                 365

Arg Asp Val Ile Gln Glu Glu Asp Ala Gly Val Arg Ser Arg Thr Val
370                 375                 380

Glu Val Thr Arg Asp Gly Lys Lys His Leu Leu Gly Val Ile Glu Ile
385                 390                 395                 400

Pro Ser Phe Tyr Phe Asp Tyr Ser Arg Arg Ala Gly Gln Gln Tyr
            405                 410                 415

Arg Ser Val Ser Glu Asp Thr Ala Asn Ala Phe Glu Ala Leu Lys Ala
            420                 425                 430

Lys Lys Val Glu Gly Ile Ile Asp Leu Arg Asn Asp Pro Gly Gly
            435                 440                 445

Ser Leu Glu Glu Val Ala Arg Met Leu Gly Gln Val Ile Lys Ser Gly
450                 455                 460

Pro Val Val Gln Ile Arg Asp Gly Asn Gly Asn Val Ser Val Phe Glu
```

```
                465                 470                 475                 480
Asp Asn Asp Gly Gly Gln Gln Ile Tyr Thr Gly Pro Leu Ala Val Leu
            485                 490                 495

Val Asn Leu Ala Ser Ala Ser Ala Ser Glu Ile Tyr Ser Ala Ala Ile
            500                 505                 510

Gln Asp Tyr Glu Arg Gly Ile Ile Ile Gly Ser Thr Thr Thr Gly Lys
            515                 520                 525

Gly Thr Ala Gln Val Gln Leu Asp Thr Leu Ala Tyr Gly Gln Ala Thr
            530                 535                 540

Leu Thr Gln Arg Lys Phe Tyr Arg Val Thr Gly Gly Ser Thr Gln Asn
545                 550                 555                 560

Lys Gly Val Val Pro Asp Ile Lys Leu Val Asp Ile Tyr Asn Glu Glu
            565                 570                 575

Phe Gly Glu Arg Lys Ser Lys Asn Ala Leu Lys Trp Asp Thr Ile Pro
            580                 585                 590

Thr Ala Pro Phe Lys Arg Glu Gly Ser Val Gln Pro Tyr Val Ala Lys
            595                 600                 605

Leu Ser Gln Leu Ser Glu Gln Arg Val Ala Val Asp Pro Gln Phe Lys
            610                 615                 620

Tyr Leu Asn Lys Arg Thr Ala Ile Ala Lys Val Thr Ser Asp Gln Lys
625                 630                 635                 640

Gln Val Val Leu Asp Ile Asp Lys Arg Ala Glu Leu Leu Ser Leu
            645                 650                 655

Glu Lys Gln Thr Leu Asp Ala Glu Asn Glu Arg Arg Ile Ala Thr Gly
            660                 665                 670

Gln Lys Pro Phe Pro Asn Trp Glu Ser Tyr Gln Ala Ser Leu Asp Ala
            675                 680                 685

Leu Ala Glu Ser Arg Ala Lys Met Lys Ala Asn Gln Arg Pro Ala Leu
            690                 695                 700

Pro Glu Glu Glu Thr Phe Val Asn Glu Ala Ala Asn Val Leu Met Asp
705                 710                 715                 720

Tyr Ala Lys Leu Gln Asn Arg
            725

<210> SEQ ID NO 22
<211> LENGTH: 728
<212> TYPE: PRT
<213> ORGANISM: Acinetobacter baumannii

<400> SEQUENCE: 22

Met Thr Arg Ile Ile Val Ala Ser Lys Glu Gly Leu Asp Val Leu Gln
1               5                   10                  15

Asp Gly Gln Leu Asn Lys Val Val Leu Asn Gln Pro Thr Ile Ile Gln
            20                  25                  30

Ile Gly Val Ser Gln Lys Asp Ile Ala Ser Met Glu Lys Gln Gly Gly
        35                  40                  45

Ser Leu Val Ile His Leu Lys Asn Gly Glu Thr Ile Val Leu Glu Asn
        50                  55                  60

Phe Phe Asn Glu Ala Thr Asn Thr Thr Glu His Ser Leu Val Phe Pro
65              70                  75                  80

Thr Glu Gln Gly Lys Phe Val Glu Ala Gln Phe Asp Ala Gln Gly Lys
                85                  90                  95

Val Ile Asp Tyr Arg Gly Leu Asn His Val Thr Asp Leu Ala Tyr Thr
            100                 105                 110
```

```
Ser Thr Ser Pro Ser Ala Ala Thr Met Ala Val Asp Asn Asp Pro Ser
        115                 120                 125

Phe Ser Met Gly Asn Val Leu Lys Ala Gly Leu Ala Val Leu Ala Ala
130                 135                 140

Glu Gly Leu Tyr Leu Trp Ala Phe Asp Lys Asp Lys Asp Ser
145                 150                 155                 160

Pro Ser Thr Pro Asp Leu Ile Ala Pro Ala Ala Pro Thr Ala Thr Leu
                165                 170                 175

Ala Asp Asp Thr Val Thr Val Thr Gly Lys Thr Glu Ala Asn Ala Lys
                180                 185                 190

Ile Tyr Ile Lys Asp Ala Ala Gly Asn Thr Val Ala Ser Gly Val Ala
                195                 200                 205

Asp Ala Ser Gly Asn Tyr Thr Ile Lys Leu Asp Lys Pro Leu Val Asn
210                 215                 220

Gly Asp Lys Leu Asn Val Ile Ala Gln Asp Ala Ala Gly Asn Asn Ser
225                 230                 235                 240

Lys Val Thr Val Thr Gly Thr Lys Asp Thr Ile Ala Pro Asp Val
                245                 250                 255

Pro Gln Ala Gln Leu Ser Asp Asp Gly Ser Leu Leu Thr Gly Lys Ala
        260                 265                 270

Glu Ala Asn Ala Lys Ile Thr Val Tyr Asp Ala Thr Gly Lys Val Leu
        275                 280                 285

Gly Thr Val Phe Ala Asn Lys Asp Gly Ile Tyr Ser Leu Lys Leu Thr
        290                 295                 300

Pro Pro Leu Thr Ser Glu Ala Gly Gly Lys Val Val Ala Glu Asp Ala
305                 310                 315                 320

Ala Gly Asn Lys Ser Glu Glu Val Lys Ile Ile Ala Gly Lys Asp Thr
                325                 330                 335

Ile Pro Pro Ala Ser Pro Phe Val Glu Val Asn Lys Glu Gly Ser Val
                340                 345                 350

Ile His Gly Lys Thr Glu Ala Asn Ala Lys Val Gln Ile Lys Asp Ala
        355                 360                 365

Asp Gly Lys Val Ile Gly Ser Gly Thr Ala Asp Ala Gln Gly Glu Phe
        370                 375                 380

Gln Ile Thr Leu Ser Pro Ala Leu Lys Glu Ala Gln Lys Gly Thr Val
385                 390                 395                 400

Val Val Glu Asp Ala Ala Gly Asn Val Ser Lys Pro Val Glu Ile Thr
                405                 410                 415

Pro Gly Phe Asp Ser Ile Ala Pro Asp Lys Pro Thr Val Gln Ile Asn
                420                 425                 430

Thr Asp Gly Thr Ser Val Thr Gly Thr Ala Glu Ala Asn Ala Lys Ile
                435                 440                 445

Glu Ile Lys Asp Thr Thr Gly Lys Val Ile Gly Ser Gly Thr Ala Asp
        450                 455                 460

Ala Asn Gly Lys Phe Thr Ile Ser Ile Ser Pro Ala Leu Thr Asp Asn
465                 470                 475                 480

Lys His Ala Ser Val Ser Ala Ile Asp Asn Ala Gly Asn Lys Ser Glu
                485                 490                 495

Val Val Asp Ile Val Gly Thr Lys Asp Thr Thr Pro Pro Ala Lys Pro
                500                 505                 510

Ile Leu Asn Ser Val Asp Asp Val Gly Ala Val Lys Gly Ala Ile
        515                 520                 525

Thr Ala Gly Ser Glu Thr Asp Asp Ala Arg Pro Lys Leu Thr Gly Ser
```

-continued

```
                530                 535                 540
Gly Glu Ala Asn Ala Thr Leu Thr Ile Tyr Asp Asn Gly Val Ala Ile
545                 550                 555                 560

Gly Val Val Thr Val Thr Ser Gly Arg Ser Trp Ser Phe Thr Phe Asp
                565                 570                 575

Lys Asp Leu Ala Leu Gly Lys His Thr Ile Thr Leu Thr Gln Thr Asp
                580                 585                 590

Ala Ala Gly Leu Thr Ser Glu Ala Ser Ser Pro Phe Thr Phe Tyr Val
                595                 600                 605

Val Ala Pro Lys Ala Ala Ser Leu Ser Glu Thr Ser Val Asp Ile Leu
                610                 615                 620

Ser Thr Glu Gly Pro Ser Leu Ala Asp Ser Val Gly Leu His Thr Leu
625                 630                 635                 640

Lys Val Ala Gln Asn Thr Thr Thr Glu Thr Asn Asn Pro Gln Lys Ser
                645                 650                 655

Val Pro Leu Asp Asp Leu Leu Lys Ser Ser Thr Ala Ser Glu Ser Asp
                660                 665                 670

Pro Ile Ala Lys Leu Leu Ser Ser Thr Ala Leu Lys Thr Thr Gln Ala
                675                 680                 685

Ser Glu Pro Ile Glu Val Asn Ala Ser Val Gly Gln Thr Thr Ser Asn
                690                 695                 700

Pro Asn His Pro Leu Pro Asp Thr Thr Ser Ser Val Leu Gln Asn Leu
705                 710                 715                 720

Leu Asp Gln Thr Tyr Pro Val Val
                725
```

<210> SEQ ID NO 23
<211> LENGTH: 754
<212> TYPE: PRT
<213> ORGANISM: Acinetobacter baumannii

<400> SEQUENCE: 23

```
Met Ser Lys Arg Ile Ile Gln Ser Val Leu Ser Val Ser Val Leu Ala
1               5                   10                  15

Ser Met Met Ser Met Ala Phe Ala Ala Gln Asn Glu Gln Glu Gln Ala
                20                  25                  30

Glu Gln Thr Leu Glu Lys Pro Ala Glu Pro Val Lys Leu Glu Thr Ile
                35                  40                  45

Phe Val Thr Ala Glu Glu Gln Val Lys Gln Ser Leu Gly Val Ser Val
            50                  55                  60

Ile Thr Lys Glu Asp Leu Glu Lys Leu Pro Val Arg Asn Asp Ile Ser
65                  70                  75                  80

Asp Tyr Val Arg Arg Met Pro Gly Val Asn Leu Thr Gly Asn Ser Ala
                85                  90                  95

Thr Gly Gln Arg Gly Asn Asn Arg Gln Ile Asp Ile Arg Gly Met Gly
                100                 105                 110

Pro Glu Asn Thr Leu Ile Leu Val Asp Gly Lys Pro Ile Asn Ser Arg
            115                 120                 125

Asn Ser Val Arg Tyr Gly Trp Lys Gly Glu Arg Asp Thr Arg Gly Asp
            130                 135                 140

Ser Asn Trp Val Pro Ala Glu Ala Ile Glu Ser Ile Glu Val Leu Arg
145                 150                 155                 160

Gly Pro Ala Ala Ala Arg Tyr Gly Ser Gly Ala Ala Gly Gly Val Val
                165                 170                 175
```

-continued

```
Asn Ile Ile Thr Lys Lys Val Thr Asn Glu Thr His Gly Ser Val Glu
            180                 185                 190
Phe Tyr Thr Ser Gln Pro Glu Asp Ser Lys Glu Gly Ser Ser Asn Arg
        195                 200                 205
Val Gly Phe Asn Val Ser Gly Pro Leu Ile Lys Asp Val Leu Ser Tyr
    210                 215                 220
Arg Leu Tyr Gly Asn Tyr Asn Lys Thr Glu Ala Asp Val Asp Ile
225                 230                 235                 240
Asn Lys Ser Ile Gly Ser Thr Ala Ala Gly Arg Glu Gly Val Lys Asn
                245                 250                 255
Lys Asp Ile Ser Gly Arg Leu Ala Trp Gln Ala Thr Asp Gln Gln Thr
            260                 265                 270
Val Leu Leu Asp Ile Ser Ser Lys Gln Gly Asn Ile Tyr Ser Gly
        275                 280                 285
Asp Ser Gln Leu Asn Ala Asn Ala Glu Ala Asp Ala Ile Leu Ser Gln
    290                 295                 300
Leu Ile Gly Lys Glu Thr Asn Thr Met Tyr Arg Asp Ser Tyr Ala Leu
305                 310                 315                 320
Thr His Glu Gly Asp Trp Ser Trp Gly Lys Ser Lys Leu Val Ala Gln
                325                 330                 335
Tyr Asp Lys Thr His Asn Lys Arg Leu Pro Glu Gly Leu Ala Gly Ser
            340                 345                 350
Val Glu Gly Lys Ile Asn Asn Leu Asp Asp Lys Ala Thr Ser Arg Leu
        355                 360                 365
Glu Thr Leu Arg Phe Asn Gly Glu Ala Asn Ile Pro Phe Glu Tyr Tyr
    370                 375                 380
Leu Pro Gln Val Leu Thr Val Gly Thr Glu Trp Val Glu Asp Arg Phe
385                 390                 395                 400
Lys Asp Asn Val Ser Thr Thr Gln Gly Lys Asp Ser Ser Gly Ser Gly
                405                 410                 415
Tyr Gly Asp Gln Leu Ala Lys Gly Asp Arg Ser Lys Met Glu Ser Arg
            420                 425                 430
Ile Ala Ser Ala Tyr Ile Glu Asp Asn Leu Lys Val Thr Asp Ser Thr
        435                 440                 445
Asp Val Val Leu Gly Leu Arg Phe Asp Asp His Ser Lys Ser Gly Ser
    450                 455                 460
Asn Trp Ser Pro Ser Leu Asn Ile Thr Gln Lys Leu Asn Asp Asn Phe
465                 470                 475                 480
Thr Leu Lys Gly Gly Val Ala Lys Ala Tyr Lys Ala Pro Asn Met Tyr
                485                 490                 495
Gln Asn Ala Glu Gly Tyr Leu Leu Ser Thr Asn Gly Asn Gly Cys Pro
            500                 505                 510
Ala Asn Ile Glu Ser Arg Cys Leu Leu Gln Gly Asn Gly Asp Leu Lys
        515                 520                 525
Pro Glu Thr Ser Val Asn Lys Glu Leu Gly Ile Gln Phe Gln Arg Asp
    530                 535                 540
Ile Val Asn Ala Ser Leu Thr Trp Phe Arg Asn Asp Tyr Lys Asp Lys
545                 550                 555                 560
Ile Val Ala Gly Thr His Val Val Gly Thr Val Asp Gly Ser Ser Thr
                565                 570                 575
Asn Ala Asn Thr Gly Ala Val Thr Asn Thr Lys Trp Asn Ile Leu Arg
            580                 585                 590
Trp Glu Asn Thr Pro Lys Ala Leu Ile Gln Gly Phe Glu Gly Ser Leu
```

```
                595                 600                 605
Gly Leu Asp Phe Gly Asp Ile Arg Trp Thr Asn Asn Phe Thr Tyr Met
610                 615                 620

Met Asp Ser Lys Asp Lys Gln Thr Gly Asn Pro Leu Ser Leu Val Pro
625                 630                 635                 640

Ile Tyr Thr Ile Asn Ser Ile Phe Asp Tyr Asp Ile Thr Asp Gln Leu
                645                 650                 655

Asp Val Asn Phe Val Phe Thr Gln Tyr Gly Arg Gln Lys Ser Arg Gln
                660                 665                 670

Phe Ala Glu Asn Arg Leu Glu Ser Gly Ile Gly Ser Gly Gly Ala Asn
                675                 680                 685

Ser Ala Leu Lys Pro Ser Thr Val Lys Ser Tyr Ser Thr Ala Gly Ile
690                 695                 700

Asn Val Gly Tyr Lys Phe Ser Asp Gln Ile Ser Thr Arg Val Gly Val
705                 710                 715                 720

Ser Asn Leu Phe Asp Lys Gln Ile Leu Arg Asp Ser Asn Ser Ile Ser
                725                 730                 735

Gln Thr Tyr Asn Glu Pro Gly Arg Ala Tyr Tyr Ala Ser Leu Lys Tyr
                740                 745                 750

Ser Phe

<210> SEQ ID NO 24
<211> LENGTH: 906
<212> TYPE: PRT
<213> ORGANISM: Acinetobacter baumannii

<400> SEQUENCE: 24

Met Pro Ser Lys Ile Lys Phe Lys Gln Ser Thr Leu Ser His Ser Met
1               5                   10                  15

His Leu Ile Leu Lys Met Gln Ser Ile Pro Lys Leu Ile Cys Ser Ser
                20                  25                  30

Leu Leu Leu Ser Leu Cys Val Thr Pro Cys Tyr Ala Gln Ser Ser Ala
                35                  40                  45

Glu Thr Val Ile Pro Glu Ala Asn Gln Thr Val Thr Asp Ser Leu Val
50                  55                  60

Gln Gln Thr Asn Thr Asn Asn Pro Ser Asp Val Pro Ile Thr Asp Val
65                  70                  75                  80

Ala Thr Leu Val Thr Gln Ala Gln Gln Gln Asp Ser Leu Ala Ile
                85                  90                  95

Leu Gln Gln Gln Glu Gln Phe Pro Asn Gln Ile Glu Glu Phe Lys Pro
                100                 105                 110

Ile Thr Leu Asp Asn Leu Glu Asp Leu Pro Val Met Pro Val Asp Gln
                115                 120                 125

Asn Met Ala Asn Glu Ile Tyr Arg Val Ala Glu Glu Ala Lys Asn Glu
                130                 135                 140

Ala Gln Asn Phe Gln Asn Gly Thr Gln Lys Gln Pro Glu Met Val Val
145                 150                 155                 160

Ser Asp Ala Ser Gln Ala Glu Leu His Glu Ile Asn Gln Ala Pro Val
                165                 170                 175

Asn Ile Asp Gln Leu Met His Glu Ile Gln Ser Asp Ser Lys Ile Val
                180                 185                 190

Val Glu Ala Asn Glu Thr Gly Lys Thr Leu Pro Glu Leu Thr Ala Ala
                195                 200                 205

Val Glu Glu Pro Pro Glu Glu Lys Gly Phe Phe Arg Arg Ile Phe Asn
```

```
            210                 215                 220
Lys Ile Arg Pro Pro Arg Val Ile Pro Met Glu Gln Ile Pro Arg Ile
225                 230                 235                 240

Thr Ala Glu Val Thr Gly Ala Pro Asp Asp Leu Ala Lys Asn Ile Lys
                    245                 250                 255

Gly Lys Leu Ser Thr Phe Thr Gln Glu Ser Phe Glu Asp Phe Asn Ala
                260                 265                 270

Ala Leu Pro Gln Leu Arg Ser Leu Ser Asn Gln Ala Ala Gln Ala Val
            275                 280                 285

Gly Tyr Tyr Asn Ala Glu Phe Arg Phe Glu Lys Leu Ser Ala Ser Arg
        290                 295                 300

Val Arg Val Asn Val Thr Pro Asn Glu Pro Val Arg Ile Asn Glu Gln
305                 310                 315                 320

Asn Ile Glu Phe Thr Gly Ala Gly Ala Lys Gln Pro Gln Phe Gln Val
                    325                 330                 335

Ile Arg Leu Val Pro Asp Gln Asp Val Gly Asp Ile Phe Asn His Gly
                340                 345                 350

Leu Tyr Glu Thr Thr Lys Ser Arg Ile Val Asp Ala Ala Ser Asp Asn
            355                 360                 365

Gly Tyr Phe Asp Ala Tyr Trp Arg Leu His Asp Val Lys Val Ser Gln
        370                 375                 380

Pro Glu Asn Lys Ala Asp Ile Asn Leu Lys Tyr Glu Thr Gly Glu Arg
385                 390                 395                 400

Tyr Lys Leu Gly Lys Val Glu Phe Arg Met Ser Asp Pro Ser Lys Pro
                    405                 410                 415

Leu Pro Leu Asn Met Asn Ile Leu Glu Ser Met Ala Pro Trp Lys Glu
                420                 425                 430

Gly Asp Asp Tyr Ala Phe Trp Arg Val Asn Val Leu Ala Asn Asn Leu
            435                 440                 445

Thr Asn Ser Arg Tyr Phe Asn Tyr Thr Leu Val Asp Ser Ile Lys Pro
        450                 455                 460

Asp Pro Ile Glu Lys Pro Leu Glu Leu Pro Pro Asp Leu Gln Ala Leu
465                 470                 475                 480

Val Asp Gln Gln Asn Val Asp Ile Asp Glu Ser Lys Leu Leu Pro Leu
                    485                 490                 495

Glu Gln Gln Gln Leu Ala Lys Ala Arg Gln Leu Ala Ser Ser Ser Lys
                500                 505                 510

Glu Val Thr Gln Asn Val Val Asp Glu Lys Gln Phe Ala Gly Thr Glu
            515                 520                 525

Ser Val Gln Ala Ala Pro Ala Ser Leu Lys Ala Ala Thr Val Gln His
        530                 535                 540

Glu Glu Gln Glu Ser Glu Gln Asp Arg Leu Gln Ala Gln Ala Arg Glu
545                 550                 555                 560

Glu Lys Arg Ile Pro Val Ile Val Thr Leu Asn Ala Asp Lys Leu Asn
                    565                 570                 575

Ser Leu Glu Thr Gly Ile Gly Tyr Gly Thr Asp Thr Gly Ala Arg Leu
                580                 585                 590

Arg Ser Gln Tyr Arg Arg Ser Ile Val Asn Lys Tyr Gly His Ser Phe
            595                 600                 605

Asp Ala Asn Leu Glu Leu Ser Gln Ile Arg Gln Ser Ile Asp Gly Arg
        610                 615                 620

Tyr Ser Ile Pro Tyr Lys His Pro Leu Asn Asp Tyr Phe Asn Ile Val
625                 630                 635                 640
```

Gly Gly Tyr Glu Arg Glu Thr Arg Asp Asp Ile Gly Pro Asp Val Ser
            645                 650                 655

Leu Leu Thr Glu Ser Ala Val Leu Gly Gly Glu Arg Val Ile Lys Lys
        660                 665                 670

Pro Leu Gly Asn Trp Gln His Thr Ile Gly Val Arg Tyr Arg Leu Asp
    675                 680                 685

Arg Leu Thr Gln Lys Gly Asn Val Asp Ile Ser Glu Leu Pro Asp Ala
690                 695                 700

Phe Lys Thr Ala Ala Ser Glu Gln Glu Ala Leu Leu Phe Ser Tyr Glu
705                 710                 715                 720

Thr Ser Lys Thr Ser Ser Asn Thr Arg Leu Asn Pro Thr Lys Ala Phe
            725                 730                 735

Lys Gln Thr Tyr Lys Leu Glu Leu Gly Ser Glu Ser Leu Leu Ser Asp
        740                 745                 750

Ala Asn Met Ala Ile Ala Thr Ala Gly Trp Arg Phe Ile Tyr Ser Leu
    755                 760                 765

Gly Glu Asn Asp Asp His Gln Phe Val Gly Arg Ser Asp Phe Ser Tyr
770                 775                 780

Ile Phe Thr Asp Glu Phe Asp Lys Val Pro Tyr Asn Leu Arg Phe Phe
785                 790                 795                 800

Thr Gly Gly Asp Gln Thr Ile Arg Gly Phe Asp Tyr Lys Ser Leu Ser
            805                 810                 815

Pro Glu Asp Asn Gly Tyr Lys Ile Gly Gly Gln Ala Leu Ala Val Gly
        820                 825                 830

Ser Leu Glu Tyr Asn Tyr Gln Phe Lys Glu Gly Trp Arg Ala Ala Val
    835                 840                 845

Phe Ser Asp Phe Gly Asn Ala Tyr Asp Lys Ser Phe Ser Asn Pro Thr
850                 855                 860

Ala Tyr Ser Val Gly Val Gly Ile Arg Trp Lys Ser Pro Ile Gly Pro
865                 870                 875                 880

Ile Arg Leu Asp Val Ala Ser Gly Ile Ser Asp Asp Asn His Pro Ile
            885                 890                 895

Arg Leu His Phe Phe Ile Gly Pro Gln Leu
        900                 905

<210> SEQ ID NO 25
<211> LENGTH: 974
<212> TYPE: PRT
<213> ORGANISM: Acinetobacter baumannii

<400> SEQUENCE: 25

Met Phe Ile Lys Ser Ile Leu Ser Ser Ile Thr Ser Ile Ile Pro Leu
1               5                   10                  15

Pro Glu Asn Ser Asn Thr Ser Ser Asn Leu Gly Asn Gly Ser Gly Asp
            20                  25                  30

Gly Leu Leu Asn Gly Ile Ser Ser Gly Asn Gly Glu His Asn Tyr Gly
        35                  40                  45

Ile Gly Asn Gly Ile Ala Asp Asp Ala Ser Ile Thr Ala Pro Ile Thr
    50                  55                  60

Ile Pro Leu Asn Leu Ser Gly Asn Ser Ile Thr Leu Ile Gly Asn Ser
65                  70                  75                  80

Ser Ser Ser Ser Val Asn Ser Ser Pro Thr Thr Thr Ser Asn Asn Val
            85                  90                  95

Asn Asp Asn Asp Val Thr Asn Asn Gly Asn Gly Ser Thr Ile Gly Ser

```
            100                 105                 110
Gly Thr Gly Asn Gly Ser Gly Asp Gly Leu Leu Asn Gly Ala Ala Ser
        115                 120                 125
Gly Asn Gly Glu His Asn Tyr Gly Ile Gly Asn Gly Ile Ala Asp Asp
    130                 135                 140
Ala Ser Ile Thr Ala Pro Leu Ser Ile Pro Ile Asn Leu Ala Gly Asn
145                 150                 155                 160
Ser Ile Thr Leu Ile Gly Asp Ser Ser Ser Ser Val Asn Asn Ser
                165                 170                 175
Ala Thr Asn Thr Ser Asn Thr Val Asn Asp Asn Asp Thr Thr Tyr Asn
            180                 185                 190
Gly Asn Gly Ser Gly Gly Asn Gly Ser Gly Asp Gly Leu Leu Asn
        195                 200                 205
Gly Ile Gly Ser Gly Asn Gly Glu Gln Asn Tyr Gly Ile Gly Asn Gly
    210                 215                 220
Ile Ala Asp Asp Ala Ser Ile Thr Ala Pro Ile Thr Leu Pro Ile Asn
225                 230                 235                 240
Leu Ser Gly Asn Ser Ile Thr Leu Ile Gly Asn Ser Ser Ala Ser Ser
                245                 250                 255
Val Asn Ser Ser Pro Thr Thr Thr Ser Asn Thr Val Asn Asp Asn Asp
            260                 265                 270
Thr Thr Tyr Asn Gly Asn Gly Thr Gly Asp Ser Gly Val Ser Ala Leu
        275                 280                 285
Gly Gly Ser Gly Asn Gly Ser Gly Asp Gly Ala Gly Asn Gly Ile Ala
    290                 295                 300
Ser Gly Asn Gly Glu His Asn Tyr Gly Ile Gly Asn Gly Asn Gly Asp
305                 310                 315                 320
Asp Val Asp Ile Thr Ala Pro Ile Thr Gly Val Leu Asn Ile Ser Gly
                325                 330                 335
Asn Ser Phe Thr Leu Ile Gly Asn Ser Ser Ser Ser Val Asn Thr
            340                 345                 350
Ala Pro Thr Thr Thr Ser Asn Thr Val Asn Asp Asn Asp Thr Ile Asp
        355                 360                 365
Asn Gly Asn Ser Gly Gly Thr Gly Ser Gly Ser Gly Asn Gly Ser Gly
    370                 375                 380
Asp Gly Leu Leu Asn Gly Ala Ala Ser Gly Asn Gly Glu His Asn Tyr
385                 390                 395                 400
Gly Ile Gly Asn Gly Asn Gly Asp Asp Val Asp Ile Thr Ala Pro Ile
                405                 410                 415
Thr Gly Val Phe Asn Phe Ser Gly Asn Ser Phe Ser Ile Ile Gly Asn
            420                 425                 430
Ser Ser Ser Ser Ile Asn Thr Ala Pro Thr Thr Thr Thr Asn Thr
        435                 440                 445
Val Asn Asp Asn Asp Val Thr Asp Asn Gly Asn Asp Gly Gly Gly Leu
    450                 455                 460
Val Gly Gly Ser Ser Gly Asn Gly Ser Gly Asp Gly Leu Leu Asn Gly
465                 470                 475                 480
Ala Ala Ser Gly Asn Gly Glu His Asn Tyr Gly Ile Gly Asn Gly Asn
                485                 490                 495
Gly Asp Asp Ala Asp Phe Thr Phe Pro Leu Thr Gly Val Leu Asn Phe
            500                 505                 510
Ser Gly Asn Ser Leu Ser Gly Phe Gly Ser Ser Ser Ser Asp Ser Val
        515                 520                 525
```

```
Asn Val Ala Pro Thr Thr Ala Thr Asn Thr Val Asn Asp Asn Asp Thr
        530                 535                 540

Ile Asp Asn Ala Asn Thr Gly Gly Leu Gly Asp Gly Ser Gly Asn Gly
545                 550                 555                 560

Ser Gly Asp Gly Leu Leu Asn Gly Ala Ala Ser Gly Asn Gly Glu His
                565                 570                 575

Asn Tyr Gly Ile Gly Asn Gly Asn Gly Asp Asp Ala Asp Phe Thr Leu
                580                 585                 590

Pro Phe Thr Gly Gly Leu Asn Ile Leu Gly Asn Ala Leu Ser Gly Ile
                595                 600                 605

Gly Gly Ser Ser Thr Asp Ser Ile Asn Ile Ser Pro Thr Thr Thr Ser
610                 615                 620

Asn Thr Val Asn Asp Asn Asp Thr Thr Asn Asn Gly Asn Thr Ser Gly
625                 630                 635                 640

Gly Val Ile Gly Ser Gly Asp Ser Gly Asn Gly Ser Gly Asp Gly Leu
                645                 650                 655

Leu Asn Gly Ile Ser Ser Gly Asn Gly Glu His Asn Tyr Gly Ile Gly
                660                 665                 670

Asn Gly Asn Gly Asp Asp Val Asp Val Val Ala Pro Ile Thr Thr Pro
                675                 680                 685

Leu Asn Val Leu Gly Asn Ser Phe Ser Phe Ile Gly Gly Glu Gly Thr
690                 695                 700

Gly Asp Ile Leu Gly Pro Ile Thr Gly Ile Ile Gly Ile Gly Ile Gly
705                 710                 715                 720

Asp Gly Asp Ile Leu Ser Pro Ile Thr Gly Ile Ile Gly Ile Gly Ile
                725                 730                 735

Gly Asp Gly Asp Ile Leu Ser Pro Ile Thr Gly Ile Ile Gly Ser Ile
                740                 745                 750

Gly Gly Ile Gly Gly Asp Leu Gly Asp Asn Pro Leu Thr Gly Ile Ile
                755                 760                 765

Gln Ser Gly Ile Asp Val Leu Gln Asn Leu Glu Ser Leu Lys Thr Gly
770                 775                 780

Leu Ile Asn Thr Gly Ile Asp Thr Ile Ala Gly Thr Ile Ile Gly Val
785                 790                 795                 800

Phe Pro Asp Ala Glu His Pro Val Gly Asp Phe Ala Asp Leu Gly Lys
                805                 810                 815

Leu Leu Phe Glu Thr Ser Arg Asp Ser Val Asn Gly Thr Leu Glu Ala
                820                 825                 830

Ile Ser Asp Leu Ala Gly Ala Asp Leu Glu Gly Ala Ser Gly Ser Ile
                835                 840                 845

Thr Gly Val Ile Asp Thr Leu Ile Thr Asn Gly Ser Thr Ala Ser Thr
                850                 855                 860

Ile Ile Gln His Ile Val Gly Asp Asp Leu Val Thr Glu Asn Gly Gly
865                 870                 875                 880

Leu Leu Gly Ser Ile Thr Thr Ile Ile Gly Gly Val Asp Ser Gly Asp
                885                 890                 895

Gly Gly Leu Leu Gly Gly Leu Asp Gly Leu Ile Ser Ile Asn Tyr Gly
                900                 905                 910

Asp Ser Asp Asn Ser Asn Ser Ile Asp Val Glu Asp Ile Leu Gly Asn
                915                 920                 925

Ile Leu Gly Ser Val Gly Ser Asn Gln Gly Ile Ala Val Gly Glu Pro
930                 935                 940
```

Asp Pro Thr Gly Gly Ser Leu Ile His Thr Ile Ser Leu Asn Thr Val
945                 950                 955                 960

Asn Gln Leu Thr Asp Gln Leu Leu His Ala Leu Pro Thr Val
            965                 970

<210> SEQ ID NO 26
<211> LENGTH: 1071
<212> TYPE: PRT
<213> ORGANISM: Acinetobacter baumannii

<400> SEQUENCE: 26

Met Tyr Lys Pro Thr Thr Phe Val Trp Gln Pro Ser Ala Ala Ser Leu
1               5                   10                  15

Phe Lys Ile Thr Val Leu Ser Ser Ala Leu Ala Ala Leu Gly Ile Thr
                20                  25                  30

Thr Gly Cys Ser Ser Thr Pro Gln Ser Ala Lys Thr Ser Lys Thr Lys
            35                  40                  45

Gln Val Ser Gly Ala Gly Tyr Leu Asp Ala Ser Ser Leu Asp Ser Leu
50                  55                  60

Glu Asp Leu Leu Ser Ala Thr Asp Met Arg Ala Val Glu Gly Asp Arg
65                  70                  75                  80

Leu Leu Ile Leu Lys His Gly Asp Val Trp Lys Arg Met Ala Val Gly
                85                  90                  95

Phe Lys Met Asp Leu Asn His Trp Asp Pro Arg Ile Glu Ala Gln Arg
            100                 105                 110

Ser Trp Phe Ile Ser Arg Gln Pro Tyr Leu Asp Arg Leu Ser Ala Arg
        115                 120                 125

Ala Ser Arg Tyr Leu Tyr His Thr Val Lys Glu Ala Glu Arg Arg Gly
130                 135                 140

Leu Pro Thr Glu Leu Ala Leu Leu Pro Val Ile Glu Ser Ser Tyr Asp
145                 150                 155                 160

Pro Ala Ala Thr Ser Ser Ala Ala Ala Gly Leu Trp Gln Phe Ile
                165                 170                 175

Pro Ser Thr Gly Arg Ile Tyr Gly Leu Gln Gln Thr Gly Met Tyr Asp
            180                 185                 190

Gly Arg Arg Asp Val Val Glu Ser Thr Arg Ala Ala Tyr Glu Phe Leu
        195                 200                 205

Gly Ser Leu Tyr Asn Gln Phe Gly Ser Trp Glu Leu Ala Leu Ala Ala
210                 215                 220

Tyr Asn Ala Gly Pro Gly Arg Ile Gln Gln Ala Ile Asn Arg Asn Gln
225                 230                 235                 240

Ala Ala Gly Leu Pro Thr Asp Tyr Trp Ser Leu Lys Leu Pro Gln Glu
                245                 250                 255

Thr Met Asn Tyr Val Pro Arg Phe Leu Ala Val Ala Gln Ile Ile Lys
            260                 265                 270

Asn Pro Arg Ala Tyr Gly Val Ser Leu Pro Pro Ile Ala Asn Arg Pro
        275                 280                 285

His Phe Arg Glu Val Thr Leu Ser Ala Pro Leu Ser Leu Asn Glu Ile
        290                 295                 300

Ala Ser Val Thr Gly Leu Ser Arg Ala Glu Leu Tyr Ala Leu Asn Pro
305                 310                 315                 320

Gly Tyr Arg Gly Glu Thr Val Asp Pro Ala Ser Pro Met Arg Ile Leu
                325                 330                 335

Ile Pro Ala Asp Ile Ser Pro Ser Val Asp Asn Lys Leu Lys Gly Met
            340                 345                 350

-continued

```
Lys Ala Gly Gly Ser Ser Gly Trp Trp Ala Ser Val Thr Ser Pro Ser
            355                 360                 365
Lys Pro Thr Thr Thr Thr Ser Thr Ser Val Thr Val Arg Thr Thr Pro
370                 375                 380
Ser Thr Pro Ala Gln Pro Val Arg Pro Ser Thr Pro Ala Lys Thr Ser
385                 390                 395                 400
Ser Ser Ser Val Thr Val Lys Thr Thr Thr Pro Arg Gly Ser Asp Ala
                405                 410                 415
Leu Ala Ala Phe Ala Ala Ser Ala Asp Val Pro Ser Ala Pro Arg Ile
            420                 425                 430
Pro Val Ala Val Thr Pro Ala Ala Asn Ile Lys Pro Val Arg Thr Glu
            435                 440                 445
Pro Pro Ile Ser Ala Thr Glu Arg Glu Lys Ile Leu Ala Ala Val Arg
            450                 455                 460
Ala Glu Gly Glu Lys Glu Thr Val Asp Gln Ala Leu Glu Pro Gln Ala
465                 470                 475                 480
Thr Gln Ala Glu Lys Asp Gln Val Val Ala Glu Leu Lys Ala Leu Ala
                485                 490                 495
Pro Gln Gly Thr Glu Ile Val Asp Pro Tyr Asp Gly Lys Ile Lys Leu
            500                 505                 510
Thr Ala Ile Gln Thr Ser Gln Ser Val Ala Glu Gln Gly Lys Glu
            515                 520                 525
Val Ser Lys Gly Phe Ala Tyr Pro Lys Thr Leu Ala Glu Asp Ala Thr
            530                 535                 540
Leu Ala Asn Ser Glu Asp Ala Gln Arg Asn Lys Asp Lys Pro Tyr Ile
545                 550                 555                 560
Lys Thr Asp Thr Asp Val Val Val Gln Pro Lys Gly Lys Arg Ser
                565                 570                 575
Thr Tyr Thr Val Gln Pro Gly Asp Thr Leu Ala Val Ile Ala Met Lys
            580                 585                 590
Asn Gly Val Asn Trp Arg Asp Val Ala Lys Trp Asn Gln Ile Asp Pro
            595                 600                 605
Glu Lys Thr Leu Phe Val Gly Thr Ser Leu Tyr Leu Tyr Asp Ala Lys
            610                 615                 620
Pro Gln Glu Ala Glu Thr Thr Ala Lys Ser Ala Ala Lys Pro Asp Val
625                 630                 635                 640
Tyr Val Val Gln Ala Asn Asp Ser Leu Thr Gly Val Ala Asn Gln Phe
                645                 650                 655
Asn Leu Ser Val Lys Gln Leu Ala Glu Tyr Asn Asp Leu Ser Val Thr
            660                 665                 670
Asp Gly Leu Phe Val Gly Gln Lys Leu Gln Leu Lys Glu Pro Lys Gly
            675                 680                 685
Asn Arg Ala Ala Lys Val Glu Pro Lys Ala Ile Gln Ala Ser Thr Arg
            690                 695                 700
Arg Ile Ala Thr Lys Ser Tyr Thr Val Lys Arg Gly Glu Tyr Leu Lys
705                 710                 715                 720
Leu Ile Ala Asp Arg Tyr Ala Leu Ser Asn Gln Glu Leu Ala Asp Leu
                725                 730                 735
Thr Pro Gly Leu Ser Ala Gly Ser Asn Leu Ile Val Gly Gln Lys Ile
            740                 745                 750
Asn Val Pro Ala Lys Glu Ile Thr Val Asp Glu Val Asp Asp Ser Lys
            755                 760                 765
```

Ala Ser Gly Lys Tyr Glu Lys Leu Ala Ala Gly Pro Ser Tyr Lys Thr
770                 775                 780

Glu Ser Tyr Lys Val Gln Arg Gly Asp Thr Leu Ser Ser Ile Ala Thr
785                 790                 795                 800

Lys Ser Lys Ile Ser Leu Ala Glu Leu Ala Glu Leu Asn Asn Leu Lys
                805                 810                 815

Ala Asn Ser His Val Gln Leu Gly Gln Thr Leu Lys Val Pro Ala Gly
            820                 825                 830

Ala Ser Val Pro Asp Gln Tyr Val Gln Ser Gly Asp Ser Leu Asn
        835                 840                 845

Ala Ile Ala Ala Lys Tyr Asn Leu Gln Thr Ser Tyr Leu Ala Asp Leu
    850                 855                 860

Asn Gly Leu Ser Arg Thr Ala Gly Leu Arg Ala Gly Gln Arg Leu Lys
865                 870                 875                 880

Leu Thr Gly Glu Val Glu Thr Thr Ser Lys Val Ser Ala Lys Asn Thr
                885                 890                 895

Lys Glu Glu Thr Pro Glu Thr Tyr Thr Val Lys Ser Gly Asp Ser Leu
            900                 905                 910

Gly Asn Ile Ala Asn Arg Tyr His Leu Gln Leu Asp Tyr Leu Ala Ala
        915                 920                 925

Leu Asn Gly Leu Ser Arg Asn Ser Asn Val Arg Val Gly Gln Arg Leu
930                 935                 940

Lys Leu Thr Gly Asp Leu Pro Thr Val Glu Thr Ala Lys Thr Asp Thr
945                 950                 955                 960

Ala Lys Ser Ser Pro Lys Ala Val Val Ala Gly Lys Asn Thr Glu Lys
                965                 970                 975

Tyr Thr Val Lys Ala Gly Glu Ser Leu Asn Ala Ile Ala Ser Arg Ala
            980                 985                 990

Gly Ile Ser Val Arg Glu Leu Ala Glu Met Asn Ala Leu Lys Ala Asn
        995                 1000                1005

Ala Asn Leu Gln Arg Gly Gln Asn Ile Val Ile Pro Lys Thr Val
    1010                1015                1020

Val Glu Tyr Lys Val Lys Arg Gly Asp Thr Leu Ile Gly Leu Ala
    1025                1030                1035

Ser Lys Tyr Gly Leu Glu Thr Thr Leu Leu Ala Glu Leu Asn Asn
    1040                1045                1050

Leu Thr Pro Ser Thr Gln Leu Arg Ile Gly Asp Ile Ile Lys Val
    1055                1060                1065

Pro Asn Leu
    1070

<210> SEQ ID NO 27
<211> LENGTH: 1110
<212> TYPE: PRT
<213> ORGANISM: Acinetobacter baumannii

<400> SEQUENCE: 27

Met Lys Arg Met Leu Ile Asn Ala Thr His Ala Glu Glu Val Arg Val
1               5                   10                  15

Ala Leu Ile Thr Gly Asn Arg Leu Tyr Asp Phe Asp Leu Glu Asn Arg
            20                  25                  30

Thr Arg Glu Gln Lys Lys Ser Asn Ile Tyr Lys Gly His Val Thr Arg
        35                  40                  45

Val Glu Pro Ser Leu Glu Ala Val Phe Val Glu Tyr Gly Ala Gly Arg
    50                  55                  60

```
Gln Gly Phe Leu Ser Met Arg Glu Ile Ala Asn Ser Tyr Phe Gln Ala
 65                  70                  75                  80

Asp Pro Arg Gln Thr Ser Asn Ile Arg Glu Leu Ile Thr Glu Gly Thr
                 85                  90                  95

Glu Leu Leu Val Gln Val Glu Lys Glu Arg Gly Asn Lys Gly Ala
            100                 105                 110

Ala Leu Ser Thr Phe Ile Ser Leu Ala Gly Arg Tyr Leu Val Leu Met
            115                 120                 125

Pro Asn Asn Pro Lys Gly Gly Ile Ser Arg Gln Ile Ser Gly Ser
130                 135                 140

Val Arg Glu Glu Leu Lys Glu Ile Leu Ala Ser Leu Asn Val Pro Arg
145                 150                 155                 160

Gly Met Ser Val Ile Val Arg Thr Ala Gly Ile Gly Arg Thr Gln Glu
                165                 170                 175

Glu Leu Gln Leu Asp Leu Gln His Leu Leu Asp Leu Trp Ala Gln Ile
            180                 185                 190

Gln Gly Thr Ala Ser Ser Gly Pro Ser Pro Met Leu Val His Gln Glu
            195                 200                 205

Ala Gly Val Val Thr Arg Ala Ile Arg Asp Tyr Leu Arg Asp Asp Val
210                 215                 220

Ala Glu Ile Leu Ile Asp Ser Glu Gln Ala Tyr Asn Glu Ala Tyr Asn
225                 230                 235                 240

Phe Val Lys Ala Val Met Pro Arg Gln Leu Asp Lys Leu Lys Thr Tyr
                245                 250                 255

Thr Leu Asn Glu Pro Leu Phe Ala His Phe Gly Ile Glu Ser Gln Ile
            260                 265                 270

Gln Thr Ala Tyr Glu Arg Glu Val Lys Leu Pro Ser Gly Gly Ser Ile
            275                 280                 285

Val Ile Asp Gln Thr Glu Ala Leu Val Ser Ile Asp Ile Asn Ser Ala
            290                 295                 300

Lys Ser Thr Arg Gly His Asp Val Glu Glu Thr Ala Leu Asn Thr Asn
305                 310                 315                 320

Leu Glu Ala Ala Glu Ile Ala Arg Gln Leu Arg Leu Arg Asp Ile
                325                 330                 335

Gly Gly Leu Val Val Ile Asp Phe Ile Asp Met Thr Lys Glu Arg Asn
            340                 345                 350

Gln Arg Met Val Glu Ala Lys Leu Arg Glu Ala Thr Gln Ser Asp Arg
            355                 360                 365

Ala Arg Ile Gln Phe Gly Gln Leu Ser Arg Phe Gly Leu Met Glu Met
            370                 375                 380

Ser Arg Gln Arg Leu Arg Pro Ser Leu Glu Glu Ala Thr Gly Tyr Val
385                 390                 395                 400

Cys Pro Arg Cys His Gly Thr Gly Met Val Arg Asp Leu Arg Ser Leu
                405                 410                 415

Ser Leu Ser Ile Met Arg Lys Val Glu Ile Ala Leu Arg Glu Arg
                420                 425                 430

His Gly Glu Val Gln Val Glu Val Pro Val Glu Ile Ala Ala Phe Leu
            435                 440                 445

Leu Asn Glu Lys Arg His Ser Leu Val Tyr Leu Glu Gln Thr Ser Gly
            450                 455                 460

Val Arg Val Thr Val Leu Pro His Pro His Leu Glu Thr Pro His Tyr
465                 470                 475                 480
```

-continued

Glu Ile Ala Tyr Asn Pro Asp Gly Phe Ala Pro Ser Ser Tyr Glu Arg
             485                 490                 495

Thr Glu Ala Thr Arg Ser Ser Glu Lys Glu Leu Gly Tyr Glu Ser Ser
        500                 505                 510

Glu Trp His Leu Glu Glu Ala Asp His Gly His Ala His Val Thr Ala
        515                 520                 525

Thr Ala Ser Thr His Ala Ala Ala Gln Lys Lys Ala Asn His Ala Thr
        530                 535                 540

Gln Pro Val Ala Gln Pro Ser Ala Gln Lys Ala Ala Ser Pro Cys Ala
545                 550                 555                 560

Trp Leu Glu Asn Leu Phe Val Gln Lys Gln Ala Gln Thr Val Asp Gln
                565                 570                 575

Ser Arg Ser Ala Gln Asn Ala Ala Ala Ala Ile Glu Gln Met Val Asn
            580                 585                 590

Thr Gly Ala Val Ser Arg Gly Gln Phe Gly Gln Val Ala Val Pro Ala
        595                 600                 605

Val Ala Glu Val Ala Pro Val Gln Ser Asn Asn Ala Tyr Ile Ser Gln
        610                 615                 620

Ser Pro Val Lys Gln Asp Val Arg Glu His Val Glu Lys Asp Asp Lys
625                 630                 635                 640

Ser Gln Gln Gln Arg Gln Asn Asn Lys Lys Arg Lys His Lys Glu Gln
                645                 650                 655

Arg Glu Gln His His Gln Ser His Glu Gln Gln His Gln Val His Glu
            660                 665                 670

Glu Val Val Gln Leu Ser Arg Gln Glu Gln Arg Glu Leu Lys Arg Gln
        675                 680                 685

Gln Lys Arg Gln Gln Gln Gln Asp Gln Gln His Gln Asn Asn Asp Val
        690                 695                 700

Gln His Thr Glu Asn Ala Val Pro Arg Arg Asp Arg Asn Asn Gln Gln
705                 710                 715                 720

Arg Pro Asn Arg Pro Asn Arg His Arg Asp Pro Ser Val Leu Asn Glu
                725                 730                 735

Asn Gln Asn Thr Leu Val Val Val Asp Glu Lys Gln Ile Lys Val Asp
            740                 745                 750

Val Ile Asp Ala Pro Lys His Asp Val Met Asn Thr Ala Leu Ile Ile
        755                 760                 765

Asn Val Asp Gln Gly Gln Ser Glu Ile Val Ala Leu Thr Pro Glu Arg
        770                 775                 780

Arg His Val Glu Arg Val Glu Thr Thr Ser Thr Glu Val Ala Gln Glu
785                 790                 795                 800

Pro Thr Pro Ala Pro Val Val Ala Glu Lys Ala Ala Val Val Glu Thr
                805                 810                 815

Lys Glu Glu Ala Gln Pro Ser Gln Glu Ala Ala Gln Pro Gln Ile Lys
            820                 825                 830

Arg Ala Ser Asn Asp Pro Arg Met Arg Arg Gln Arg Glu Ala
        835                 840                 845

Lys His Ala Lys Ala Ala Thr Pro Ser Ile Ala Pro Ser Gln Ile Pro
850                 855                 860

Thr Leu Ala Gln His Thr Ile Gly Ser Leu Ile Arg His Val Tyr Gly
865                 870                 875                 880

Glu Asp Cys Thr Val Leu Ile Glu Gln Phe Gly Leu Val Pro Thr Phe
                885                 890                 895

Asn Arg Ala Leu Gln Lys Phe Ala Glu Gln Tyr Ala Ser Thr Leu Val

```
                    900                 905                 910
        Val Glu Val Thr Ala Glu Thr Glu Lys Lys Pro Val Thr Arg Asp
                        915                 920                 925

Ala Glu Leu Pro Ser His Lys Pro Ala Glu Glu Ala Glu Pro Ala Pro
                    930                 935                 940

Val Leu Pro Leu Thr Pro Pro Gln Ala Pro Ala Pro Arg Val Ala Asn
        945                 950                 955                 960

Asp Pro Arg Glu Arg Arg Leu Ala Lys Leu Ala Ala Glu Gln Ala
                        965                 970                 975

Phe Glu Gln Val Lys Gln Gln His Ser Ala Gln Glu Glu Val Ala Thr
                    980                 985                 990

Pro Ala Pro Val Ala Glu Glu Thr  Val Ala Ala Pro Thr  Ala Glu Thr
                    995                 1000                1005

Gln Ala  Thr Val Glu Pro Ala  Gln Gln Pro Leu Glu  Leu Asn Gln
                    1010                1015                1020

Ser Thr  Glu Val Val Gln Pro  Glu Ala Ala Pro Ala  Glu Glu Lys
                    1025                1030                1035

Ala Thr  Glu Glu Thr Val Ala  Glu Ala Pro Ala Ala  Lys Glu Pro
                    1040                1045                1050

Ala Pro  Ser Lys Ala Ala Ser  Lys Ala Lys Ala Ala  Ala Glu Glu
                    1055                1060                1065

Thr Val  Ala Pro Thr Glu Ala  Thr Thr Asp Ala Glu  Ser Glu Asp
                    1070                1075                1080

Val Lys  Ala Asp Lys Asp Lys  Pro Ser Arg Pro Arg  Arg Pro Arg
                    1085                1090                1095

Gly Arg  Pro Pro Lys Lys Ala  Asn Pro Val Ala Glu
                    1100                1105                1110

<210> SEQ ID NO 28
<211> LENGTH: 1228
<212> TYPE: PRT
<213> ORGANISM: Acinetobacter baumannii

<400> SEQUENCE: 28

Met Ser Thr Leu Ala Thr Leu Lys Ala Leu Leu Ala Lys Arg Ile Leu
1               5                   10                  15

Ile Ile Asp Gly Ala Met Gly Thr Met Ile Gln Arg His Lys Leu Glu
            20                  25                  30

Glu Ala Asp Tyr Arg Gly Glu Arg Phe Ala Asp Trp Ala His Asp Leu
        35                  40                  45

Lys Gly Asn Asn Asp Leu Leu Val Leu Thr Gln Pro Gln Ile Ile Gln
    50                  55                  60

Gly Ile His Glu Ala Tyr Leu Asp Ala Gly Ala Asp Ile Ile Glu Thr
65                  70                  75                  80

Asn Ser Phe Asn Gly Thr Arg Val Ser Met Ser Asp Tyr His Met Glu
                85                  90                  95

Asp Leu Val Pro Glu Ile Asn Arg Glu Ala Ala Arg Leu Ala Lys Ala
            100                 105                 110

Ala Cys Glu Lys Tyr Ser Thr Pro Asp Lys Pro Arg Phe Val Ala Gly
        115                 120                 125

Val Leu Gly Pro Thr Ser Arg Thr Cys Ser Ile Ser Pro Asp Val Asn
    130                 135                 140

Asn Pro Ala Phe Arg Asn Ile Ser Phe Asp Glu Leu Lys Glu Asn Tyr
145                 150                 155                 160
```

-continued

```
Ile Glu Ala Thr His Ala Leu Ile Glu Gly Ala Asp Ile Ile Leu
                165                 170                 175
Ile Glu Thr Val Phe Asp Thr Leu Asn Cys Lys Ala Ala Ile Phe Ala
            180                 185                 190
Val Lys Glu Val Phe Lys Gln Ile Gly Arg Glu Leu Pro Ile Met Ile
        195                 200                 205
Ser Gly Thr Ile Thr Asp Ala Ser Gly Arg Thr Leu Thr Gly Gln Thr
    210                 215                 220
Ala Glu Ala Phe Trp Asn Ser Val Arg His Gly Asp Leu Leu Ser Ile
225                 230                 235                 240
Gly Phe Asn Cys Ala Leu Gly Ala Asp Ala Met Arg Pro His Val Lys
                245                 250                 255
Thr Ile Ser Asp Val Ala Asp Thr Phe Val Ser Ala His Pro Asn Ala
            260                 265                 270
Gly Leu Pro Asn Ala Phe Gly Glu Tyr Asp Glu Thr Pro Glu Gln Thr
        275                 280                 285
Ala Ala Phe Leu Lys Glu Phe Ala Glu Ser Gly Leu Ile Asn Ile Thr
    290                 295                 300
Gly Gly Cys Cys Gly Thr Thr Pro Asp His Ile Arg Ala Ile Ala Asn
305                 310                 315                 320
Ala Val Lys Asp Ile Ala Pro Arg Gln Val Pro Glu Thr Val Pro Ala
                325                 330                 335
Cys Arg Leu Ser Gly Leu Glu Pro Phe Asn Ile Tyr Asp Asp Ser Leu
            340                 345                 350
Phe Val Asn Val Gly Glu Arg Thr Asn Val Thr Gly Ser Lys Lys Phe
        355                 360                 365
Leu Arg Leu Ile Arg Glu Glu Asn Phe Ala Glu Ala Leu Glu Val Ala
    370                 375                 380
Gln Gln Gln Val Glu Ala Gly Ala Gln Ile Ile Asp Ile Asn Met Asp
385                 390                 395                 400
Glu Gly Met Leu Asp Ser Gln Asn Ala Met Val His Phe Leu Asn Leu
                405                 410                 415
Val Ala Ser Glu Pro Asp Ile Ser Arg Val Pro Ile Met Ile Asp Ser
            420                 425                 430
Ser Lys Trp Glu Ile Ile Glu Ala Gly Leu Lys Cys Val Gln Gly Lys
        435                 440                 445
Pro Val Val Asn Ser Ile Ser Leu Lys Glu Gly Tyr Asp Glu Phe Val
    450                 455                 460
Glu Lys Ala Arg Leu Cys Arg Gln Tyr Gly Ala Ala Ile Ile Val Met
465                 470                 475                 480
Ala Phe Asp Glu Val Gly Gln Ala Asp Thr Ala Glu Arg Lys Arg Glu
                485                 490                 495
Ile Cys Lys Arg Ser Tyr Asp Ile Leu Val Asn Glu Val Gly Phe Pro
            500                 505                 510
Ala Glu Asp Ile Ile Phe Asp Pro Asn Val Phe Ala Val Ala Thr Gly
        515                 520                 525
Ile Glu Glu His Asn Asn Tyr Ala Val Asp Phe Ile Glu Ala Thr Gly
    530                 535                 540
Trp Ile Lys Gln Asn Leu Pro His Ala Met Ile Ser Gly Gly Val Ser
545                 550                 555                 560
Asn Val Ser Phe Ser Phe Arg Gly Asn Glu Pro Val Arg Glu Ala Ile
                565                 570                 575
His Ser Val Phe Leu Tyr His Ala Ile Lys Gln Gly Met Thr Met Gly
```

```
                580             585             590
Ile Val Asn Ala Gly Gln Met Ala Ile Tyr Asp Asp Ile Pro Thr Glu
            595             600             605

Leu Lys Glu Ala Val Glu Asp Val Ile Leu Asn Gln Asn Gln Gly Glu
    610             615             620

Ser Gly Gln Ala Ala Thr Glu Lys Leu Leu Glu Val Ala Glu Lys Tyr
625             630             635             640

Arg Gly Gln Gly Gly Ala Thr Lys Glu Ala Glu Asn Leu Glu Trp Arg
                645             650             655

Asn Glu Ser Val Glu Lys Arg Leu Glu Tyr Ala Leu Val Lys Gly Ile
        660             665             670

Thr Thr Tyr Ile Asp Gln Asp Thr Glu Glu Ala Arg Leu Lys Ser Lys
            675             680             685

Arg Pro Leu Asp Val Ile Glu Gly Pro Leu Met Asp Gly Met Asn Val
    690             695             700

Val Gly Asp Leu Phe Gly Ser Gly Lys Met Phe Leu Pro Gln Val Val
705             710             715             720

Lys Ser Ala Arg Val Met Lys Gln Ala Val Ala Trp Leu Asn Pro Tyr
                725             730             735

Ile Glu Ala Glu Lys Thr Glu Gly Gln Ser Lys Gly Lys Val Leu Met
        740             745             750

Ala Thr Val Lys Gly Asp Val His Asp Ile Gly Lys Asn Ile Val Gly
            755             760             765

Val Val Leu Gly Cys Asn Gly Tyr Asp Ile Val Asp Leu Gly Val Met
    770             775             780

Val Pro Cys Glu Lys Ile Leu Gln Thr Ala Ile Asp Glu Lys Cys Asp
785             790             795             800

Ile Ile Gly Leu Ser Gly Leu Ile Thr Pro Ser Leu Asp Glu Met Val
                805             810             815

Phe Val Ala Lys Glu Met Gln Arg Lys Gly Phe Asn Ile Pro Leu Leu
        820             825             830

Ile Gly Gly Ala Thr Thr Ser Lys Ala His Thr Ala Val Lys Ile Asp
            835             840             845

Pro Gln Tyr Gln Asn Asp Ala Val Ile Tyr Val Ala Asp Ala Ser Arg
    850             855             860

Ala Val Gly Val Ala Thr Thr Leu Leu Ser Lys Glu Met Arg Gly Ala
865             870             875             880

Phe Ile Glu Glu His Arg Ala Glu Tyr Ala Lys Ile Arg Glu Arg Leu
                885             890             895

Ala Asn Lys Gln Pro Lys Ala Ala Lys Leu Thr Tyr Lys Glu Ser Val
        900             905             910

Glu Asn Gly Phe Lys Ile Asp Glu Ser Tyr Val Pro Pro Lys Pro Asn
            915             920             925

Leu Leu Gly Thr Gln Val Leu Lys Asn Tyr Pro Leu Ala Thr Leu Val
    930             935             940

Asp Tyr Phe Asp Trp Thr Pro Phe Phe Ile Ser Trp Ser Leu Thr Gly
945             950             955             960

Lys Phe Pro Lys Ile Leu Glu Asp Glu Val Val Gly Glu Ala Ala Thr
                965             970             975

Asp Leu Tyr Asn Gln Ala Gln Ala Met Leu Lys Asp Ile Ile Asp Asn
        980             985             990

Asn Arg Phe Asp Ala Arg Ala Val Phe Gly Met Phe Pro Ala Gln Arg
            995             1000            1005
```

-continued

Thr Asp Ala Asp Thr Val Ser Val Phe Asp Glu Ala Gly Gln Asn
    1010                1015                1020

Val Thr His Thr Phe Glu His Leu Arg Gln Gln Ser Asp Lys Val
    1025                1030                1035

Thr Gly Lys Pro Asn Leu Ser Leu Ala Asp Tyr Ile Arg Ala Asp
    1040                1045                1050

Arg Glu Gln Gln Asp Tyr Leu Gly Gly Phe Thr Val Ser Ile Phe
    1055                1060                1065

Gly Ala Glu Glu Leu Ala Asn Glu Tyr Lys Ala Lys Gly Asp Asp
    1070                1075                1080

Tyr Ser Ala Ile Leu Val Gln Ser Leu Ala Asp Arg Phe Ala Glu
    1085                1090                1095

Ala Phe Ala Glu His Leu His Glu Arg Ile Arg Lys Glu Phe Trp
    1100                1105                1110

Gly Tyr Lys Ala Asp Glu Gln Leu Ser Asn Glu Glu Leu Ile Lys
    1115                1120                1125

Glu Lys Tyr Val Gly Ile Arg Pro Ala Pro Gly Tyr Pro Ala Cys
    1130                1135                1140

Pro Glu His Ser Glu Lys Ala Val Leu Phe Asp Trp Leu Gly Ser
    1145                1150                1155

Thr Asp Lys Ile Gly Thr Lys Leu Thr Glu His Phe Ala Met Met
    1160                1165                1170

Pro Pro Ser Ser Val Ser Gly Phe Tyr Tyr Ser His Pro Gln Ser
    1175                1180                1185

Glu Tyr Phe Asn Val Gly Lys Ile Ser Gln Asp Gln Leu Glu Asp
    1190                1195                1200

Tyr Ala Lys Arg Lys Gly Trp Thr Leu Asp Glu Ala Lys Arg Trp
    1205                1210                1215

Leu Ala Pro Asn Leu Asp Asp Ser Ile Val
    1220                1225

<210> SEQ ID NO 29
<211> LENGTH: 1284
<212> TYPE: PRT
<213> ORGANISM: Acinetobacter baumannii

<400> SEQUENCE: 29

Met Lys Leu Lys Leu Lys Asn Phe Lys Pro Asn Asn Leu Trp Tyr Ala
1               5                   10                  15

Val Cys Ser Ser Ser Met Ile Phe Thr Trp Leu Met Thr Ser Ser Val
                20                  25                  30

Val Gln Ala Ser Asp Leu Gln Ile Tyr Ala Ser Pro Thr Ala Gly Lys
        35                  40                  45

Lys Thr Ile Val Met Met Leu Asp Thr Ser Gly Ser Met Thr Asn Asn
50                  55                  60

Ser Tyr Gly Glu Asn Arg Leu Ala Met Leu Lys Asn Gly Met Asn Ala
65                  70                  75                  80

Phe Leu Ala Ser Asn Asn Pro Val Leu Asn Asp Thr Arg Val Gly Leu
                85                  90                  95

Gly Asn Phe Ser Ala Asn Gly Asp Ser Arg Ser Gly Gln Ile Leu Val
                100                 105                 110

Ala Ala Ala Pro Leu Gly Asp Ala Ser Thr Leu Asn Thr Val Gly Ser
        115                 120                 125

Gln Arg Tyr Lys Leu Lys Gln Ala Val Ala Asn Leu Thr Ala Gly Gly

-continued

```
            130                 135                 140
Ser Thr Pro Ser Ala His Ala Tyr Ala Glu Ala Ala Tyr Leu Met
145                 150                 155                 160

Gly Thr Thr Thr Tyr Ser Glu Thr Asn Tyr Ala Ile Arg Lys Asp Ser
                165                 170                 175

Tyr Ile Lys Arg Val Arg Arg Ser Asp Asn Arg Thr Glu Tyr Ser Tyr
            180                 185                 190

Cys Thr Asn Tyr Arg Asp Ser Gln Ile Asp Thr Ala Asn Leu Trp Gln
        195                 200                 205

Pro Cys Arg Ser Asn Ser Tyr Trp Ser Ser Trp Ser Thr Asn Asn Pro
    210                 215                 220

Gly Val Asp Asn Ala Thr Ala Tyr Asp Thr Ser Ser Asp Trp Thr Tyr
225                 230                 235                 240

Tyr Tyr Thr Tyr Tyr Tyr Thr Thr Phe Asn Tyr Ala Val Ala Asn Ala
                245                 250                 255

Asp Ser Gly Ile Pro Lys Ser Lys Ser Asn Asp Thr Ala Ser Asn Pro
            260                 265                 270

Asn Ile Val Val Asp Arg Asn Ala Thr Asn Ser Asn Ala Val Tyr Gln
        275                 280                 285

Ser Pro Leu Pro Ala Val Ala Asn Arg Gln Ser Cys Asp Gly Gln Gly
    290                 295                 300

Ile Tyr Phe Leu Ser Asp Gly Glu Pro Asn Asn Thr Thr Asn Thr Arg
305                 310                 315                 320

Ser Ala Ser Val Met Ser Thr Ala Leu Gly Ser Thr Phe Gly Ala Asp
                325                 330                 335

Phe Asn Cys Ser Gly Gly Leu Ser Asn Thr Thr Ala Asp Ser Gly Trp
            340                 345                 350

Ala Cys Met Gly Glu Phe Ala Lys Arg Leu Phe Asp Lys Thr Lys Asn
        355                 360                 365

Pro Ala Gly Val Ser Ile Gln Thr Ala Phe Val Gly Phe Gly Ser Asp
    370                 375                 380

Phe Ser Ser Leu Asn Ser Ser Asp Val Lys Asn Ala Cys Arg Leu Ser
385                 390                 395                 400

Ser Arg Thr Gln Ser Asp Arg Lys Gly Asp Asp Ala Cys Ser Pro Asn
                405                 410                 415

Gln Ser Thr Asn Ala Val Ala Ala Pro Gly Tyr Gly Asn Gly Gly Phe
            420                 425                 430

Phe Pro Thr Gln Ser Ser Gln Gly Val Thr Asp Ser Val Ile Ala Phe
        435                 440                 445

Ile Asn Asn Leu Asp Lys Val Pro Leu Glu Pro Leu Thr Thr Gly Ala
    450                 455                 460

Ile Ser Val Pro Tyr Asp Ala Leu Asn Pro Lys Asn Leu Gln Glu Tyr
465                 470                 475                 480

Gly Tyr Leu Arg Ala Phe Glu Pro Asn Pro Ala Asn Thr Tyr Leu Thr
                485                 490                 495

Trp Arg Gly Asn Leu Lys Lys Tyr His Val Val Leu Ser Gly Ala Asn
            500                 505                 510

Ala Gly Ala Phe Glu Ala Asn Ser Gly Gly Leu Val Tyr Asn Ala Ser
        515                 520                 525

Gly Ala Phe Arg Thr Gly Thr Lys Asp Tyr Trp Asn Ser Ser Thr Tyr
    530                 535                 540

Thr Asp Gly Gly Lys Val Phe Leu Gly Gly Ser Tyr Ala Asn Val Pro
545                 550                 555                 560
```

```
Leu Pro Ile Ala Gly Gln Pro Glu Thr Arg Asp Ala Glu Gly Asn Ile
                565                 570                 575

Thr Lys Tyr Tyr Tyr Ala Val Gln Ser Lys Ile Arg Asn Leu Phe Thr
            580                 585                 590

Asp Val Ser Ala Val Ala Ala Asp Gly Ser Leu Thr Lys Ile Ser Thr
            595                 600                 605

Ser Gly Thr Asn Leu Leu Lys Ile Pro Ala Ala Pro Pro Glu Glu Thr
        610                 615                 620

Asn Pro Phe Asp Thr Val Ala Asn Thr Ala Ser Tyr Val Leu Gly Lys
625                 630                 635                 640

Phe Asp Pro Ser Thr Gly Gln Asn Ile Leu Lys Ala Phe Pro Ile Ser
                645                 650                 655

Leu Lys Leu Lys Ile Leu Asn Tyr Leu Gly Tyr Ser Thr Asp Ile Asn
                660                 665                 670

Ala Thr Thr Leu Pro Ser Ser Leu Val Thr Ser Asn Glu Pro Tyr Leu
            675                 680                 685

Ser Met Gly Gly Ser Ile His Ser Leu Pro Val Gln Leu Thr Tyr Asn
        690                 695                 700

Gly Thr Leu Asp Asp Asn Gly Asn Leu Thr Ser Ala Arg Glu Gln Ser
705                 710                 715                 720

Ile Leu Tyr Gly Thr Met Glu Gly Gly Leu His Ile Val Asp Ala Ser
                725                 730                 735

Ser Gly Ile Glu Gln Met Val Phe Val Pro Ala Asp Ile Leu Asn Asp
            740                 745                 750

Ser Val Ala Ser Lys Ala Leu Val Gly Gln Ser Asp Ala Ser Ala
            755                 760                 765

Pro Ala His Gly Met Asp Gly Ala Trp Val Ser Asp Pro Ala Tyr Asn
770                 775                 780

Ile Thr Thr Val Gly Ser Gly Ser Ser Ala Val Ser Lys Val Thr Ala
785                 790                 795                 800

Lys Gln Met Asn Ile Tyr Gly Gly Met Arg Met Gly Ser Ser Tyr
            805                 810                 815

Tyr Gly Leu Asp Val Leu Ser Pro Thr Ser Pro Lys Leu Leu Phe Arg
            820                 825                 830

Ile Gly Ala Asp Gln Asn Asp Tyr Ser Arg Met Gly Gln Ser Trp Ser
            835                 840                 845

Lys Pro Val Leu Ala Asn Ile Arg Tyr Asn Gly Ser Ile Arg Arg Val
850                 855                 860

Leu Ile Val Gly Gly Tyr Asp Gln Cys Tyr Glu Lys Pro Asn Ile
865                 870                 875                 880

Thr Leu Thr Asp Ala Cys Phe Thr Asn Gly Lys Ala Lys Gly Asn Ala
                885                 890                 895

Val Tyr Ile Ile Asp Ala Lys Thr Gly Gln Arg Leu Trp Trp Thr Ser
            900                 905                 910

Asp Thr Gly Ser Asn Thr Asp Asn Ala Asn Met Lys His Ser Ile Val
        915                 920                 925

Ser Arg Ile Ser Thr Leu Asp Arg Asp Ala Asp Gly Leu Val Asp His
    930                 935                 940

Leu Tyr Phe Gly Asp Leu Gly Gly Gln Ile Phe Arg Val Asp Leu Asn
945                 950                 955                 960

Asn Asn Gln Thr Lys Thr Asn Ser Thr Tyr Ser Ser Phe Gly Val Arg
                965                 970                 975
```

```
Val Val Arg Leu Ala Asn Leu Ala Thr Asn Asp Ser Thr Tyr Asp Gly
            980                 985                 990

Thr Asn Asp Tyr Thr Gly Gly Asn Ala Pro Arg Phe Tyr Glu Pro Pro
        995                1000                1005

Thr Val Thr Ile His Asp Tyr Gly Ile His Thr Phe Ile Thr Val
    1010                1015                1020

Gly Ile Ala Ser Gly Asp Arg Ser Thr Pro Leu Asp Val Tyr Pro
    1025                1030                1035

Leu Thr Gly Arg Glu Gly Met Thr Pro Ala Ser Ala Leu Ser Gly
    1040                1045                1050

Arg Pro Val Asn Asn Val Tyr Gly Ile Ile Asp Arg Asp Phe Val
    1055                1060                1065

Lys Lys Asn Leu Met Ser Leu Thr Asp Asn Gln Leu Glu Thr Lys
    1070                1075                1080

Asp Ile Thr Arg Thr Gly Leu Arg Lys Asn Pro Gln Ile Leu Arg
    1085                1090                1095

Thr Gly Glu Thr Arg Val Ala Gln Ile Phe Phe Pro Thr Thr Gly
    1100                1105                1110

Val Gly Lys Gly Gly Trp Tyr Arg Ser Leu Ser Ser Thr Ser Asp
    1115                1120                1125

Gly Thr Glu Lys Ala Asn Asn Ser Phe Arg Ile Lys Gly Gly Leu
    1130                1135                1140

Lys Ala Phe Glu Glu Pro Met Ala Ile Thr Gly Asn Leu Ile Ile
    1145                1150                1155

Leu Val Tyr Asp Pro Gln Gly Thr Gly Ile Val Ala Ala Asp Pro
    1160                1165                1170

Cys Leu Pro Arg Val Val Gly Glu Thr Asp Arg Gln Thr Tyr Cys
    1175                1180                1185

Leu Pro Phe Gly Ala Cys Leu Asn Ser Asp Gly Ser Ile Asp Gln
    1190                1195                1200

Asn Lys Glu Asn His Ser Gly Phe Glu Thr Gln Thr Gly Thr Asn
    1205                1210                1215

Cys Pro Val Gly Ala Ser Glu Cys Asn Lys Asn Val Ile Gly Ser
    1220                1225                1230

Gly Ile Arg Ser Val Thr Phe Val Pro Thr Glu Asp Asn Pro Pro
    1235                1240                1245

Thr Thr Asn Ser Cys Gly Lys Leu Lys Leu Ser Gly Asn Glu Gln
    1250                1255                1260

Gly Thr Gly Gln Trp Gln Cys Thr Ser His Leu Val Pro Thr Arg
    1265                1270                1275

Trp Tyr Glu Arg Tyr Arg
    1280

<210> SEQ ID NO 30
<211> LENGTH: 3047
<212> TYPE: PRT
<213> ORGANISM: Acinetobacter baumannii

<400> SEQUENCE: 30

Met Thr Asp Ala Ala Gly Asn Thr Ser Glu Gln Ala Val Gln Lys Val
1               5                   10                  15

Val Val Asp Thr Thr Ala Pro Gln Ala Gly Glu Leu Thr Leu Ser Asp
            20                  25                  30

Leu Ser Asp Thr Gly Ile Ser Ala Thr Asp Gln Ile Thr Gln Asp Lys
        35                  40                  45
```

```
Asn Phe Asn Leu Lys Leu Glu Gly Gln Glu Ser Gly Ser Arg Val Thr
 50                  55                  60
Tyr Leu Val Ser Thr Asp Glu Gly Lys Thr Trp Gln Glu Thr Thr Ile
 65                  70                  75                  80
Ala Gln Lys Asp Leu Thr Asp Gly Val Tyr Gln Tyr Lys Ala Val Val
                 85                  90                  95
Thr Asp Ala Ala Gly Asn Thr Ser Glu Thr Ala Val Gln Lys Val Val
                100                 105                 110
Val Asp Thr Thr Thr Pro Gln Ala Gly Glu Leu Thr Leu Ser Asp Leu
            115                 120                 125
Asn Asp Thr Gly Val Ser Val Thr Asp Gln Ile Thr Gln Asp Lys Asn
130                 135                 140
Phe Asn Leu Lys Leu Glu Gly Gln Glu Thr Gly Ser Arg Val Thr Tyr
145                 150                 155                 160
Leu Val Ser Thr Asp Glu Gly Lys Thr Trp Gln Glu Thr Thr Ile Ala
                165                 170                 175
Gln Lys Asp Leu Ala Asp Gly Val Tyr Lys Tyr Lys Ala Val Val Thr
            180                 185                 190
Asp Ala Ala Gly Asn Thr Ser Glu Thr Ala Val Gln Lys Val Val Val
            195                 200                 205
Asp Thr Thr Ala Pro Gln Ala Gly Lys Leu Thr Leu Ser Asp Leu Asn
210                 215                 220
Asp Thr Gly Val Ser Ala Thr Asp Gln Ile Thr Gln Asp Asn Ser Phe
225                 230                 235                 240
Thr Leu Lys Leu Ala Gln Pro Ile Val Ile Gly Glu Gln Ala Ala Leu
                245                 250                 255
Leu Asp His Tyr Glu Val Ser Lys Asp Glu Gly Lys Thr Trp Gln Glu
            260                 265                 270
Thr Thr Ala Asp Gln Lys Asp Leu Ala Asp Gly Ile Tyr Gln Tyr Lys
            275                 280                 285
Ala Ile Val Thr Asp Leu Ala Gly Asn Ile Ser Glu Ser Ala Ile Gln
290                 295                 300
Lys Val Val Val Asp Asn Ser Leu Asn Val Glu Ser Thr Thr Val Ile
305                 310                 315                 320
Val Lys Pro Ile Thr Glu Asp Asn Thr Ile Ser Leu Val Glu Lys Asp
                325                 330                 335
Gln Val Ile Ser Ile Arg Leu Glu Ile Ala Asn Leu Pro Thr Asp Leu
            340                 345                 350
Asn Ser Ser Leu Thr Ser Val Asn Thr Thr Leu Gly Asn Val Thr Tyr
            355                 360                 365
Asn Phe His Phe Asp Glu Val Thr Gln Glu Trp Val Thr Glu Ile Pro
370                 375                 380
Ala Glu Phe Leu Trp Ser Val Glu Pro Gln Thr Asn Ile Ser Ile Glu
385                 390                 395                 400
Ile Ser Leu Thr Asp Gln Ala Gly Asn Thr Ala Ile Ile Lys His Thr
                405                 410                 415
Gln Asn Tyr Asn Val Asp His Thr Pro Asn Ser Pro Thr Leu Asp Ser
            420                 425                 430
Leu Thr Phe Asn Asn Ile Asp Gly Ala Ile Ile Ser Gly Ser Ala Tyr
            435                 440                 445
Lys Gly Ser Lys Val Asp Ile Tyr Asn Lys Asn Gly Asp Trp Leu Ala
450                 455                 460
```

```
Ser Thr Ile Thr Asn Glu Glu Gly Lys Phe Thr Leu Gln Asp Leu Ser
465                 470                 475                 480

Ile Asn Ser Asn Gln Glu Val Tyr Ala Val Ala Thr Tyr Asn Gly Tyr
            485                 490                 495

Ser Ser Glu Asn Ser Ser Ile Gly Leu Val Thr Glu Val Pro Ala Ile
            500                 505                 510

Ser Ile Thr Arg Ile Ser Pro Glu Gly Val Ile Ser Gly Tyr Ala Thr
            515                 520                 525

Glu Gly Ser His Phe Ile Val Lys Asp Gln Asn Gly Asn Ile Leu Gln
            530                 535                 540

Glu Phe Asn Ser Asn Val Phe Asp Ser Ser Gly Ile Thr Pro Phe Ser
545                 550                 555                 560

Val Met Ala Leu Gly Glu Val Arg Pro Phe Ile Leu Ser Leu Asp Gln
            565                 570                 575

Pro Leu Glu Glu Gly Ala Gln Ile Ile Ile Ser Ile Asp Lys Asp Asn
            580                 585                 590

Ile Ser Gly His Pro Gln Tyr Ile Thr Ala Asp Tyr Thr Pro Ala Val
            595                 600                 605

Phe Leu Glu Thr Pro Gln Phe Asp Ile Ser Gly Glu Thr Leu Ser Val
610                 615                 620

His Val Asn Glu Pro Asn Ser Phe Ile Arg Ala Phe Ser Gly Glu Gly
625                 630                 635                 640

Asn Leu Ile Ala Thr Gly Phe Thr Asp Glu Gln Gly Phe Ala Ser Leu
            645                 650                 655

Gln Val Phe Gln Phe Leu Lys Glu Gly Glu Thr Val Ser Val Gln Val
            660                 665                 670

Val Asp Lys Asn Gln Asn Thr Ser Glu Thr Leu Ile Glu Val Pro Asn
            675                 680                 685

Phe Ala Tyr Ile Pro His Val Glu Arg Ile Thr Gln Glu Gly Leu Ile
            690                 695                 700

Ser Gly Val Ala Glu Asp Asn Ser Thr Val Ile Val Arg Asp Ala Asp
705                 710                 715                 720

Gly Asn Glu Leu Gly Lys Val Thr Leu Gly Asp Asp Asn Ser Trp Ser
            725                 730                 735

Asp Phe Ser His Phe Ser Leu Ser Val Asn Arg Pro Leu Ile Asp Gly
            740                 745                 750

Glu Lys Ile Ser Val Gln Ile Ile Asp Asn Lys Gly Leu Met Ser Pro
            755                 760                 765

Glu Gln Asn Ile Ile Val Asp Leu Thr Pro Pro Ala Pro Thr Glu
            770                 775                 780

Leu Asn Phe Asn Asp Ala Gly Asp Leu Val Tyr Gly His Ala Glu Pro
785                 790                 795                 800

Phe Ser Glu Ile Leu Val Lys Asp Gly Gln Gly Asn Ile Leu Asn Lys
            805                 810                 815

Trp Phe Trp Asn Asn Trp Thr Asp Glu Ser Gly Ser Phe Ser Ile Glu
            820                 825                 830

Leu Gly Thr Phe Leu Thr Asn Ala Glu Thr Val Tyr Val Thr Ala Thr
            835                 840                 845

Asp Val Asn Gly Asn Val Ser Leu Ala Ala Gln Ile Gln Ala Pro Asn
850                 855                 860

Tyr Ala Phe Ala Pro Tyr Val Asp Ser Phe Thr Ser Asp Gly Val Ile
865                 870                 875                 880

Ser Gly Gln Ala Glu Asn Asn Ser Thr Leu Val Val Lys Asp Ala Lys
```

-continued

```
                885                 890                 895
Gly Asp Val Val Ala Glu Ile Lys Val Gly Glu Asp Asn Gly Trp Asn
                    900                 905                 910
Gly Ser Ser Tyr Phe Lys Leu Gln Leu Asp Arg Pro Leu Val Asp Gly
                    915                 920                 925
Glu Gln Phe Phe Leu Ser Ile Lys Asp Ala Arg Gly Gln Val Ser Ala
                    930                 935                 940
Asp Thr Val Ile Thr Ala Asp Thr Val Ala Pro Thr Pro Ala Ser Asn
945                 950                 955                 960
Leu Val Phe Ser Glu Asp Gly Ser Tyr Leu Thr Gly Val Ala Glu Leu
                    965                 970                 975
Asn Thr Thr Ile Gln Val Phe Asp His Asn Gly Gln Leu Val Asn Ile
                    980                 985                 990
Trp Asn Asn Thr Ile Asn Ser Asp Gly Thr Phe Thr Ile Tyr Leu Gly
                    995                 1000                1005
Ser Asn Asn Leu His Gly Glu Ala Phe Thr Val Thr Val Lys Asp
    1010                1015                1020
Gln Ala Gly Asn Val Ser Glu Ala Ile Ser Ile Asn Ala Pro Leu
    1025                1030                1035
Asp Asp Ile Ala Pro Asn Pro Ile Lys Asn Ile Leu Leu Asp Ala
    1040                1045                1050
Asn Gly Gln Asn Phe Thr Ala Gln Ala Glu Ala Asn Ser Gln Ile
    1055                1060                1065
Glu Val Phe Asp Ser Leu Gly Asn Gln Thr Gly Trp Gly Ser Thr
    1070                1075                1080
Asp Ser Ala Gly Asn Val Ser Gly Ser Phe Asn Gln Thr Tyr Leu
    1085                1090                1095
His Gly Glu Glu Leu Thr Phe Val Val Ile Asp Arg Ala Gly Asn
    1100                1105                1110
Arg Ser Ile Glu Phe Lys Gln Asn Ala Leu Ile Asp Thr Ile Ala
    1115                1120                1125
Pro Asn Pro Ile Ala Asn Ile Ile Phe Asn Glu Asp Gly Gln Ser
    1130                1135                1140
Phe Thr Ala Gln Ala Glu Ala Gly Ser Ser Ile Asp Val Leu Asp
    1145                1150                1155
Gln Thr Gly Asn Lys Ile Gly Phe Gly Tyr Thr Asp Ser Ser Gly
    1160                1165                1170
Asn Val Ser Gly Tyr Phe Gln Val Tyr Leu His Gly Glu Glu
    1175                1180                1185
Leu Thr Phe Val Val Ile Asp Arg Ala Gly Asn Arg Ser Ala Glu
    1190                1195                1200
Val Lys Gln Ser Ala Leu Asn Asp Asp Val Val Pro Asn Pro Ile
    1205                1210                1215
Glu Asn Ile Val Leu Asp Leu Asn Gly Gln Asn Phe Thr Ala Gln
    1220                1225                1230
Ala Glu Ala Asn Ser Gln Ile Glu Ile Lys Asn Asn Asn Gly Asp
    1235                1240                1245
Val Val Gly Tyr Gly Ser Ala Asp Ser Ala Gly Asn Val Ser Gly
    1250                1255                1260
Tyr Leu Tyr Gln Val His Leu His Gly Glu Glu Leu Thr Phe Ile
    1265                1270                1275
Val Val Asp Arg Ala Gly Asn Arg Ser Thr Glu Val Lys Gln Asn
    1280                1285                1290
```

```
Ala Leu Ile Asp Asp Ile Ala Pro Asn Pro Ile Glu Asn Ile Val
1295                1300                1305

Leu Asp Ile Asn Gly Gln Asn Phe Thr Ala Gln Ala Glu Ala Asn
1310                1315                1320

Thr Gln Ile Glu Val Lys Asn Ala Val Gly Glu Ile Val Gly Leu
1325                1330                1335

Gly Tyr Val Asp Gly Ala Gly Asn Val Ser Gly Tyr Leu Tyr Gln
1340                1345                1350

Val Tyr Leu His Gly Glu Glu Leu Thr Phe Val Val Asp Arg
1355                1360                1365

Ala Gly Asn Arg Ser Thr Glu Val Lys Gln Asn Ala Leu Ile Asp
1370                1375                1380

Asp Ile Ala Pro Asn Pro Ile Glu Asn Ile Val Leu Asp Ile Asn
1385                1390                1395

Gly Gln Asn Phe Thr Ala Gln Ala Glu Ala Asn Thr Gln Ile Glu
1400                1405                1410

Val Lys Asn Ala Val Gly Glu Ile Val Gly Leu Gly Tyr Val Asp
1415                1420                1425

Gly Ala Gly Asn Val Ser Gly Tyr Leu Tyr Gln Val Tyr Leu His
1430                1435                1440

Gly Glu Glu Leu Thr Phe Val Val Val Asp Arg Ala Gly Asn Arg
1445                1450                1455

Ser Thr Glu Val Lys Gln Asn Ala Leu Ile Asp Asp Ile Ala Pro
1460                1465                1470

Asn Pro Ile Glu Asn Ile Leu Leu Asp Ala Asn Gly Gln Asn Phe
1475                1480                1485

Thr Ala Gln Ala Glu Ala Asn Thr Gln Ile Glu Val Lys Asn Thr
1490                1495                1500

Ala Gly Glu Val Ile Gly Ser Gly Ser Thr Asp Ser Met Gly Asn
1505                1510                1515

Val Ser Gly Tyr Phe Tyr Gln Val Tyr Leu His Gly Glu Glu Leu
1520                1525                1530

Thr Phe Val Val Val Asp Arg Ala Gly Asn Arg Ser Thr Glu Val
1535                1540                1545

Lys Gln Asn Ala Leu Ile Asp Asp Ile Ala Pro Asn Ala Ile Glu
1550                1555                1560

Asn Ile Ile Phe Asn Glu Asn Gly Gln Asn Phe Thr Ala Gln Ala
1565                1570                1575

Glu Ala Asn Ser Lys Val Glu Val Lys Asn Ala Ala Gly Glu Val
1580                1585                1590

Val Gly Ser Gly Tyr Val Asp Ser Val Gly Asn Val Ser Gly Tyr
1595                1600                1605

Leu Asn Gln Val Tyr Leu Lys Gly Glu Glu Leu Thr Phe Val Val
1610                1615                1620

Ile Asp Gln Ala Gly Asn Arg Ser Ile Glu Val Lys Gln Thr Ala
1625                1630                1635

Phe Leu Asp Asn Thr Ala Pro Glu Asn Ala Thr Asn Leu Val Phe
1640                1645                1650

Ser Glu Asp Gly Ser Tyr Leu Ser Gly Met Ala Glu Pro Asn Ala
1655                1660                1665

Thr Ile Gln Ile Phe Asp Gln Tyr Gly Gln Leu Leu Asn Gln Trp
1670                1675                1680
```

```
Asn Asn Asn Val Asn Trp Asp Gly Thr Phe Asn Ile Tyr Leu Asn
    1685            1690                1695

Ser Asn Tyr Met His Gly Glu Val Phe Lys Val Val Val Asp
    1700            1705                1710

His Ala Gly Asn Leu Ser Gly Glu Val Thr Val Lys Ala Pro Leu
    1715            1720                1725

Asp Asp Ile Ala Pro Val Ala Ala Ser Asp Leu Val Phe Asn Glu
    1730            1735                1740

Asp Gly Ser Ser Leu Ser Gly Val Ala Glu Pro Asn Thr Phe Ile
    1745            1750                1755

Gln Ile Phe Asp Gln Asn Gly Gln Gln Met Asn Thr Trp Ser Gln
    1760            1765                1770

Ser Val Asn Ala Asp Gly Thr Phe Thr Ile Phe Phe Gly Thr Tyr
    1775            1780                1785

Asn Leu His Gly Glu Glu Phe Thr Val Ile Val Lys Asp Leu Ala
    1790            1795                1800

Gly Asn Val Ser Glu Ala Val Ser Val Lys Ala Pro Leu Asp Asp
    1805            1810                1815

Ile Ala Pro Lys Pro Ile Lys Asn Ile Val Phe Asp Ala Asn Gly
    1820            1825                1830

Gln Ser Phe Thr Ala Gln Ala Glu Ala Asn Ser Gln Ile Glu Ile
    1835            1840                1845

Phe Asp Ser Phe Gly Ser Gln Ile Gly Trp Gly Ser Thr Asp Ser
    1850            1855                1860

Thr Gly Ser Val Thr Gly Tyr Phe Tyr Gln Val Tyr Leu His Gly
    1865            1870                1875

Glu Glu Leu Thr Phe Val Val Ile Asp Arg Val Gly Asn Arg Ser
    1880            1885                1890

Asp Glu Met Lys Leu Asn Ala Leu Met Asp Thr Ile Ala Pro Lys
    1895            1900                1905

Pro Ile Glu Asn Ile Ile Phe Asn Glu Asn Gly Gln Asn Phe Thr
    1910            1915                1920

Ala Gln Ala Glu Ala Asn Ser Phe Ile Ser Val Lys Asn Ala Ala
    1925            1930                1935

Gly Glu Phe Val Gly Tyr Gly Tyr Val Asp Ser Thr Gly Asn Val
    1940            1945                1950

Ser Gly His Phe Asn Gln Val Tyr Leu Lys Gly Glu Glu Leu Thr
    1955            1960                1965

Phe Ile Val Ile Asp Lys Ala Gly Asn Gln Ser Ile Glu Tyr Lys
    1970            1975                1980

Gln Asn Ala Leu Thr Asp Asp Ile Ala Pro Asn Pro Ile Glu Asn
    1985            1990                1995

Ile Val Leu Asn Lys Asn Gly Gln Asn Phe Thr Ala Gln Ala Glu
    2000            2005                2010

Ala Asp Ser Gln Ile Glu Val Lys Asn Thr Ala Gly Glu Val Val
    2015            2020                2025

Gly Ser Gly Tyr Val Asp Ser Ile Gly Asn Val Ser Gly Ser Phe
    2030            2035                2040

Asn Gln Val Tyr Leu His Gly Glu Glu Leu Thr Phe Val Val Val
    2045            2050                2055

Asp Arg Ala Gly Asn Arg Ser Thr Glu Val Lys Gln Asn Ala Leu
    2060            2065                2070

Ile Asp Asp Ile Ala Pro Asn Gln Ile Glu Asn Ile Val Phe Asp
```

```
                2075                2080                2085
Val Asn Gly Gln Tyr Phe Thr Gly His Ala Glu Ala Asp Thr Arg
    2090                2095                2100
Ile Glu Val Leu Asp Gln Phe Gly Asn Arg Ala Gly Trp Gly Tyr
    2105                2110                2115
Val Asp Ser Gln Gly Asn Val Ile Gly Tyr Phe Asn Gln Val Tyr
    2120                2125                2130
Leu His Gly Glu Glu Leu Thr Phe Ile Val Val Asp Ile Ala Gly
    2135                2140                2145
Asn Arg Ser Val Glu Val Lys Gln Asn Ala Leu Ile Asp Asn Val
    2150                2155                2160
Ala Pro Pro Ala Ala Ala Asn Ile Thr Leu Thr Ser Asp Gly Leu
    2165                2170                2175
Leu Phe Gly Glu Ala Glu Pro Asn Ser Thr Val Glu Ile Ile Asp
    2180                2185                2190
Gln Tyr Gly Ala Val Ile Thr Thr Thr Tyr Val Trp Tyr Asp Gly
    2195                2200                2205
Thr Phe Asn Gln Trp Ile Asn Leu Ser Gln Tyr Gln Thr Gln Asn
    2210                2215                2220
Leu Ser Ile Val Val Lys Asp Gln Ala Gly Asn Arg Ser Glu Val
    2225                2230                2235
Val His Glu Leu Val Pro Val Phe Thr Asn Ser Pro Ile Ala Ala
    2240                2245                2250
Thr Glu Leu Lys Leu Asp Ile Asp Gly His Ile Leu Thr Gly Lys
    2255                2260                2265
Ala Thr Val Gly Met Ser Val Val Thr Ser Thr Asp Gly Gln
    2270                2275                2280
Thr Ile Asn Gly Gly Trp Asn Asn Ala Val Asn Glu Asp Gly Ser
    2285                2290                2295
Phe Ala Ile Gln Leu Asn Asp Tyr Tyr Leu Gln Gly Gln Thr Leu
    2300                2305                2310
Gln Val Arg Val Tyr Asp Gln Asn Thr Asn Gln Tyr Ser Leu Ile
    2315                2320                2325
Ser Glu Ile Ile Ala Pro Leu Asp Asn Ile Ala Pro Val Ile Asn
    2330                2335                2340
Glu Val Val Ile Asn Asn Asp Gly Tyr Gly Ile Thr Gly Gln Thr
    2345                2350                2355
Asp Ser Lys Ala Ile Ile Gln Val Met Asp Ala Asp Gly Asp Leu
    2360                2365                2370
Arg Ala Glu Phe Gln Ala Asp Glu Thr Gly Tyr Phe Asn Ala Ser
    2375                2380                2385
Ile Tyr Pro Pro Ile Leu Arg Gly Glu Gln Leu Phe Ile Thr Ala
    2390                2395                2400
Ile Asp Leu Ala Lys Asn Ile Ser Lys Pro Phe Asn Ile Thr Phe
    2405                2410                2415
Asn Ala Asp Thr Asn Ala Pro Pro Ser Ala Glu His Ile Val Val
    2420                2425                2430
Ser Glu Asn Gly Phe Phe Ile Glu Gly Thr Ala Val Ala Ile Ser
    2435                2440                2445
Thr Val His Ile Phe Asp Val His Ser Asn His Val Ala Thr Asn
    2450                2455                2460
Val Ala Asp Glu Ala Gly Asn Phe Asn Ile Gln Leu Tyr Pro Pro
    2465                2470                2475
```

```
Leu Ala Ser Gly Gln Ile Leu Arg Ile Val Val Glu Tyr Asn Gly
    2480            2485                2490
Tyr Gln Ser Ala Tyr Thr Glu Ile Thr Ala Pro Ile Asp Thr Val
    2495            2500                2505
Ala Pro Asn Ala Ala Thr Gln Leu Leu Leu Glu Asp Gly Asn Val
    2510            2515                2520
Leu Ser Gly Gln Ala Glu Ala Tyr Ser Ile Val Asn Ile Phe Asp
    2525            2530                2535
Ala Asn Asn Asn Leu Val Gly Gln Thr Asn Val Gly Ser Asp Gly
    2540            2545                2550
Ala Phe Leu Thr His Leu Trp Tyr Glu Tyr Trp His Gly Glu Thr
    2555            2560                2565
Leu Thr Val Lys Val Val Asp Ala Asn Gln Asn Val Ser Val Gly
    2570            2575                2580
Thr Thr Ile Val Ala Ile Asn Asp Thr Val Val Pro Asp Val Val
    2585            2590                2595
Thr Gln Leu Ala Ile Asp Glu Trp Gly Ser Leu Thr Gly Arg Val
    2600            2605                2610
Glu Ser Tyr Ala Thr Val Glu Leu Thr Tyr His Phe Thr Asp Gln
    2615            2620                2625
Pro Leu Ser Val Thr Ser Thr Thr Ala Leu Ala Asn Gly Met Phe
    2630            2635                2640
Phe Ile Tyr Leu Asp Arg Asn Ala Thr Ser Leu Asp Leu Thr Val
    2645            2650                2655
Ile Asp Arg Ala Gly Asn Arg Ser Glu Thr Ile Ser Gln Ile Ile
    2660            2665                2670
Ser Asp Leu Pro Thr Val Ile Ile Asp His Phe Lys Gly Asp Ala
    2675            2680                2685
Thr Asp Asn Thr Tyr Asn Ile Asp Thr Ile Asp Phe Val Gln
    2690            2695                2700
Glu Tyr Ile Val Glu Pro Tyr Ala Ile Tyr Lys Asp Val Trp Ile
    2705            2710                2715
Asp Asn Ser Tyr Met Tyr Ser Asp Trp Val Ile Glu Gly His Tyr
    2720            2725                2730
Glu Gln Ile Trp Phe Val Asp Gly Tyr Tyr Glu Ser Gln Trp Ala
    2735            2740                2745
Thr Ser Gly Tyr Ser Thr Val Gln Asn Ile Tyr Gln Asn Gln Asn
    2750            2755                2760
Gly Ile Thr Tyr Ile Asp Asn Gly Thr Ala Asp Ser Asp Tyr Ser
    2765            2770                2775
Arg Tyr Glu Gln Gln Tyr Tyr Asp Phe Val Asn Gly Gln Trp Gln
    2780            2785                2790
Glu Gly Tyr Glu Leu Thr Tyr Ile Arg Ser Glu Gly Trp Val
    2795            2800                2805
Asp Thr Ser His Tyr Glu Asp Val Tyr Ile Asp Thr Ser His Tyr
    2810            2815                2820
Glu Glu Val Trp Val Asp Thr Ser His Tyr Gln Asp Ile Trp Val
    2825            2830                2835
Glu Asn Ser Tyr Trp Glu Ser Gln Leu Val Glu Ser Gly Arg Arg
    2840            2845                2850
Asp Val Asp Leu Gly Gly His Asp Lys Ile Ile Ser Ser Val Asn
    2855            2860                2865
```

| | | | | | | | | | | |
|---|---|---|---|---|---|---|---|---|---|---|
| Tyr | Ser | Leu | Val | Gly | Leu | Tyr | Gln | Thr | Val | Asn | Asp | Pro | Thr | Thr |
| | 2870 | | | | 2875 | | | | 2880 | |
| Val | Asp | Ser | Phe | Leu | Glu | Ser | Gly | Arg | Tyr | Val | Glu | Asp | Leu | Glu |
| 2885 | | | | | 2890 | | | | | 2895 | |
| Leu | Val | Gly | Ser | Ala | His | Leu | Asn | Ala | Thr | Gly | Asn | Ala | Leu | Asp |
| 2900 | | | | | 2905 | | | | | 2910 | |
| Asn | Leu | Leu | Thr | Gly | Asn | Ser | Gly | Asn | Asn | Val | Leu | Asn | Gly | Arg |
| 2915 | | | | | 2920 | | | | | 2925 | |
| Glu | Gly | Asn | Asp | Thr | Tyr | Ile | Thr | Asn | Glu | Gly | Thr | Asp | Thr | Ile |
| | 2930 | | | | 2935 | | | | | 2940 | |
| Val | Phe | Gln | Leu | Leu | Asn | Ser | Gln | Asp | Ala | Thr | Gly | Gly | Asn | Gly |
| | 2945 | | | | 2950 | | | | | 2955 | |
| His | Asp | Thr | Val | Leu | Asp | Phe | Thr | Leu | Gly | Asp | Ile | Arg | Thr | Asn |
| | 2960 | | | | 2965 | | | | | 2970 | |
| Leu | Gln | Ala | Asp | Lys | Ile | Asp | Leu | Ser | Glu | Leu | Leu | Ile | Asp | Tyr |
| | 2975 | | | | 2980 | | | | | 2985 | |
| Ser | Lys | Asp | Val | Ser | Ala | Leu | Ala | Lys | Phe | Ile | Thr | Val | Glu | Gln |
| | 2990 | | | | 2995 | | | | | 3000 | |
| Asp | Ala | Gly | Asn | Thr | Thr | Ile | Ser | Leu | Asp | Arg | Asp | Gly | Glu | Gly |
| | 3005 | | | | 3010 | | | | | 3015 | |
| Thr | Met | Phe | Asn | Ser | Val | Ser | Leu | Leu | Thr | Leu | Asn | Gln | Val | Asn |
| | 3020 | | | | 3025 | | | | | 3030 | |
| Thr | Thr | Leu | Asp | Glu | Leu | Leu | Asn | Asn | Gln | Gln | Ile | Ile | Val |
| | 3035 | | | | 3040 | | | | | 3045 | |

<210> SEQ ID NO 31
<211> LENGTH: 183
<212> TYPE: DNA
<213> ORGANISM: Acinetobacter baumannii

<400> SEQUENCE: 31

```
atgacacagc tcattaataa aggtggcttt cgtgaaagag ccaatagaag ccgaaaatat    60
caacaatctg aaaacaagca gtagctctg ccttcaaaaa agtatcaacc tcaaactaaa   120
ctccaagata tcaaagcga gatgattcaa gcaaaagcag gtactgctga aacttcagat   180
taa                                                                183
```

<210> SEQ ID NO 32
<211> LENGTH: 201
<212> TYPE: DNA
<213> ORGANISM: Acinetobacter baumannii

<400> SEQUENCE: 32

```
atgaaattag ctaaaacttt actcgctact accctagctt taactgctgc ttcaactttc    60
gctgcttcta agcacgacca agcacataac actgctggtg aagaaaaagt tgttgtttca   120
actcaagagc aagcaaacac tgcaaatgct gcttctgacg ctgtaggttc tgcttctgaa   180
gctgctcctg caactcgtta a                                             201
```

<210> SEQ ID NO 33
<211> LENGTH: 201
<212> TYPE: DNA
<213> ORGANISM: Acinetobacter baumannii

<400> SEQUENCE: 33

```
atgatagatg aagaaaagcc tttaaatttt gaagatgatg acgagcctct tgattttgaa    60
gatgaagaat tcatagacga taaaaaagag gacgaaatgt ataactcgat tactaaggat   120
```
ggctctagtg tcgatcctgc tgatgatggg acacgacata ttcgtcctga agacggcgat    180
ccgattgaaa ttgatgagta a                                              201

<210> SEQ ID NO 34
<211> LENGTH: 222
<212> TYPE: DNA
<213> ORGANISM: Acinetobacter baumannii

<400> SEQUENCE: 34
atgagcacta ctaataatca agcaaatcaa cgcaataatc agcagcaaca acaacagcaa    60
aatgacaacc gtaatcaaca gcaacacggt aaccaacagc aaaacgatca acagcaacaa    120
aataaccagc aacaacagca aaatgataac cgcggtcaac aacaaggatc taatcaaaaa    180
gattctggcc aacaaaactc aaataacaac caacaacgtt aa                       222

<210> SEQ ID NO 35
<211> LENGTH: 327
<212> TYPE: DNA
<213> ORGANISM: Acinetobacter baumannii

<400> SEQUENCE: 35
atgtcagcaa aactagttgt tactttgtta gcaaccagtc ttttaactgt aggctgtgtt    60
gcttatacag atgatcctta ttatcgcggt ggttatggtt accatgatca tgacgacgat    120
cgttatgacc gtaacgatgg acgtcgatat agtgagtggg aacgcaaacg ttgggaagag    180
cgtaaaagat tatatgaaca caacgcaaaa gatattcgtg aacagcaaaa ggatcgtcgt    240
gaatgggaaa acgacaccg tgaatgggag aagaaacgct tagaagaccg agatcatgat     300
catagagatt atcgtcatga tgactaa                                        327

<210> SEQ ID NO 36
<211> LENGTH: 345
<212> TYPE: DNA
<213> ORGANISM: Acinetobacter baumannii

<400> SEQUENCE: 36
atgaataaat tacttgttgc tttaggtctt gctgcgactg ttgcccttgt tggttgtaat    60
aaagataaag ctccagaaac tggtgctact acaggtgaac acttagaaaa tgctgctcaa    120
caagcaacag cagatatcaa atctgctggt gatcaagctc gagcgatat tgcaactgca     180 acagacaacg cttcagctaa aattgatgct gctgctgacc atgctgctga tcgactgct     240 aaagctgcag ctgaaacaga agctactgca cgtaaagcga ctgctgatac agctcaagct    300
gttgaaaatg cagctgctga tgtgaaaaaa gatgctcaac actaa                    345

<210> SEQ ID NO 37
<211> LENGTH: 381
<212> TYPE: DNA
<213> ORGANISM: Acinetobacter baumannii

<400> SEQUENCE: 37
atgaaaatga cggctaaaat tgcattattc agtgcagcaa ttgtaactat gggtagtttg    60
gctgcttgtc aatcaacaac tcaaccaccct aagccagaac atggcatgat gcaagatggc   120
ccacgtgatg gtcaccacca tcgtatgaaa caccgtgaat ttacgcctga acaaaaagca    180
gcatgggaac aacaccgtgc agagcgtaaa gctcgttttg agcaaattca aaaagcatgt    240
gaaggtaaag ttgttggaca aactgtcaat gttcaagttg gagataaaac acttgaaggt    300

```
acatgtaacc tccgctttga gccaaaacgt cctcaaccac cagtcaatgc ccctgctcca    360
gtagcgactc aagcaaaata a                                              381

<210> SEQ ID NO 38
<211> LENGTH: 420
<212> TYPE: DNA
<213> ORGANISM: Acinetobacter baumannii

<400> SEQUENCE: 38
atgaaagcca taaaaatttt atgtattaca agctctatct tggtttcatc atctctcttt    60
gctgaaacac ctcaacctca acaagtgaat gaagcaactt ctaagacaat gccttatggt   120
gataatccaa gcttaggccg cgtactgtta tacaaaacag gaaaaggcat tcaaaattta   180
ggagattcta ttcaaggcgc ttctgaaaaa acttcaaata aaattagtga aaaatggaaa   240
gatacgaaag aatttaccgc cgaaaaagca gaagttgttc aacaaaaagc ggatacagcc   300
aaagtattta ctgaacagaa aatagaacaa gctaagcaaa atatcaccag cagtagaaac   360
ggtgaaaata ttccaatcga acaaggtgag ctaagtaaat ctagtacgac tgccaattaa   420

<210> SEQ ID NO 39
<211> LENGTH: 480
<212> TYPE: DNA
<213> ORGANISM: Acinetobacter baumannii

<400> SEQUENCE: 39
atgaaaaaat cattattagc aattgcactt atgagtactc ttcttgtcgc atgtaataaa    60
catgaaaata aaacagaaac aacctctgat gcatcactc ctgtacaaac tgctcaatca   120
aataataatg aagcggtaga tacagcacat acagccgaga attctttaga ttgggatggt   180
aaatataaag gtacgcttcc ttgtgcagac tgtgaaggca tcaaaactga attagagtta   240
aaagatgata aacttatga gctaacagaa acctatcttg gtaaaggtga tgcaaaccca   300
tttgaaaccc atggtaagtt tactttcgat aaagacaata cttctgttat taccttagat   360
gataaagctc aaaaccgtaa attctttatt ggtgaaaata cagcgacagc tttagatatg   420
gaaggtaaaa aagttgaagg ttctttagct gaacattatg ttttgaaaaa agaagattaa   480

<210> SEQ ID NO 40
<211> LENGTH: 489
<212> TYPE: DNA
<213> ORGANISM: Acinetobacter baumannii

<400> SEQUENCE: 40
atggcaaata aaaaactttt aatctgtgct gcaattgcgg ctggactatt gttaaccgca    60
tgcgttaaaa aagagacacc gaaagaagaa gagcaagaca aggttgaaac tgctgtttca   120
gaacctcaac cacagaagcc tgcaaaattt gaatctttag agagtgtaga tactcaagaa   180
gctcaagttc aagagcaacc acaagttgaa gttcatcgtg aagaaactgc taacacgaca   240
actgaaattc gccgtgaaac tcgtcctgcg cgttctgatg aatcttcaca gacacaagtt   300
gctgaacaac ctaaatctga cacccaaaaa gtagaaccta accagaaaaa aaaacctgag   360
cctaaagctg aacctaaacc ggaaaaagct cagtcaaaac cagctgctaa ggcaactgag   420
cctgcgaaca cagaagatga tgccgttgct gctgctattg ctgctgcaac accagcactt   480
aagaactaa                                                            489

<210> SEQ ID NO 41
<211> LENGTH: 501
```

```
<212> TYPE: DNA
<213> ORGANISM: Acinetobacter baumannii

<400> SEQUENCE: 41
atgactactg aaaataaatt agatgaatta aaggcaaacg cggctgatgc aaaagtacaa      60
ggtgaaaaag cttggacga tttaaaagaa aatgtaaaag agaaacaaac tgcgggtaaa     120
gaagcaattg cagataaagt agatgagcta agaccaaag cggccgatgc aaaagtacaa     180
ggtgaaaaag ccttggaaga tttaaaggaa aatgtaaaag aaaaacaagc tgctgcaaaa     240
gaggcagttg aagataaagc tagtgatttg aaaggcaaac ttgatgatgc tcagcatagc     300
ctgcaagaca agtttgatca tttacgtact gaagcagcgc ataaacttga tgatgctaaa     360
gccaaagctg cagaattaaa ggaagaggcg gctacaaaat ttgatgagtt aaaaactcaa     420
gcaactgcga aatttgatga gttgaagaaa acagctaccg aaaaacttaa taaattgaaa     480
aatcatgatt ctgctgaata a                                                501

<210> SEQ ID NO 42
<211> LENGTH: 693
<212> TYPE: DNA
<213> ORGANISM: Acinetobacter baumannii

<400> SEQUENCE: 42
atgcacacgc gtcgtatttt attagcgttt tcacttgccg cttcggcagc atcggttgct      60
tttgcagatt atcaaaatat taccaatct actgattcag atcgattgga acagttatca     120
aaaacactat ctcaaggctc atatactcat cctgatgatt tagatcttcc ggcgagtgca     180
aaagtttcag tgactttacg tgagaaaaca gttgaactca acaatgattc actggcaaag     240
aaatacggca caacgacagc taaaaactca tttaaaaacct cttcttcaaa tccttattct     300
tggttagttt ctcatcctct tcctgataca gtacgtgttt cttctaactt tggtggtcgt     360
accatgggtg tcgtgcaga gcatcatggt ggtttagata tggctgcacc aagtggtacg     420
ccaatctatg ccactggtcc gggtattgtg actaaatcag gctggggcac aggttatggc     480
caatatgttg aaattaacca tggtaatggt tatttaacac gttatgcgca tgcttcacgc     540
ttaatggttc gggtaggtga tcaggtttct gcgggtgacc atattgctaa tgttggttgt     600
acaggccgct gtactggtcc acatttacat tacgaagtag ttaaagatgg tcaacgtaag     660
aatccatcaa cttacttagc aatgttgcct taa                                  693

<210> SEQ ID NO 43
<211> LENGTH: 717
<212> TYPE: DNA
<213> ORGANISM: Acinetobacter baumannii

<400> SEQUENCE: 43
atgggcatga cttttacaga catagaaaat aaatctgcca aacgcctaat tggtattgct      60
gcagtcattt ttctgcatct tcttgttgcc tatattctga tgtcaggttt agcaaacaat     120
attcaaaaac cagcagaaaa acctgtggaa ttacaaatta ttcaggatat taagccacct     180
cctccaccaa agccggaaga gccgaaacca aaggaaaaac cacctgagcc accaaaaatg     240
gtagaaaaag ttgccaaggt tcctgagcca ccaaaagaag tagagaaagt agcaacacca     300
gtacaaaaaa cgacgccagt agctcaaacg actaaagtcg ctactccggc tcctgctgca     360
cctagtactc cttctccgag ccctgttgct gcaccagctc cagtggcagc tgctgcacca     420
gcacttaaac ccgctggtgt aactcgtggt gtttcagaag gctctgcggg ctgcgaaaaa     480
```

| | |
|---|---|
| ccagaatatc cacgcgaagc actcatgaac gaagagcaag gtacggtgcg tatacgtgtt | 540 |
| ttagttgata cttccggcaa agtcattgat gccaaagtaa aaaaatcgag tggtagcaaa | 600 |
| accttagata aagcagcaac taaagcctac agcttatgta cgttcaaacc agcaatgaaa | 660 |
| gatggcgtac ctcagcaaga ctggtatgaa attgaatatc cattcgtaat tgaataa | 717 |

<210> SEQ ID NO 44
<211> LENGTH: 762
<212> TYPE: DNA
<213> ORGANISM: Acinetobacter baumannii

<400> SEQUENCE: 44

| | |
|---|---|
| atgaaaatga tgaaaacagc tatcgttact gcaagtgtac ttgcttctgc ctctattttt | 60 |
| gcacaaagtg cgggcgttaa tgcaggtgca tctgctcaag tcaacgtaca accaggtggt | 120 |
| cttgttagtg gcgtagccaa tacagtcaaa aatactgcac atactgtagg gaacacagca | 180 |
| aaacatgctg gtcacgtagc tgctgacaca accgttaaag ctacaaaaaa aacaacaggt | 240 |
| aaagtaactg aactttcttc taaagctgct actggtacta acatgtagc aagtgaagct | 300 |
| gtaactggta ctaaacattt tgctaccgaa gcagcaacag gtacaaaaaa tttagcgact | 360 |
| aaggctgcaa ctggcactaa aaacctagca gttgaagcta aagcagatac aaaagcacat | 420 |
| cttgatgctg taaaaactaa ggtagcagaa aaacaagctg accaaaaaga atttactgct | 480 |
| gaaaaacagg ccgatgctca agcacgtgta gatgctgtta agctcgtgt agcacaaaat | 540 |
| caagctgagc aaaaagaatt cgttgctgac actaaagctg atgctcaagc aaaattaaat | 600 |
| acagctcaac cagctcatgg agttaacgct caaacaggt aaacgttgg tgttaatgtt | 660 |
| gctggtatta tgcaaatgc aaacgtaaat gcaggcgctc aagcgtctac acaaaaaggc | 720 |
| gaaaagaaat cttttattaa aggtctttc ggtactaact aa | 762 |

<210> SEQ ID NO 45
<211> LENGTH: 885
<212> TYPE: DNA
<213> ORGANISM: Acinetobacter baumannii

<400> SEQUENCE: 45

| | |
|---|---|
| atgcaaatga agaagcattc tttattattt attgccttaa tgagcaccac ttctctatac | 60 |
| gcaaatatcc ctatcgagtc tcgtggttta agtcaaaatg atggtagtgc atctaatact | 120 |
| tcttcaagca atatttcagt tcctacaaat ttaaactggg aactcatgca aaaaaaccaa | 180 |
| caattagaaa atgatattcg tacattaaga ggtcagcttg aagaacaagc taatgatatt | 240 |
| gagcaattaa agaaagatct agcaaaccga tataccgact tagatcaacg tttagaatta | 300 |
| ttacaccaaa aagttgaccc tgacagtgct acacaagatg atagttcgaa tgcaacgtcc | 360 |
| gataacacta ctcctgctag tgcaccagcc cctcaaacca cggagagtaa taaagtagct | 420 |
| gccgtaccag ccacacaaac ttctgagcag cagcctagcg caccaacaac cactactcaa | 480 |
| ccagcaccag ctgctgcgca aaaccagtca aattccctcg aattagaaaa agctgcttat | 540 |
| actgtagctt tagatgcgta taaacaaggc ggtgctaaaa aagcaattgc tccaatgcaa | 600 |
| aactttataa aaaccatcc taatagtatc tatacaggta atgcttattt ttggttagcc | 660 |
| gagtttcatt tagcgacaga tccagtaaat tataatgaag caagaaaaa ctataatgtc | 720 |
| gtagctaacc aatacccaaa ttcaagtaag gcacctcgag cattgtacca actttatagt | 780 |
| atcgctaaaa tgttgataaa gaatactgtg tcagcaaatc aatacaagaa caagttactt | 840 |
| agccaatatc caaaatctga agaagcaaaa ttctttaaca aataa | 885 |

<210> SEQ ID NO 46
<211> LENGTH: 1071
<212> TYPE: DNA
<213> ORGANISM: Acinetobacter baumannii

<400> SEQUENCE: 46

| | | | | | |
|---|---|---|---|---|---|
| atgtcaatga | ataacaaaca | acgctggatg | ggtggcgttg | ttttattagg | tggtggtgtt | 60 |
| ttattggcag | cattacttct | aaaaggaaat | gaagaaataa | aacaggtaga | tgttcaaccc | 120 |
| caaacttcaa | catcaccgaa | attacaagct | aagccaaagc | aatcagcaca | agaagggcag | 180 |
| atggtacagc | tacagccact | tgcagttgat | gttgaaacga | aaaaacgtct | tcttgaagaa | 240 |
| cagcgccgtt | ctcgtgaaaa | agctgtagca | gaacaagagg | ctcgtgctgc | cgaattcttg | 300 |
| gcaatgcaac | aacaggcaga | agcggatgca | gctcgtaaag | ctgctgctga | atatgccgcg | 360 |
| attaatgctc | gccgagctgc | tgcacaagaa | agttccgata | atattcctcc | tgaagtcgcg | 420 |
| ggtagtgaga | ataaggcaaa | aggacagcaa | actgatacaa | aaaagtcagt | agatctggct | 480 |
| aaagcggatg | cagataaaaa | agctgctgaa | gcgaaacgct | agctgaggc | ggataagaaa | 540 |
| gcggctgagc | aaaacgtca | ggcagaagca | gacaagaaag | cagcagaggc | taaacgccaa | 600 |
| gcagaagcag | ataagaaagc | agctgaggca | aaacgtcagg | cagaagcgga | taagaaagca | 660 |
| gcagaggcga | agcgccaagc | agaagcggac | aaaaaggctg | ctgaagctaa | acgtcaagca | 720 |
| gaagcagata | agaaagcagc | tgaagcgaaa | cgtaaggcag | aggccgagaa | aaaagctgaa | 780 |
| gcagagaaag | cacgtgagtt | gcttgaaaat | ggtgataaaa | aatggatggt | acaggttgca | 840 |
| ttggctgcta | accaagcaaa | tgcagatgct | gtagtctcta | aattacgtgc | aaaaggctat | 900 |
| aaggtcacga | cgagtccaac | cagtaaaggt | atccgtatta | tggttggtcc | tgcaaaagat | 960 |
| agagatacgg | cagatactac | acgtaagaaa | attacttctg | acgccagttt | aaatatgaag | 1020 |
| tcagcttggg | tgattgactg | ggtgccttta | gatcagcgta | agtcagatta | a | 1071 |

<210> SEQ ID NO 47
<211> LENGTH: 1104
<212> TYPE: DNA
<213> ORGANISM: Acinetobacter baumannii

<400> SEQUENCE: 47

| | | | | | |
|---|---|---|---|---|---|
| atggctaata | ctagatatga | agatgataac | aatagttcag | gtacttcaaa | tcgtggattt | 60 |
| gcaagtatgg | atcctgaaag | agtcagagaa | atagccagta | aaggtgggcg | agctgcacat | 120 |
| gccagtggca | atgcgcatga | atttacttca | gaagaagctc | gtgaagctgg | ccgtgctgca | 180 |
| catgccagtg | gtaacgcaca | tgaatttacc | tcagaagagg | ctcgtgaagc | tggtgcttta | 240 |
| agtcataaaa | acgatgatcg | taatggtcgt | ggtcgcagcc | gttatgatga | cgacgaagat | 300 |
| gatgaccgcg | gccgttcaag | tggtcgaggc | cgtggccgca | gtcgttatga | tgatgacgac | 360 |
| gaagatgatg | atcgcggtcg | ctcaggcggt | cgtggccgtg | gtcgcggtcg | tgatgatgac | 420 |
| gacgaagatg | atgatcgcgg | tcgctcaggt | ggccgaggcc | gtggtcgcag | tcgtgatgat | 480 |
| gacgatgaag | atgatgatcg | cggtcgttca | ggtggccgag | gtcgtggtcg | cagccgccgt | 540 |
| gatgatgacg | atgaagatga | tgatcgcggt | cgttcaggcg | gtcgaggtcg | tggccgcagc | 600 |
| cgtcgtgatg | acgacgatga | agatgatgat | cgcggtcgct | caggtggccg | aggtcgtggt | 660 |
| cgcagccgtt | atgatgacga | cgatgaagat | gatgaccgtg | gccgttcagg | cggtcgaggt | 720 |
| cgtggccgca | gccgtcgtga | cgatgatgac | gaagatgatg | atcgtggtcg | ttcaggtggc | 780 |

| | |
|---|---|
| cgaggccgtg gccgcagtcg ttatgatgac gacgatgaag atgatgatcg tggccgttca | 840 |
| ggtggccgag gtcgtggccg cagccgtcgt gatgatgacg atgaagatga tgatcgcggt | 900 |
| cgttcaggtg gtcgaggccg tggccgcagt cgttatgatg atgacgatga agatgatgat | 960 |
| cgtggtcgtt caggtggccg aggccgtggt cgcagccgtc gtgatgacga tgacgacgat | 1020 |
| gatgaccgcc gtggccgttc agacggtcgt ggtcagaact ctcgtaatca aaaacgcgat | 1080 |
| gcttatggac gctttacgtc ttaa | 1104 |

<210> SEQ ID NO 48
<211> LENGTH: 1263
<212> TYPE: DNA
<213> ORGANISM: Acinetobacter baumannii

<400> SEQUENCE: 48

| | |
|---|---|
| atgttatatg tgattccgtt tatcatatta ctcgtggtcg ccgttatttt aaaaaaacgc | 60 |
| gagaatagtc aaaaacaaga ggccacttcc ccaaaaaata taaatagaaa atccggcaaa | 120 |
| aaagcgagtg ctaaatcaag caaaagctcg cgtgaaaaaa taaaagccaa ggtcattgag | 180 |
| gaaaatattc ctgctatccc tcaaagtaat cctgtaccgg aagctttacg acacaatatt | 240 |
| caacagctca ttcaagaaaa acagttttca gcagctgaag ctcaagtcaa tcaggcgcta | 300 |
| aaaaaagata atactcaaca tgaactgtat ttattacttc ttgaaattca tattgctcag | 360 |
| aaagatgaat ttgcaattca acagttgatt agccatattc gtagcttggg tttaaatgaa | 420 |
| atagcagctc aagcagaaac tcgacaaaaa gaatatgaat catccagcca acctgatgct | 480 |
| attgatttcc ctcaagctca aacatatgaa gaaccgaaaa acacagatac aacggctcag | 540 |
| ttcgatgaat taacaacaag ttcttccgag gcttcttttg atgacctaca gaaagactat | 600 |
| accccctgtaa aacaagaacc tgctattgaa attgaacctt tagagtttaa cttttcattc | 660 |
| gaacagaatt cggctacgga aaataccaac caaccagcac aacaacctga gttatcatcc | 720 |
| actcaagaaa caaatgagct ggccgattta gagttttctt ttgacttggc ccctctgcat | 780 |
| gaaactgagg aaaaatctca agcagtagag gtaaaagcag accaagaaaa tagcatcaat | 840 |
| gcattagatt ttaactttga cttaaatcct tcaagttcag agacgaaatc tgttcaacaa | 900 |
| gctccctcat tagatgaaat taagctcata gaacaagccc cattagaagc gacttctatc | 960 |
| gcacctcttg agttttcgtt agatgagcct gccttagttc cagcaccaga gcttgaaact | 1020 |
| caaaaccata tagatgtagt aaatgaagca gccactcaaa cccaaataga ggatccgctt | 1080 |
| ttagaagctt ttccagaatt aaaacaaata aatgaaaatg aactcgattt aaaattggct | 1140 |
| gaacaataca ttaagtttgg cgcaaaccaa gcagcgcgta atttactaca gggtgatgag | 1200 |
| caaaaattca acacagaaca acaacaacat gcgaaaaacc tacttaatcg catagcttct | 1260 |
| tag | 1263 |

<210> SEQ ID NO 49
<211> LENGTH: 1338
<212> TYPE: DNA
<213> ORGANISM: Acinetobacter baumannii

<400> SEQUENCE: 49

| | |
|---|---|
| atgccaaaaa taaagccaat taaactcgta attattgtcg tctgtatcgc cattattgct | 60 |
| gtcttagctt ggaaattctt aaaagcctaaa caacagcaac ctcaatatat tacagcagag | 120 |
| gtaactcgtg gggatattga gaataatgta cttgcaaccg gtacacttga tgcaaccaag | 180 |
| ctcattagtg tgggtgctca ggtatctggt caggttaaaa agatgtatgt gcagcttggt | 240 |

```
gatcaagtaa aacaaggtca acttattgca caaattgact cgaccaccca agaaaacagt      300
ttaaaaacat ctgatgctaa tattaaaaat ttagaggcac agcgtcttca gcaaatcgct      360
tctttaaacg agaaacaact cgaatatcgt cgtcaacaac aaatgtatgc tcaagatgca      420
acacctcgtg cagatttaga gtcggctgaa gctgcttata aaacagctca ggcacaagtt      480
aaagcattag atgcacaaat tgagtctgca aaataacgc gttcaacagc acaaccaat       540 attggctata cccgtattgt tgcgccaact gatggtacgg ttgttgcgat gtgactgaa      600 gaaggtcaaa cggtaaacgc aaaccaaagt gctcctacta tcgtcaaaat tgcaaaactt      660
caaaatatga cgattaaagc acaggtgagt gaagccgata ttatgaaagt ggaaaaaggt      720
cagcaggtct atttcacgac cttaggtgat gaaaccaagc gctatgcaac cttacgtcaa      780
atcgaacctg ctccagattc aatctctagt gaatcaaaca gcaccacaag ttcaacaaca      840
agctcagctg tttactacaa cgctttattt gatgttccaa atacggacgg caaattgcgt      900
attgatatga ctgcacaagt ttatatcgta ttaaattcag caaaaaatgc cttattggtt      960
ccatcttctg cgttaagtag caaacaattt tctggccaaa gaaaacaggg gcaatcggca     1020
gataaagcaa gttctactcc aagtgcagaa cgcaagcatc aaggtaacgg cgtccgttta     1080
gaacgcttaa atttaactcc tgaacaaaaa caacttattg aacaaggcaa agcaactctg     1140
agtgtagttc gcgttttaca agcagatggt acgactaaac aacacaaat tttggtaggt     1200 attaataacc gtgtaaatgc acaagtactt gccggattaa acaaggtga ccaagttgtg      1260 attgctgata gttcagaaaa ctctgcagct tctgcaaaca gtggtaataa ccgccgccgt     1320
ggcccaatgg gaatgtaa                                                   1338

<210> SEQ ID NO 50
<211> LENGTH: 2136
<212> TYPE: DNA
<213> ORGANISM: Acinetobacter baumannii

<400> SEQUENCE: 50
atgaatatcc cacctcgacc atttaagttg tctgtaatcg cctgcgcgat ttgttatgcc       60
aacctcacct atgcccaaga tgcacaggta caagctttgc aaacgattca ggtcaaagca      120
tcaaatgcag agcagtcttc tgaacagacc aaggcatata atgttaaaaa ctcaagtagt      180
gcaaccaagc ttaatattga ggctaaggaa acaccccaaa ccattaatgt cgttactcgt      240
cagcaaattg aagattttgg ccttaccagt actcgtgatg ttttaagaaa taccccctggt      300 gtaacagtct ctaatcaaga aactgagcga accactaata tggctcgtgg ttttgagatt      360
tcaaatatct tgacggatgg cgtaggcttt cctctttcag ttataacta ataataacg       420 aatcctgata cttacttta tgatcgtgta gaagtagtta aaggagctga ctcgttaact      480
aatgcctttg gcgatccgag tgcaaccatc aataatattc gaaaacgtcc aacccaagaa      540
tttcaagcaa gcggtggtgt aagttacggt tcatgggata cgcagcgcta tgaagctgac      600
gtatctggct caattctacc aagtggaaaa gtacgtggcc gtattatggg ctatgaacaa      660
actggtgatt cttacctaga ccgatattct gcggaaaaaa acggctttgc tggtattgtt      720
gaagccgatt taacagatag cactttactt accgcaggtt atagccaaga acaaaataaa      780
cccaatgcaa acaactgggg tgcactacct ttattagatg ccaacggtaa acaaatttcc      840
tatgaccgct catataatcc aaaccctgat tgggcacatt gggataatga acacaaaat      900 gcttttgttg aattaaagca aaaacttaat gaccaatgga atgctaaact gacttacaac      960
```

```
tatcttgata cgaagcataa tagccgtctt ctctattact atggttaccc aaaagctgat    1020
gggtccggtg tttctctaac gccttggggt ggacaagaac atcaagaaaa acatgctgta    1080
gattttaatc tcgaagggac ctataagcta tttaaccgag aacatgaagc aactctaggc    1140
tacagctatg tacgtaatca tcaacaagat aaacaatcta caggaacgat taacgatagt    1200
aacgttataa agtcaactac gaccgattgg gcaagttgga caccgcaatc tataacttgg    1260
tcagatttca cagaagcggc taactataaa caaaatatta actcaattta tgccgcgaca    1320
cgtttacatc ttaatgaaga tttaaaactt ttacttggtg caaactatgt tcaagctgag    1380
agtaaaggcg aaagttatag ctcaccaatg tcatatagtg aaagtaaagt ttctccatat    1440
gtcggattaa cctataattt tacacctgaa tatacgggtt acatgagtta tacctctatt    1500
ttccgtccac aaactggtat tgataaagat accaatcaag ctttaaaacc tattgagggt    1560
aaaagctatg aaatgggtgt aaaaagctca tggctagatg accgtttaac aggcacactt    1620
tcagtattta aaactgaaca aaacaattac cctttacgta actcggatgg aaacccactt    1680
aaccgaaaag taccaacgag tgatctagaa tcgcaaggtg tagaagtcgg tctatcaggt    1740
caaattactg ataacgtaaa tctttctttc ggctatgctc aatttagtat taaagacact    1800
aaaaatggtg gcgaagcaag aacatacaat ccaaaccaga cacttaactt gctaactacc    1860
tatactccgc cagttttacc taagcttaaa gttggtgcag gtttacagtg gcaagatggg    1920
ataaagttat atgactcaaa tgtaaacggt acgatcaaac aagatgcata tgctttagtc    1980
aatttaatgg caagctatga agtcaatgat catattacgc ttcaagcaaa tggtaataat    2040 attttgaca agaaatattt aaatagtttc ccagatgggc aggcttttta tggtgcccca    2100
gccaactata cagttgctgt aaagtttaaa tattaa                              2136

<210> SEQ ID NO 51
<211> LENGTH: 2184
<212> TYPE: DNA
<213> ORGANISM: Acinetobacter baumannii

<400> SEQUENCE: 51
atgaaacttc aaactatagc ttgtgcagta gcaatcgcga ctggcggttt attcttctct      60
catacgatga acgaagcaag agcagcaacc aatactgctg ctgtttctca atcgatccag     120
ccaacgcaag agcaagcctt ggtggctcgt caactggcaa ctttagtaga ccgccaacat     180
tatttaaata tgcgtctgga tgcgaacaca tctaaccgta ttcttgatat gtacttagac     240
agtcttgatc cggaccactc attatttttta gacgctgaag ttcaaaacta taaaaagctc     300
tatggttcaa attttggtgc ttcattaaaa gcggggaatt taactgggcc atttgctatt     360
caccagcaat atcgtgagcg cttaaagcag ttttatgagt tcatgcttgc tgagttgaag     420
aaaccacaaa acttaaaaca gccaaatact tttattgaag tagatcgcga aaaagcaccg     480
tattttaaaa cgtcagctga acagcaaaat cactggcgta aaatgctggt ttctcagtta     540
attaatttaa cgattagccg tgaagaagag caggcgaaac aaaaggcgtt aaaagaaaac     600
ccttcacttg ctgatggtca agacttaaca ggcccagaag atttaacgcc agctcagact     660
ttgactaagc gttatacgcg tcagcttgaa agaattagtc gtgtgaaaag cgacgatgtg     720
ttggataaaa cattaaatgc aatgttggca acttatgatc cgcacagtaa ctattatccg     780
ccaattgatg cgatagaact gaaccgccaa acaaccttac agcttgaagg tattggggta     840
tcgattcgcc cagaacgtgg taatgaagat tacaccaaga ttgaaactat tgtagaaggt     900
ggtcctgcaa gtaagtctgg tcaagtgaaa tcaggagacc gaatcgttgg tgtcgctcaa     960
```

```
gagggcggca aaatgatcga tgtggtcggc tggtcgagtt cggaaattgt tgggttgatt    1020
cgtggtaagc gcggtacaaa agtaacgttg aagcttcttg gtgctggtgc atcaatgagt    1080
caagcacgca atgtgacttt ggtacgtgat gttattcaag aagaagatgc cggtgttcgt    1140
tcacgtacag ttgaagtgac acgtgatggt aaaaagcatc tattaggtgt gattgaaatt    1200
ccatcgttct attttgacta tcgttcacgt cgtgctggtc agcaatatcg ctcagtttct    1260
gaagatactg caaatgcgtt tgaggcatta aaagccaaga agttgaagg tattattatt     1320 gacttgcgta atgacccagg tggttcatta agaagttg cacgtatgct cggacaagtg      1380
attaagtcag gtccagttgt gcaaattcgt gatggcaatg gcaacgtaag tgtatttgaa    1440
gacaacgatg gtggtcagca aatctataca ggtccactcg ctgtattggt gaacttggca    1500
tcagcatctg caagtgaaat ttactctgct gcaattcaag attatgagcg tggcattatc    1560
attggtagta caactacagg taaaggtaca gctcaggttc aactcgatac tttggcatat    1620
ggtcaagcaa ccttaactca gcgtaaattc taccgtgtaa cgggtggtag tacacaaaac    1680
aaaggtgtag tgccagatat taagcttgtt gatatctata cgaagagtt tggtgagcgt     1740 aaatcgaaaa atgcgttgaa gtgggatacg attccgactg caccatttaa gcgtgaaggt    1800
tcagtgcagc catatgtagc gaagctgtct caactttcgg aacaacgtgt tgctgttgat    1860
ccacagttta agtatttaaa taaacgtacg gcaattgcga aggttacgag tgaccagaaa    1920
caagttgtgc ttgatattga taagcgccgt gcagagcttt tgagtttaga aaagcaaact    1980
ttagatgctg aaaatgaacg tcgtatagca acaggtcaaa acctttccc taactgggaa     2040 agctatcagg cttctctaga tgctctagct gaatctcgtg ccaaaatgaa agctaatcaa    2100
cgtcctgcgt tgccagaaga agaaacgttc gtaaatgaag ctgcgaatgt attgatggat    2160
tatgcgaaat tgcagaaccg ttaa                                          2184
```

<210> SEQ ID NO 52
<211> LENGTH: 2187
<212> TYPE: DNA
<213> ORGANISM: Acinetobacter baumannii

<400> SEQUENCE: 52

```
atgacaagaa taattgtagc atccaaagag ggtttggacg ttctgcaaga tggtcagctc     60
aataaggtgg tttttaaacca acctactatt attcaaattg gtgtaagtca aaagagatatc   120 gcatcgatgg aaaagcaggg tggaagtcta gtcatccatt taaaaaatgg agaaacaatt    180
gtcttagaaa atttctttaa tgaagcaacg aatacaacag agcattcact cgttttttcca   240 actgaacaag gaaaatttgt tgaagcacaa tttgatgctc aaggtaaggt tatagattat    300
agaggcttaa atcatgttac ggatttggcc tataccagta ccagcccttc agctgcaaca    360
atggccgttg ataatgatcc aagcttttcg atgggtaatg tactaaaagc aggcttagca    420
gttttagccg ctgaaggttt atatctttgg gcatttgata agatgataa agatgattca     480 cccagtactc ccgatttaat agcacctgct gctcctacag ctacgcttgc tgatgatact    540
gtgacagtga ctggcaaaac tgaagcaaat gcgaaaatct acattaaaga tgcagcaggt    600
aatacagtgg cctcaggtgt tgctgatgcg agcggaaatt acgcgattaa attagataag    660
ccgttagtga atgggataa attaaatgtt attgcccaag atgcggctgg aaataattct     720
aaagttactg tggtaacagg aacaaaagat acaattgccc cagatgttcc acaagctcaa    780
ttgagtgatg atggttcctt attgacaggt aaagcagaag caaatgcaaa aatcactgtt    840
```

```
tatgatgcca ctggcaaagt attaggaact gttttttgcga ataaagatgg tatttattct    900
ttaaaactta ctccaccatt aaccagtgaa gcgggcggta aagtggttgc cgaagatgct    960
gcgggtaaca aatctgagga agttaaaatt attgcgggta aagataccat accgccagca   1020
tctccttttg ttgaagtaaa taagaaggg tcggtaatac atggtaaaac tgaagcaaat   1080
gcaaaagttc aaataaaaga tgccgatggt aaagtgattg aagtgggac cgccgatgct    1140
caaggtgaat ttcaaattac actttcacct gctttaaaag aggcgcaaaa gggcacagtg   1200
gttgtggaag atgctgctgg taatgtatct aaaccagttg aaattacgcc aggctttgac   1260
tcgattgcac cagataaacc gactgttcaa attaatacag atggtacttc tgtaaccggt   1320
acggctgagg caaatgccaa aattgaaatt aaagatacaa caggcaaggt aattggtagt   1380
ggaacagcgg atgcgaatgg aaaatttaca atttctattt caccagcttt aacggataat   1440
aaacatgctt cggtatcagc tatagataat gctggaaata agtctgaagt tgttgatatt   1500
gtaggtacaa aagatacaac accaccagca aaacctatat aaatagcgt agatgatgat    1560
gtaggtgctg ttaaaggagc tataacgget ggttctgaaa ctgacgatge tagaccaaaa   1620
cttacaggct caggtgaagc aaatgcaact cttactattt atgataatgg tgttgcaatt   1680
ggagttgtga cggtaacaag tggtagatct tggtcattta catttgataa agacttagct   1740
cttggtaagc atactattac tttgactcaa actgatgcgg caggccttac cagtgaggca   1800
agttctccat ttacctttta tgtagttgct ccaaaggctg cgagtctgtc tgaaacttca   1860
gtagatattt taagtacaga gggaccatct ttggcagata tgttggatt gcatacttta    1920
aaggtagcgc aaaatacaac aactgagacg aataaccegc agaaatcggt tcctttagat   1980
gatttattaa aaagttctac ggctagtgaa tcagacccaa tcgcaaaact tctctcatca   2040
acagcgttaa aaacgactca ggcatctgag ccaatcgaag taaatgcatc agttggtcag   2100
acaacatcaa atcctaatca tccctttacct gatacaactt cttcggtttt acaaaacctt   2160
ttagatcaaa cttatccagt tgttag                                       2187

<210> SEQ ID NO 53
<211> LENGTH: 2265
<212> TYPE: DNA
<213> ORGANISM: Acinetobacter baumannii

<400> SEQUENCE: 53
atgtcgaagc gtattatcca gtcagtgctt tctgtttcag tactggcaag tatgatgtct    60
atggcttttg ctgcacaaaa tgagcaagaa caagctgaac aaacattaga aaagcctgct   120
gaacctgtga aattggaaac aattttcgta acagctgaag agcaagtgaa gcaatcgctc   180
ggtgtatcgg ttattaccaa agaagattta gaaaaactac cagttcgtaa tgatatttct   240
gactatgtac gtcgtatgcc aggtgtcaac ctgacaggca atagtgctac tgggcagcgt   300
ggtaataata gacaaattga tattcgcgga atgggccctg aaaacacgct tattttagtg   360
gacggtaaac caattaactc tcgtaattca gtccgttatg gctggaaagg agagcgtgat   420
acacgaggcg actcaaactg gtaccagcag aagccatcg agtcgatcga agttttacgc    480
ggaccagcag ctgctcgata tggttctggt gcggcaggtg gggtggttaa catcattact   540
aaaaagtga ctaatgaaac tcatggttca gtagagtttt atacttcaca gcctgaagac   600
tccaagaag gttcatcaaa tcgtgttggt tttaacgtaa gtgggccact aattaaggac   660
gttttatctt atcgtttata tggtaattat aataaaacag aagctgatga tgttgatatt   720
aataaatcaa ttggtagtac cgcagctggc cgtgaaggtg ttaaaaataa agatatttca   780
```

```
ggccgtttag cttggcaagc aacagaccag caaactgtct tgctcgatat ttcttctagc    840
aaacaaggta atatttattc tggtgactct cagttaaatg caaatgctga agcggatgcg    900
atactttcgc agctcattgg taaagaaacc ataccatgt atcgtgatag ctatgcatta    960
acgcatgaag gtgattggtc ttggggtaag agtaagttag ttgctcaata tgataagacc   1020
cataacaaac gtctacctga aggcttggcg ggaagtgtag aaggaaaaat taataatctt   1080
gatgataaag ccacttcgcg tttagaaact cttcgcttta acggcgaggc taatattcct   1140
tttgaatact atttaccca gtattaact gtaggtaccg aatgggttga agacagattt   1200
aaagataatg tctcgacaac tcaaggtaaa gacagcagtg gttcaggtta tggcgatcaa   1260
ttagcgaaag gtgatcgtag taaaatggag tcacgtattg cttctgcata tattgaagat   1320
aacctgaaag ttacagacag cacagatgtt gtattaggtt tacgttttga tgaccatagt   1380
aaatctggtt ctaattggag tccaagctta atattactc aaaaactcaa tgataatttc   1440
actttaaaag gtggggtagc aaaagcttat aaagcaccaa atatgtatca aaatgccgaa   1500
gggtatttat taagtacaaa tggcaatggc tgtcctgcta atattgagtc gcgttgttta   1560
ttacaaggta atggtgattt aaaacctgaa acatcggtaa acaaagagct cggcattcag   1620
ttccaaagag atatcgtgaa tgcgagctta acttggttcc gtaatgatta taagataag   1680 attgttgcgg gtactcatgt tgtcggaaca gttgatggct caagtacaaa tgcaaataca   1740
ggagctgtga ccaatacgaa gtggaatatt ttgcgttggg aaaatacgcc taaagcctta   1800
attcaaggtt ttgaaggaag tttgggggta gacttcggtg atatccgctg gactaataac   1860
tttacctaca tgatggactc gaaagacaag caaactggga atccattatc tttagttcca   1920
atctatacaa ttaactcaat tttgattat gacattactg atcaattgga tgtaaatttt   1980
gtatttactc aatatggtcg tcaaaaatca cgtcaatttg cagagaatag acttgaatcc   2040
ggtataggtt caggaggtgc gaattctgcg cttaagccaa gtacggtaaa agctatagt   2100 actgctggta ttaatgttgg ttataagttt tcagaccaaa ttagtacgcg tgttggtgtg   2160
agtaatctgt ttgataaaca aattttaaga gacagcaatt ctattagcca aacttataat   2220
gagccaggtc gagcttatta tgcatcttta aaatattctt tctaa                   2265

<210> SEQ ID NO 54
<211> LENGTH: 2721
<212> TYPE: DNA
<213> ORGANISM: Acinetobacter baumannii

<400> SEQUENCE: 54
atgccttcta aaattaagtt taaacagtca actctttctc actctatgca tttaatctta     60
aaaatgcaga gtatacctaa acttatttgt agcagcttat tattaagttt atgtgttact    120
ccttgttatg ctcaaagttc ggctgagacc gttataccag aagcaaacca gacggtaaca    180
gattcattgg tacaacaaac taatacaaat aacccaagtg atgttccaat taccgatgtc    240
gctactcttg taactcaagc acagcaacaa caagatagct tggctatatt gcaacaacaa    300
gaacaatttc cgaatcagat tgaagaattt aagccaatta cgcttgataa tcttgaagac    360
ttacctgtta tgcctgttga tcagaatatg gcaaatgaaa tttatcgggt agcagaagag    420
gcaaaaaacg aggctcaaaa cttccagaat ggtacgcaaa acaaccaga atggtggtg    480 agtgacgcat cacaagcaga attacatgaa attaatcagg cccctgtaaa tattgaccag    540
ctcatgcatg agattcaatc tgatagtaag attgtggttg aagccaatga aacaggaaaa    600
```

```
actttacctg agcttactgc tgccgttgaa gaaccacccg aggaaaaagg tttcttttaga   660
cgtatattca ataaaatccg tccacctcgg gtaattccaa tggagcagat accccgtatt   720
actgctgagg ttacgggtgc gccagatgat ttagctaaaa atatcaaagg taaattatct   780
acatttaccc aagaatcatt tgaagatttt aatgcagcgc taccgcaact taggagctta   840
agtaatcagg ctgctcaagc tgtaggttat tacaatgccg agtttcgttt tgaaaagtta   900
agtgccagtc gcgtacgtgt taatgtaacg ccaaatgaac cagtacggat taatgaacaa   960
aacattgaat ttactggtgc tggtgcaaaa cagccacaat ttcaggtcat tcgtttagtt  1020
cctgaccaag atgtaggtga tattttttaat catggccttt acgaaaccac aaaaagccga  1080
attgtcgatg ctgcatcgga taatggttat tttgatgctt attggcgttt acatgacgta  1140
aaagtgagcc aacctgaaaa taaagcggat attaacctca agtatgagac tggtgagcgt  1200
tataagcttg gtaaggttga gtttcgcatg agcgatccat caaaaccatt acctttaaat  1260
atgaatattc ttgaaagcat ggcaccgtgg aaagagggtg atgactatgc ttttttggcgt  1320
gtaaatgttt tagcaaataa cctgactaac tcacgctatt ttaactatac cttggttgat  1380
tcaattaaac ccgacccaat tgaaaaacca cttgagttac caccccgattt acaagcgttg  1440
gtcgatcagc agaatgttga tattgacgaa tcgaagctgc ttcctttaga gcaacaacaa  1500
cttgccaaag cacgccagtt ggcttcctca agtaaagaag taacacaaaa tgtggtagat  1560
gaaaaacaat ttgccggaac tgaaagtgta caagccgcac ctgcatcttt aaaagctgca  1620
actgtacaac atgaagaaca agagtctgaa caagaccgtt tacaggctca agctcgggaa  1680
gaaaaacgta taccagtgat tgtgacgtta aatgccgata aactaaatag tctggaaaca  1740
ggtattggtt atggtaccga cactggcgcc cgtttacgta gccaatatag acgttcgatt  1800
gtgaataaat acggtcattc atttgacgca aacttggagc tttcccaaat tcgtcaatct  1860
atagatgggc gctatagtat tccttataaa catccgttaa atgattactt taatattgtg  1920
ggtggttatg agcgtgaaac gagggatgat attggtccgg atgtaagttt actcacggaa  1980
tcggcagttt taggggggtga gcgagttatt aaaaaaccac tcggaaactg gcaacatact  2040
attgggtac gttatcgtct cgaccgccta actcaaaagg ggaatgtgga tatctctgag  2100
ctaccagatg catttaaaac tgctgcatca gagcaagaag cattattatt tagttatgag  2160
acctctaaaa cttcaagtaa tacacgctta aacccgacca aagctttttaa acaaacttat  2220
aaattagaat taggtagcga aagtttactt tcagatgcca atatggcgat tgccacagcg  2280
ggttggagat ttatttattc tttaggtgaa aatgatgacc atcagtttgt tgggcggtcc  2340
gatttttagtt atattttttac cgatgagttt gataaagttc catacaattt aagattctttt  2400
actggtggtg accagacaat tcgtggtttt gattataaaa gtctttcacc agaagataat  2460
ggatataaga ttggtggaca ggctctagca gtaggctctt tagaatataa ctatcaattc  2520
aaagagggtt ggcgagcagc tgttttttct gattttggta atgcttacga taagagttttt  2580
agtaatccga cggcctatag tgtgggtgtt ggtattcgtt ggaagtcccc aattggacca  2640
attcgtttag acgtggcttc tggtatttct gatgataacc atccgattcg tttgcatttc  2700
tttattggtc cacaaccttta a                                              2721
```

<210> SEQ ID NO 55
<211> LENGTH: 2925
<212> TYPE: DNA
<213> ORGANISM: Acinetobacter baumannii

<400> SEQUENCE: 55

```
atgtttatta aaagtatttt atcttcgatt actagtatta tcccacttcc tgaaaatagt      60
aacacaagca gtaatttagg taacggctct ggtgacggcc tacttaatgg aatatcttcc     120
ggaaatggtg aacacaacta tggtattggc aatggtattg ccgatgacgc aagcattacc     180
gccccaatta ccattcccct caacctctct ggtaactcaa ttactctcat aggcaattca     240
tcttcaagtt cggtgaatag ctctccaacc accacttcaa ataacgttaa tgacaacgat     300
gtaacaaata atggtaacgg ctctaccatt ggtagcggta caggcaatgg ctctggtgac     360
gggcttttaa atggcgccgc ttctggtaat ggtgaacaca actatggaat cggtaatggt     420
attgccgatg acgcaagcat tactgcccca ctttcaattc caattaacct tgcgggtaac     480
tctattaccc taattggtga ctcatcttct agttcggtca caactctgc aaccaataca      540 tcaaataccg tgaatgataa cgacaccacc tataacggca atggctcagg tggtggtaat     600
ggttcgggcg atggcttgtt aaatggaatt ggctctggca atggcgagca aaactacggt     660
atcggaaatg ggattgcgga tgcgcaagt attacagccc caattacgct tcctattaac      720
ttgtctggta actcaattac tctaattggc aattcatctg caagttctgt taattcctcg     780
ccaactacaa cgtcaaatac tgtgaatgac aacgacacca cctataacgg taatggtact     840
ggtgatagcg gcgtgagcgc tctgggcggt tctggcaatg gttcaggtga tggcgcaggt     900
aatggtatcg cttctggcaa tggtgaacat aactatggta ttggcaatgg taacggcgac     960
gatgttgata ttactgctcc gattaccggc gttctaaaca tttcagggaa ctcatttact    1020
ctcattggta attcttcatc aagttctgtc aataccgcac caacaaccac atcaaataca    1080
gtgaacgaca atgacaccat tgataatggt aatagcggcg gcacaggtag tggttcaggc    1140
aatggctctg gtgatggttt acttaatggc gctgcttctg gcaatggcga gcataactac    1200
ggcattggca acggaaatgg tgatgatgta gatattaccg caccaattac aggtgttttt    1260
aatttctctg gtaactcttt ctcaatcatt ggcaattcat cttctagttc aattaatact    1320
gctccaacta caacgaccaa tacagttaat gacaatgacg taactgataa tggaaatgat    1380
ggaggcggac ttgttggtgg aagttctgga aatggctctg gtgacggact gttaaacggc    1440
gctgcttctg gcaatggcga acacaactac ggtattggta acggaaacgg tgatgatgca    1500
gatttcacct tccctcttac tggtgtactt aacttttccg gcaactcgct ttcaggcttt    1560
ggcagttcat ctagtgactc ggtaaatgta gcaccaacca cagcaaccaa taccgtcaat    1620
gataatgaca ccattgataa tgccaataca ggcggccttg gtgacggttc gggcaatggc    1680
tctggcgatg gtctttttaa atggtgcagcg tctggtaatg gcgagcataa ctatggcatt    1740
ggtaacggaa acggtgacga tgcagacttt acgcttccat ttactggcgg tttaaatatt    1800
ctgggcaatg ctttatcagg tatcggcggt tcttcgaccg actctattaa tatttccacca    1860 acaactactt caaacacagt caatgacaat gacactacca caacggcaa cacttcaggt     1920 ggtgtgattg ttctggcga ctcaggcaac ggctctggtg atggcttatt aaatggcatc     1980
tcatcaggta acggtgaaca taattatggc attggcaacg gtaatggcga tgatgttgac    2040
gttgttgccc ctatcactac accacttaat gtattaggca actctttctc atttattggt    2100
ggtgaaggta caggcgatat cttaggtccg attactggca ttattggtgg tattggcggt    2160
gatggagata tcctaagtcc aattactggc attatcggtg gtattggtgg tgatggagat    2220
atcctaagcc cgattactgg cattatcggt agcattggcg gcatcggggg tgatctgggc    2280
gataacccac ttacaggtat tattcaaagc ggtattgacg ttctacaaaa tttagaaagc    2340
```

| | |
|---|---|
| ctaaaaacag gtttgattaa tacaggtatt gatacgattg ccggaacaat tattggtgtt | 2400 |
| ttccctgatg cagagcaccc tgtcggtgat tttgcagatc ttggaaaact acttttcgag | 2460 |
| acttcacgtg atagtgttaa cggcacgctt gaagctattt ctgaccttgc aggcgctgac | 2520 |
| cttgaggggg caagtggctc gattactggt gtaattgata cccttattac caatggttca | 2580 |
| acggcatcta ccattattca gcatattgta ggtgatgacc tagtcactga aaacggtggc | 2640 |
| ctcttgggtt caatcaccac gattattggt ggtgttgaca cgcgcgacgg tggtttactg | 2700 |
| ggtggcctag atggcttaat tagcattaac tatggcgact cagacaatag taattctata | 2760 |
| gatgtagaag atattttagg aaatatcctc ggctcggttg gttcaaatca aggtattgct | 2820 |
| gttggtgaac ctgatccaac gggcggtagt ttgattcata cgatttcact taacacagta | 2880 |
| aatcagttaa ctgaccaact tttacatgct ttaccgactg tctaa | 2925 |

<210> SEQ ID NO 56
<211> LENGTH: 3216
<212> TYPE: DNA
<213> ORGANISM: Acinetobacter baumannii

<400> SEQUENCE: 56

| | |
|---|---|
| atgtataaac caaccacatt tgtgtggcag ccatctgcag catcattatt caaaattaca | 60 |
| gtccttagct ctgctttagc tgcgttgggt attacaacag gctgttcttc gactccgcaa | 120 |
| tctgcaaaaa cctcgaaaac aaaacaggtg agtggagcag gctatcttga tgcaagcagt | 180 |
| ctggactctt tagaagactt actttcagca acagatatgc gtgctgtaga gggcgaccgt | 240 |
| ttacttattt taaaacacgg tgatgtctgg aagcgtatgg ctgtaggctt caaaatggac | 300 |
| ctcaatcatt gggatccacg tattgaagcg cagcgtagtt ggtttatctc acgtcagccc | 360 |
| taccttgacc gcttaagtgc tcgcgcaagt cgttatttat atcatactgt taagaagca | 420 |
| gaacgccgtg gtcttccaac cgaacttgcg ttattaccag tgattgaaag ttcatatgac | 480 |
| ccagctgcaa caagtagtgc ggcggcgcg ggtttatggc aatttattcc tagtactggt | 540 |
| cgtatttatg gtttacaaca aacgggtatg tacgacggac gccgtgatgt tgtggaatct | 600 |
| actcgtgctg cctatgagtt tttaggaagc ttatataacc agttcggttc atgggaatta | 660 |
| gctttggctg cttataacgc tggtccgggt cgtattcaac aagcgattaa ccgaaatcag | 720 |
| gctgctggtt tgccaacaga ctattggtca ctaaaattac cgcaagaaac catgaactat | 780 |
| gttccgcgtt tcttggctgt cgctcaaatt attaaaaacc cacgcgctta tggggttcg | 840 |
| ttaccgccga ttgcaaatag gccccatttc cgtgaagtta ccttatctgc accattatct | 900 |
| ttaaatgaaa tcgcgtcggt gacgggtctt agccgtgctg agtatatgc attaaaccca | 960 |
| ggctatcgtg gtgaaacagt agaccctgca agtccaatgc gtattttgat tccagctgat | 1020 |
| ataagtcctt cagtggataa caagttaaaa ggaatgaaag caggtggaag ttcaggctgg | 1080 |
| tgggcaagtg ttacttcgcc gtctaaaccg accacaacaa cttcaacctc agtcacagtt | 1140 |
| agaactactc catcaactcc agctcagcca gtaagaccat cgacgcctgc taaaacaagt | 1200 |
| agcagctcgg taacggtaaa aactacaaca cctcgtggtt ctgatgcgct agctgctttt | 1260 |
| gcagcgtcag ctgatgtacc aagtgcacca cgtattcctg ttgcggtcac tccggctgca | 1320 |
| aatatcaaac ctgtgagaac ggaaccgcca atttcagcaa ctgaacgcga gaaaatttta | 1380 |
| gcggcagtgc gtgctgaagg ggaaaaggaa acagttgatc aagctttaga acctcaagct | 1440 |
| actcaagctg aaaaagatca agttgttgcc gagttaaaag cacttgcacc tcagggtaca | 1500 |
| gaaattgtcg atccgtatga cggcaaaatt aagttaaccg caattcagac cagccaatct | 1560 |

```
gttgctgagc agcaaggtaa agaagtaagt aaaggttttg cttatccaaa aactttagct    1620
gaagatgcaa ctcttgcaaa ctctgaagat gctcagcgca ataaagataa gccttatatt    1680
aaaactgata cagatgttgt ggttgtacaa cctaaaggta agcgtagtac ttatacagta    1740
cagcctggcg atactttagc agttattgcc atgaagaatg tgtgaactg gcgtgatgta     1800 gctaaatgga accagattga ccctgaaaag actttatttg taggaaccag tctatatctc    1860
tatgatgcta agcctcaaga ggcggaaact acggcaaaat cggcagctaa acctgatgtc    1920
tatgttgttc aagcaaatga cagtttaaca ggagtggcaa atcaatttaa tttgtcagtg    1980
aaacagctag ctgaatataa cgatttgtct gtaacagatg gcttgtttgt agggcaaaaa    2040
ttacagttaa aagaacctaa aggtaatcgt gctgctaaag tagagccaaa ggcaattcaa    2100
gcaagtacac gtcgtattgc aacaaagagt tatacggtta aacgtggcga atacttgaaa    2160
ttaattgcag accgttatgc attatctaat caagagttgg cagacctaac accagggtta    2220
tcagctggta gtaatttaat tgtaggccaa aaaattaatg tacctgcaaa agaaatcact    2280
gttgatgaag ttgatgacag caaggcttct ggtaaatatg aaaagcttgc agcaggtcca    2340
tcatataaaa ctgaaagtta taagtgcag cgtggtgata cattatcaag cattgcgacc     2400
aagtctaaaa ttagcctagc tgagcttgct gaactgaaca atttaaaagc gaacagtcat    2460
gtccaactgg gacaaactct aaaagttccg gctggtgcat cagttcctga ccaatatgtt    2520
gtgcagtcag gcgatagctt aaatgcaatt gcagctaaat ataacttaca aaccagttat    2580
ttggctgatt tgaatggttt gtcacgtact gcaggccttc gtgctggtca gcgtttaaaa    2640
ttaactggtg aagttgaaac aactagcaaa gtttcggcta aaaataccaa agaagaaacg    2700
ccagagacct acacagttaa atctggtgat agcttaggaa atatcgctaa ccgctatcat    2760
ttacagttag attacctcgc tgcattgaac ggtttgtctc gcaacagtaa tgttcgtgtt    2820
ggtcaacgct taaaattaac aggtgattta ccaacagtag aaacagctaa aacggatacg    2880
gcgaaatcgt ctccaaaagc tgtagttgca ggaaaaaata ctgaaaagta cacggttaaa    2940
gctggtgagt cgttaaatgc tattgcgagt cgtgcgggta tttcagttcg tgaacttgct    3000
gaaatgaatg cattaaaagc aaatgccaat ttacagcgtg acaaaatat tgtgattcca     3060 aaaactgtag tggaatacaa agtcaaacgt ggtgatacct taattggtct tgcgagtaaa    3120
tatggtttag aaaccacttt attggcggaa ctcaacaacc taacaccgtc gactcaattg    3180
cgtattggcg atatcattaa agtgcctaat ttatag                              3216
```

<210> SEQ ID NO 57
<211> LENGTH: 3333
<212> TYPE: DNA
<213> ORGANISM: Acinetobacter baumannii

<400> SEQUENCE: 57

```
atgaaacgta tgttgattaa tgcaactcat gccgaagaag ttcgcgttgc acttatcact      60
ggtaatcgtc tttacgattt tgatttagag aatcgtaccc gagaacagaa aaaatccaat    120
atctataaag gccatgtcac ccgcgtagaa ccatctttag aagctgtttt tgttgaatat    180
ggcgcaggtc gtcaaggctt cttgtctatg cgtgaaattg ctaacagcta ttttcaggca    240
gacccacgtc aaacttcaaa cattcgtgaa cttattactg aaggcacaga gcttttagtt    300
caggttgaaa aagaagaacg tggtaataaa ggtgcagcac tttctacgtt tatttccctt    360
gcaggccgtt atttagttct tatgccaaat aacccgaaag gtggtggtat tagccgtcaa    420
```

```
atttcaggtt cagtacgtga agaattaaaa gaaattttag cttctttaaa tgtacctcgt    480
ggtatgagcg ttattgtacg taccgctggt attggacgta cccaagaaga attacaactc    540
gatttgcaac acttgcttga cctttgggca caaatccaag gtacagccag ctcaggccct    600
tctccgatgc ttgttcatca agaagcgggt gtagtaacac gtgcaattcg tgattactta    660
cgtgatgacg ttgctgaaat cttaattgat agcgaacaag cttataacga agcatataac    720
tttgttaaag cagtgatgcc gcgtcaatta gacaaattaa aaacttatac tttaaacgag    780
ccattgtttg ctcattttgg tattgaaagc caaattcaaa ctgcttacga gcgtgaagta    840
aaacttcctt ctggcggttc aattgtgatt gaccagactg aagctttagt ttcaatcgat    900
attaactctg cgaaatcgac tcgtggacat gatgttgaag aaactgcact gaatactaac    960
cttgaagcag cagaagaaat tgctcgccaa cttcgtttac gtgacattgg cggtttagtt   1020
gttatcgact tcatcgatat gactaaagaa cgcaatcaac gtatggttga agcaaaactt   1080
cgtgaagcaa cacaaagcga tcgtgcacgt atccagttcg gtcaattgtc tcgttttggc   1140
ttaatggaaa tgagccgtca acgcttacgc ccatcgcttg aagaagcaac aggttatgta   1200
tgccctcgct gtcatggtac aggcatggtt cgtgatttac gttcgctttc tctttcaatt   1260
atgcgtaaag ttgaagagat tgcacttcgt gaacgtcatg gtgaagttca agttgaagtt   1320
ccagttgaaa ttgcagcctt tttgcttaat gaaaaacgcc atagtctggt gtatttagag   1380
caaacttctg gtgtacgtgt gactgtattg ccacacccgc acttagaaac tccacattac   1440
gaaattgcat ataacccaga tggctttgct ccatctagct atgaacgtac agaagcaacc   1500
cgttctagcg agaaagagtt aggttatgag tcttctgaat ggcatttaga agaagcagat   1560
catggccatg ctcatgtaac tgctacagct tcaactcatg ctgcggctca gaaaaaagca   1620
aatcatgcaa ctcaacctgt agcacaacct tctgctcaaa aagcagcaag cccatgtgca   1680
tggttagaaa acctgtttgt tcaaaaacaa gcgcaaacag ttgatcaatc tcgttcagca   1740
caaaatgctg ctgctgcgat tgagcaaatg gtgaatacag cgcagtaagc cgcggacag    1800
ttcggtcaag tagccgtacc tgctgttgcg gaagttgcgc cagttcaatc aaataacgct   1860
tatatttcac agtcacctgt gaaacaagac gttcgtgaac atgttgaaaa agatgataaa   1920
tctcagcaac aacgtcagaa caacaaaaag cgtaaacata agagcaacg tgaacaacat    1980
caccaatcac atgaacagca acatcaagtt catgaagaag tggttcaatt gtcacgccaa   2040
gaacaacgtg agttaaaacg tcagcaaaaa cgtcaacagc agcaagatca gcaacatcaa   2100
aataatgatg tacaacacac tgaaaatgct gtgccacgtc gtgaccgtaa taatcaacaa   2160
cgtccaaacc gtccaaatcg ccaccgcgat ccaagtgtat taaatgaaaa tcaaaataca   2220
ctggttgttg ttgatgaaaa acaaattaag gttgatgtga ttgatgcacc taagcatgat   2280
gtcatgaaca ctgctttaat catcaatgtt gatcaaggtc aaagtgagat tgttgcactt   2340
acacctgagc gtcgtcacgt tgagcgagtt gaaacgactt ctactgaagt tgctcaagag   2400
ccaactccag ctcctgttgt agccgagaaa gctgctgtag ttgaaaccaa agaagaagct   2460
cagccaagcc aagaagctgc tcagccacaa atcaaacgtg ctagcaatga ccctcgtatg   2520
cgtcgtcgtc agcaacgtga ggctaaacac gctaaggcag ctacaccatc tattgcgcca   2580
tcgcaaattc caactttggc acaacacaca atcggtagtt taatccgtca tgtgtatggt   2640
gaagattgca ccgtattgat tgaacaattt ggtctagtcc caacgtttaa tcgtgctttg   2700
cagaaatttg cagaacagta cgcaagtacg ttagtagttg aagttactgc tgaaacggaa   2760
gagaaaaagc cggtaactcg tgatgcagaa cttccaagcc ataaaccagc tgaagaagca   2820
```

-continued

| | |
|---|---|
| gaacctgcac cagtacttcc gcttactccg ccgcaagcac cagctccacg tgttgcaaat | 2880 |
| gacccgcgtg agcgccgtcg tttagcaaaa cttgctgcgg aacaagcatt tgagcaagtg | 2940 |
| aaacaacaac attctgctca agaagaagtt gctactcctg ctcctgtagc agaagaaacc | 3000 |
| gttgctgctc caactgctga acacaagca acagttgaac cagcacaaca accgcttgaa | 3060 |
| cttaatcagt caactgaagt cgtacaacct gaagctgctc ctgcagagga aaaagctaca | 3120 |
| gaagaaacag tagctgaagc tcctgcggca aggaacctg cgccatcaaa agcagcaagc | 3180 |
| aaagcaaaag cagcggctga agaaacagta gctccgactg aagcaacaac tgatgccgaa | 3240 |
| tcagaagacg ttaaggcaga taaggacaaa ccgagtcgcc ctcgtcgccc tcgtggccgt | 3300 |
| ccgccaaaaa aagctaatcc tgtagctgag taa | 3333 |

<210> SEQ ID NO 58
<211> LENGTH: 3687
<212> TYPE: DNA
<213> ORGANISM: Acinetobacter baumannii

<400> SEQUENCE: 58

| | |
|---|---|
| atgtctacgc ttgccaccct aaaagcgctt cttgctaaac gcattctgat tattgatggt | 60 |
| gcaatgggaa ccatgatcca cgccataaaa ttggaagaag ctgactatcg tggtgagcgt | 120 |
| tttgctgatt gggcacatga tttaaaaggt aacaatgacc ttttggttct aacacagcct | 180 |
| caaatcattc aaggtattca tgaagcctac ctcgatgctg gtgcagatat tattgaaacc | 240 |
| aacagcttta tggcacacg tgtttcaatg tctgactacc acatggaaga tcttgttcca | 300 |
| gagattaacc gtgaagcagc acgtttagcc aaagcagctt gcgaaaaata ttcgactcca | 360 |
| gacaaaccgc gttttgtggc aggtgtactg gggccaacat ctcgtacatg ttcaatctct | 420 |
| ccagatgtga acaaccctgc ttttcgtaac attagctttg atgaactaaa agaaaattat | 480 |
| attgaagcga ctcatgcact aattgaaggt ggtgcagaca ttatcctgat tgaaaccgta | 540 |
| tttgatactt taaattgtaa agcagcgatt tttgcagtca agaagtatt caaacaaatt | 600 |
| ggtcgcgaat taccaattat gatttcaggg accattaccg atgcatcagg ccgtactta | 660 |
| acaggtcaga cagcggaagc tttctggaat tcggttcgtc atggcgattt gctttcaatc | 720 |
| ggttttaact gtgcccttgg tgcagatgcc atgcgccctc acgtaaaaac tatttccgat | 780 |
| gtcgcagata cctttgtttc agcgcaccca atgcaggct taccaaacgc atttggtgaa | 840 |
| tatgacgaaa ctccagagca aactgcagct ttcttaaaag agtttgctga agcggtttg | 900 |
| attaacatta ctggtggttg ctgtggtacg acaccagacc atattcgagc tattgccaat | 960 |
| gcggtaaaag acattgcgcc tcgccaagtg cctgaaaccg tacctgcttg ccgcttaagt | 1020 |
| ggtttagaac catttaatat ttatgatgat tcattgtttg taaacgttgg tgaacgtact | 1080 |
| aacgttaccg ttctaaaaa attcttacgt ctcattcgtg aagagaactt tgcagaagct | 1140 |
| ttagaagttg cacagcaaca agtcgaagct ggcgcacaga ttattgacat caacatggat | 1200 |
| gaagggatgc tcgactcgca aaatgcgatg gtgcattttt taaaccttgt agcatccgaa | 1260 |
| cctgacattt cacgtgtacc gatcatgatt gactcatcga atgggaaat cattgaagcc | 1320 |
| ggcttaaaat gcgtacaagg taaaccggtt gttaactcaa tttccttaaa agaaggttat | 1380 |
| gacgagtttg ttgaaaaggc ccgcctctgc cgtcaatatg gtgctgcaat cattgtgatg | 1440 |
| gcctttgacg aagtaggtca ggccgacact gctgaacgta acgtgaaat ctgtaagcgc | 1500 |
| tcttatgaca ttttagtaaa cgaagtaggc ttccctgctg aagatattat ttttgacccg | 1560 |

```
aacgtgtttg cagttgcgac tggtattgaa gaacacaaca actacgcagt cgatttatt    1620 gaagcaacgg gctggattaa acagaactta ccgcacgcca tgatttctgg tggtgtgtct   1680
aacgtttcgt tctcattccg tggtaatgag ccagttcgtg aagccattca ctctgtattc   1740
ttgtaccatg ccatcaagca aggcatgacc atgggtattg tgaacgcagg tcaaatggct   1800
atttatgatg atattcctac cgagctaaaa gaagcggttg aagatgtcat tttaaatcag   1860
aatcaaggtg agtctggtca ggctgcgact gaaaaattac ttgaagttgc agaaaaatac   1920
cgtggacaag gtggtgcaac aaaagaagcc gaaaaccttg aatggcgtaa tgagtcagtt   1980
gaaaaacgtc ttgaatatgc cttggttaaa ggtattacga cttatattga ccaagacacc   2040
gaagaagccc gcttaaaatc aaaacgtcct ttagatgtaa ttgaagggcc actgatggac   2100
ggcatgaatg tggtcggtga cttgttcggt tcaggcaaaa tgttcttgcc acaagttgta   2160
aaatctgccc gagtcatgaa acaagcagtg gcatggctca acccgtacat cgaagctgaa   2220
aagacagaag gacagtctaa aggtaaagtc ctaatggcaa cggttaaagg tgacgtacac   2280
gatattggta aaaatattgt aggcgtagta cttggctgta atggctatga cattgttgac   2340
cttggcgtaa tggtccccttg cgagaaaatc ttgcaaactg caattgatga aaaatgtgac   2400
atcattgggt tatctggtct gatcacccca tctttagatg aaatggtatt tgttgctaaa   2460
gaaatgcagc gtaaaggctt taacattcct ttattgattg tggtgcaac cacttctaaa    2520 gcccacacag cagtaaaaat tgaccctcag tatcaaaacg atgcagtaat ttatgttgct   2580
gatgcttctc gtgctgttgg tgtagcgaca accttgcttt cgaaagaaat gcgtggtgca   2640
tttattgaag aacatcgtgc tgaatatgcc aaaattcgtg agcgtttagc caacaaacaa   2700
ccaaaagcgg ccaaactgac ttataaagag tcggttgaaa atggttttaa aattgatgaa   2760
agctatgtgc caccaaaacc aaatcttttg ggaactcaag ttttaaagaa ttatccgctt   2820
gcaacactcg tggattattt tgactggacg ccattcttta tttcttggag tttaactggc   2880
aaattcccga aaatttaga agatgaagtg gtcggcgaag cagcaactga cttgtacaac   2940
caagcacaag caatgttgaa agatattatc gacaacaacc gttttgatgc tcgtgctgta   3000
tttggtatgt tccctgctca gcgtacagat gcagataccg tcagcgtatt tgatgaagct   3060
ggtcaaaatg ttacgcatac ttttgagcac ttacgccagc aatctgacaa agtgacaggc   3120
aaaccaaact tgtctttagc agattacatt cgtgctgacc gcgagcagca agactacttg   3180
ggcggattca ctgtatcgat ttttggtgca gaagaactgg ccaatgaata caaagccaaa   3240
ggtgatgact actctgcaat tttagtacag tcattagctg accgttttgc tgaagccttt   3300
gcagaacatt tacatgaacg tattcgtaaa gagttctggg gctataaagc ggatgagcag   3360
ctcagcaatg aagagctgat taagagaaa tatgtcggta ttcgccctgc accaggttat   3420
cctgcttgcc ctgagcactc tgaaaaagca gtgttatttg actggttagg ctctaccgac   3480
aaaattggta ctaaactgac tgagcacttt gcaatgatgc cgccatcttc ggtaagcggt   3540
ttctattatt ctcatcctca aagtgaatac tttaacgtgg gtaaaattc tcaagaccaa    3600 cttgaagatt atgcaaaacg taaggttgg acactggatg aagcgaagcg ttggttagct    3660
ccgaatttag atgactcgat tgtttag                                       3687
```

<210> SEQ ID NO 59
<211> LENGTH: 3855
<212> TYPE: DNA
<213> ORGANISM: Acinetobacter baumannii

<400> SEQUENCE: 59

```
atgaaactaa aattgaagaa ttttaagcca aataatttat ggtatgccgt ctgttcaagc    60
tcaatgatat tcacatggct gatgacaagc tctgtggtgc aagcaagtga tttacaaatt   120
tatgcctcac ctacagcagg taaaaaaaca attgtgatga tgttggatac atcaggaagt   180
atgaccaaca atagttatgg tgaaaaccgc ttagccatgc ttaaaaatgg tatgaatgct   240
tttttggcta gcaataaccc tgtcttaaat gatacgcgag taggtttagg aaatttctcg   300
gcaaatggtg acagccgaag tggacaaatt ttagtggctg ctgctccttt aggtgatgca   360
agtactttaa atacggtagg ctcacaacgt tataaattaa acaagctgt tgctaattta    420
actgcgggag gctcaacacc ttcagcccac gcttatgctg aagcagctgc ttacttaatg   480
gggacaacca catattcaga gacgaattat gctattcgta agatagtta tcaaacgt     540
gtaagaagat ctgataatag aactgaatat tcatattgta ctaattaccg tgattcgcaa   600
attgatacag ccaacctatg caaccttgt cgttcaaata gttattggag tagctggtca    660
acaaataatc caggtgtgga taatgctact gcttatgata cttcatctga ctggacttat   720
tactatactt attactacac cacttttaat tatgctgtag caaatgcaga tagcggtatt   780
ccaaaatcta atcaaacga tacagctagc aatccgaata ttgttgtaga ccgaaatgct    840
actaactcca atgcagtgta tcagtcacct ttacctgcag tagcgaatcg ccagagttgt   900
gatggacaag gtatttactt cttatcggat ggcgaaccga acaatacaac aaatacacgt   960
tcggcaagtg tcatgtcgac tgctttaggt agtacttttg gagctgattt taattgttct  1020
ggaggtttat ctaacactac ggcagactct ggttgggctt gtatgggaga gtttgcaaaa  1080
agattatttg ataaaacaaa gaaccctgcc ggagtttcta ttcaaacagc atttgtcggt  1140
tttggtagtg actttttctag tttgaattct tctgatgtaa aaaatgcctg ccgtttaagt  1200
tcgagaaccc agtctgaccg aaaaggagat gatgcgtgtt caccgaatca atctacaaat  1260
gcggtagctg caccaggtta tggaaatggt ggttttttcc ctactcagag ttcacaaggc  1320
gtaacagaca gcgttatcgc atttattaat aatttagata aagttccttt agaacccta   1380
accacaggtg ctatctcagt tccatatgat gcattgaatc ccaaaaattt acaggaatat  1440
ggttatttac gagcttttga gccaaatcca gctaacacgt acttaacatg gcgtggaaat  1500
ttaaagaaat atcatgttgt tttatctgga gcgaatgctg gtgcttttga ggccaattct  1560
ggcggattag tctacaatgc aagtgggct tttagaactg gaacaaagga ttattggaat   1620
agctctactt atactgacgg aggcaaagtc tttttaggtg gttcatatgc gaatgtgcct  1680
ttacccattg ctggacaacc tgaaacacgt gatgcagaag ggaatatcac aaaatattat  1740
tacgcagtac aaagtaaaat ccgcaactta tttactgatg tttccgccgt tgcagcagat  1800
ggtagcttaa cgaaaatttc aacttctgga actaatttgc taaaaattcc agctgctcca  1860
ccagaagaaa ctaatccttt tgatacggtg gctaatacag caagttatgt tttaggtaaa  1920
tttgatccat caactggaca aaatatttta aaagctttc ctataagctt gaaattaaaa   1980
atattaaatt atttaggtta ttcaacagat attaatgcaa caactctgcc ttcatctttg  2040
gttacatcga atgaaccta tttatcgatg gggggaagta ttcactcttt accggttcaa   2100
ctaacctaca atggaaccct agatgataat gggaatttaa catctgcccg agaacaatcc  2160
atcctctatg gaactatgga aggcggatta catattgtgg atgcttcatc tggtattgag  2220
caaatggtct tgttcctgc agatatttta aatgattcag ttgcttccaa agctttagtt   2280
gttggtcaaa gtgatgcttc agctcccgct catggtatgg acggagcttg ggtatctgat  2340
```

```
ccagcctata atattactac agtgggaagt ggtagctcgg cagtatcaaa agtaactgca   2400
aagcaaatga atatttatgg cggcatgcgt atgggaggaa gtagctacta cggactagat   2460
gtattaagcc ctacttcacc gaaactgctt tttagaatag gggcagacca gaatgactat   2520
agccgtatgg gtcaaagctg gtctaaaccc gtactcgcga acatccgtta taacggttct   2580
attagacgcg tcctgattgt tggcggtggt tatgatcagt gttatgaaaa accaaatatt   2640
acgttgactg acgcttgctt taccaatgga aaagcaaaag gaaatgctgt ctatattatt   2700
gacgcaaaaa ctggtcagcg tttgtggtgg acaagtgata caggttctaa tactgataac   2760
gccaatatga agcatagtat tgttagccgt attagtactt tagaccgtga tgctgatggc   2820
ttagtcgacc atctatattt tggagattta ggcggacaaa ttttcgcgt agaccttaat    2880 aataatcaga caaaaaccaa ttcgacctat agcagttttg tgtcagagt tgtgcgttta    2940 gcgaatttag caacaaatga ttcaacttat gatggcacaa atgattatac aggtgggaat   3000
gctcctcgtt tttatgagcc tccaacagta acgatccacg attatggaat tcacactttt   3060
attacagtag gaattgcatc aggagaccgt agtacacctt tagatgttta cccactcaca   3120
ggtcgtgaag gtatgacgcc tgcaagtgca ttaagtggac gtcctgtaaa taatgtatat   3180
ggaattattg atagagactt tgttaaaaag aacttaatgt ctttaactga taatcagctt   3240
gaaacaaaag atattacacg gacaggctta agaaaaaatc cacaaattct aagaacaggt   3300
gaaacaagag tagctcaaat tttcttccca actacaggag taggtaaagg tggttggtat   3360
cgctcgcttt ctagtacgag cgatggtaca gaaaaagcta ataatagttt tcgtattaaa   3420
ggaggactca agcttttga ggaaccaatg gcaattacgg gtaatttaat tattctagtt    3480
tatgaccctc aaggaacggg aattgttgcg gcagatcctt gcctacctcg tgttgtggga   3540
gaaacagacc gacaaactta ttgtttacca tttggagctt gtcttaattc tgatgggtca   3600
atcgatcaaa ataaagagaa tcacagtggg tttgaaacac aaactggtac taattgccca   3660 gtagggctt ctgaatgtaa taaaaacgtt attggctctg gtattcgtag cgtaacattt    3720
gtaccaacgg aggataaccc acctacgact aatagttgtg ggaaattaaa gctgtctggt   3780
aatgagcaag ggactggaca gtggcaatgt acgagtcatt tagttcctac gcgttggtat   3840
gagcgttatc gttaa                                                    3855
```

<210> SEQ ID NO 60
<211> LENGTH: 9144
<212> TYPE: DNA
<213> ORGANISM: Acinetobacter baumannii

<400> SEQUENCE: 60

```
atgacagacg ctgctggcaa tacttcggaa caggctgtac aaaaagtagt tgtggatact     60
accgcgccgc aagcaggtga actgacttta tctgacttga gtgatacagg tatttcagca   120
acagatcaga tcacgcaaga taaaaacttc aatttaaagc ttgaaggaca ggaaagcggc   180
agccgagtaa catatttagt ttctaccgat gaaggaaaaa cttggcagga aaccacgata   240
gcccaaaaag atttaactga tggtgtttac caatataaag ctgtagtgac agacgctgcc   300 ggcaataccct cggaaacggc tgtacaaaaa gtggttgtgg atactaccac accacaagca   360
ggtgaactga ctctatctga cttgaatgat acaggcgttt cagtaacaga tcagatcacg   420
caagataaaa acttcaattt aaagcttgaa ggacaggaaa ctggtagccg agtaacatat   480 ttagttttcca ctgatgaagg aaaaacgtgg caggaaacca cgatagccca aaaagatttg   540
gctgatggtg tttacaaata taagctgta gtgacagacg ctgccggcaa tacctcggaa    600
```

-continued

| | |
|---|---|
| acggctgtac aaaaagtggt tgtggatact accgcaccgc aagcaggtaa actcacttta | 660 |
| tctgatttga atgatacagg tgtttcagca acagatcaga ttacgcaaga taatagtttt | 720 |
| actttaaagc tagctcaacc gattgtgatt ggggaacaag ccgctttact agaccactat | 780 |
| gaagtttcaa aagatgaagg aaaaacttgg caagagacaa cagctgatca aaaagattta | 840 |
| gctgatggta tttaccaata taaagctata gtgacagacc ttgcaggcaa tatctcagaa | 900 |
| tctgctatac aaaagttgt tgtagataat tccttaaatg ttgaatcaac cacagtgatt | 960 |
| gtaaagccga ttactgaaga caatacaata agtctagttg aaaaagatca agttatttct | 1020 |
| ataagacttg aaatagctaa tttacccaca gatttaaata gctcactgac atcagtaaat | 1080 |
| acgacattag gcaatgttac ttataatttt cattttgatg aagtcacgca agaatgggtt | 1140 |
| actgaaattc cagcagagtt tctttggtca gtagagccgc aaaccaatat atcaattgag | 1200 |
| attagtctta ctgatcaagc tggtaataca gccattatca acatacccca aaattataat | 1260 |
| gtggatcata ctccgaattc accaacccta gattcactga ctttcaacaa tatagatgga | 1320 |
| gctatcattt caggtagtgc atataaagga agtaaggtcg atatctacaa taaaaatggt | 1380 |
| gattggcttg caagtacaat aactaatgaa gaagtaaat ttactttaca agatctttca | 1440 |
| attaactcaa atcaagaagt ttacgcagtc gctacttata atggttatag cagtgaaaat | 1500 |
| tcatcaattg ggttagttac tgaagttcca gctattagta ttacacgaat tagtccagaa | 1560 |
| ggcgtgatta gtggttatgc gactgaaggt agtcatttta ttgtaaaaga tcagaatgga | 1620 |
| aatatttac aagaatttaa ttctaatgta tttgatagct ctggtattac accatttagt | 1680 |
| gtaatggcat taggcgaagt aagaccatt attttgtccc tcgatcagcc tttagaggaa | 1740 |
| ggggctcaaa ttattatctc tatagataaa gataatattt caggccatcc acaatatatt | 1800 |
| actgcagact atactccagc agtattttta gaaactccac aatttgatat tagtggtgaa | 1860 |
| actttatcag tacatgttaa tgaacctaac agctttattc gtgcattttc tggagaaggc | 1920 |
| aatttaattg ctacaggttt taccgatgag caaggctttg caagtttaca ggtgttccaa | 1980 |
| tttttaaaag aaggcgaaac ggtttctgta caagtagtag ataaaaatca aaatacgagt | 2040 |
| gaaaccctaa tcgaggttcc aaactttgct tatattccac atgttgaacg tattacacaa | 2100 |
| gaaggcttaa tttctggagt tgctgaagat aatagtacgg taattgtacg tgatgctgat | 2160 |
| ggcaatgaat taggaaaggt tacattaggt gatgataata gttggagtga ctttagtcat | 2220 |
| tttagcttga gtgtaaaccg ccccttta att gatggagaga aaatttccgt tcaaattatt | 2280 |
| gataataaag ggttaatgag tcctgagcaa aatatcatcg tagatctgac tcctccacct | 2340 |
| gctccaacgg agttaaattt taatgatgct ggtgatttag tttatggtca tgcagaacct | 2400 |
| ttctctgaaa ttttagttaa agatgggcaa ggaaatattc ttaataaatg gttttggaat | 2460 |
| aactggaccg atgagagtgg aagtttctca atagaactag gtacattttt aaccaatgct | 2520 |
| gagacggttt atgtcacggc taccgatgta aatggaaacg taagtttagc agctcagata | 2580 |
| caagcaccta attatgcctt tgctccatat gttgatagct ttacttcgga tggcgtgata | 2640 |
| agtgggcaag ctgaaaataa tagtactctc gttgttaaag acgccaaagg tgacgttgta | 2700 |
| gctgaaatta agttggtga agataacggt tggaatggat caagttattt taaactccag | 2760 |
| cttgatcgtc ctcttgtcga tggtgagcag tttttcttat caattaagga tgcacgtggg | 2820 |
| caagtaagtg ctgatactgt aattaccgct gatacggttg ctcctacacc agccagcaat | 2880 |
| ttagttttct cagaagatgg ttcatatctt acgggtgtag cagaactgaa tactacgatt | 2940 |

```
caggtttttg atcataatgg tcagctagtg aatatatgga ataacaccat taactctgac    3000
ggtacattta ctatttactt aggtagtaac aatttacatg gagaagcatt cacagtcact    3060
gttaaagacc aagccggaaa tgtgagtgag gctatttcaa taaacgcgcc acttgacgat    3120
attgcaccga atccaattaa aaatatttta cttgatgcaa atggccaaaa ctttacagca    3180
caagcagaag caaatagtca gatcgaagtt tttgattcat tgggtaatca gacaggttgg    3240
ggttctacag atagtgcagg taatgttttct ggttctttca atcaaactta tttcacggt    3300 gaggaactca cttttgttgt tatagatcga gcaggtaatc gcagtatcga atttaagcaa    3360
aatgctttaa ttgataccat tgcaccaaat ccgattgcaa atatcatctt caacgaagat    3420
ggccaaagtt ttacagctca ggcagaagcc ggaagttcta ttgatgtatt agatcagact    3480
ggaaataaga ttggttttgg ttacaccgat agctcaggta atgtatctgg ttattttcaa    3540
caagtttact tacacggtga ggaacttact tttgtcgtga tcgatcgagc aggtaaccgc    3600
agtgcagagg tcaagcagag tgctttgaat gatgacgtcg taccaaatcc gattgaaaat    3660
attgtattag atctcaatgg ccagaacttt acagctcagg cagaagcaaa tagccaaatt    3720
gaaatcaaaa ataataacgg tgacgtcgta ggttatggat cagcagatag tgcaggtaat    3780
gtttcaggat atttgtatca agtgcattta catggcgaag agctcacttt tattgtagtt    3840
gaccgagcgg gtaaccgcag tacagaggtt aagcagaatg ccttgattga tgatattgcg    3900
ccaaatccga ttgaaaatat tgtattagat atcaatgggc aaaattttac agcgcaagca    3960
gaagcaaata ctcaaattga agttaaaaat gctgttggtg agattgtagg tttaggttat    4020
gtggatggcg ctggtaacgt gtcaggttat ttatatcaag tctatttaca tggagaagag    4080 ctcactttttg ttgtcgttga ccgagcgggt aaccgcagta cagaggttaa gcagaatgcc    4140
ttgattgatg atattgcgcc aaatccgatt gaaaatattg tattagatat caatgggcaa    4200
aattttacag cgcaagcaga agcaaatact caaattgaag ttaaaaatgc tgttggtgag    4260
attgtaggtt taggttatgt ggatggcgct ggtaacgtgt caggttattt atatcaagtc    4320
tatttacatg gagaagagct cacttttgtt gtcgttgacc gagcgggtaa ccgcagtaca    4380
gaggtcaagc agaacgcctt gattgatgat atcgcaccaa atccgattga gaatatttta    4440
cttgatgcga acggacagaa cttttacagct caggcagaag caaacactca aattgaagtc    4500
aaaaatactg ctggtgaagt cataggatct ggttcaaccg atagtatggg taatgttttct    4560 ggttacttct atcaggtcta tttacatggt gaagaactca cttttgttgt agttgatcga    4620
gctggtaacc gcagtacaga ggtcaagcag aatgccttga ttgatgacat tgctccgaat    4680
gcgattgaaa acattatctt taatgaaaat ggtcaaaact ttacagcgca agcagaagca    4740
aatagcaaag ttgaagttaa aaatgctgcg ggtgaggttg taggttctgg ttatgtggat    4800
agtgttggta atgtgtcagg ttacttgaat caagtttatt taaaggtgga ggagctcact    4860
tttgttgtga ttgatcaagc tggtaatcgt agcattgaag taaaacaaac agcctttctt    4920
gataatacag caccggaaaa tgcgactaat ttagtattta gtgaagatgg ctcatatcta    4980
agtggtatgg ctgagccaaa tgcgacgatt caaatatttg atcagtatgg tcaattatta    5040
aatcagtgga ataataatgt taattgggac ggaacatttta acatctatttt aaacagtaac    5100 tacatgcatg gagaagtatt taaagtagtt gtagttgatc acgctggtaa tttgagtggt    5160
gaggttactg taaaagcacc gcttgatgat attgctcctg tagctgcaag tgatctggtc    5220
tttaatgaag atggttcatc cctttctggt gtagctgagc caaatacctt catccagatt    5280
tttgatcaaa atggtcagca gatgaatacg tggagtcaga gtgtaaatgc tgatggtaca    5340
```

```
tttactattt ttttcggtac ttacaattta catggtgaag agtttacagt cattgttaaa    5400
gaccttgctg gaaatgtgag tgaagctgtt tcagttaagg cgccgcttga tgatattgcc    5460
ccaaaaccga ttaaaaatat tgtatttgat gcaaatggcc aaagctttac ggcacaagca    5520
gaagcaaata gtcagattga aatttttgac tcatttggta gtcagatagg ttggggctct    5580
accgatagca ctggtagtgt gacgggttac ttctatcaag tgtatttaca tggagaagaa    5640
ttaacgttcg ttgttataga ccgagtaggt aaccgtagtg atgaaatgaa gttaaatgct    5700
ttgatggata ccattgcacc aaagccgatt gaaaacatca tctttaatga aaatgggcaa    5760
aattttacag cacaagcaga agccaatagt tttattagtg tcaaaaatgc tgcgggtgag    5820
tttgttggct atggttatgt cgatagtact ggtaatgtgt ccggtcactt caatcaggtt    5880
tacttaaaag gtgaggaact cacttttatt gttatagata aagcaggtaa tcaaagtatt    5940
gaatataagc aaaatgcttt aactgatgat attgcaccaa atccgattga aacatcgtc     6000 ttaaataaaa atggacaaaa ctttacagcg caagcggaag ccgatagcca aatcgaagtt    6060
aaaaatactg cgggtgaggt cgtaggttct ggttatgtag atagtattgg taatgtgtca    6120 ggttcttta atcaagtcta tttacatgga gaagagctta cttttgttgt agttgaccga    6180
gcaggtaacc gtagtacaga ggtcaagcag aatgctttga ttgatgatat cgcacctaat    6240
caaattgaga atattgtttt tgatgtaaat ggtcagtact ttacggggca tgctgaagca    6300
gatactcgaa ttgaagtact agatcaattt ggcaatcgcg ctggttgggg atatgttgat    6360
agccaaggta acgtgatagg ttatttcaat caggtttatt tacatggaga ggaattaact    6420
ttcatcgttg tagatatagc tggtaaccga agtgttgaag ttaagcaaaa tgctttaatt    6480
gataatgtcg caccgccagc agcagcaaat attacattaa cctcagacgg attgcttttt    6540
ggtgaggcgg agccaaactc aactgttgaa attattgatc aatatggtgc agttatcaca    6600
acaacttatg tttggtacga tggcacattt aatcaatgga ttaatctgag tcaataccag    6660
acacaaaatt taagtattgt tgtcaaagat caagcaggta accgcagtga agttgtacat    6720
gaattagtac cagtatttac caactcacca attgctgcaa cagagctaaa actggatata    6780
gatggtcata ttctgacagg taaggcgaca gtaggaatgt cggttgttgt tacatctact    6840
gatggtcaga ccattaacgg agggtggaat aatgctgtga atgaagatgg tagttttgct    6900
attcagttaa atgattacta tctacaggga cagacattac aagttcgagt ttatgatcag    6960
aatacgaatc aatatagcct aatctctgaa attattgcgc ctttagacaa tattgctcca    7020
gtaattaatg aagtggtaat taacaatgat ggttatggta ttactgggca aactgattca    7080
aaagcaatca ttcaggtaat ggatgcggat ggagatttac gagcagaatt tcaagcggat    7140
gagactggat attttaacgc tagtatttat ccacctatat acgtggaga gcagttattc     7200 atcactgcga tagatttagc caaaaatata agtaagccat ttaatattac ttttaatgca    7260
gatactaatg caccgccatc agcagagcat attgtgtat ctgaaaatgg tttttttatt      7320
gagggaaccg ctgtagcaat tagtactgtg catatttttg atgtgcatag taaccatgtt    7380
gccactaatg ttgcagatga agctggaaac tttaatattc agttgtatcc acctctagcg    7440
agtggacaaa ttttacgcat tgttgtggaa tacaatggga tcaaagtgc ttacaccgaa      7500 attacggcac ctatagacac tgtcgcacca aatgcagcaa ctcagcttct cttagaagat    7560
ggaaatgtac tttcaggaca agcggaagca tattcaattg ttaatatttt tgatgctaat    7620
aataatttgg ttggtcagac taatgttgga agtgatggtc ctttcttaac acacctatgg    7680
```

| | |
|---|---:|
| tatgagtatt ggcatggcga acattaacg gtaaaagtag ttgatgccaa tcaaaatgtg | 7740 |
| agtgtgggga caacgattgt tgctataaat gatacggtag ttccagatgt agttacgcag | 7800 |
| cttgctatag atgaatgggg ttcgctcaca gggagggtag aaagttatgc tactgttgag | 7860 |
| cttacctatc attttactga ccaaccgctt tctgtaacga gcactacagc attggcaaat | 7920 |
| ggaatgttct ttatctatct ggatagaaat gcaacttcac ttgaccttac tgttattgat | 7980 |
| cgtgctggaa accgtagtga aaccattagc caaataatta gtgatttacc gactgttatt | 8040 |
| attgatcact ttaaaggtga tgctacagat aatacttata acattgatac tatagatgat | 8100 |
| tttgttcaag aatatattgt tgagccgtat gcaatatata aagacgtctg gattgataat | 8160 |
| agctatatgt attcagattg ggtcattgaa ggccattatg aacagatatg gtttgttgat | 8220 |
| ggatattatg aatcgcaatg ggccacaagt ggttattcaa ctgtacaaaa tatttatcaa | 8280 |
| aatcaaaatg gtataactta tattgataat ggcacggcag atagcgatta tagtcgatat | 8340 |
| gaacaacaat attatgattt cgtgaatggc caatggcaag aaggctatga attaacttat | 8400 |
| atacgttcag aagaaggatg ggttgataca agtcattatg aagatgttta tattgataca | 8460 |
| agtcattatg aagaggtttg ggtagatact agccactatc aagatatttg ggtagaaaat | 8520 |
| agttattggg agagtcaact tgttgaatct ggccgtagag atgtggattt aggcgggcat | 8580 |
| gataaaatta tcagttctgt taattatagt ttggttggtt tatatcaaac agtaaatgat | 8640 |
| ccaacgactg tagattcgtt tttggaaagt ggtcgttatg tagaagactt ggagctggtt | 8700 |
| ggttctgctc atctaaatgc aacaggcaat gctttagata atctttttaac aggtaactct | 8760 |
| ggtaataacg ttttgaatgg gcgtgaaggt aacgatacct atatcactaa tgaaggtact | 8820 |
| gataccattg tgttccaatt gctaaatagc caagatgcaa ctggcgggaa tggacatgac | 8880 |
| acggtgttag attttacttt aggtgatata agaactaacc ttcaagctga caaaatcgat | 8940 |
| ttaagtgaac tattaattga ctattctaaa gatgtaagcg cattagctaa atttattact | 9000 |
| gtagagcaag atgctgggaa cacgactatt agtcttgacc gagatggcga aggtacaatg | 9060 |
| tttaatagtg tgtcactgtt aactctaaat caagtaaata caacattaga cgaattacta | 9120 |
| aacaaccagc aaattattgt ttaa | 9144 |

<210> SEQ ID NO 61
<211> LENGTH: 183
<212> TYPE: RNA
<213> ORGANISM: Acinetobacter baumannii

<400> SEQUENCE: 61

| | |
|---|---:|
| augacacagc ucauuaauaa agguggcuuu cgugaaagag ccaauagaag ccgaaaauau | 60 |
| caacaaucug aaaacaagca aguagcucug ccuucaaaaa aguaucaacc ucaaacuaaa | 120 |
| cuccaagaua aucaaagcga gaugauucaa gcaaaagcag guacugcuga aacuucagau | 180 |
| uaa | 183 |

<210> SEQ ID NO 62
<211> LENGTH: 201
<212> TYPE: RNA
<213> ORGANISM: Acinetobacter baumannii

<400> SEQUENCE: 62

| | |
|---|---:|
| augaaauuag cuaaaacuuu acucgcuacu acccuagcuu uaacugcgc uucaacuuuc | 60 |
| gcugcuucua agcacgacca agcacauaac acugcugug aagaaaaagu uguuguuuca | 120 |
| acucaagagc aagcaaacac ugcaaaugcu gcuucgacg cuguagguuc ugcuucugaa | 180 |

```
gcugcuccug caacucguua a                                          201

<210> SEQ ID NO 63
<211> LENGTH: 201
<212> TYPE: RNA
<213> ORGANISM: Acinetobacter baumannii

<400> SEQUENCE: 63
augauagaug aagaaaagcc uuuaaauuuu gaagaugaug acgagccucu ugauuugaa   60 gaugaagaau ucauagacga uaaaaagag gacgaaaugu auaacucgau uacuaaggau  120
ggcucuagug ucgauccugc ugaugauggg acacgacaua uucguccuga agacggcgau 180
ccgauugaaa uugaugagua a                                          201

<210> SEQ ID NO 64
<211> LENGTH: 222
<212> TYPE: RNA
<213> ORGANISM: Acinetobacter baumannii

<400> SEQUENCE: 64
augagcacua cuaauaauca agcaaaucaa cgcaauaauc agcagcaaca acaacagcaa  60
aaugacaacc guaaucaaca gcaacacggu aaccaacagc aaaacgauca acagcaacaa 120
aauaaccagc aacaacagca aaaugauaac cgcggucaac aacaaggauc uaaucaaaaa 180
gauucuggcc aacaaaacuc aaauaacaac caacaacguu aa                   222

<210> SEQ ID NO 65
<211> LENGTH: 327
<212> TYPE: RNA
<213> ORGANISM: Acinetobacter baumannii

<400> SEQUENCE: 65
augucagcaa aacuaguugu uacuuuguua gcaaccaguc uuuuaacugu aggcugcguu  60
gcuuauacag augauccuua uuaucgcggu gguuaugguu accaugauca ugacgacgau 120
cguuaugacc guaacgaugg acgucgauau agugaguggg aacgcaaacg uuggaagag  180 cguaaaagau uauaugaaca caacgcaaa gauauucgug aacagcaaaa ggaucgucgu  240
gaaugggaaa acgacaccg ugaaugggag aagaaacgcu agaagaccg agaucaugau  300 cauagagauu aucgucauga ugacuaa                                    327

<210> SEQ ID NO 66
<211> LENGTH: 345
<212> TYPE: RNA
<213> ORGANISM: Acinetobacter baumannii

<400> SEQUENCE: 66
augaauaaau uacuuguugc uuuaggucuu gcugcgacug uugcccuugu ugguuguaau  60
aaagauaaag cuccagaaac uggugcuacu acaggugaac acuuagaaaa ugcugcucaa 120
caagcaacag cagauaucaa aucucugguu gaucaagcug cgagcgauau ugcaacugca 180
acagacaacg cuucagcuaa aauugaugcu gcugcugacc augcugcuga ugcgacgcu  240 aaagcugcag cugaaacaga agcuacgca cguaaagcga cugcugauac agcucaagcu  300
guugaaaaug cagcugcuga ugugaaaaaa gaugcucaac acuaa                345

<210> SEQ ID NO 67
<211> LENGTH: 381
<212> TYPE: RNA
```

<213> ORGANISM: Acinetobacter baumannii

<400> SEQUENCE: 67

| | |
|---|---|
| augaaaauga cggcuaaaau ugcauuauuc agugcagcaa uuguaacuau ggguaguuug | 60 |
| gcugcuuguc aaucaacaac ucaaccaccu aagccagaac auggcaugau gcaagauggc | 120 |
| ccacgugaug gucaccacca ucguaugaaa caccgugaau uuacgccuga acaaaaagca | 180 |
| gcaugggaac acaccgugc agagcguaaa gcucguuuug agcaaauuca aaagcaugu | 240 |
| gaagguaaag uuguuggaca aacugucaau guucaaguug gagauaaaac acuugaaggu | 300 |
| acauguaacc uccgcuuuga gccaaaacgu ccucaaccac cagucaaugc cccugcucca | 360 |
| guagcgacuc aagcaaaaua a | 381 |

<210> SEQ ID NO 68
<211> LENGTH: 420
<212> TYPE: RNA
<213> ORGANISM: Acinetobacter baumannii

<400> SEQUENCE: 68

| | |
|---|---|
| augaaagcca uaaaaauuuu auguauuaca agcucuaucu ugguuucauc aucucucuuu | 60 |
| gcugaaacac cucaaccuca acaagugaau gaagcaacuu cuaagacaau gccuauggu | 120 |
| gauaauccaa gcuuaggccg cguacuguua uacaaaacag gaaaaggcau caaaauuua | 180 |
| ggagauucua uucaaggcgc uucugaaaaa acuucaaaua aaauuaguga aaauggaaa | 240 |
| gauacgaaag aauuuaccgc cgaaaaagca gaaguuguuc aacaaaaagc ggauacagcc | 300 |
| aaaguauuua cugaacagaa aauagaacaa gcuaagcaaa auaucaccag caguagaaac | 360 |
| ggugaaaaua uuccaaucga caaggugag cuaaguaaau cuaguacgac ugccaauuaa | 420 |

<210> SEQ ID NO 69
<211> LENGTH: 480
<212> TYPE: RNA
<213> ORGANISM: Acinetobacter baumannii

<400> SEQUENCE: 69

| | |
|---|---|
| augaaaaaau cauuauuagc aauugcacuu augaguacuc uucuugucgc auguaauaaa | 60 |
| caugaaaaua aaacagaaac aaccucugau gcaucuacuc cuguacaaac ugcucaauca | 120 |
| aauaauaaug aagcgguaga uacagcacau acagccgaga auucuuuaga uugggauggu | 180 |
| aaauauaaag guacgcuucc uugugcagac ugugaaggca ucaaaacuga auuagaguua | 240 |
| aaagaugaua aaacuuauga gcuaacagaa accaucuuug guaaaggga ugcaaaccca | 300 |
| uuugaaaccc augguaaguu uacuuucgau aaagacaaua cuucguuau uaccuuagau | 360 |
| gauaaagcuc aaaaccguaa auucuuuauu ggugaaaaua cagcgacagc uuuagauaug | 420 |
| gaagguaaaa aaguugaagg uucuuuagcu gaacauuaug uuugaaaaa agaagauuaa | 480 |

<210> SEQ ID NO 70
<211> LENGTH: 489
<212> TYPE: RNA
<213> ORGANISM: Acinetobacter baumannii

<400> SEQUENCE: 70

| | |
|---|---|
| auggcaaaua aaaaacuuuu aaucugugcu gcaauugcgg cuggacuauu guuaaccgca | 60 |
| ugcguuaaaa aagagacacc gaaagaagaa gagcaagaca agguugaaac ugcuguuuca | 120 |
| gaaccucaac cacagaagcc ugcaaaauuu gaaucuuuag agaguguaga uacucaagaa | 180 |
| gcucaaguuc aagagcaacc acaaguugaa guucaucgug aagaaacugc uaacacgaca | 240 |

```
acugaaauuc gccgugaaac ucguccugcg cguucugaug aaucuucaca gacacaaguu      300
gcugaacaac cuaaaucuga gacaccaaaa guagaaccua aaccagaaaa aaaaccugag      360
ccuaaagcug aaccuaaacc ggaaaaagcu cagucaaaac cagcugcuaa ggcaacugag      420
ccugcgaaca cagaagauga ugccguugcu gcugcuauug cugcugcaac accagcacuu      480
aagaacuaa                                                             489
```

<210> SEQ ID NO 71
<211> LENGTH: 501
<212> TYPE: RNA
<213> ORGANISM: Acinetobacter baumannii

<400> SEQUENCE: 71

```
augacuacug aaaauaaauu agaugaauua aaggcaaacg cggcugaugc aaaaguacaa       60
ggugaaaaag cuuuggacga uuuaaaagaa aauguaaaag agaaacaaac ugcgg guaaa     120 gaagcaauug cagauaaagu agaugagcua aagaccaaag cggccgaugc aaaaguacaa     180
ggugaaaaag ccuuggaaga uuuaaaggaa auguaaaag aaaaacaagc ugcugcaaaa      240
gaggcaguug aagauaaagc uagugauuug aaaggcaaac uugaugaugc ucagcauagc     300
cugcaagaca aguuugauca uuuacguacu gaagcagcgc auaaacuuga ugaugcuaaa     360
gccaaagcug cagaauuaaa ggaagaggcg gcuacaaaau uugaugaguu aaaaacucaa     420
gcaacugcga auuugauga guugaagaaa acagcuaccg aaaaacuuaa uaaauugaaa     480
aaucaugauu cugcugaaua a                                               501
```

<210> SEQ ID NO 72
<211> LENGTH: 693
<212> TYPE: RNA
<213> ORGANISM: Acinetobacter baumannii

<400> SEQUENCE: 72

```
augcacacgc gucguauuuu auuagcguuu ucacuugccg cuucggcagc aucgguugcu       60
uuugcagauu aucaaaauau uaaccaaucu acugauucag aucgauugga acaguuauca     120
aaacacuauu cucaaggcuc auauacucau ccugaugauu uagaucuucc ggcgagugca     180
aaaguuucag ugacuuuacg ugagaaaaca guugaacuca acaaugauuc acuggcaaag     240
aaauacggca aacgacagc uaaaaacuca uuuaaaccu cuucuucaaa uccuauuucu       300
ugguuaguuu cucauccucu uccugauaca guacguguuu cuucuaacuu ggguggucgu     360
accaugggug gucgugcaga gcaucaugu gguuagauua uggcugcacc aaguggauacg     420 ccaaucuaug ccacuggucc gggauugug acuaaaucag gcuggggcac agguuauggc     480
caauauguug aaauuaacca ugguaauggu uauuuaacac guuaugcgca ugcuucacgc     540
uuaaugguuc ggguagguga ucagguuucu gcgggugacc auauugcuaa guuggguugu    600
acaggccgcu guacuggucc acauuuacau uacgaaguag uuaaagaugg ucaacguaag     660
aauccaucaa cuuacuuagc aauguugccu uaa                                  693
```

<210> SEQ ID NO 73
<211> LENGTH: 717
<212> TYPE: RNA
<213> ORGANISM: Acinetobacter baumannii

<400> SEQUENCE: 73

```
augggcauga cuuuuacaga cauagaaaau aaaucugcca aacgccuaau ugguauugcu       60
```

```
gcagucauuu uucugcaucu ucuuguugcc uauauucuga ugucagguuu agcaaacaau    120
auucaaaaac cagcagaaaa accguggaa uuacaaauua uucaggauau uaagccaccu    180
ccuccaccaa agccggaaga gccgaaacca aaggaaaaac caccugagcc accaaaaaug    240
guagaaaaag uugccaaggu uccgagcca caaaagaag uagagaaagu agcaacacca     300
guacaaaaaa cgacgccagu agcucaaacg acuaaagucg cuacuccggc uccugcugca    360
ccuaguacuc cuucuccgag cccguuugcu gcaccagcuc cagugcagc ugcugcacca     420 gcacuuaaac ccgcuggugu aacucguggu guuucagaag cucugcggg cugcgaaaaa     480 ccagaauauc cacgcgaagc acucaugaac gaagagcaag uacggugcg uauacguguu     540 uuaguugaua cuuccggcaa agucauugau gccaaaguaa aaaaaucgag gguagcaaa     600 accuuagaua aagcagcaac uaaagccuac agcuuaugua cguucaaacc agcaaugaaa    660
gauggcguac cucagcaaga cugguaugaa auugauauc cauucguaau ugaauaa       717
```

<210> SEQ ID NO 74
<211> LENGTH: 762
<212> TYPE: RNA
<213> ORGANISM: Acinetobacter baumannii

<400> SEQUENCE: 74

```
augaaauga ugaaaacagc uaucguuacu gcaaguguac uugcuucugc cucuauuuuu     60
gcacaaagug cgggcguuaa ugcaggugca ucugcucaag ucaacguaca accagguggu    120
cuuguuagug gcguagccaa ucagucaaa aauacugcac auacuguagg gaacacagca    180
aaacaugcug gucacguagc ugcugacaca accguuaaag cucaaaaaaa aacaacaggu    240
aaaguaacug aacuuucuuc uaaagcugcu acugguacua acauguagc aagugaagcu    300 guaacuggua cuaaacauuu ugcuaccgaa gcagcaacag uacaaaaaaa uuuagcgacu    360
aaggcugcaa cuggcacuaa aaaccuagca guugaagcua agcagauac aaaagcacau    420 cuugaugcug uaaaaacuaa gguagcagaa aaacaagcgc accaaaaaga uuuacugcu    480 gaaaaacagg ccgaugcuca agcacgugua gaugcuguua agcucgugu agcacaaaau    540 caagcugagc aaaaagaauu cguucugac acuaaagcug augcucaagc aaaauuaaau    600
acagcucaac cagcucaugg aguuaacgcu caaacaggug uaaacguugg uguuaauguu    660
gcugguauua augcaaagc aaacguaaau gcaggcgcuc aagcgucuac acaaaaaggc    720 gaaaagaau cuuuuuauua aaggucuuuuc gguacuaacu aa                      762
```

<210> SEQ ID NO 75
<211> LENGTH: 885
<212> TYPE: RNA
<213> ORGANISM: Acinetobacter baumannii

<400> SEQUENCE: 75

```
augcaaauga agaagcauuc uuuauuuauuu auugccuuaa ugagcaccac uucucuauac    60
gcaaauaucc cuaucgaguc ucguggguuua agucaaaaug augguagugc aucuaauacu   120
ucuucaagca auauuucagu uccuacaaau uuaaacuggg aacucaugca aaaaaaccaa   180
caauuagaaa augauauucg uacauuaaga ggucagcuug aagaacaagc uaugauauu    240 gagcaauuaa agaaagaucu agcaaaccga uauaccgacu uagaucaacg uuuagaauua    300
uuacaccaaa aaguugaccc ugacagugcu acacaagaug auaguucgaa ugcaacgucc    360
gauaacacua cuccugcuag ugcaccagcc ccucaaacca cggagaguaa uaaaguagcu    420
gccguaccag ccacacaaac uucugagcag cagccuagcg caccaacaac cacuacucaa    480
```

```
ccagcaccag cugcugcgca aaaccaguca aauucccucg aauuagaaaa agcugcuuau      540
acuguagcuu uagaugcgua uaacaaggc ggugcuaaaa aagcaauugc uccaaugcaa       600
aacuuuauaa aaaaccaucc uaauaguauc uauacaggua augcuuauuu uugguuagcc     660
gaguuucauu uagcgacaga uccaguaaau uauaaugaag caagaaaaa cuauaaugu       720 guagcuaacc aauacccaaa uucaaguaag gcaccucgag cauuguacca acuuuauagu     780
aucgcuaaag auguugauaa gaauacgug ucagcaaauc aauacaagaa caaguuacuu     840
agccaauauc caaaaucuga agaagcaaaa ucuuuaaca aauaa                      885
```

<210> SEQ ID NO 76
<211> LENGTH: 1071
<212> TYPE: RNA
<213> ORGANISM: Acinetobacter baumannii

<400> SEQUENCE: 76

```
augucaauga auaacaaaca acgcuggaug gguggcguug uuuuauuagg ugguggguguu     60 uuauuggcag cauuacuucu aaaaggaaau gaagaaauaa aacagguaga uguucaaccc     120
caaacuucaa caucaccgaa auuacaagcu aagccaaagc aaucagcaca agaagggcag     180
augguacagc uacagccacu ugcaguugau guugaaacag aaaaacgucu ucuugaagaa     240
cagcgccguu ucugugaaaa agcuguagca gaacaagagg cucgugcugc cgaauucuug    300
gcaaugcaac aacaggcaga agcggaugca gcucguaaag cugcugcuga auaugccgcg     360
auuaaugcuc gccgagcugc ugcacaagaa aguccgauua auauuccucc ugaagucgcg     420
gguagugaga auaaggcaaa aggacagcaa acugauacaa aaaagucagu agaucuggcu    480
aaagcggaug cagauaaaaa agcugcugaa gcgaaacgcu uagcgaggc ggauaagaaa     540 gcggcugagg caaaacguca ggcagaagca gacaagaaag cagcagaggc uaaacgccaa    600
gcagaagcag auaagaaagc agcugaggca aaacgucagg cagaagcgga uaagaaagca     660
gcagaggcga agcgccaagc agaagcggac aaaaaggcug cugaagcuaa acgucaagca    720
gaagcagaua agaaagcagc ugaagcgaaa cguaaggcag aggccgagaa aaaagcugaa    780
gcagagaaag cacgugaguu gcuugaaaau ggugauaaaa aauggauggu acagguugca    840
uuggcugcua accaagcaaa ugcagaugcu guagucucua aauuacgugc aaaaggcuau     900
aaggucacga cgaguccaac caguaaaggu auccguauua ugguuggucc ugcaaaagau     960
agagauacgg cagauacuac acguaagaaa auuacuucug acgccaguuu aaauaugaag     1020
ucagcuuggg ugauugacug ggugccuuua gaucagcgua agucagauua a              1071
```

<210> SEQ ID NO 77
<211> LENGTH: 1104
<212> TYPE: RNA
<213> ORGANISM: Acinetobacter baumannii

<400> SEQUENCE: 77

```
auggcuaaua cuagauauga agaugauaac aauaguucag guacuucaaa ucugggauuu    60
gcaaguaugg auccugaaag agucagagaa auagccagua aaggugggcg agcugcacau    120
gccaguggca augcgcauga auuuacuuca gaagaagcuc ugaagcugg ccgugcugca    180 caugccagug guaacgcaca ugaauuuacc ucagaagagg cucgugaagc uggugcuuua    240
agucauaaaa acgaugaucg uaauggucgu ggucgcagcc guuaugauga cgacgaagau     300
gaugaccgcg gccguucaag uggucgaggc cguggccgca gucguuauga ugaugacgac     360
```

| | | |
|---|---|---|
| gaagaugaug aucgcggucg cucaggcggu cguggccgug gucgcggucg ugaugaugac | 420 | |
| gacgaagaug augaucgcgg ucgcucaggu ggccgaggcc ggucgcag ucgugaugau | 480 | |
| gacgaugaag augaugaucg cggucguuca gguggccgag gucguggucg cagccgccgu | 540 | |
| gaugaugacg augaagauga ugaucgcggu cguucaggcg gucgaggucg uggccgcagc | 600 | |
| cgucgugaug acgacgauga agaugaugau cgcggucgcu caggguggccg aggucguggu | 660 | |
| cgcagccguu augaugacga cgaugaagau gaugaccgug gccguucagg cggucgaggu | 720 | |
| cguggccgca gccgucguga cgaugaugac gaagaugaug aucguggucg uucaggugggc | 780 | |
| cgaggccgug gccgcagucg uuaugaugac gacgaugaag augaugaucg uggccgguuca | 840 | |
| gguggccgag gucguggccg cagccgucgu gaugaugacg augaagauga ugaucgcggu | 900 | |
| cguucaggug gucgaggccg uggccgcagu cguuaugaug augacgauga agaugaugau | 960 | |
| cguggucguu caggggccg aggccgguggu cgcagccguc gugaugacga ugacgacgau | 1020 | |
| gaugaccgcc guggccguuc agacggucgu ggucagaacu cucguaauca aaaacgcgau | 1080 | |
| gcuuauggac gcuuuacguc uuaa | 1104 | |

<210> SEQ ID NO 78
<211> LENGTH: 1263
<212> TYPE: RNA
<213> ORGANISM: Acinetobacter baumannii

<400> SEQUENCE: 78

| | | |
|---|---|---|
| auguuauaug ugauuccguu uaucauauua cucgguggucg ccguuauuuu aaaaaaacgc | 60 | |
| gagaauaguc aaaacaaga ggccacuucc ccaaaaaaua uaaauagaaa auccggcaaa | 120 | |
| aaagcgagug cuaaaucaag caaaagcucg cgugaaaaaa uaaaagccaa ggucauugag | 180 | |
| gaaaauauuc cugcuauccc ucaaaguaau ccuguaccgg aagcuuuacg acacaauauu | 240 | |
| caacagcuca uucaagaaaa acaguuuuca gcagcugaag cucaagucaa ucaggcgcua | 300 | |
| aaaaaagaua auacucaaca ugaacuguau uuauuacuuc uugaaauuca uauugcucag | 360 | |
| aaagaugaau uugcaauuca acaguugauu agccauauuc guagcuuggg uuuaaaugaa | 420 | |
| auagcagcuc aagcagaaac ucgacaaaaa gaauaugaau cauccagcca accugaugcu | 480 | |
| auugauuucc cucaagcuca aacauaugaa gaaccgaaaa acacagauac aacggcucag | 540 | |
| uucgaugaau uaacaacaag uucuuccgag gcuucuuuug augaccuaca gaaagacuau | 600 | |
| accccuguaa acaagaacc ugcuauugaa auugaaccuu uagaguuuaa cuuucauuc | 660 | |
| gaacagaauu cggcuacgga aaauaccaac caaccagcac aacaaccuga guuaucaucc | 720 | |
| acucaagaaa caaaugagcu ggccgauuua gaguuucuu uugacuuggc cccucugcau | 780 | |
| gaaacugagg aaaaaucuca agcaguagag guaaaagcag accaagaaaa uagcaucaau | 840 | |
| gcauuagauu uuaacuuga cuuaaauccu ucaaguucag agacgaaauc uguucaacaa | 900 | |
| gcuccccucau uagaugaaau uaagcucaua gaacaagccc cauugagaagc gacuucuauc | 960 | |
| gcaccucuug aguuuucguu agaugagccu gccuuaguuc cagcaccaga gcuugaaacu | 1020 | |
| caaaaccaua uagauguagu aaaugaagca gccacucaaa cccaaauaga ggauccgcuu | 1080 | |
| uuagaagcuu uuccagaauu aaaacaaaua aaugaaaaug aacucgauuu aaaauuggcu | 1140 | |
| gaacaauaca uuaaguuugg cgcaaaccaa gcagcgcgua auuuacuaca ggguggaugag | 1200 | |
| caaaaauuca acacagaaca acaacaacau gcgaaaaacc uacuuaaucg cauagcuucu | 1260 | |
| uag | 1263 | |

<210> SEQ ID NO 79
<211> LENGTH: 1338
<212> TYPE: RNA
<213> ORGANISM: Acinetobacter baumannii

<400> SEQUENCE: 79

| | | | | | |
|---|---|---|---|---|---|
| augccaaaaa | uaaagccaau | uaaacucgua | auuauugucg | ucuguaucgc | cauuauugcu | 60 |
| gucuuagcuu | ggaaauucuu | aaagccuaaa | caacagcaac | cucaauauau | uacagcagag | 120 |
| guaacucgug | gggauauuga | gaauaaugua | cuugcaaccg | guacacuuga | ugcaaccaag | 180 |
| cucauuagug | ugggugcuca | gguaucuggu | cagguuaaaa | agauguaugu | gcagcuuggu | 240 |
| gaucaaguaa | aacaagguca | acuuauugca | caaauugacu | cgaccaccca | agaaaacagu | 300 |
| uuaaaaacau | cugaugcuaa | uauuaaaaau | uuagaggcac | agcgucuuca | gcaaaucgcu | 360 |
| ucuuuaaacg | agaaacaacu | cgaauaucgu | cgucaacaac | aaaauguagc | ucaagaugca | 420 |
| acaccucgug | cagauuuaga | gucggcugaa | gcugcuuaua | aaacagcuca | ggcacaaguu | 480 |
| aaagcauuag | augcacaaau | ugagcucgca | aaaauaacgc | guucaacagc | acaaaccaau | 540 |
| auuggcuaua | cccguauugu | ugcgccaacu | gaugguacgg | uuguugcgau | ugugacugaa | 600 |
| gaaggucaaa | cgguaaacgc | aaaccaaagu | gcuccuacua | ucgucaaaau | ugcaaaacuu | 660 |
| caaaauauga | cgauuaaagc | acaggugagu | gaagccgaua | uuaugaaagu | ggaaaaaggu | 720 |
| cagcaggucu | auuucacgac | cuuaggugau | gaaaccaagc | gcuaugcaac | cuuacgucaa | 780 |
| aucgaaccug | cuccagauuc | aaucucuagu | gaaucaaaca | gcaccacaag | uucaacaaca | 840 |
| agcucagcug | uuuacuacaa | cgcuuuauuu | gauguuccaa | auacggacgg | caaauugcgu | 900 |
| auugauauga | cugcacaagu | uuauaucgua | uuaaauucag | caaaaaaugc | cuuauugguu | 960 |
| ccaucuucug | cguuaaguag | caaacaauuu | ucuggccaaa | gaaaacaggg | gcaaucggca | 1020 |
| gauaaagcaa | guucuacucc | aagugcagaa | cgcaagcauc | aagguaacgg | cguccguuua | 1080 |
| gaacgcuuaa | auuuaacucc | ugaacaaaaa | caacuuauug | aacaaggcaa | agcaacucug | 1140 |
| aguguaguuc | gcguuuuaca | agcagauggu | acgacuaaac | caacacaaau | uuggguaggu | 1200 |
| auuaauaacc | guguaaaugc | acaaguacuu | gccggauuaa | aacaagguga | ccaaguugug | 1260 |
| auugcugaua | guucagaaaa | cucugcagcu | ucugcaaaca | gugguaauaa | ccgccgccgu | 1320 |
| ggcccaaugg | gaauguaa | | | | | 1338 |

<210> SEQ ID NO 80
<211> LENGTH: 2136
<212> TYPE: RNA
<213> ORGANISM: Acinetobacter baumannii

<400> SEQUENCE: 80

| | | | | | |
|---|---|---|---|---|---|
| augaauaucc | caccucgacc | auuuaaguug | ucuguaaucg | ccugcgcgau | uuguuaugcc | 60 |
| aaccucaccu | augcccaaga | ugcacaggua | caagcuuugc | aaacgauuca | ggucaaagca | 120 |
| ucaaaugcag | agcagucuuc | ugaacagacc | aaggcauaua | auguuaaaaa | ucaaguagu | 180 |
| gcaaccaagc | uuaauauuga | ggcuaaggaa | acaccccaaa | ccauuaaugu | cguuacucgu | 240 |
| cagcaaauug | aagauuuugg | ccuuaccagu | acucgugaug | uuuuaagaaa | uaccccuggu | 300 |
| guaacagucu | cuaucaagda | aacgagcga | accacuauua | uggcucgggg | uuuugagauu | 360 |
| ucaaauaucu | ugacggaugg | cguaggcuuu | ccucuuucag | guuauaacua | uaauaauacg | 420 |
| aauccugaua | cuuacuuuua | ugaucgugua | gaaguaguua | aaggagcuga | cucguuaacu | 480 |
| aaugccuuug | gcgauccgag | ugcaaccauc | aauaauauuc | gaaaacgucc | aacccaagaa | 540 |

-continued

| | |
|---|---|
| uuucaagcaa gcgguggugu aaguuacggu ucaugggaua cgcagcgcua ugaagcugac | 600 |
| guaucuggcu caauucuacc aaguggaaaa guacgguggcc guauuauggg cuaugaacaa | 660 |
| acuggugauu cuuaccuaga ccgauauucu gcggaaaaaa acggcuuugc gguauuguu | 720 |
| gaagccgauu uaacagauag cacuuuacuu accgcaggguu auagccaaga acaaaauaaa | 780 |
| cccaaugcaa acaacugggg ugcacuaccu uuauuagaug ccaacgguaa acaaauuucc | 840 |
| uaugaccgcu cauauaaucc aaacccugau ugggcacauu gggauaauga dacacaaaau | 900 |
| gcuuuuguug aauuaaagca aaaacuuaau gaccaaugga augcuaaacu gacuuacaac | 960 |
| uaucuugaua cgaagcauaa uagccgucuu cucuauuacu augguuaccc aaaagcugau | 1020 |
| gggaccggug uuucucuaac gccuuggggu ggacaagaac aucaagaaaa acaugcugua | 1080 |
| gauuuuaauc ucgaagggac cuauaagcua uuuaaccgag aacaugaagc aacucuaggc | 1140 |
| uacagcuaug uacguaauca ucaacaagau aaacaaucua caggaacgau uaacgauagu | 1200 |
| aacguuauaa agucaacuac gaccgauugg gcaaguugga caccgcaauc uauaacuugg | 1260 |
| ucagauuuca cagaagcggc uaacuauaaa caaauauuua acucaauuua ugccgcgaca | 1320 |
| cguuuacauc uuaaugaaga uuuaaaacuu uuacuggug caaacuaugu ucaagcugag | 1380 |
| aguaaaggcg aaaguuauag cucaccaaug ucauauaagu aaaguaaagu uucuccauau | 1440 |
| gucggauuaa ccuauaauuu uacaccugaa uauacggguu acaugaguua uaccucuauu | 1500 |
| uuccguccac aaacugguau ugauaaagau accaaucaag cuuuaaaaaccc uauugagggu | 1560 |
| aaaagcuaug aaaugggugu aaaaagcuca uggcuagaug accguuuaac aggcacacuu | 1620 |
| ucaguauuua aaacugaaca aaacaauuac ccuuuacgua acucggaugg aaacccacuu | 1680 |
| aaccgaaaag uaccaacgag ugaucuagaa ucgcaaggug uagaagucgg ucuaucaggu | 1740 |
| caaauuacug auaacguaaa ucuuucuuuc ggcuaugcuc aauuuaguau uaagacacu | 1800 |
| aaaaauggug gcgaagcaag aacauacaau ccaaaccaga cacuuaacuu gcuaacuacc | 1860 |
| uauacuccgc caguuuuacc uaagcuuaaa guugugcag guuuacagug caagauggg | 1920 |
| auaaaguuau augacucaaa uguaaacggu acgaucaaac aagaugcaua ugcuuuaguc | 1980 |
| aauuuaaugg caagcuauga agucaaugau cauauuacgc uucaagcaaa ugguaauaau | 2040 |
| auuuuugaca agaaauauuu aaauaguuuc ccagaugggc aggcuuuuua uggugccccca | 2100 |
| gccaacuaua caguugcugu aaaguuuaaa uauuaa | 2136 |

<210> SEQ ID NO 81
<211> LENGTH: 2184
<212> TYPE: RNA
<213> ORGANISM: Acinetobacter baumannii

<400> SEQUENCE: 81

| | |
|---|---|
| augaaacuuc aaacuauagc uugugcagua gcaaucgcga cuggcgguuu auucuucucu | 60 |
| cauacgauga acgaagcaag agcagcaacc aauacugcug cuguuucuca aucgauccag | 120 |
| ccaacgcaag agcaagccuu ggugcucgu caacuggcaa cuuuaguaga ccgccaacau | 180 |
| uauuuaaaua ugcgucugga ugcgaacaca ucuaaccgua uucuugauau guacuuagac | 240 |
| agucuugauc cggaccacuc auuauuuuua gacgcugaag uucaaaacua uaaaaagcuc | 300 |
| uaugguucaa auuugguugc uucauuaaaa gcggggaauu uaacugggcc auuugcuauu | 360 |
| caccagcaau aucgugagcg cuuaaagcag uuuuaugagu ucaugcuugc ugaguugaag | 420 |
| aaaccacaaa acuuaaaaca gccaaauacu uuuauugaag uagaucgcga aaaagcaccg | 480 |
| uauuuuaaaa cgucagcuga acagcaaaau cacuggcgua aaaugcuggu uucucaguua | 540 |

| | |
|---|---|
| auuaauuuaa cgauuagccg ugaagaagag caggcgaaac aaaaggcguu aaaagaaaac | 600 |
| ccuucacuug cugaugguca agacuuaaca ggcccagaag auuuaacgcc agcucagacu | 660 |
| uugacuaagc guuauacgcg ucagcuugaa agaauuaguc gugugaaaag cgacgaugug | 720 |
| uuggauaaaa cauuaaaugc aauguuggca acuuaugauc cgcacaguaa cuauuauccg | 780 |
| ccaauugaug cgauagaacu gaaccgccaa acaaccuuac agcuugaagg uauuggggua | 840 |
| ucgauucgcc cagaacgugg uaaugaagau uacaccaaga uugaaacuau guagaaggu | 900 |
| gguccugcaa guaagucugg ucaagugaaa ucaggagacc gaaucguugg ugucgcucaa | 960 |
| gagggcggca aaaugaucga uggucggc uggucgaguu cggaaauugu ggguugauu | 1020 |
| cguguaagc gcguacaaa aguaacguug aagcuucuug gugcuggugc aucaaugagu | 1080 |
| caagcacgca augugacuuu ggacgcgau guuauucaag aagaagaugc cggguucgu | 1140 |
| ucacguacag uugaagugac acgugauggu aaaaagcauc uauuaggugu gauugaaauu | 1200 |
| ccaucguucu auuuugacua ucguucacgu cgugcugguc agcaauaucg cucaguuucu | 1260 |
| gaagauacug caaaugcguu ugaggcauua aaagccaaga aaguugaagg uauuauuauu | 1320 |
| gacuugcgua augacccagg ugguucauua gaagaaguug cacguaugcu cggacaagug | 1380 |
| auuaagucag guccaguugu gcaaauucgu gauggcaaug gcaacguaag uguauuugaa | 1440 |
| gacaacgaug guggucagca aaucuauaca gguccacucg cuguauuggu gaacuuggca | 1500 |
| ucagcaucug caagugaaau uuacucugcu gcaauucaag auuaugagcg uggcauuauc | 1560 |
| auugguagua caacuacagg uaaagguaca gcucagguuc aacgauac uuuggcauau | 1620 |
| ggucaagcaa ccuuaacuca gcguaaauuc uaccguguaa cggugguag uacacaaaac | 1680 |
| aaaggguguag ugccagauau uaagcuuguu gauaucuaua cgaagaguu ggugagcgu | 1740 |
| aaaucgaaaa augcguugaa gugggauacg auuccgacug caccauuuaa gcugaaggu | 1800 |
| ucagugcagc cauauguagc gaagcugucu caacuucgg aacaacgugu ugcuguugau | 1860 |
| ccacaguuua aguauuuaaa uaaacguacg gcaauugcga agguuacgag ugaccagaaa | 1920 |
| caaguuugugc uugauauuga uaagcgccgu gcagagcuuu ugaguuuaga aaagcaaacu | 1980 |
| uuagaugcug aaaaugaacg ucguauagca acaggucaaa aaccuuuccc uaacugggaa | 2040 |
| agcuaucagg cuucucuaga ugcucuagcu gaaucgug ccaaaaugaa agcuaaucaa | 2100 |
| cguccugcgu ugccagaaga agaaacguuc guaaaugaag cugcgaaugu auugauggau | 2160 |
| uaugcgaaau ugcagaaccg uuaa | 2184 |

<210> SEQ ID NO 82
<211> LENGTH: 2187
<212> TYPE: RNA
<213> ORGANISM: Acinetobacter baumannii

<400> SEQUENCE: 82

| | |
|---|---|
| augacaagaa uaauuguagc auccaaagag gguuggacg uucugcaaga uggucagcuc | 60 |
| aauaaggugg uuuuaaacca accuacuauu auucaaauug guguaaguca aaaagauauc | 120 |
| gcaucgaugg aaaagcaggg uggaagcua gucauccauu uaaaaaaugg agaaacaauu | 180 |
| gucuuagaaa auuucuuuaa ugaagcaacg aauacaacag agcauucacu cguuuuucca | 240 |
| acugaacaag gaaaauuugu ugaagcacaa uuugaugcuc aagguaaggu uauagauuau | 300 |
| agaggcuuaa aucauguuac ggauuuggcc uauaccagua ccagcccuuc agcugcaaca | 360 |
| auggccguug auaaugaucc aagcuuuucg augggauaug uacuaaaagc aggcuuagca | 420 |

```
guuuuagccg cugaagguuu auaucuuugg gcauuugaua aagaugauaa agaugauuca    480
cccaguacuc ccgauuuaau agcaccugcu gcuccuacag cuacgcuugc ugaugauacu    540
gugacaguga cuggcaaaac ugaagcaaau gcgaaaaucu acauuaaaga ugcagcaggu    600
aauacagugg ccucaggugu ugcugaugcg agcggaaauu acacgauuaa auuagauaag    660
ccguuaguga augggauaa auuaaauguu auugcccaag augcggcugg aaauaauucu     720
aaaguuacug ugguaacagg aacaaaagau acaauugccc cagaguuccc acaagcucaa    780
uugagugaug augguuccuu auugacaggu aaagcagaag caaaugcaaa aaucacuguu    840
uaugaugcca cuggcaaagu auuaggaacu guuuuugcga auaaagaugg uauuuauucu    900
uuaaaacuua cuccaccauu aaccagugaa gcgggcggua aaguгguugc cgaagaugcu    960
gcgggu aaca aaucgagga aguuaaaauu auugcgggua aagauaccau accgccagca   1020
ucuccuuuug uugaaguaaa uaagaagggg ucgguaauac augguaaaac ugaagcaaau   1080
gcaaaaguuc aaauaaaaga ugccgauggu aagugauug gaagugggac cgccgaugcu   1140
caaggugaau ucaaauuac acuuucaccu gcuuaaaaag aggcgcaaaa gggcacagug   1200
guugguggaag augcugcugg uaauguaucu aaaccaguug aaauuacgcc aggcuuugac   1260
ucgauugcac cagauaaacc gacuguucaa auuaauacag augguacuuc uguaaccggu   1320
acggcgagg caaaugccaa aauugaaauu aaagauacaa caggcaaggu aauugguagu   1380
ggaacagcgg augcgaaugg aaaauuuaca auuucuauuu caccagcuuu aacgggauaau   1440
aaacaugcuu cgguaucagc uauagauaau gcuggaaaua aguucugaagu guuugauauu   1500
guaggucacaa aagauacaac accaccagca aaaccuauau uaauuagcgu agaugaugau   1560
guagg gucug uuaaaggagc uauaacggcu gguucugaaa cugacgaugc uagaccaaaa   1620
cuuacaggcu caggugaagc aaaugcaacu cuuacuauuu ugauaaugg uguugcaauu   1680
ggaguuguga cgguaacaag ugguagaucu uggucauuua cauuugauaa agacuuagcu   1740
cuuggu aagc auacuauuac uuugacucaa acugaugcgg caggccuuac cagugaggca   1800
aguucuccau uuaccuuuua uguaguugcu ccaaaggcug cgagucuguc ugaaacuuca   1860
guagauauuu uaaguacaga gggaccaucu uggcagauua uguuggauu gcauacuuua   1920
aaгguagcgc aaaauacaac aacugagacg auuaacccgc agaaaucggu uccuuuagau   1980
gauuuauuaa aaaguucuac ggcuaguaa ucagacccaa ucgcaaaacu cucucauca    2040
acagcguuaa aaacgacuca ggcaucugag ccaaucgaag uaaaugcauc aguuggucag   2100
acaacaucaa auccuaauca uccuuuaccu gauacaacuu cuucgguuuu acaaaaccuu   2160
uuagaucaaa cuuauccagu uguuuag                                      2187
```

<210> SEQ ID NO 83
<211> LENGTH: 2265
<212> TYPE: RNA
<213> ORGANISM: Acinetobacter baumannii

<400> SEQUENCE: 83

```
augucgaagc guauuaucca gucagugcuu ucuguuucag uacuggcaag uaugaugucu     60
auggcuuuug cugcacaaaa ugagcaagaa caagcugaac aaaacauuaga aaagccugcu   120
gaaccuguga aauuggaaac aauuuucgua acagcugaag agcaagugaa gcaaucgcuc   180
gguguaucgg uuauuaccaa agaagauuua gaaaaacuac caguucguaa ugauauuucu   240
gacuauguac gucguaugcc aggugucaac cugacaggca auagcucuac ugggcagcgu   300
gguaauaaua gacaaauuga uauucgcgga augggcccug aaaacacgcu auuuuagug   360
```

```
gacgguaaac caauuaacuc ucguaauuca guccguuaug gcuggaaagg agagcgugau    420
acacgaggcg acucaaacug gguaccagca gaagccaucg agucgaucga aguuuuacgc    480
ggaccagcag cugcucgaua ugguucuggu gcggcaggug ggugguuaa caucauuacu     540
aaaaaaguga cuaaugaaac ucaugguuca guagaguuuu auacuucaca gccugaagac    600
uccaaagaag guucaucaaa ucguguuggu uuuaacguaa gugggccacu aauuaaggac    660
guuuuaucuu aucguuuaua ugguaauuau aauaaaacag aagcugauga guugauauu     720
aauaaaucaa uugguaguac cgcagcuggc cgugaaggug uuaaaaauaa agauauuuca    780
ggccguuuag cuuggcaagc aacagaccag caaacugucu ugcucgauau uucuucuagc    840
aaacaaggua auauuuauuc uggugacucu caguuaaaug caaaugcuga agcggaugcg    900
auacuuucgc agcucauugg uaagaaaacc aauaccaugu aucgugauag cuaugcauua    960
acgcaugaag gugauggguc uuggggguaag aguaaguuag uugcucaaua ugauaagacc    1020
cauaacaaac gucuaccuga aggcuuggcg ggaaguguag aaggaaaaau uaauaaucuu    1080
gaugauaaag ccacuucgcg uuuagaaacu cuucgcuuua acggcgaggc uaauauuccu    1140
uuugaauacu auuuaccccca aguauuaacu guaggugaccg aaugguuga agacagauuu    1200
aaagauaaug ucucgacaac ucaagguaaa gacagcagug guucagguua uggcgaucaa    1260
uuagcgaaag gugaucguag uaaaauggag ucacguauug cuucugcaua uauugaagau    1320
aaccugaaag uuacagacag cacagauguu guauuagguu uacguuuuga ugaccauagu    1380
aaaucugguu cuaauuggag uccaagcuua aauauuacuc aaaaacucaa ugauaauuuc    1440
acuuuaaaag gugggguagc aaaagcuuau aaagcaccaa auauguauca aaaugccgaa    1500
ggguauuuau uaaguacaaa uggcaauggc uguccugcua auauugaguc gcguuguuua    1560
uuacaaggua auggugauuu aaaaccugaa acaucgguaa acaaagagcu cggcauucag    1620
uuccaaagag auaucgugaa ugcgagcuua acugguuucc guaaugauua uaaagauaag    1680
auuguugcgg guacucaugu ugucggaaca guugauggcu caaguacaaa ugcaaauaca    1740
ggagcuguga ccaauacgaa guggaauauu uugcguuggg aaaauacgcc uaaagccuua    1800
auucaagguu uugaaggaag uuuggggguua gacuucggug auauccgcug gacuaauaac    1860
uuuaccuaca ugauggacuc gaaagacaag caaacuggga auccauuauc uuuaguucca    1920
aucuauacaa uuaacucaau uuuugauuau gacauuacug aucaauggga guaaauuuu     1980
guauuuacuc aauauggucg ucaaaaauca cgucauuuug cagagaauag acuugaaucc    2040
gguauagguu caggaggugc gaauucgcgc cuuaagccaa gucguaaaa agcuauagu     2100
acugcuggua uuaauguugg uuauaaguuu ucagaccaaa uuaguacgcg uguuggugug    2160
aguaaucugu uugauaaaca aauuuuaaga gacagcaauu cuauuagcca aacuauaau    2220
gagccagguc gagcuuauua ugcaucuuua aaauauucuu ucuaa                    2265

<210> SEQ ID NO 84
<211> LENGTH: 2721
<212> TYPE: RNA
<213> ORGANISM: Acinetobacter baumannii

<400> SEQUENCE: 84
augccuucua aaauuaaguu uaaacaguca acucuuucuc acucuaugca uuuaaucuua     60
aaaaugcaga guauaccuaa acuuauugu agcagcuuau uauuaaguuu augguuuacu    120
ccuuguuaug cucaaaguuc ggcugagacc guuuuaccag aagcaaaccca gacgguaaca    180
```

```
gauucauugg uacaacaaac uaauacaaau aacccaagug auguuccaau uaccgauguc    240
gcuacucuug uaacucaagc acagcaacaa caagauagcu uggcuauauu gcaacaacaa    300
gaacaauuuc cgaaucagau ugaagaauuu aagccaauua cgcuugauaa ucuugaagac    360
uuaccuguua ugccuguuga ucagaauaug gcaaaugaaa uuuaucgggu agcagaagag    420
gcaaaaaacg aggcucaaaa cuuccagaau gguacgcaaa aacaaccaga aaugguggug    480
agugacgcau cacaagcaga auuacaugaa auuaaucagg ccccuguaaa uauugaccag    540
cucaugcaug agauucaauc ugauaguaag auugugguug aagccaauga aacaggaaaa    600
acuuuaccug agcuuacgc ugccguugaa gaaccacccg aggaaaaagg uuucuuuaga    660
cguauauuca auaaaauccg uccaccucgg guaauuccaa uggagcagau accccguauu    720
acugcugagg uuacgggugc gccagaugau uuagcuaaaa auaucaaagg uaauuaucu     780
acauuuaccc aagaaucauu ugaagauuuu aaugcagcgc uaccgcaacu uaggagcuua    840
aguaaucagg cugcucaagc uguagguauu acaaugccg aguuucguuu ugaaaaguua     900
agugccaguc gcguacgugu uaaugaacg ccaaaugaac caguacggau uaaugaacaa      960
aacauugaau uuacggugc uggugcaaaa cagccacaau ucaggucau ucguuuaguu      1020
ccugaccaag auaggguga uauuuuuaau cauggccuuu acgaaaccac aaaaagccga     1080
auugucgaug cugcaucgga uaaugguuau uuugaugcuu auuggcguuu acaugacgua    1140
aaagugagcc aaccgaaaa uaaagcggau auuaaccuca aguaugagac ugguagcgu      1200
uauaagcuug guaagguuga guuucgcaug agcgauccau caaaaccauu accuuuaaau    1260
augaauauuc uugaaagcau ggcaccgugg aaagagggug augacuaugc uuuuggcgu     1320
guaaauguuu uagcaaauaa ccugacuaac ucacgcuauu uuaacuauac cuggguuug     1380
ucaauuaaac ccgacccaau ugaaaaacca cuugaguuac cacccgauuu acaagcguug    1440
gucgaucagc agaauguuga uauugacgaa ucgaagcugc uccuuuaga gcaacaacaa     1500
cuugccaaag cacgccaguu ggcuucccuca aguaaagaag uaacacaaaa uguggugau    1560
gaaaaacaau uugccggaac ugaaagugua caagccgcac cugcaucuuu aaaagcugca    1620
acuguacaac augaagaaca agaugucgaa caagaccguu uacaggcuca agcucgggaa    1680
gaaaacgua uaccaguga ugugacguua aaugccgaua aacuaaaaug ucuggaaaca      1740
gguauugguu augguaccga cacuggcgcc cguuuacgua gccaauauag acguucgauu    1800
gugaauaaau acgucauuc auuugacgca aacuggagc uuuccaaau cgucaaucu        1860
auagaugggc gcuauaguau uccuuauaaa cauccguuaa augauuacuu uaauauugug    1920
gguggguaug agcgugaaac gagggaugau auugguccgg auguaaguuu acucacggaa    1980
ucggcaguuu uagggguga gcgaguuauu aaaaaaccac ucggaaacug gcaacauacu    2040
auuggguac guuaucgucu cgaccgccua acucaaaagg ggaaugugga uaucucugag     2100
cuaccagaug cauuuaaaac ugcugcauca gagcaagaag cauuauuau uaguauaug      2160
accucuaaaa cuucaaguaa uacacgcuua aacccgacca agcuuuuaa acaaacuua      2220
aaauuagaau uaggagcga aaguuacuu ucagaugcca auaggcgau ugccacagcg       2280
gguuggagau uuauuuauuc uuuaggugaa aaugaugacc aucaguuugu ugggcgguc     2340
gauuuuaguu auauuuuac cgaugaguuu gauaaaguuc cauacaauuu aagauucuuu     2400
acugguggug accagacaau ucgguguuu gauuauaaaa gucuucacc agaagauaau      2460
ggauauaga uugguggaca ggcucuagca guaggcucuu uagaauauaa cuaucaauuc     2520
aaagagggu ggcgagcagc uguuuuucu gauuuugga augcuuacga uaagaguuuu       2580
```

| | |
|---|---|
| aguaauccga cggccuauag uguggguguu gguauucguu ggaaguccccc aauuggacca | 2640 |
| auucguuuag acguggcuuc ugguauuucu gaugauaacc auccgauucg uuugcauuuc | 2700 |
| uuuauugguc cacaacuuua a | 2721 |

<210> SEQ ID NO 85
<211> LENGTH: 2925
<212> TYPE: RNA
<213> ORGANISM: Acinetobacter baumannii

<400> SEQUENCE: 85

| | |
|---|---|
| auguuuauua aaaguauuuu aucuucgauu acuaguauua ucccacuucc ugaaaauagu | 60 |
| aacacaagca guauuuuagg uaacggcucu ggugacggcc acuuaaugg aauaucuucc | 120 |
| ggaaauggug aacacaacua ugguauuggc aauggauauu ccgaugacgc aagcauuacc | 180 |
| gccccaauua ccauuccccu caaccucucu gguaacucaa uuacucucau aggcaauuca | 240 |
| ucuucaaguu cggugaauag cucuccaacc accacuucaa auaacguuaa ugacaacgau | 300 |
| guaacaaaua augguaacgg cucuaccauu gguagcggua caggcaaugg cucuggugac | 360 |
| ggcuuuuaa auggcgccgc uucugguaau ggugaacaca acuauggaau cgguaauggu | 420 |
| auugccgaug acgcaagcau uacugcccca cuuucaauuc caauuaaccu ugcgguaac | 480 |
| ucuauuaccc uaauugguga cucaucuucu aguccgguca acaacucugc aaccaauaca | 540 |
| ucaaauaccg ugaaugauaa cgacaccacc uauaacggca auggcucagg uggugguaau | 600 |
| gguucgggcg auggcuuguu aaauggaauu ggcucuggca auggcgagca aaacuacggu | 660 |
| aucggaaaug ggauugcgga ugacgcaagu auuacagccc caauuacgcu uccuauuaac | 720 |
| uugucuggua acucaauuac ucuaauuggc aauucaucug caaguucugu aauuccucg | 780 |
| ccaacuacaa cgucaaauac ugugaaugac aacgacacca ccuauaacgg uaaugguacu | 840 |
| ggugauagcg gcgugagcgc ucugggcggu ucuggcaaug guucagguga uggcgcaggu | 900 |
| aaugguaucg cuucuggcaa uggugaacau aacuauggua uggcaauggu uaacggcgac | 960 |
| gaugguugaua uuacugcucc gauuaccggc guucuaaaca uuucagggaa ucauuuacu | 1020 |
| cucauuggua auucuucauc aaguucuguc aauaccgcac caacaaccac aucaaauaca | 1080 |
| gugaacgaca augacaccau ugauaauggu aauagcggcg gcacagguag gguucaggc | 1140 |
| aauggcucug gugaugguuu acuuaauggc gcugcuucug caauggcga gcauaacuac | 1200 |
| ggcauuggca acggaaaugg ugaugaugua gauauuaccg caccaauuac aggguguuuu | 1260 |
| aauuucucug guaacucuuu ucaaucauu ggcaauucau cuucuaguuc aauuaauacu | 1320 |
| gcuccaacua caacgaccaa uacaguuaau gacaaugacg uaacugauaa uggaaaugau | 1380 |
| ggaggcggac uuguuggugg aaguucggaa auggcucug ugacggacu guuaacggc | 1440 |
| gcugcuucug gcaauggcga acacaacuac gguauuggua acggaaacgg ugaugaugca | 1500 |
| gauuucaccu ucccucuuac ugguauacuu aacuuuccg gcaacucgcu ucaggcuuu | 1560 |
| ggcaguucau cuagugacuc gguaaaugua gcaccaacca cagcaaccaa uaccgucaau | 1620 |
| gauaaugaca ccauugauaa ugccaauaca ggcggccuug gugacgguuc gggcaauggc | 1680 |
| ucuggcgaug gucuuuuaaa uggugcagcg ucuggguaaug gcgagcauaa cuauggcauu | 1740 |
| gguaacggaa acggugacga ugcagacuuu acgcuuccau uuacuggcgg uuuaaauauu | 1800 |
| cugggcaaug cuuuaucagg uaucggcggu ucuucgaccg acuucuauaa uauuucacca | 1860 |
| acaacuacuu caaacacagu caaugacaau gacacuacca caacggcaa cacuucaggu | 1920 |

| | |
|---|---|
| ggugugauug guucuggcga cucaggcaac ggcucugguq augqcuuauu aaauggcauc | 1980 |
| ucaucaggua acggugaaca uaauuauggc auuggcaacg uaauggcga ugauguugac | 2040 |
| guuguugccc cuaucacuac accacuuaau guauuaggca acucuuucuc auuuauuggu | 2100 |
| ggugaaggua caggcgauau cuuaggucq auuacuggca uuauuggugg uauuggcggu | 2160 |
| gauggagaua uccuaagucc aauuacuggc auuaucggug uauugguqg ugauggagau | 2220 |
| auccuaagcc cgauuacugg cauuaucggu agcauuggcg gcaucggggg ugaucugggc | 2280 |
| gauaacccac uuacagguau uauucaaagc gguauugacg uucuacaaaa uuuagaaagc | 2340 |
| cuaaaaacag guuugauuaa uacagguauu gauacgauug ccggaacaau auuggugu | 2400 |
| uucccugaug cagagcaccc ugucggugau uuugcagauc uuggaaaacu acuuuucgag | 2460 |
| acuucacgug auaguguuaa cggcacgcuu gaagcuauuu cugaccuugc aggcgcugac | 2520 |
| cuugaggggg caaguggcuc gauuacuggu guaauugaua cccuuauuac caauggguuca | 2580 |
| acggcaucua ccauuauuca gcauauugua ggugaugacc uagucacuga aaacggugqc | 2640 |
| cucuuggguu caaucaccac gauuauugu gguguugaca gcqqcgacgg uqguuuacug | 2700 |
| gguqgccuag augcuuaau uagcauuaaa uaugqcqacu cagacaauag uaauucuaua | 2760 |
| gauguagaag auauuuuagg aaauauccuc ggcucgquqg uucaaauca agguauugcu | 2820 |
| guuggugaac cugauccaac gggcqquagu uqauucaua cgauuucacu uaacacagua | 2880 |
| aaucaguuaa cugaccaacu uuuacaugcu uuaccgacug ucuaa | 2925 |

<210> SEQ ID NO 86
<211> LENGTH: 3216
<212> TYPE: RNA
<213> ORGANISM: Acinetobacter baumannii

<400> SEQUENCE: 86

| | |
|---|---|
| auguauaaac caaccacauu ugugugqcag ccaucugcag caucauuauu caaaauuaca | 60 |
| guccuuagcu cugcuuuagc ucqcguuqggu auuacaacag gcuguucuuc gacuccqcaa | 120 |
| ucugcaaaaa ccucgaaaac aaaacaqqug aguggagcag gcaucuuga ugcaagcagu | 180 |
| cuggacucuu uagaagacuu acuuucagca acagauaugc gugcuguaga gggcgaccgu | 240 |
| uuacuuauuu uaaaacacgg ugaugucugg aaqcguauqg cuguaqgcuu caaaauqgac | 300 |
| cucaaucauu gggauccacg uauugaaqcg cagcguagu gguuuaucuc acqucagccc | 360 |
| uaccuugacc gcuuaagugc ucqcgcaagu cquauuuuau aucauacugu uaagaagca | 420 |
| gaacgccgug ucuuccaac cgaacuuqcq uuauuaccag ugauugaaaq uucauaugac | 480 |
| ccagcugcaa caaquagqugc ggcggcggcg gguuuauggc aauuuauucc uaguacuggu | 540 |
| cguauuuaug guuuacaaca aacggqgauq uacgacqgac gccgugaugu ugqggaaucu | 600 |
| acucgugcug ccuaugaguu uuuaggaaqc uuauauaacc aquucgqquc augggaauua | 660 |
| gcuugggcug cuauaacgc uggccgggu cguauucaac aagcgauuaa ccgaaaucag | 720 |
| gcugcuqgguu ugccaacaga cuauuqgqucq cuaaaauuac cgcaagaaac caugaacuau | 780 |
| guuccgcguu ucuuggcuqu cqcucaaauu auuaaaaacc cacqcgcuua uggqguuucg | 840 |
| uuaccgccga uugcaaauag gccccauuuc cgugaaguua ccuuaucqc accauuaucu | 900 |
| uuaaaugaaa ucgcgucggu gacgqqucuu aqccgugcuq aguauaugc auuaaacca | 960 |
| ggcuaucqgu gugaaacagu agacccugca agccaauqgc guauuuugau ccagcugau | 1020 |
| auaaguccuu caguggauaa caaguuaaaa qqaaugaaaq caggqqqaaq uucagqcuqq | 1080 |
| uqgqcaagug uuacuucgcc qucuaaaccg accacaacaa cuucaacccuc agucacaquu | 1140 |

```
agaacuacuc caucaacucc agcucagcca guaagaccau cgacgccugc uaaaacaagu    1200
agcagcucgg uaacgguaaa aacuacaaca ccucgugguu cugaugcgcu agcugcuuuu    1260
gcagcgucag cugauguacc aagugcacca cguauccugu ugcggucac uccggcugca    1320 aauaucaaac cugugagaac ggaaccgcca auuucagcaa cugaacgcga gaaaauuuua    1380
gcggcagugc gugcugaagg ggaaaaggaa acaguugauc aagcuuuaga accucaagcu    1440
acucaagcug aaaagauca aguuguugcc gaguuaaaag cacuugcacc ucagggguaca   1500 gaaauugucg auccguauga cggcaaaauu aaguuaaccg caauucagac cagccaaucu    1560
guugcugagc agcaagguaa agaaguaagu aaagguuuug cuuauccaaa aacuuuagcu    1620
gaagaugcaa cucuugcaaa cucugaagau gcucagcgca auaaagauaa gccuuauauu    1680
aaaacugaua cagauguugu gguuuacaa ccuaaaggua agcguaguac uuauacagua     1740
cagccuggcg auacuuuagc aguuauugcc augaagaaug gugugaacug gcugaugua    1800 gcuaaaugga accagauuga cccugaaaag acuuuauuug uaggaaccag ucuauaucuc    1860
uaugaugcua agccucaaga ggcggaaacu acggcaaaau cggcagcuaa accgaugcuc    1920
uauguuguuc aagcaaauga caguuuaaca ggaguggcaa aucaauuuaa uuugucagug    1980
aaacagcuag cugaauauaa cgauuugucu guaacagaug gcuuguuugu agggcaaaaa    2040
uuacaguuaa aagaaccuaa agguaaucgu gcugcuaaag uagagccaaa ggcaauucaa    2100
gcaaguacac gucguauugc aacaaagagu auacgguuaa acgtggcga auacugaaa     2160 uuaauugcag accguauagc auuaucuaau caagaguugg cagaccuaac accagggUUa    2220
ucagcuggua guauuuaau uguaggccaa aaaauuaaug uaccugcaaa agaaaucacu     2280
guugaugaag uugaugacag caaggcuucu gguaaauaug aaaagcuugc agcaggucca    2340
ucauauaaaa cugaaaguua uaaagugcag cguggugaua cauuaucaag cauugcgacc    2400
aagucuaaaa uuagccuagc ugagcuugcu gaacugaaca auuuaaaagc gaacagucau    2460
guccaacugg acaaacucu aaaaguuccg gcuggugcau caguuccuga ccauauguu     2520 gugcagucag gcgauagcuu aaaugcaauu gcagcuaaau auaacuuaca aaccaguuau    2580
uuggcugauu ugaauggUUU gucacguacu gcaggccuuc gugcugguca gcguuuaaaa    2640 uuaacggug aaguugaaac aacuagcaaa guuucggcua aaaauaccaa agaagaaacg    2700
ccagagaccu acacaguuaa aucgugugau agcuuaggaa auaucgcuaa ccgcuaucau    2760
uuacaguuag auuaccucgc ugcauugaac gguuugucuc gcaacaguaa uguucgguuu    2820
ggucaacgcu uaaauuaac agguauuua ccaacaguag aaacagcuaa aacgauacg      2880 gcgaaaucgu cuccaaaagc uguaguugca ggaaaaaaua cugaaaagua cacgguuaaa    2940
gcuggugagu cguuaaugc uauugcgagu cgucgggua uucaguucg ugaacugcu      3000 gaaaugaaug cauuaaaagc aaagccaau uuacagcgug acaaaauau gugauucca     3060 aaacuguag uggaauacaa agucaaacgu ggugauaccu uauuggucu ugcgaguaaa    3120 uaugguuuag aaaccacuuu auuggcggaa cucaacaacc uaacaccguc gacucaauug    3180
cguauuggcg auaucauuaa agugccuaau uuauag                             3216
```

<210> SEQ ID NO 87
<211> LENGTH: 3333
<212> TYPE: RNA
<213> ORGANISM: Acinetobacter baumannii

<400> SEQUENCE: 87

| | | | | |
|---|---|---|---|---|
| augaaacgua | uguugauuaa | ugcaacucau | gccgaagaag | uucgcguugc acuuaucacu | 60 |
| gguaaucguc | uuuacgauuu | ugauuuagag | aaucguaccc | gagaacagaa aaaauccaau | 120 |
| aucuauaaag | gccaugucac | ccgcguagaa | ccaucuuuag | aagcuguuuu uguugaauau | 180 |
| ggcgcagguc | gucaaggcuu | cuugucuaug | cgugaaauug | cuaacagcua uuucaggca | 240 |
| gacccacguc | aaacuucaaa | cauucgugaa | cuuauuacug | aaggcacaga gcuuuuaguu | 300 |
| cagguugaaa | aagaagaacg | ugguaauaaa | ggugcagcac | uucuacguu uauucccuu | 360 |
| gcaggccguu | auuuaguucu | uaugccaaau | aacccgaaag | guggugguau uagccgucaa | 420 |
| auuucagguu | caguacguga | agaauuaaaa | gaaauuuuag | cuucuuuaaa uguaccucgu | 480 |
| gguaugagcg | uuauuguacg | uaccgcuggu | auuggacgua | cccaagaaga auuacaacuc | 540 |
| gauuugcaac | acuugcuuga | ccuuuggca | caaauccaag | uacagccag cucaggcccu | 600 |
| ucuccgaugc | uuguucauca | agaagcgggu | guaguaacac | gugcaauucg ugauuacuua | 660 |
| cgugaugacg | uugcugaaau | cuuaauugau | agcgaacaag | cuuauaacga agcauauaac | 720 |
| uuuguuaaag | cagugaugcc | gcgucaauua | gacaaauuaa | aaacuauac uuuaaacgag | 780 |
| ccauuguuug | cucauuuugg | uauugaaagc | caaauucaaa | cugcuuacga gcgugaagua | 840 |
| aaacuuccuu | cuggcgguuc | aauugugauu | gaccagacug | aagcuuuagu uucaaucgau | 900 |
| auuaacucug | cgaaaucgac | ucguggacau | auguuggag | aaacugcacu gaauacuaac | 960 |
| cuugaagcag | cagaagaaau | ugcucgccaa | cuucguuuac | gugacauugg cgguuuagu | 1020 |
| guuaucgacu | ucaucgauau | gacuaaagaa | cgcaaucaac | guaugguuga agcaaaacuu | 1080 |
| cgugaagcaa | cacaaagcga | ucgugcacgu | auccaguucg | gucaauuguc ucguuuuggc | 1140 |
| uuaauggaaa | ugagccguca | acgcuuacgc | ccaucgcuug | aagaagcaac agguuaugua | 1200 |
| ugcccucgcu | gucauggcuac | aggcaugguu | cgugauuuac | guucgcuuuc ucuuucaauu | 1260 |
| augcguaaag | uugaagagau | ugcacuucgu | gaacgucaug | ugaaguuca aguugaaguu | 1320 |
| ccaguugaaa | uugcagccuu | uuugcuuaau | gaaaaacgcc | auagucuggu guauuuagag | 1380 |
| caaacuucug | uguacgugu | gacuguauug | ccacacccgc | acuuagaaac uccacauuac | 1440 |
| gaaauugcau | auaacccaga | uggcuuugcu | ccaucuagcu | augaacguac agaagcaacc | 1500 |
| cguucuagcg | agaaagaguu | agguuaugag | ucuucugaau | ggcauuuaga agaagcagau | 1560 |
| cauggccaug | cucauguaac | ugcuacagcu | caacucaug | cugcggcuca gaaaaaagca | 1620 |
| aaucaugcaa | cucaaccugu | agcacaaccu | ucugcucaaa | aagcagcaag cccaugugca | 1680 |
| ugguuagaaa | accguuugu | ucaaaaacaa | gcgcaaacag | uugaucaauc ucguucagca | 1740 |
| caaaaugcug | cugcugcgau | ugagcaaaug | gugaauacag | gcgcaguaag ccgcggacag | 1800 |
| uucggucaag | uagccguacc | ugcuguugcg | gaaguugcgc | caguucaauc aaauaacgcu | 1860 |
| uauauuucac | agucaccugu | gaaacaagac | guucgugaac | auguugaaaa agaugauaaa | 1920 |
| ucucagcaac | aacgucagaa | caacaaaaag | cguaaacaua | aagagcaacg ugaacaacau | 1980 |
| caccaaucac | augaacagca | acaucaaguu | caugaagaag | ugguucaauu gcacgccaa | 2040 |
| gaacaacgug | aguuaaaacg | ucagcaaaaa | cgucaacagc | agcaagauca gcaacaucaa | 2100 |
| aauaaugaug | uacaacacac | ugaaaaugcu | gugccacguc | ugaccguaa uaaucaacaa | 2160 |
| cguccaaacc | guccaaaucg | ccaccgcgau | ccaaguguau | uaaaugaaaa ucaaaauaca | 2220 |
| cugguuguug | uugaugaaaa | acaaauuaag | guugaugaga | uugaugcacc uaagcaugau | 2280 |
| gucaugaaca | cugcuuuaau | caucaauguu | gaucaagguc | aaagugagau uguugcacuu | 2340 |
| acaccugagc | gucgucacgu | ugagcgaguu | gaaacgacuu | cuacugaagu ugcucaagag | 2400 |

```
ccaacuccag cuccuguugu agccgagaaa gcugcuguag uugaaaccaa agaagaagcu    2460
cagccaagcc aagaagcugc ucagccacaa aucaaacgug cuagcaauga cccucguaug    2520
cgucgucguc agcaacguga ggcuaaacac gcuaaggcag cuacaccauc uauugcgcca    2580
ucgcaaauuc caacuuuggc acaacacaca aucgguaguu uaauccguca uguguauggu    2640
gaagauugca ccguauugau ugaacaauuu ggucuagucc caacguuuaa ucgugcuuug    2700
cagaaauuug cagaacagua cgcaaguacg uuaguaguu aaguuacgc ugaaacggaa    2760
gagaaaaagc cgguaacucg ugaugcagaa cuuccaagcc auaaaccagc ugaagaagca    2820
gaaccugcac caguacuucc gcuuacuccg ccgcaagcac cagcuccacg uguugcaaau    2880
gacccgcgug agcgccgucg uuuagcaaaa cuugcugcgg aacaagcauu ugagcaagug    2940
aaacaacaac auucugcuca agaagaaguu gcuacuccug cuccuguagc agaagaaacc    3000
guugcugcuc caacugcuga aacacaagca acaguugaac cagcacaaca accgcuugaa    3060
cuuaaucagu caacugaagu cguacaaccu gaagcugcuc cugcagagga aaaagcuaca    3120
gaagaaacag uagcugaagc uccugcggca aaggaaccug cgccaucaaa agcagcaagc    3180
aaagcaaaag cagcggcuga agaaacagua gcuccgacug aagcaacaac ugaugccgaa    3240
ucagaagacg uuaaggcaga uaaggacaaa ccgagucgcc cucgucgccc ucguggccgu    3300
ccgccaaaaa aagcuaauucc uguagcugag uaa    3333
```

<210> SEQ ID NO 88
<211> LENGTH: 3687
<212> TYPE: RNA
<213> ORGANISM: Acinetobacter baumannii

<400> SEQUENCE: 88

```
augucuacgc uugccacccu aaaagcgcuu cuugcuaaac gcauucugau uauugauggu      60
gcaaugggaa ccaugaucca gcgccauaaa uggaagaag cugacuaucg ugguagcgu      120
uuugcugauu gggcacauga uuuaaaaggu aacaaugacc uuuugguucu aacacagccu     180
caaaucauuc aagguauuca ugaagccuac cucgaugcug gugcagauau uauugaaacc     240
aacagcuuua auggcacacg uguuucaaug ucgacuacc acauggaaga ucuuguucca     300
gagauuaacc gugaagcagc acguuuagcc aaagcagcuu gcgaaaaaua uucgacucca     360
gacaaaccgc guuuugugcc aggcucuacug gggccaacau cucguacaug uucaaucucu     420
ccagauguga acaacccugc uuuucguaac auuagcuuug augaacuaaa agaaauuau     480
auugaagcga cucaugcacu aauugaaggu ggucagaca uuauccgau ugaaaccgua     540
uuugauacuu uaaauuguaa agcagcgauu uuugcaguca agaaguauu caaacaaauu     600
ggucgcgaau uaccaauuau gauucaggg accauuaccg augcaucagg ccguacuuua     660
acaggucaga cagcggaagc uuucuggaau ucgguucguc auggcgauuu gcuucaauc     720
gguuuuaacu gucccuuugg ucagaugcc augcgcccuc acguaaaaac uauuuccgau     780
gucgcagaua ccuuuguuuc agcgcacccca aaugcaggcu accaaacgc auuggugaa     840
uaugacgaaa cuccagagca aacugcagcu uucuuaaaag aguugcuga agcgguuug     900
auuaacauua cuggugguug cuggugacg acaccagacc auauucgagc uauugccaau     960
gcgguaaaag acauugcgcc ucgccaagug ccugaaaccg uaccugcuug ccgcuuaagu    1020
gguuuagaac cauuuaauau uuaugaugau ucauuguuug uaaacguugg ugaacguacu    1080
aacguuaccg guucuaaaaa auucuuacgu cucauucgug aagagaaacuu ugcagaagcu    1140
```

```
uuagaaguug cacagcaaca agucgaagcu ggcgcacaga uuauugacau caacauggau   1200
gaagggaugc ucgacucgca aaaugcgaug gugcauuuuu uaaaccuugu agcauccgaa   1260
ccugacauuu cacguguacc gaucaugauu gacucaucga aaugggaaau cauugaagcc   1320
ggcuuaaaau gcguacaagg uaaaccgguu guuaacucaa uuuccuuaaa agaagguuau   1380
gacgaguuug uugaaaaggc ccgccucugc cgucaauaug gugcugcaau cauugugaug   1440
gccuuugacg aaguaggca ggccgacacu gcugaacgua aacgugaaau cuguaagcgc   1500
ucuuaugaca uuuuaguaaa cgaaguaggc uucccugcug aagauauuau uuugacccg   1560 aacguguuug caguugcgac ugguauugaa gaacacaaca acuacgcagu cgauuuuauu   1620
gaagcaacgg gcuggauuaa acagaacuua ccgcacgcca ugauuucugg gguguguucu   1680
aacguuucgu ucucauuccg ugguaaugag ccaguucgug aagccauuca cucuguauuc   1740
uuguaccaug ccaucaagca aggcaugacc auggguauug gaacgcagg ucaauggcu   1800 auuuaugaug auauuccuac cgagcuaaaa gaagcgguug aagaugucau uuuaaaucag   1860
aaucaaggug agucuggca ggcugcgacu gaaaaauuac uugaaguugc agaaaaauac   1920
cguggacaag guggugcaac aaaagaagcc gaaaaccuug aauggcguaa ugagucaguu   1980
gaaaaacguc uugaauaugc cugguuaaaa gguauuacga cuuauauuga ccaagacacc   2040
gaagaagccc gcuuaaaauc aaaacguccu uuagaugaua uugaagggcc acugauggac   2100
ggcaugaaug uggucggua cuuguucggu ucagcaaaaa uguucuugcc acaaguugua   2160
aaaucugccc gagucaugaa acaagcagug gcauggcuca acccguacau cgaagcugaa   2220
aagacagaag gacagucuaa agguaaaguc cuaauggcaa cgguuaaagg ugacguacac   2280
gauauuggua aaauauugu aggcguagua cuuggcugua auggcuauga cauuguugac   2340
cuuggcguaa uguccccuug cgagaaaauc uugcaaacug caauugauga aaaaugugac   2400
aucauugggu uaucggucu gaucaccca ucuuuagaug aaaugguauu uguugcuaaa   2460
gaaaugcagc guaaaggcuu uaacauuccu uuauugauu guggugcaac cacuucuaaa   2520
gcccacacag caguaaaaau ugacccucag uaucaaaacg augcaguaau uuauguugcu   2580
gaugcuucuc gugcuguugg uguagcgaca accuugcuuu cgaaagaaau gcguggugca   2640
uuuauugaag aacaucgugc ugaauaugcc aaaauucgug agcguuuagc caacaaacaa   2700
ccaaaagcgg ccaaacugac uuauaaagag ucgguugaaa augguuuuaa aauugaugaa   2760
agcuaugugc caccaaaacc aaaucuuuug gaacucaag uuuaaagaa uuaccgcuu   2820 gcaacacucg uggauuauuu ugacuggacg ccauucuuua uuucuggag uuaacuggc   2880 aaauucccga aaauuuuaga agaugaagug gucggcgaag cagcaacuga cuuguacaac   2940
caagcacaag caauguugaa agauauuauc gacaacaacc guuuugaugc ucgugcugua   3000
uuugguaugu ucccugcuca gcguacagau gcagauaccg ucagcguauu ugaugaagcu   3060
ggucaaaaug uuacgcauac uuuugagcac uuacgccagc aaucgacaa agugacaggc   3120 aaaccaaacu ugucuuuagc agauuacauu cgucugaccc gcgagcagca agacuacuug   3180
ggcggauuca cuguaucgau uuuuggugca gaagaacugg ccaaugaaua caaagccaaa   3240
ggugaugacu acucugcaau uuuaguacag ucauuagcug accguuugc ugaagccuuu   3300 gcagaacauu uacaugaacg uauucguaaa gaguucuggg gcuauaaagc ggaugagcag   3360
cucagcaaug aagagcugau uaaagaaaa uaugucggua uucgccugcc accagguuau   3420
ccugcuugcc cugagcacuc ugaaaaagca guguauuuu acugguuagg cucuaccgac   3480
aaaauuggua cuaaacugac ugagcacuuu gcaaugaugc cgccaucuuc gguaagcggu   3540
```

```
uucuauuauu cucauccuca aagugaauac uuuaacgugg guaaaauuuc ucaagaccaa    3600
cuugaagauu augcaaaacg uaaagguugg acacuggaug aagcgaagcg uugguuagcu    3660
ccgaauuuag augacucgau uguuuag                                        3687
```

<210> SEQ ID NO 89
<211> LENGTH: 3855
<212> TYPE: RNA
<213> ORGANISM: Acinetobacter baumannii

<400> SEQUENCE: 89

```
augaaacuaa aauugaagaa uuuuaagcca aauaauuuau gguaugccgu cuguucaagc      60
ucaaugauau ucacauggcu gaugacaagc ucuguggugc aagcaaguga uuuacaaauu    120
uaugccucac cuacagcagg uaaaaaaaca auugugauga uguuggauac aucaggaagu    180
augaccaaca auaguuaugg ugaaaaccgc uuagccaugc uuaaaaaugg uaugaaugcu    240
uuuuuggcua gcaauaaccc ugucuuaaau gaaugcgag uagguuuagg aaauuucucg     300
gcaaauggug acagccgaag uggacaaauu uuagggcug cugucccuuu aggugaugca    360
aguacuuuaa aucgguuagg cucacaacgu uauaaauuaa aacaagcugu ugcuaauuua    420
acugcgggag gcucaacacc uucagcccac gcuuaugcug aagcagcugc uuacuuaaug    480
gggacaacca cauauucaga gacgaauuau gcauucgua aagauaguua uaucaaacgu      540
guaagaagau cugauaauag aacgaauau ucauaugua cuaauuaccg ugauucgcaa      600
auugauacag ccaaccuaug gcaaccuugu cguucaaaua guuauggag uagcuggua      660 acaaauaauc cagguguga uaaugcuacu gcuuaugaua cuucaucuga cuggacuuau    720
uacuauacuu auuacuacac cacuuuuaau uaugcguag caaagcaga uagcgguauu    780 ccaaaaucua aaucaaacga uacagcuagc aauccgaaua uuguugaga ccgaaaugcu    840 acuaacucca augcagugua ucagucaccu uuaccgcag uagcgaaucg ccagaguugu    900
gauggacaag guauuuacuu cuuaucggau ggcgaaccga acaauacaac aaauacacgu    960
ucggcaagug ucaugucgac ugcuuuaggu aguacuuuug gagcugauuu uaauuguucu    1020
ggagguuuau cuaacacuac ggcagacucu gguuggccuu uauggggaga guugcaaaa     1080 agauuauuug auaaaacaaa gaacccugcc ggaguuucua ucaaacagc auuugucggu    1140 uuugguagug acuuuucuag uuugaauucu ucugauguaa aaaugccug ccguuuaagu    1200 ucgagaaccc agucugaccg aaaaggagau gaugcguguu caccgaauca aucuacaaau    1260
gcgguagcug caccagguua uggaaauggu gguuuuucc cuacucagag uucacaaggc     1320
guaacagaca gcguuaucgc auuuauuaau aauuuagaua aguuccuuu agaacccuua    1380 accacagggu cuaucucagu uccauaugau gcauugaauc ccaaaauuu acaggaauau    1440 gguuauuuac gagcuuuuga gccaaauccu gcuaacacgu acuuaacaug gcguggaaau    1500
uuaaagaaau aucauguugu uuuaucugga gcgaaugcug gugcuuuuga ggccaauucu    1560
ggcggauuag ucuacaaugc aagugggcu uuuagaacug gaacaaagga uuauuggaau    1620
agcucuacuu auacgacgg aggcaaaguc uuuuuaggug guucauaugc gaaugugccu    1680
uuacccauug cuggacaacc ugaaacacgu gaugcagaag ggaauaucac aaaauauuau    1740
uacgcaguac aaaguaaau ccgcaacuua uuuacgaug uuccgccgu ugcagcagau       1800 gguagcuuua cgaaaauuuc aacuucugga acuaauuugc uaaaaauucc agcugcucca    1860
ccagaagaaa cuaauccuuu ugauacggug gcuaauacag caaguuaugu uuuagguaaa    1920
```

| | |
|---|---:|
| uuugauccau caacuggaca aaauauuuua aaagcuuuuc cuauaagcuu gaaauuaaaa | 1980 |
| auauuaaauu auuuagguua uucaacagau auuaaugcaa caacucugcc uucaucuuug | 2040 |
| guuacaucga augaaccuua uuuaucgaug gggggaagua uucacucuuu accgguucaa | 2100 |
| cuaaccuaca auggaacccu agaugauaau gggaauuuaa caucugcccg agaacaaucc | 2160 |
| auccucuaug gaacuaugga aggcggauua cauauugugg augcuucauc ugguauugag | 2220 |
| caaauggucu uuguuccugc agauauuuua aaugauucag uugcuccaa agcuuuaguu | 2280 |
| guuggucaaa gugaugcuuc agcucccgcu cauggauugg acggagcuug gguaucugau | 2340 |
| ccagccuaua auauuacuac aguggggaagu gguagcucgg caguaucaaa aguaacugca | 2400 |
| aagcaaauga auauuuaugg cggcaugcgu augggaggaa uagcuacua cggacuagau | 2460 |
| guauuaagcc cuacuucacc gaaacugcuu uuuagaauag gggcagacca gaaugacuau | 2520 |
| agccguaugg gucaaagcug gucuaaaccc guacucgcga acauccguua uaacgguucu | 2580 |
| auuagacgcg uccugauugu uggcggguggu uaugaucagu guuaugaaaa accaaauauu | 2640 |
| acguugacug acgcuugcuu uaccaaugga aaagcaaaag gaaaugcugu cuauauuauu | 2700 |
| gacgcaaaaa cuggucagcg uuugugguggg acaagugaua cagguucuaa uacugauaac | 2760 |
| gccaauauga agcauaguau uguuagccgu auuaguacuu uagaccguga ugcugauggc | 2820 |
| uuagucgacc aucuauauuu uggagauuua ggcggacaaa uuuuucgcgu agaccuuaau | 2880 |
| aauaaucaga caaaaaccaa uucgaccau agcaguuuug gugucagagu gugcguuua | 2940 |
| gcgaauuuag caacaaauga uucaacuuau gauggcacaa augauuauac agguggaau | 3000 |
| gcuccucguu uuuaugagcc uccaacagua acgauccacg auuauggaau ucacacuuuu | 3060 |
| auuacaguag gaauugcauc aggagaccgu aguacaccuu uagauguuua cccacucaca | 3120 |
| ggucgugaag guaugacgcc ugcaagugca uuaaguggac guccuguaaa uaauguauau | 3180 |
| ggaauuauug auagagacuu uguuaaaag aacuuaaugu cuuuaacuga uaaucagcuu | 3240 |
| gaaacaaaag auauuacacg gacaggcuua agaaaaaauc cacaaauucu aagaacaggu | 3300 |
| gaaacaagag uagcucaaau uuucuuccca acuacaggag uagguaaagg ugguuggua | 3360 |
| cgcucgcuuu cuaguacgag cgauggguaca gaaaaagcua auaauaguuu ucguauuaaa | 3420 |
| ggaggacuca aagcuuuuga ggaaccaaug gcaauuacgg guaauuaau uauucuaguu | 3480 |
| uaugacccuc aaggaacggg aauuguugcg cagauccuu ccuaccucg uguuguggga | 3540 |
| gaaacagacc gacaaacuua uuguuuacca uuuggagcuu gucuuaauc ugauggguca | 3600 |
| aucgaucaaa auaaagagaa ucacaguggg uuugaaacac aaacugguac uaauugccca | 3660 |
| guaggggcuu cugaauguaa uaaaaacguu auuggcucug uauucguag cguaacauuu | 3720 |
| guaccaacgg aggauaaccc accuacgacu auuaguugug ggaaauuaaa gcugucuggu | 3780 |
| aaugagcaag ggacuggaca guggcaaugu acgagucauu uaguuccuac gcguugguau | 3840 |
| gagcguuauc guuaa | 3855 |

<210> SEQ ID NO 90
<211> LENGTH: 9144
<212> TYPE: RNA
<213> ORGANISM: Acinetobacter baumannii

<400> SEQUENCE: 90

| | |
|---|---:|
| augacagacg cugcuggcaa uacuucggaa caggcuguac aaaaaguagu gugggauacu | 60 |
| accgcgccgc aagcagguga acugacuuua ucugacuuga gugauacagg uauuucagca | 120 |
| acagaucaga ucacgcaaga uaaaaacuuc aauuuaaagc uugaaggaca ggaaagcggc | 180 |

-continued

```
agccgaguaa cauauuuagu uucuaccgau gaaggaaaaa cuuggcagga aaccacgaua    240
gcccaaaaag auuuaacuga ugguguuuac caauauaaag cuguagugac agacgcugcc    300
ggcaauaccu cggaaacggc uguacaaaaa gugguugugg auacuaccac accacaagca    360
ggugaacuga cucuaucuga cuugaaugau acaggcguuu caguaacaga ucagaucacg    420
caagauaaaa acuucaauuu aaagcuugaa ggacaggaaa cugguagccg aguaacauau    480
uuaguuucca cugaugaagg aaaaacgugg caggaaacca cgauagccca aaagauuug     540 gcugauggug uuuacaaaua uaaagcugua gugacagacg cugccggcaa uaccucggaa    600
acggcuguac aaaagugguu guggauacu accgcaccgc aagcagguaa acucacuuua    660
ucugauuuga augauacagg uguucagca acagaucaga uuacgcaaga uaauaguuuu    720
acuuuaaagc uagcucaacc gauugugauu ggggaacaag ccgcuuuacu agaccacuau    780 gaaguucaa aagaugaagg aaaaacuugg caagagacaa cagcugauca aaaagauuua    840
gcugauggua uuuaccaaua uaaagcuaua gugacagacc uugcaggcaa uaucucagaa    900
ucugcuauac aaaaguugu uguagauaau uccuuaaaug uugaaucaac cacagugauu    960
guaaagccga uuacugaaga caauacaaua agcuaguug aaaaagauca aguuauuucu    1020
auaagacuug aaauagcuaa uuuacccaca gauuuaaaua gcucacugac aucaguaaau    1080
acgacauuag gcaauguuac uuauaauuuu cauuuugaug aagucacgca agaaugggu     1140 acugaaauuc cagcagaguu ucuuggca guagagccgc aaaccaauau aucaauugag      1200
auuagucuua cugaucaagc ugguaauaca gccauuauca aacauacccca aaauuauaau    1260 guggaucaua cuccgaauuc accaacccua gauucacuga cuucaacaa uauagaugga    1320 gcuaucauuu caggagugc auauaaagga aguaaggucg auaucuacaa uaaaaauggu    1380
gauuggcuug caaguacaau aacuaaugaa gaagguaaau uuacuuuaca agaucuuuca    1440
auuaacucaa aucaagaagu uuacgcaguc gcuacuuaua augguauag cagugaaaau    1500 ucaucaauug gguuaguuac ugaaguucca gcuauuagua uuacacgaau uaguccagaa    1560
ggcgugauua ugguuauge gacugaaggu agucauuuua uuguaaaaga ucagaaugga    1620
aauauuuuac aagaauuuaa uucuaaugua uuugauagcu cugguauuac accauuuagu    1680
guaauggcau uaggcgaagu aagaccauuu auuuugcccc ucgaucagcc uuuagaggaa    1740
ggggcucaaa uuauuaucuc uauagauaaa gauauauuu caggccaucc acaauauauu    1800
acugcagacu auacuccagc aguauuuuua gaaacuccac aauuugauau uaguggugaa    1860
acuuuaucag uacauguuaa ugaaccuaac agcuuuauuc gugcauuuuc uggagaaggc    1920
aauuuaauug cuacaggguu uaccgaugag caaggcuuug caaguuuaca gguguccaa     1980 uuuuuaaaag aaggcgaaac gguuucgua caaguaguag auaaaaauca aaaucgagu       2040 gaaacccuaa ucgagguucc aaacuuugcu uauauuccac auguugaacg uauuacacaa    2100
gaaggcuuaa uuucugagu ugcugaagau aauaguacgg uaauuguacg ugaugcugau    2160
ggcaaugaau uaggaaaggu uacauuaggu gaugauaaua guuggaguga cuuuagucau    2220
uuuagccuug guguaaaccg cccuuuuaauu gauggagaga aaauuccgu ucaaauuauu    2280 gauaauaaag gguaaugag uccgagcaa aauaucaucg uagaucugac uccuccaccu      2340
gcuccaacgg aguuaaauuu uaaugaugcu ggugauuuag uuuaugguca ugcagaaccu    2400
uucucugaaa uuuuaguuaa agaugggcaa ggaaauauuc uuaauaaaug guuuggaau     2460 aacuggaccg augagagugg aaguuucuca auagaacuag guacauuuuu aaccaaugcu    2520
```

-continued

```
gagacgguuu augucacggc uaccgaugua aauggaaacg uaaguuuagc agcucagaua    2580
caagcaccua auuaugccuu ugcuccauau guugauagcu uuacuucgga uggcgugaua    2640
agugggcaag cugaaaauaa uaguacucuc guuguuaaag acgccaaagg ugacguugua    2700
gcugaaauua aaguugguga agauaacggu uggaauggau caaguuauuu uaaacuccag    2760
cuugaucguc cucuugucga guggugagcag uuuuucuuau caauuaagga ugcacguggg    2820
caaguaagug cugauacugu aauuaccgcu gauacgguug cuccuacacc agccagcaau    2880
uuaguuuucu cagaagaugg uucauaucuu acggguguag cagaacugaa uacuacgauu    2940
cagguuuuug aucauaaugg ucagcuagug aauauaugga auaacaccau uaacucugac    3000
gguacauuua cuauuuacuu agguaguaac aauuuacaug gagaagcauu cacagucacu    3060
guuaaagacc aagccggaaa ugugagugag gcuauuucaa uaaacgcgcc acuugacgau    3120
auugcaccga auccaauuaa aaauauuuua cuugaugcaa auggccaaaa cuuuacagca    3180
caagcagaag caaauaguca gaucgaaguc uuugauucau ugguaauca gacagguugg    3240
gguucuacag auagugcagg uaauguuucu gguucuuuca aucaaacuua uuuacacggu    3300
gaggaacuca cuuugugugu auagaucga gcagguaauc gcaguaucga auuuaagcaa    3360
aaugcuuuaa uugauaccau ugcaccaaau ccgauugcaa auaucaucuu caacgaagau    3420
ggccaaaguu uuacagcuca ggcagaagcc ggaaguucua ugauguauu agaucagacu    3480
ggaaauaaga uugguuuugg uuacaccgau agcucaggua auguaucgg uuauuuucaa    3540
caaguuuacu uacacgguga ggaacuuacu uuugucguga ucgaucgagc agguaaccgc    3600
agugcagagg ucaagcagag ugcuuugaau gaugacgucg uaccaaaucc gauugaaaau    3660
auuguauuag aucucaaugg ccagaacuuu acagcucagg cagaagcaaa uagccaaauu    3720
gaaaucaaaa auaauaacgg ugacgucgua gguuauggau cagcagauag ugcagguaau    3780
guuucaggau auuuguauca agugcauuua caugcgaag agcucacuuu uauugagauu    3840
gaccgagcgg guaccgcag uacagagguu aagcagaaug ccuugauuga ugauauugcg    3900
ccaaauccga uugaaaauau uguauuagau aucaaugggc aaaauuuuac agcgcaagca    3960
gaagcaaaua cucaaauuga aguuaaaaau gcguuggug agauuguagg uuagguaa    4020
guggauggcg cugguaacgu gucagguuau uuauaucaag ucuauuuaca uggagaagag    4080
cucacuuuug uugucguuga ccgagcgggu aaccgcaguua cagagguuaa gcagaaugcc    4140
uugauugaug auauugcgcc aaauccgauu gaaauauug uauuagauau caaugggcaa    4200
aauuuuacag cgcaagcaga agcaaauacu caaauugaag uuaaaaaugc guuggugag    4260
auuguagguu agguuaaugu ggauggcgcu gguaacgugu cagguuauuu aaucaaguc    4320
uauuuacaug gagaagagcu cacuuuugu ucguugacc gagcgguaa ccgcaguaca    4380
gaggucaagc agaacgccuu gaugaugau aucgcaccaa auccgauuga gaauauuuua    4440
cuugaucgca acgacagaa cuuuacagcu caggcagaag caaacacuca aauugaaguc    4500
aaaauacug cugugaagu cauaggaucu gguucaaccg auagauggg uaauguuucu    4560
gguuacuucu aucaggucua uuuacaugg gaagaacuca cuuuuguugu aguugaucga    4620
gcugguaacc gcaguacaga ggucaagcag aaugccuuga ugaugacau ugcuccgaau    4680
gcgauugaaa acauuaucuu uaaugaaau ggucaaaacu uucagcgca agcagaagca    4740
aauagcaaag uugaaguuaa aaaugcgcg ggugagguug uagguucgg uuaguggau    4800
aguguugguua uguguccagg uuacuugaau caaguuuaau uaaaagguga ggagcucacu    4860
uuuguuguga uugaucaagc ugguaaucgu agcauugaag uaaaacaaac agccuuucuu    4920
```

-continued

```
gauaauacag caccggaaaa ugcgacuaau uuaguauuua gugaagaugg cucauaucua    4980
agugguaugg cugagccaaa ugcgacgauu caaauauuug aucaguaugg ucaauuauua    5040
aaucagugga auaauaaugu uaauugggac ggaacauuua acaucuauuu aaacaguaac    5100
uacaugcaug gagaaguauu uaaaguaguu guaguugauc acgcggguaa uuugaguggu    5160
gagguuacug uaaaagcacc gcuugaugau auugcuccug uagcugcaag ugaucgguc     5220 uuuaaugaag augguucauc ccuuucuggu guagcugagc caaauaccuu cauccagauu    5280
uuugaucaaa auggucagca gaugaauacg uggagucaga guguaaaugc ugaugguaca    5340
uuuacuauuu uuuucgguac uuacaauuua cauggugaag aguuuacagu cauuguuaaa    5400
gaccuugcug gaaaugugag ugaagcuguu ucaguuaagg cgccgcuuga ugauauugcc    5460
ccaaaaccga uuaaaaauau uguauuugau gcaaauggcc aaagcuuuac ggcacaagca    5520
gaagcaaaua gucagauuga aauuuugac ucauuggua gucagauagg uuggggcucu      5580
accgauagca cuggaguguu gacggguuac uucuaucaag uguauuuaca uggagaagaa    5640
uuaacguucg uuguuauaga ccgaguaggu aaccguagug augaaaugaa guuaaaugcu    5700
uugauggaua ccauugcacc aaagccgauu gaaaacauca ucuuuaauga aaaugggcaa    5760
aauuuuacag cacaagcaga agccaauagu uuuauuagu caaaaaugc ugcgggugag      5820 uuuguuggcu augguaugu cgauagauacu gguaaugugu ccggucacuu caaucagguu    5880
uacuuaaaag gugaggaacu cacuuuuauu guuauagaua aagcagguaa ucaaaguauu    5940
gaauauaagc aaaaugcuuu aacgaugau auugcaccaa auccgauuga aaacaucguc    6000
uuaaauaaaa auggacaaaa cuuuacagcg caagcggaag ccgauagcca aaucgaaguu    6060
aaaaauacug cggguaggu cguagguucu gguauguag auaguauugg uaauguguca     6120
gguucuuuua aucaagucua uuuacaugga gaagagcuua cuuuuguugu aguugaccga    6180
gcagguaacc guauacaga ggucaagcag aaugcuuuga uugaugauau cgcaccuaau    6240
caaauugaga auauuguuu ugauguaaau ggucaguacu uacggggca ugcugaagca    6300 gauacucgaa uugaaguacu agaucaauuu ggcaaucgcg cugguugggg auauguugau    6360
agccaaggua acgugauagg uuauuucaau cagguuuauu uacauggaga ggaauuaacu    6420
uucaucguug uagauauagc ugguaaccga aguguugaag uuaagcaaaa ugcuuuaauu    6480
gauaaugucg caccgccagc agcagcaaau auuacauuaa ccucagacgg auugcuuuu     6540 ggugaggcgg agccaaacuc aacuguugaa auuauugauc aauuaggugc aguuaucaca    6600
acaacuuaug uuuggacga uggcacauuu aaucaaugga uuaaucugag ucaauaccag    6660
acacaaaauu uaaguauugu ugucaaagau caagcagguua accgcaguga aguugucau    6720 gaauuaguac caguauuuac caacucacca auugcugcaa cagagcuaaa acuggauaua    6780
gauggucaua uucugacagg uaaggcgaca guaggaaugu cgguuguugu uacaucuacu    6840
gauggucaga ccauuaacgg aggugggaau aaugcuguga augaagaugg uaguuugcu     6900 auucaguuaa augauuacua ucuacaggga cagacauuac aaguucgagu uuaugaucag    6960
aauacgaauc aauauagccu aaucucugaa auuauugcgc cuuuagacaa uauugcucca    7020
guaauuaaug aaguguaau uaacaaugau gguaugua uacgggca aacgauuca         7080 aaagcaauca uucagguaau ggaugcggau ggagauuuac gagcagaauu caagcggau    7140 gagacuggau auuuuaacgc uagauuuau ccaccauauau uacgggaga gcaguuauuc    7200 aucacugcga uagauuuagc caaaaauaua aguaagccau uuaauauuac uuuuaaugca    7260
```

```
gauacuaaug caccgccauc agcagagcau auuguggu au cugaaaaugg uuuuuuuauu    7320
gagggaaccg cuguagcaau uaguacugug cauauuuuug augugcauag uaaccauguu    7380
gccacuaaug uugcagauga agcuggaaac uuuaauauuc aguuguaucc accucuagcg    7440
aguggacaaa uuuuacgcau uguuguggaa uacaaugggu aucaaagugc uuacaccgaa    7500
auuacggcac cuauagacac ugucgcacca aaugcagcaa cucagcuucu cuuagaagau    7560
ggaaauguac uuucaggaca agcggaagca uauucaauug uuaauauuuu ugaugcuaau    7620
aauaauuugg uuggucagac uaauguugga agugauggug cuuucuuaac acaccuaugg    7680
uaugaguauu ggcauggcga aacauuaacg guaaaaguag uugaugccaa ucaaaaugug    7740 aguguggga caacgauugu ugcuauaaau gauacgguag uuccagaugu aguuacgcag    7800
cuugcuauag augaaugggg uucgcucaca gggagggu aa aaaguuaugc uacguugag    7860 cuuaccuauc auuuuacuga ccaaccgcuu ucuguaacga gcacuacagc auuggcaaau    7920
ggaauguucu uuaucuaucu ggauagaaau gcaacuucac uugaccuuac uguuauugau    7980
cgugcuggaa accguaguga aaccauuagc caaauaauua gugauuuacc gacguuuauu    8040
auugaucacu uuaaagguga ugcuacagau aauacuuaua acauugauac uauagaugau    8100
uuuguucaag aauauauugu ugagccguau gcaauauaua aagacgucug gauugauaau    8160
agcuauaugu auucagauug ggucauugaa ggccauuaug aacagauaug guugguugau    8220
ggauauuaug aaucgcaaug ggccacaagu ugguuaucaa cuguacaaaa uauuuaucaa    8280
aaucaaaaug guauaacuua uauugauaau ggcacggcag auagcgauua uagucgauau    8340
gaacaacaau auuaugauuu cgugaauggc caauggcaag aaggcuauga auuaacuuau    8400
auacguucag aagaaggaug gguugauaca agcauuaug aagauguuua uauugauaca    8460
agucauuaug aagagguuug gguagauacu agccacuauc aagauauuug gguagaaaau    8520
aguuauuggg agagucaacu uguugaaucu ggccguagag auguggauuu aggcgggcau    8580
gauaaaauua ucaguucugu uaauauagu uugguggu uauaucaaac aguaaaugau    8640
ccaacgacug uagauucguu uuuggaaagu ggucguuaug uagaagacuu ggagcugguu    8700
gguucugcuc aucuaaaugc aacaggcaau gcuuagauua aucuuuuaac agguaacucu    8760
gguaauaacg uuuugaaugg gcugaaggu acgauaccu auaucacuaa ugaaggu acu    8820 gauaccauug uguccaauu gcuaaauagc caagaugcaa cuggcgggaa uggacaugac    8880
acgguguuag auuuuacuuu agguaauaua agaacuaacc uucaagcuga caaaaucgau    8940
uuaagugaac uauuaauuga cuauucuaaa gauguaagcg cauuagcuaa auuuauuacu    9000
guagagcaag augcugggaa cacgacuauu agucuugacc gagauggcga agguacaaug    9060
uuuaauagug ugcacuguu aacucuaaau caaguaaaua caacauuaga cgaauuacua    9120
aacaaccagc aaauuauugu uuaa                                          9144
```

<210> SEQ ID NO 91
<211> LENGTH: 10
<212> TYPE: DNA
<213> ORGANISM: Artificial sequence
<220> FEATURE:
<223> OTHER INFORMATION: Alignment model sequence

<400> SEQUENCE: 91
attcggaacc                                                          10

```
<210> SEQ ID NO 92
<211> LENGTH: 10
<212> TYPE: DNA
<213> ORGANISM: Artificial sequence
<220> FEATURE:
<223> OTHER INFORMATION: Alignment model sequence

<400> SEQUENCE: 92
atacgggacc                                                          10
```